(12) United States Patent
Alcazar et al.

(10) Patent No.: US 11,897,872 B2
(45) Date of Patent: *Feb. 13, 2024

(54) AZASPIROCYCLES AS MONOACYLGLYCEROL LIPASE MODULATORS

(71) Applicant: Janssen Pharmaceutica NV, Beerse (BE)

(72) Inventors: Jesus Alcazar, Toledo (ES); Michael K. Ameriks, San Diego, CA (US); Cynthia B. Berry, Poway, CA (US); Pablo Garcia-Reynaga, San Diego, CA (US); Andrew V. Samant, Cardiff, CA (US); J. A. Vega-Ramiro, Toledo (ES)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/051,130

(22) Filed: Oct. 31, 2022

(65) Prior Publication Data
US 2023/0227438 A1    Jul. 20, 2023

Related U.S. Application Data

(63) Continuation of application No. 17/212,338, filed on Mar. 25, 2021, now Pat. No. 11,505,546.

(60) Provisional application No. 63/000,306, filed on Mar. 26, 2020.

(51) Int. Cl.
| | |
|---|---|
| C07D 413/06 | (2006.01) |
| C07D 413/14 | (2006.01) |
| C07D 401/06 | (2006.01) |
| C07D 401/14 | (2006.01) |
| C07D 403/06 | (2006.01) |

(52) U.S. Cl.
CPC ......... C07D 413/06 (2013.01); C07D 401/06 (2013.01); C07D 401/14 (2013.01); C07D 403/06 (2013.01); C07D 413/14 (2013.01)

(58) Field of Classification Search
CPC .. C07D 413/06; C07D 401/06; C07D 401/14; C07D 403/06; C07D 413/14
USPC ................................................... 514/210.16
See application file for complete search history.

(56) References Cited

U.S. PATENT DOCUMENTS

| | | | |
|---|---|---|---|
| 8,415,341 B2 | 4/2013 | Chevalier et al. | |
| 11,505,546 B2* | 11/2022 | Alcazar ................ | C07D 413/06 |
| 2017/0283406 A1 | 10/2017 | Ikeda et al. | |
| 2020/0255439 A1 | 8/2020 | Kamata et al. | |

FOREIGN PATENT DOCUMENTS

| | | |
|---|---|---|
| EP | 3438109 A1 | 2/2019 |
| WO | 2004013144 A1 | 2/2004 |
| WO | 2009095253 A1 | 8/2009 |
| WO | 2013049289 A1 | 4/2013 |
| WO | 2017171100 A1 | 10/2017 |
| WO | 2019065791 A1 | 4/2019 |
| WO | 2020211798 A1 | 10/2020 |
| WO | 2021160602 A1 | 8/2021 |
| WO | 2021191384 A1 | 9/2021 |
| WO | 2021191390 A1 | 9/2021 |
| WO | 2021191391 A1 | 9/2021 |

OTHER PUBLICATIONS

Ahn et al., "Enzymatic Pathways That Regulate Endocannabinoid Signaling in the Nervous System", Chem Rev., 2008, p. 1687-1707, vol. 108, No. 5.
Alhouayek et al., "Increasing endogenous 2-arachidonoylglycerol levels counteracts colitis and related systemic Inflammation", FASEB J., Aug. 2011, 2711-2721, vol. 25, No. 8.
Bedse et al., "Functional Redundancy Between Canonical Endocannabinoid Signaling Systems in the Modulation of Anxiety", Biol Psychiatry, Oct. 1, 2017, 488-499, vol. 82, No. 7.
Bedse et al., "Therapeutic endocannabinoid augmentation for mood and anxiety disorders: comparative profiling of Faah, Magl and dual inhibitors", Transl Psychiatry, Apr. 26, 2018, 92, vol. 8, No. 1.
Benito et al., "Cannabinoid CB2 Receptors in Human Brain Inflammation", British Journal of Pharmacology, 2008, 277-285, vol. 153.
Berge, S.M. et al., "Pharmaceutical Salts", J. Pharm. Sci., 1977, pp. 1-19, vol. 66 Issue 1.
Bernal-Chico et al., "Blockade of monoacylglycerol lipase inhibits oligodendrocyte excitotoxicity and prevents demyelination in vivo", Glia, Jan. 2015, 163-176, vol. 63, No. 1.

(Continued)

*Primary Examiner* — Kristin A Vajda

(57) ABSTRACT

Azaspirocycle compounds of Formula (I), and pharmaceutically acceptable salts, isotopes, N-oxides, solvates, and stereoisomers thereof, pharmaceutical compositions containing them, methods of making them, and methods of using them including methods for treating disease states, disorders, and conditions associated with MGL modulation, such as those associated with pain, psychiatric disorders, neurological disorders (including, but not limited to major depressive disorder, treatment resistant depression, anxious depression, autism spectrum disorders, Asperger syndrome, bipolar disorder), cancers and eye conditions:

(I)

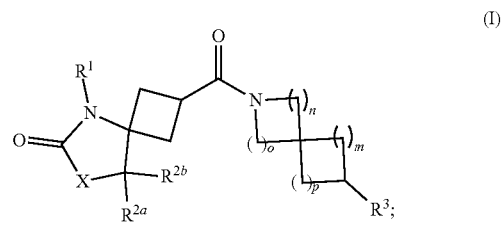

wherein X, $R^1$, $R^{2a}$, $R^{2b}$, $R^3$, m, n, o, and p are defined herein.

15 Claims, No Drawings

(56) References Cited

OTHER PUBLICATIONS

Buczynski and Parsons, "Quantification of brain endocannabinoid levels: methods, interpretations and pitfalls", Brit J Pharmacol, 2010, 423-442, vol. 160, No. 3.

Cancer [online], Medline plus trusted health information for you, [retrieved on Jul. 6, 2007]. Retrieved from the internet, URL http://www.nlm.nih.gov/medlineplus/cancer.html.

Cavuoto et al., "The Expression of Receptors for Endocannabinoids in Human and Rodent Skeletal Muscle", Biochemical and Biophysical Research Communications, 2007, 105-110, vol. 364.

Chen et al., "Monoacylglycerol Lipase Is a Therapeutic Target for Alzheimer's Disease", Cell Rep., Nov. 29, 2012, 1329-1339, vol. 2, No. 5.

Chinnadurai et al, "Monoacylglycerol lipase inhibition as potential treatment for interstitial cystitis", Medical Hypotheses, Oct. 2019, 109321, vol. 131.

Christensen et al., "Efficacy and safety of the weight-loss drug rimonabant: a meta-analysis of randomised trials", The Lancet, 2007, 1706-1713, vol. 370.

Covey et al., "Inhibition of endocannabinoid degradation rectifies motivational and dopaminergic deficits in the Q175 mouse model of Huntington's disease", Neuropsychopharmacology, 2018, 2056-2063, vol. 43.

Curry et al., "Monoacylglycerol Lipase Inhibitors Reverse Paclitaxel-Induced Nociceptive Behavior and Proinflammatory Markers in a Mouse Model of Chemotherapy-Induced Neuropathy", J Pharmacol Exp Ther., Jul. 2018, 169-183, vol. 366, No. 1.

Devane et al., "Isolation and structure of a brain constituent that binds to the cannabinoid receptor", Science, 1992, 1946-1949, vol. 258.

Di Marzo et al., "Endocannabinoids and the regulation of their levels in health and disease", Curr Opin Lipidol, 2007, 129-140, vol. 18.

Di Marzo et al., "Plant, Synthetic, and Endogenous Cannabinoids in Medicine", Annu Rev Med., 2006, 553-574., vol. 57.

Dinh et al, "Brain monoglyceride lipase participating in endocannabinoid inactivation", Proc Natl Acad Sci USA, Aug. 6, 2002, 10819-10824, vol. 99, No. 16.

Folkes et al., "An endocannabinoid-regulated basolateral amygdala-nucleus accumbens circuit modulates sociability", J Clin Invest., 2020, 1728-1742., vol. 130, Issue 4.

Ghosh et al., "The monoacylglycerol lipase inhibitor JZL 184 suppresses inflammatory pain in the mouse carrageenan model", Life Sci., Mar. 19, 2013, 498-505, vol. 92, No. 8-9.

Golub, et al., Molecular Classification of cancer: Class Discovery and class prediction by gene expression monitoring, Science, 1999, pp. 531-537, vol. 286.

Guindon et al., "Peripheral antinociceptive effects of inhibitors of monoacylglycerol lipase in a rat model of Inflammatory pain", Br J Pharmacol., 2011, 1464-1478, vol. 163.

Hajrasouliha et al., "Endogenous cannabinoids contribute to remote ischemic preconditioning via cannabinoid CB2 receptors in the rat heart", Eur J Pharmacol, 2008, 246-252, vol. 579.

Hauer et al., "Glucocorticoid-endocannabinoid interaction in cardiac surgical patients: relationship to early cognitive dysfunction and late depression", Rev Neurosci., 2012, 681-690, vol. 23, No. 5-6.

Herkenam et al., "Cannabinoid receptor localization in brain", Proc. Nat. Acad. Sci., 1990, 1932-1936, vol. 87, No. 5.

Hernandez-Torres et al., "A Reversible and Selective Inhibitor of Monoacylglycerol Lipase Ameliorates Multiple Sclerosis", Angew Chem Int Ed Engl., Dec. 8, 2014, 13765-13770, vol. 53, No. 50.

Hill et al., "Circulating endocannabinoids and N-acyl ethanolamines are differentially regulated in major depression and following exposure to social stress", Psychoneuroendocrinology, Sep. 3, 2009, 1257-1262, vol. 34, No. 8.

Hill et al., "Reductions in circulating endocannabinoid levels in individuals with post-traumatic stress disorder following exposure to the World Trade Center attacks", Psychoneuroendocrinology, 2013, 2952-2961, vol. 38, No. 12.

Hill et al., "Serum Endocannabinoid Content is Altered in Females with Depressive Disorders: A Preliminary Report", Pharmacopsychiatry, Mar. 2008, 48-53, vol. 41, No. 2.

Ikeda et al., "Design and Synthesis of Novel Spiro Derivatives as Potent and Reversible Monoacylglycerol Lipase (MAGL) Inhibitors: Bioisosteric Transformation from 3-Oxo-3,4-dihydro-2H-benzo[b][1,4]oxazin-6-yl Moiety", J. Med. Chem., 2021, https://doi.org/10.1021/acs.jmedchem.1c00432.

International Search Report and Written Opinion for International Application No. PCT/EP2021/053062 dated Mar. 18, 2021.

International Search Report and Written Opinion for International Application No. PCT/EP2021/057820 dated Jun. 7, 2021.

International Search Report and Written Opinion for International Application No. PCT/EP2021/057833 dated Jun. 7, 2021.

International Search Report and Written Opinion for International Application No. PCT/EP2021/057838 dated Jun. 7, 2021.

Jung et al., "Uncoupling of the endocannabinoid signalling complex in a mouse model of fragile X syndrome", Nature Communications, 2012, 1080., vol. 3.

Katz et al., "Endocannabinoid Degradation Inhibition Improves Neurobehavioral Function, Blood-Brain Barrier Integrity, and Neuroinflammation following Mild Traumatic Brain Injury", J Neurotrauma, Mar. 1, 2015, 297-306, vol. 32, Issue 5.

Kinsey et al., "Blockade of Endocannabinoid-Degrading Enzymes Attenuates Neuropathic Pain", J Pharmacol Exp Ther., Sep. 2009, 902-910, vol. 330, No. 3.

Lala, Peeyush K. et al., Role of Nitric Oxide in Tumor Progression: Lessons from Experimental Tumors, Cancer and Metastasis Reviews, 1998, pp. 91-106, vol. 17, Kluwer Academic Publishers.

Ligresti et al., "From endocannabinoid profiling to 'endocannabinoid therapeutics'", Curr Opin Chem Biol., Jun. 2009, 321-331, vol. 13, No. 3.

Long et al., "Characterization of Monoacylglycerol Lipase Inhibition Reveals Differences in Central and Peripheral Endocannabinoid Metabolism", Chem Biol., Jul. 31, 2009, 744-753, vol. 16, No. 7.

Long et al., "Selective blockade of 2-arachidonoylglycerol hydrolysis produces cannabinoid behavioral effects", Nat Chem Biol., Jan. 2009, 37-44, vol. 5, No. 1.

Matsuda et al., "Structure of a cannabinoid recepter and functional expresion of the cloned cDNA", Nature, 1990, 561-564, vol. 346.

Mechoulam et al., "Identification of an endogenous 2-monoglyceride, present in canine gut, that binds to cannabinoid receptors", Biochem Pharmacol, 1995, 83-90, vol. 50.

Miller et al., "Controlled-deactivation cb1 receptor ligands as a novel strategy to lower intraocular pressure", Pharmaceuticals, 2018, 1-8, vol. 11, No. 50.

Mulvihill et al., "Therapeutic potential of monoacylglycerol lipase inhibitors", Life Sci., Mar. 19, 2013, 492-497, vol. 92, No. 8-9.

Munro et al., "Molecular characterization of a peripheral receptor for cannabinoids", Nature, 1993, 61-65, vol. 365.

Nithipatikom et al., "2-Arachidonoylglycerol: a novel inhibitor of androgen-independent prostate cancer cell invasion", Cancer Res., Dec. 15, 2004, 8826-8830, vol. 64, No. 24.

Nithipatikom et al., "A new class of inhibitors of 2-arachidonoylglycerol hydrolysis and invasion of prostate cancer cells", Biochem Biophys Res Commun., Jul. 15, 2005, 1028-1033, vol. 332, No. 4.

Nithipatikom et al., "Anti-proliferative effect of a putative endocannabinoid, 2-arachidonylglyceryl ether in prostate carcinoma cells", Prostaglandins Other Lipid Mediat., Feb. 9, 2011, 34-43, vol. 94, No. 1-2.

Nomura et al., "Endocannabinoid Hydrolysis Generates Brain Prostaglandins That Promote Neuroinflammation", Science, Nov. 11, 2011, 809-813, vol. 334, No. 6057.

Pacher et al., "Pleiotropic effects of the CB2 cannabinoid receptor activation on human monocyte migration: implications for atherosclerosis and inflammatory diseases", Amer J Physiol, 2008, H1133-H1134, vol. 294.

Pasquarelli et al., "Contrasting effects of selective MAGL and FAAH inhibition on dopamine depletion and GDNF expression in a chronic MPTP mouse model of Parkinson's disease", Neurochem Int., Nov. 2017, 14-24, vol. 110.

(56) References Cited

OTHER PUBLICATIONS

Pasquarelli et al., "Evaluation of monoacylglycerol lipase as a therapeutic target in a transgenic mouse model of ALS", Neuropharmacology, Sep. 15, 2017, 157-169, vol. 124.

Patel et al., "The endocannabinoid system as a target for novel anxiolytic drugs", Neurosci Biobehav Rev., May 2017, 56-66, vol. 76, Part A.

Piomelli, "The molecular logic of endocannabinoid signalling", Nat Rev Neurosci, 2003, 873-884, vol. 4.

Piro et al., "A Dysregulated Endocannabinoid-Eicosanoid Network Supports Pathogenesis in a Mouse Model of Alzheimer's Disease", Cell Rep., Jun. 28, 2012, 617-623, vol. 1, No. 6.

Ramesh et al, "Blockade of Endocannabinoid Hydrolytic Enzymes Attenuates Precipitated Opioid Withdrawal Symptoms in Mice", J Pharmacol Exp Ther., Oct. 2011, 173-185, vol. 339, No. 1.

Schlosburg et al., "Chronic monoacylglycerol lipase blockade causes functional antagonism of the endocannabinoid system", Nat Neurosci., Sep. 13, 2010, 1113-1119, vol. 9.

Sticht et al., "Inhibition of monoacylglycerol lipase attenuates vomiting in Suncus murinus and 2-arachidonoyl glycerol attenuates nausea in rats", Br J Pharmacol., Apr. 2012, 2425-2435, vol. 165, No. 8.

Straiker et al., "Monoacylglycerol Lipase Limits the Duration of Endocannabinoid-Mediated Depolarization-Induced Suppression of Excitation in Autaptic Hippocampal Neurons", Mol Pharmacol., Dec. 2009, 1220-1227, vol. 76, No. 6.

Sugiura et al., "2-Arachidonoylgylcerol: A Possible Endogenous Cannabinoid Receptor Ligand in Brain", Biochem Biophys Res Commun, 1995, 89-97, vol. 215.

Sugiura et al., "Biosynthesis and degradation of anandamide and 2-arachidonoylglycerol and their possible physiological significance", Prostaglandins Leukot Essent Fatty Acid, Feb.-Mar. 2002, 173-192, vol. 66, No. 2-3.

Suguira et al "Biochemistry, pharmacology and physiology of 2-arachidonoylglycerol, an endogenous cannabinoid receptor ligand", Prog Lipid Res, 2006, 405-446, vol. 45, No. 5.

Terrone et al., "Inhibition of monoacylglycerol lipase terminates diazepam-resistant status epilepticus in mice and its effects are potentiated by a ketogenic diet", Epilepsia, Jan. 2018, 79-91, vol. 59, No. 1.

Tuo et al., "Therapeutic Potential of Fatty Acid Amide Hydrolase, Monoacylglycerol Lipase, and N-Acylethanolamine Acid Amidase Inhibitors", J Med Chem., Jan. 12, 2017, 4-46, vol. 60, No. 1.

Von Ruden et al., "Inhibition of monoacylglycerol lipase mediates a cannabinoid 1-receptor dependent delay of kindling progression in mice", Neurobiol Dis., May 2015, 238-245, vol. 77.

Walter et al., "ATP Induces a Rapid and Pronounced Increase in 2-Arachidonoylglycerol Production by Astrocytes, a Response Limited by Monoacylglycerol Lipase", J Neurosci., Sep. 15, 2004, 8068-8074, vol. 24, No. 37.

Wang et al., "Treating a novel plasticity defect rescues episodic memory in Fragile X model mice", Mol Psychiatry, 2018, 1798-1806, vol. 23, No. 8.

Wenzel et al., "Novel multi-target directed ligand-based strategies for reducing neuroinflammation in Alzheimer's disease", Life Sci., Aug. 15, 2018, 314-322, vol. 207.

Wilkerson et al., "The Selective Monoacylglycerol Lipase Inhibitor MJN110 Produces Opioid-Sparing Effects in a Mouse Neuropathic Pain Model", J Pharmacol Exp Ther., Apr. 2016, 145-156, vol. 357, No. 1.

Wilson et al., "A high-throughput-compatible assay for determining the activity of fatty acid amide hydrolase", Anal Biochem., Jul. 15, 2003, 270-275, vol. 318, No. 2.

Yi et al., "Reductions in circulating endocannabinoid 2-arachidonoylglycerol levels in healthy human subjects exposed to chronic stressors", Progress in Neuro-Psychopharmacology and Biological Psychiatry, 2016, 92-97, vol. 67, No. 3.

Zhang et al, "Inhibition of monoacylglycerol lipase prevents chronic traumatic encephalopathy-like neuropathology in a mouse model of repetitive mild closed head injury", J Cereb Blood Flow Metab., Mar. 31, 2015, 706, vol. 35, Issue No. 4.

* cited by examiner

AZASPIROCYCLES AS MONOACYLGLYCEROL LIPASE MODULATORS

CROSS-REFERENCE TO RELATED APPLICATIONS

This application is a continuation of U.S. patent application Ser. No. 17/212,338, filed on Mar. 25, 2021, which is pending, which claims priority to U.S. Patent Application No. 63/000,306, filed on Mar. 26, 2020, each of which are incorporated herein in their entirety.

FIELD OF THE INVENTION

The present invention is related to certain azaspirocycle chemical entities having MGL modulating properties, pharmaceutical compositions comprising these chemical entities, chemical processes for preparing these chemical entities and their use in the treatment of diseases, disorders or conditions associated with MGL receptor activity in subjects, in particular humans.

BACKGROUND OF THE INVENTION

Cannabis sativa and analogs of $\Delta^9$-tetrahydrocannabinol have been used since the days of folk medicine for therapeutic purposes. The endocannabinoid system consists of two G-protein coupled receptors, cannabinoid receptor type 1 (CB1) (Matsuda et al., Nature, 1990, 346, 561-4) and cannabinoid receptor type 2 (CB2) (Munro et al., Nature, 1993, 365, 61-5). CB1 receptor is one of the most abundant G-protein coupled receptor expressed in the brain (Herkenam et al., Proc. Nat. Acad. Sci., 1990, 87 (5), 1932-1936). CB1 is also expressed peripherally in the liver, gastrointestinal tract, pancreas, adipose tissue, and skeletal muscles (Di Marzo et al., Curr Opin Lipidol, 2007, 18, 129-140). CB2 is predominantly expressed in immune cells such as monocytes (Pacher et al., Amer J Physiol, 2008, 294, H1133-H1134) and under certain conditions (inflammation) in the brain ((Benito et al., Brit J Pharmacol, 2008, 153, 277-285) and in skeletal (Cavuoto et al., Biochem Biophys Res Commun, 2007, 364, 105-110) and cardiac muscles (Hajrasouliha et al., Eur J Pharmacol, 2008, 579, 246-252).

In 1992, N-arachidonoylethanolamine (AEA or anandamide) was found to be an endogenous ligand for cannabinoid receptors (Devane et al., Science, 1992, 258, 1946-9). Subsequently, 2-arachidonoylglycerol (2-AG) was also identified as an additional endogenous ligand for the cannabinoid receptors (Mechoulam et al., Biochem Pharmacol, 1995, 50, 83-90; Sugiura et al., Biochem Biophys Res Commun, 1995, 215, 89-97). Concentrations of 2-AG were reported to be at least 100 times higher than these of anandamide in the rat brain (Buczynski and Parsons, Brit J Pharmacol, 2010, 160 (3), 423-42). Therefore 2-AG may play more essential physiological roles than anandamide in the brain endocannabinoid system (Sugiura et al. Prostaglandins Leukot Essent Fatty Acids., 2002, February-March, 66(2-3):173-92). The endocannabinoid 2-AG is a full agonist for CB1 and CB2 receptors, while anandamide is a partial agonist for both receptors (Suguira et al., Prog Lipid Res, 2006, 45(5):405-46). Unlike many classical neurotransmitters, endocannabinoids signal through a retrograde mechanism. They are synthesized on demand in postsynaptic neurons and then rapidly degraded following binding to presynaptic cannabinoid receptors (Ahn et al., Chem Rev. 2008, 108(5):1687-707). Monoacylglycerol lipase (MGLL, also known as MAG lipase and MGL) is the serine hydrolase responsible for the degradation of 2-AG into arachidonic acid and glycerol in the central nervous system (Mechoulam et al., Biochem Pharmacol, 1995, 50, 83-90; Sugiura et al., Biochem Biophys Res Commun, 1995, 215, 89-97; Long et al., Nat Chem Biol. 2009 January; 5(1):37-44), Schlosburg et al, Nat Neurosci., 2010, September; 13(9):1113-9) and peripheral tissues (Long et al., Chem Biol., 2009 Jul. 31; 16(7):744-53). Anandamide is hydrolyzed by fatty acid amide hydrolase (FAAH) (Piomelli, Nat Rev Neurosci, 2003, 4, 873-884). MGL exists in both soluble and membrane bound forms (Dinh et al., Proc Natl Acad Sci USA., 2002, Aug. 6; 99(16):10819-24). In the brain MGL is located in presynaptic neurons (Straiker et al., Mol Pharmacol., 2009, December; 76(6):1220-7) and astrocytes (Walter et al., J Neurosci., 2004, Sep. 15; 24(37):8068-74) within regions associated with high CB1 receptor density. Compared to wild-type controls, genetic ablation of MGL expression produces 10-fold increase in brain 2-AG levels without affecting anandamide concentration (Schlosburg et al., Nat Neurosci., 2010, September; 13(9):1113-9).

Thus, MGL modulation offers an interesting strategy for potentiating the cannabinoid system. The primary advantage of this approach is that only brain regions where endocannabinoids are actively produced will be modulated, potentially minimizing the side effects associated with exogenous CB1 agonists. Pharmacological inactivation of MGL by covalent inhibitors in animals increase 2-AG content in brain and peripheral tissues and has been found to produce antinociceptive, anxiolytic and anti-inflammatory effects that are dependent on CB1 and/or CB2 receptors (Long et al., Nat Chem Biol., 2009, January, 5(1):37-44; Ghosh et al., Life Sci., 2013, Mar. 19, 92(8-9):498-505; Bedse et al., Biol Psychiatry., 2017, Oct. 1, 82(7):488-499; Bernal-Chico et al., Glia., 2015, January, 63(1):163-76; Patel et al. Neurosci Biobehav Rev., 2017, May, 76(Pt A): 56-66; Betse et al., Transl Psychiatry., 2018, Apr. 26, 8(1):92). In addition to the role of MGL in terminating 2-AG signaling, MGL modulation, including MGL inhibition also promotes CB1/2-independent effects on neuroinflammation (Nomura et al., Science., 2011, Nov. 11; 334(6057):809-13). MGL modulation, including MGL inhibition leads to reduction in proinflammatory prostanoid signaling in animal models of traumatic brain injury (Katz et al., J Neurotrauma., 2015, Mar. 1; 32(5):297-306; Zhang et al., J Cereb Blood Flow Metab., 2015, Mar. 31; 35(4): 443-453), neurodegeneration including Alzheimer's disease (Piro et al., Cell Rep., 2012, Jun. 28, 1(6):617-23; Wenzel et al., Life Sci., 2018, Aug. 15, 207: 314-322; Chen et al., Cell Rep., 2012, Nov. 29, 2(5):1329-39), Parkinson's disease (Nomura et al., Science, 2011, Nov. 11, 334(6057), 809-13; Pasquarelli et al., Neurochem Int., 2017, November, 110:14-24), amyotrophic lateral sclerosis (Pasquarelli et al., Neuropharmacology, 2017, Sep. 15, 124: 157-169), multiple sclerosis (Hernadez-Torres et al., Angew Chem Int Ed Engl., 2014, Dec. 8, 53(50):13765-70; Bernal-Chico et al., Glia., 2015, January, 63(1):163-76), Huntington's disease (Covey et al., Neuropsychopharmacology, 2018, 43, 2056-2063), Tourette syndrome and status epilepticus (Terrone et al., Epilepsia., 2018, January, 59(1), 79-91; von Ruden et al., Neurobiol Dis., 2015, May; 77:238-45).

Therefore, by potentiating the cannabinoid system and attenuating proinflammatory cascades, MGL modulation, including MGL inhibition offers a compelling therapeutic approach for the treatment of a vast array of complex diseases. Importantly, MGL modulation, including MGL inhibition in animals does not produces the full spectrum of neurobehavioral effects observed with $\Delta^9$-tetrahydrocannabinol and other CB1 agonists (Tuo et al., *J Med Chem.*, 2017, Jan. 12, 60(1), 4-46; Mulvihill et al., *Life Sci.*, 2013, Mar. 19, 92(8-9), 492-7).

Endocannabinoid hypoactivity is a risk factor for the treatment of depression, anxiety and post-traumatic stress disorders. Millennia of human use of *Cannabis sativa*, and a brief period in which humans were treated with the endocannabinoid antagonist, rimonabant, provide support for that hypothesis. 2-AG levels are decreased in individuals with major depression (Hill et al., *Pharmacopsychiatry.*, 2008, March; 41(2): 48-53; Hill et al., *Psychoneuroendocrinology.*, 2009, September; 34(8): 1257-1262.). Low circulating 2-AG levels predict rates of depression (Hauer et al., *Rev Neurosci.*, 2012, 23(5-6):681-90). Reduced circulating 2-AG has been found in patient with post-traumatic stress disorder (PTSD) (Hill et al., *Psychoneuroendocrinology*, 2013, 38 (12), 2952-2961). Healthy volunteers exposed to chronic stressors exhibited progressively diminished circulating 2-AG levels which correlated with the onset of reductions in measures of positive emotions (Yi et al., *Progress in Neuro-Psychopharmacology and Biological Psychiatry*, 2016, 67 (3), 92-97). The CB1 receptor inverse agonist/antagonist Rimonabant has been withdrawn from the market due to the high incidence of severe depression and suicidal ideation (Christensen et al., *The Lancet*, 2007, 370, 1706-1713). Therefore, MGL modulators are potentially useful for the treatment of mood disorders, anxiety, PTSD, autism spectrum disorders, and Asperger syndrome (Folkes et al., *J Clin Invest.* 2020; 130(4):1728-1742, Jung et al., *Nature Communications*, 2012, 3, 1080; Wang et al., Mol Psychiatry, 2018 August, 23(8): 1798-1806).

Cannabinoid receptor agonists are clinically used to treat pain, spasticity, emesis, and anorexia (Di Marzo, et al., Annu Rev Med., 2006, 57:553-74; Ligresti et al., *Curr Opin Chem Biol.*, 2009, June; 13(3):321-31). Therefore, MGL modulators, including MGL inhibitors are also potentially useful for these indications. MGL exerts CB1-dependant antinociceptive effects in animal models of noxious chemical, inflammatory, thermal and neuropathic pain (Guindon et al., *Br J Pharmacol.*, 2011, August; 163(7):1464-78; Kinsey et al., *J Pharmacol Exp Ther.*, 2009, September; 330(3):902-10; Long et al., *Nat Chem Biol.*, 2009, January; 5(1):37-44). MGL blockade reduces mechanical and acetone induced cold allodynia in mice subjected to chronic constriction injury of the sciatic nerve (Kinsey et al., *J Pharmacol Exp Ther.*, 2009, September; 330(3):902-10). MGL inhibition produces opiate-sparing events with diminished tolerance, constipation, and cannabimimetic side effects (Wilkerson et al., *J Pharmacol Exp Ther.*, 2016, April; 357(1):145-56). MGL blockade is protective in model of inflammatory bowel disease (Alhouayek et al., *FASEB J.*, 2011, August; 25(8): 2711-21). MGL inhibition also reverse Paclitaxel-induced nociceptive behavior and proinflammatory markers in a mouse model of chemotherapy-induced neuropathy (Curry et al., *J Pharmacol Exp Ther.*, 2018, July; 366(1):169-18). MGL inhibitors are also potentially useful for the treatment of chronic inflammatory condition of the urinary bladder like interstitial cystitis (Chinnadurai et al., 2019, October; 131: 109321).

Inhibition of 2-AG hydrolysis exerts anti-proliferative activity and reduction in prostate cancer cell invasiveness (Nithipatikom et al., *Cancer Res.*, 2004, Dec. 15, 64(24): 8826-Nithipatikom et al., *Biochem Biophys Res Commun.*, 2005, Jul. 15,332(4):1028-33; Nithipatikom et al., *Prostaglandins Other Lipid Mediat.*, 2011, February, 94(1-2):34-43). MGL is upregulated in aggressive human cancer cells and primary tumors where it has a unique role of providing lipolytic sources of free fatty acids for synthesis of oncogenic signaling lipids that promote cancer aggressiveness. Thus, beyond the physiological roles of MGL in mediated endocannabinoid signaling, MGL in cancer plays a distinct role in modulating the fatty acid precursor pools for synthesis of protumorigenic signaling lipids in malignant human cancer cells.

MGL blockade shows anti-emetic and anti-nausea effects in a lithium chloride model of vomiting in shrews (Sticht et al., *Br J Pharmacol.*, 2012, April, 165(8):2425-35).

MGL modulators, including MGL inhibitors may have utility in modulating drug dependence of opiates. MGL blockade reduce the intensity of naloxone-precipitated morphine withdrawal symptoms in mice. MGL blockade also attenuated spontaneous withdrawal signs in morphine-dependent mice (Ramesh et al., *J Pharmacol Exp Ther.*, 2011, October, 339(1):173-85).

MGL modulators are also potentially useful for the treatment of eye conditions, including but not limited to, glaucoma and disease states arising from elevated intraocular pressure (Miller et al., *Pharmaceuticals*, 2018, 11, 50).

SUMMARY OF THE INVENTION

Embodiments of the present invention relate to chemical entities, pharmaceutical compositions containing them, methods of making and purifying them, and methods for using them the treatment of diseases, disorders, and conditions associated with the MGL modulation. An additional embodiment of the invention is a method of treating a subject suffering from or diagnosed with a disease, disorder, or condition associated with the MGL modulation using at least one chemical entity of the invention.

Additional embodiments, features, and advantages of the invention will be apparent from the following detailed description and through practice of the invention.

Described herein are compounds of Formula (I):

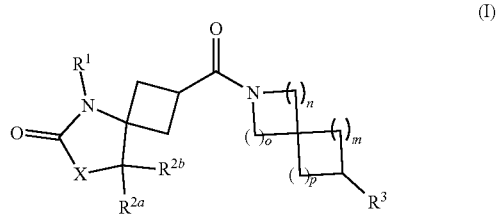

wherein
X is $CH_2$ or O;
$R^1$ is H;
$R^{2a}$ and $R^{2b}$ are each independently selected from H and $C_{1-4}$alkyl;
$R^3$ is selected from:
(i) phenyl, benzyl, or monocyclic heteroaryl, each optionally substituted with one, two, or three substituents selected from: halo, $C_{1-6}$alkyl, $C_{1-6}$haloalkyl, $C_{1-6}$alkyl-OH, $OC_{1-6}$alkyl, $OC_{1-6}$alkyl, $SC_{1-6}$alkyl, $SF_5$, $Si(CH_3)_3$, $NR^aR^b$, $C_{3-6}$cycloalkyl, $OC_{3-6}$cycloalkyl, phenyl, O-phenyl, and O-pyridyl, wherein each cycloalkyl, phenyl, or pyridyl is optionally substituted with one or two $C_{1-4}$alkyl, $C_{1-4}$haloalkyl, or halo groups; or two adjacent ring substituents on the phenyl, benzyl, or monocyclic heteroaryl, taken together with the atoms to which they are attached form a fused monocyclic $C_{5-6}$cycloalkyl or heterocycloalkyl ring, each ring optionally substituted with one or two $C_{1-4}$alkyl, $C_{1-4}$haloalkyl, or halo groups;
wherein $R^a$ and $R^b$ are each independently H or $C_{1-4}$alkyl;
(ii) a bicyclic heteroaryl optionally substituted with $C_{1-4}$alkyl or halo; and
(iii) $C_{3-6}$alkyl or $C_{3-6}$cycloalkyl optionally substituted with $C_{1-4}$alkyl, $C_{1-4}$haloalkyl, or halo; and
n, m, o, and p are each independently 1 or 2;
and pharmaceutically acceptable salts, isotopes, N-oxides, solvates, and stereoisomers thereof.

In some embodiments are compounds of Formula (I):

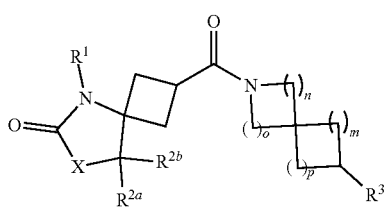
(I)

wherein
X is $CH_2$ or O;
$R^1$ is H;
$R^{2a}$ and $R^{2b}$ are each independently selected from H and $C_{1-4}$alkyl;
$R^3$ is selected from: $C_{3-6}$cycloalkyl; $C_{3-6}$cycloalkyl substituted with $C_{1-4}$alkyl; phenyl; phenyl substituted with one or two members each independently selected from: halo, $C_{1-6}$alkyl, $C_{1-6}$haloalkyl, $OC_{1-6}$alkyl, $OC_{1-6}$haloalkyl, and $C_{3-6}$cycloalkyl optionally substituted with $CH_3$ or $CF_3$; pyridyl substituted with one or two members each independently selected from: halo, $C_{1-6}$alkyl, and $C_{1-6}$haloalkyl; pyrimidinyl substituted with $C_{1-6}$alkyl;

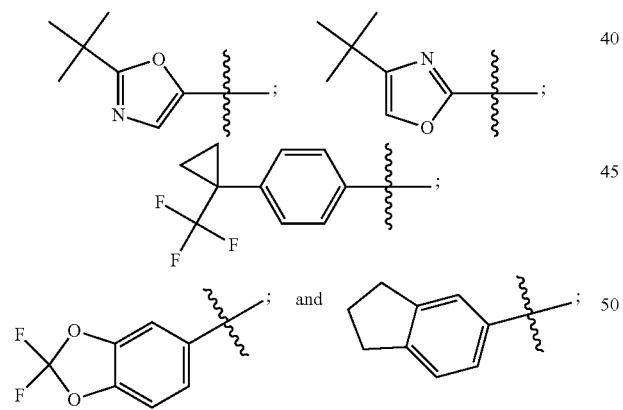

and
n, m, o, and p are each independently 1 or 2;
and pharmaceutically acceptable salts, isotopes, N-oxides, solvates, and stereoisomers thereof.

DETAILED DESCRIPTION OF THE INVENTION

As used herein, the terms "including", "containing" and "comprising" are used in their open, non-limiting sense.

Unless qualified specifically in particular instances of use, the term "alkyl" refers to a straight- or branched-chain alkyl group having from 1 to 8 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. "$C_1$-$C_4$alkyl" refers to straight- or branched-chain alkyl group having from 1 to 4 carbon atoms in the chain.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

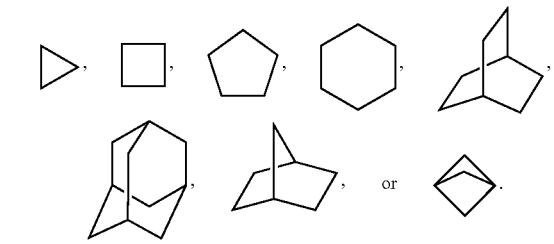

The term "halogen" or "halo" represents chlorine, fluorine, bromine, or iodine.

The term "haloalkyl" refers to a straight- or branched-chain alkyl group having from 1 to 6 carbon atoms in the chain optionally substituting hydrogens with halogens. The term "$C_1$-$C_4$ haloalkyl" as used here refers to a straight- or branched-chain alkyl group having from 1 to 4 carbon atoms in the chain, optionally substituting hydrogens with halogens. Examples of "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl ($CF(CF_3)_2$), and groups that in light of the ordinary skill in the art and the teachings provided herein would be considered equivalent to any one of the foregoing examples.

The term "aryl" refers to a monocyclic, aromatic carbocycle (ring structure having ring atoms that are all carbon) having 6 atoms per ring (Carbon atoms in the aryl groups are sp2 hybridized.)

The term "phenyl" represents the following moiety:

The term "pyridinyl" or "pyridyl" represents the following moiety:

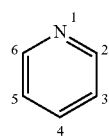

The pyridinyl or pyridyl moiety can be attached through any one of the 2-, 3-, 4-, 5-, or 6-position carbon atoms.

The term "pyrimidinyl" represents the following moiety:

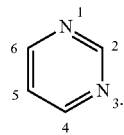

The pyrimidinyl moiety can be attached through any one of the 2-, 4-, 5-, or 6-position carbon atoms.

The term "heteroaryl" as used herein, refers to an aromatic monocyclic or multicyclic ring system comprising 5 to 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is monocyclic and has 5 or 6 ring atoms and at least one nitrogen ring atom. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring.

The term "heterocycloalkyl" as used herein, refers to a ring system which is non-aromatic, 1 to 4 of the ring atoms is independently O, N or S and the remaining ring atoms are carbon atoms, which may optionally be fused to another ring (aromatic or heteroaromatic). Non-limiting examples of illustrative heterocycloalkyl include:

Those skilled in the art will recognize that the species of heteroaryl, heterocycloalkyl, cycloalkyl, aryl groups listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

The term "variable point of attachment" means that a group is allowed to be attached at more than one alternative position in a structure. The attachment will always replace a hydrogen atom on one of the ring atoms. In other words, all permutations of bonding are represented by the single diagram, as shown in the illustrations below.

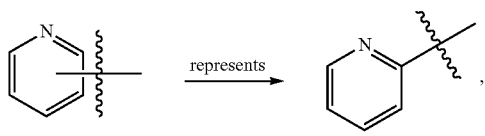

Those skilled in the art will recognize that that if more than one such substituent is present for a given ring; the bonding of each substituent is independent of all of the others. The groups listed or illustrated above are not exhaustive.

Those skilled in the art will recognize that the species of cycloalkyl or aryl groups listed or illustrated above are not exhaustive, and that additional species within the scope of these defined terms may also be selected.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

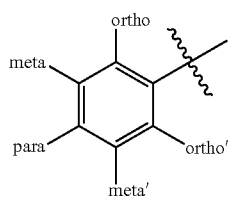

When referring to substituents on a pyridyl group, the terms "para", "meta", and "ortho" refer to the placement of a substituent relative to the point of attachment of the pyridyl ring. For example, the structure below is described as 3-pyridyl with the $X^1$ substituent in the ortho position, the $X^2$ substituent in the meta position, and $X^3$ substituent in the para position:

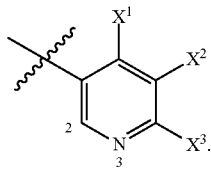

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of such formula. The compounds of this invention may possess one or more asymmetric centers; such compounds can therefore be produced as individual (R)- or (S)-stereoisomers or as mixtures thereof. Thus, any formula given herein is intended to represent a racemate, one or more of its enantiomeric forms, one or more of its diastereomeric forms, and mixtures thereof. Additionally, any formula given herein is intended to refer also to any one of: hydrates, solvates, polymorphs and of such compounds, and mixtures thereof, even if such forms are not listed explicitly.

The term "R" at a stereocenter designates that the stereocenter is purely of the R-configuration as defined in the art; likewise, the term "S" means that the stereocenter is purely of the S-configuration. As used herein, the term "RS" refers to a stereocenter that exists as a mixture of the R- and S-configurations.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Unlabeled stereocenters drawn without stereo bond designations are a mixture of the R- and S-configurations. For unlabeled stereocenters drawn with stereo bond designations, the absolute stereochemistry is as depicted.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of: for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number in an enriched form. Examples of isotopes that can be incorporated into compounds of the invention in a form that exceeds natural abundances include isotopes of hydrogen, carbon, nitrogen, oxygen, phosphorous, fluorine, chlorine, and iodine, such as $^2$H (or chemical symbol D), $^3$H (or chemical symbol T), $^{11}$C, $^{13}$C, $^{14}$C, $^{15}$N, $^{18}$O, $^{17}$O, $^{31}$P, $^{32}$P, $^{35}$S, $^{36}$Cl, and $^{125}$I, respectively. Such isotopically labelled compounds are useful in metabolic studies (preferably with $^{14}$C), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$, or D) may afford certain therapeutic advantages resulting from greater metabolic stability, for example increased in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for such variable appearing elsewhere. In other words, where a variable appears more than once, the choice of the species from a specified list is independent of the choice of the species for the same variable elsewhere in the formula, unless stated otherwise.

The term $C_{n-m}$ alkyl refers to an aliphatic chain, whether straight or branched, with a total number N of carbon members in the chain that satisfies $n \leq N \leq m$, with $m > n$.

When the same plurality of substituents is assigned to various groups, the specific individual substituent assignment to each of such groups is meant to be independently made with respect to the specific individual substituent assignments to the remaining groups. By way of illustration, but not as a limitation, if each of groups Q and R can be H or F, the choice of H or F for Q is made independently of the choice of H or F for R, so the choice of assignment for Q does not determine or condition the choice of assignment for R, or vice-versa, unless it is expressly indicated otherwise. Illustrative claim recitation in this regard would read as "each of Q and R is independently H or F", or "each of Q and R is independently selected from H and F".

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

In another example, a zwitterionic compound would be encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts, and dipolar ions in the known and well-established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$," is accordingly used herein for the sake of brevity, but not by way of limitation. The foregoing first example on substituent terminology, which is stated in generic terms, is meant to illustrate the various substituent assignments described herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein.

The nomenclature "$C_i$-$C_j$" with $j > i$, when applied herein to a class of substituents, is meant to refer to embodiments of this invention for which each and every one of the numbers of carbon members, from i to j including i and j, is independently realized. By way of example, the term $C_1$-$C_3$ or $C_{1-3}$ refers independently to embodiments that have one carbon member ($C_1$), embodiments that have two carbon members ($C_2$), and embodiments that have three carbon members ($C_3$).

A "pharmaceutically acceptable salt" is intended to mean a salt of an acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002.

Preferred pharmaceutically acceptable salts are those that are pharmacologically effective and suitable for contact with the tissues of patients without undue toxicity, irritation, or allergic response.

A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

Compounds of Formula (I) may contain at least one nitrogen of basic character, so desired pharmaceutically acceptable salts may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents.

Compounds of Formula (I) may contain a carboxylic acid moiety, a desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, piperazine, N-methyl-glucamine and tromethamine and inorganic salts derived from sodium, calcium, potassium, magnesium, manganese, iron, copper, zinc, aluminum, and lithium.

The compounds of the invention, including their pharmaceutically acceptable salts, whether alone or in combination, (collectively, "active agent" or "active agents") of the present invention are useful as MGL-modulators in the methods of the invention. Such methods for modulating MGL comprise the use of a therapeutically effective amount of at least one chemical entity of the invention.

In some embodiments, the MGL modulator is an inhibitor and is used in a subject diagnosed with or suffering from a disease, disorder, or condition associated with MGL receptor activity, such as those described herein. Symptoms or disease states are intended to be included within the scope of "disease, disorders or conditions."

Accordingly, the invention relates to methods of using the active agents described herein to treat subjects diagnosed with or suffering from a disease, disorder, or condition associated with the MGL receptor activity. The term "treat" or "treating" as used herein is intended to refer to administration of an active agent or composition of the invention to a subject for the purpose of effecting a therapeutic or prophylactic benefit through modulation of MGL receptor activity. Treating includes reversing, ameliorating, alleviating, inhibiting the progress of, lessening the severity of, or preventing a disease, disorder, or condition, or one or more symptoms of such disease, disorder or condition associated with the MGL modulation. The term "subject" refers to a mammalian patient in need of such treatment, such as a human.

The term "composition" refers to a product that includes the specified ingredients in therapeutically effective amounts, as well as any product that results, directly, or indirectly, from combinations of the specified ingredients in the specified amounts.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme. The disclosure is directed to methods for treating, ameliorating and/or preventing diseases, conditions, or disorders associated with pain (including inflammatory pain), and also psychiatric disorders, neurological disorders, cancers and eye conditions by the administration of therapeutically effective amounts of MGL modulators to subjects in need thereof.

The term "modulators" include both inhibitors and activators, where "inhibitors" refer to compounds that decrease, prevent, inactivate, desensitize, or down-regulate the MGL expression or activity, and "activators" are compounds that increase, activate, facilitate, sensitize, or up-regulate MGL expression or activity.

As used herein, unless otherwise noted, the term "affect" or "affected" (when referring to a disease, condition or disorder that is affected by inhibition of MGL) includes a reduction in the frequency and/or severity of one or more symptoms or manifestations of said disease, condition or disorder; and/or include the prevention of the development of one or more symptoms or manifestations of said disease, condition or disorder or the development of the disease, condition or disorder.

In treatment methods according to the invention, a therapeutically effective amount of at least one active agent according to the invention is administered to a subject suffering from or diagnosed as having such a disease, disorder, or condition. A "therapeutically effective amount" means an amount or dose sufficient to generally bring about the desired therapeutic or prophylactic benefit in subjects in need of such treatment for the designated disease, disorder, or condition. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. For a 70-kg human, an illustrative range for a suitable dosage amount is from about 1 to 1000 mg/day in single or multiple dosage units (e.g., BID, TID, QID or as required by modality).

Once improvement of the subject's disease, disorder, or condition has occurred, the dose may be adjusted for preventive or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Subjects may, however, require intermittent treatment on a long-term basis upon any recurrence of symptoms.

In addition, the compounds of the invention are envisaged for use alone, in combination with one or more of other compounds of this invention, or in combination with additional active ingredients in the treatment of the conditions discussed below. The additional active ingredients may be co-administered separately with at least one compound of the invention, with active agents of the invention or included with such an agent in a pharmaceutical composition according to the invention. In an illustrative embodiment, additional active ingredients are those that are known or discovered to be effective in the treatment of conditions, disorders, or diseases associated with the MGL modulation, such as another MGL inhibitor or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

When referring to inhibiting the target, an "effective amount" means an amount sufficient to affect MGL modulation.

The active agents of the invention are envisaged for use, alone or in combination with one or more additional active ingredients, to formulate pharmaceutical compositions of the invention. A pharmaceutical composition of the invention comprises a therapeutically effective amount of at least one active agent in accordance with the invention.

Pharmaceutically acceptable excipients commonly used in pharmaceutical compositions are substances that are non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of such excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using pharmaceutically acceptable excipients and compounding techniques known or that become available to those of ordinary skill in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. The compositions may be formulated for any one of a plurality of administration routes, such as intravenous infusion, topical administration, or oral administration. Preferably, the compositions may be formulated for oral administration.

For oral administration, the active agents of the invention can be provided in the form of tablets or capsules, or as a solution, emulsion, or suspension. To prepare the oral compositions, the active agents may be formulated to yield a dosage of, e.g., for a 70-kg human, an illustrative range for a suitable dosage amount is from about 1 to 1000 mg/day in single or multiple dosage units.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract or may be coated with an enteric coating.

Capsules for oral administration include hard and soft gelatin or (hydroxypropyl)methyl cellulose capsules. To prepare hard gelatin capsules, active ingredient(s) may be mixed with a solid, semi-solid, or liquid diluent. Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethyl cellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository, enema or foam. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For topical administration, the agents may be mixed with a pharmaceutical carrier at a concentration of about 0.01% to about 20% of drug to vehicle, preferably 0.1% to 10%. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

In a further embodiment, the invention is directed to a method of treating a subject suffering from or diagnosed with a disease, disorder, or condition associated with MGL modulation, comprising administering to the subject in need of such treatment a therapeutically effective amount of the active agent.

The compounds of Formula (I) are useful in methods for treating, ameliorating and/or preventing a disease, a condition or a disorder that is affected by the inhibition of MGL. Such methods comprise administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

In particular, the compounds of Formula (I), or pharmaceutically acceptable salts, isotopes, N-oxides, solvates and stereoisomers thereof, are useful for treating, ameliorating and/or preventing diseases, conditions, or disorders causing pain, psychiatric disorders, neurological disorders, cancers and eyes conditions. More particularly, the compounds of Formula (I), or pharmaceutically acceptable salts, isotopes, N-oxides, solvates and stereoisomers thereof, are useful for treating, ameliorating and/or preventing inflammatory pain, major depressive disorder, treatment resistant depression, anxious depression or bipolar disorder by administering to a subject in need thereof a therapeutically effective amount of a compound of Formula (I), or a pharmaceutically acceptable salt, isotope, N-oxide, solvate or stereoisomer thereof as herein defined.

1) Pain

Examples of inflammatory pain include, but are not limited to, pain due to a disease, condition, disorder, or a pain state including inflammatory bowel disease, visceral pain, migraine, post-operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia/hypersensitivity. Examples of inflammatory hyperalgesia include a disease, condition, disorder, or pain state including inflammation, osteoarthritis, rheumatoid arthritis, back pain, joint pain, abdominal pain, musculoskeletal diseases, skin diseases, post-operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity and/or dermal allergy, itch, eczema, pharyngitis, enteritis, irritable bowel syndrome, inflammatory bowel diseases including Crohn's Disease, ulcerative colitis, benign prostatic hypertrophy, and nasal hypersensitivity.

In an embodiment, the present invention is directed to a method for treating, ameliorating and/or preventing inflammatory visceral hyperalgesia in which an enhanced visceral irritability exists, comprising, consisting of, and/or consisting essentially of the step of administering to a subject in need of such treatment a therapeutically effective amount of a compound of Formula (I) or a pharmaceutically acceptable salt, isotope, N-oxide, solvate or stereoisomer thereof. In a further embodiment, the present invention is directed to a method for treating inflammatory somatic hyperalgesia in which a hypersensitivity to thermal, mechanical and/or chemical stimuli exists, comprising administering to a subject in need of such treatment a therapeutically effective amount of a compound of Formula (I), or a pharmaceutically acceptable salt, isotope, N-oxide, solvate or stereoisomer thereof.

A further embodiment of the present invention is directed to a method for treating, ameliorating and/or preventing neuropathic pain. Examples of a neuropathic pain include pain due to a disease, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, vidian neuralgia or chemotherapy-induced neuropathy.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising administering to a subject in need of such treatment a therapeutically effective amount of a compound of Formula (I) or a pharmaceutically acceptable salt, isotope, N-oxide, solvate or stereoisomer thereof 2) Psychiatric Disorders Examples of psychiatric disorders include, but are not limited to, anxieties such as, social anxiety, post-traumatic stress disorder, phobias, social phobia, special phobias, panic disorder, obsessive-compulsive disorder, acute stress disorder, separation anxiety disorder, and generalized anxiety disorder, as well as depression such as, major depression, bipolar disorder, seasonal affective disorder, post-natal depression, manic depression, and bipolar depression, mood disorders and mood affective disorders that can be treated according to the present invention include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, anxious depression, bipolar disorder, depressive disorder with postpartum onset, depressive disorders with psychotic symptoms; persistent mood disorders, such as cyclothymia, dysthymia, euthymia; premenstrual dysphoric disorder; psychoses; and developmental disorders such as autism spectrum disorders, and Asperger syndrome.

3) Neurological Disorders

Examples of neurological disorder include, but are not limited to, tremors, dyskinesias, dystonias, spasticity, Tourette's Syndrome; neuromyelitis optica, Parkinson's disease; Alzheimer's disease; senile dementia; Huntington's disease; Epilepsy/seizure disorders and sleep disorders.

4) Cancers

Examples of cancers include, but are not limited to, benign skin tumors, prostate tumors, ovarian tumors and cerebral tumors (glioblastomas, medulloepitheliomas, medulloblastomas, neuroblastomas, tumors of embryonic origin, astrocytomas, astroblastomas, ependymomas, oligodendrogliomas, neuroepitheliomas, epiphyseal tumor, ependymoblastomas, malignant meningiomas, sarcomatosis, malignant melanomas, schwannomas).

Eye Conditions

Examples of eye conditions include, but are not limited to, ocular hypertension, glaucoma, degeneration, and apoptosis of retinal ganglion cells and neuroretinal cells.

Other embodiments of this invention provide for a method for modulating MGL receptor activity, including when such receptor is in a subject, comprising exposing MGL receptor to a therapeutically effective amount of at least one compound selected from compounds of the invention.

In some embodiments of Formula (I), X is $CH_2$. In some embodiments, X is O.

In some embodiments, $R^{2a}$ and $R^{2b}$ are each H. In some embodiments, $R^{2a}$ and $R^{2b}$ are each $CH_3$. In some embodiments, $R^{2a}$ is H and $R^{2b}$ is $CH_3$.

In some embodiments, $R^3$ is cyclopropyl, cyclobutyl, cyclopentyl or cyclohexyl. In some embodiments, $R^3$ is

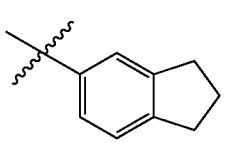 or 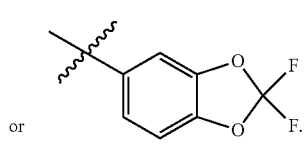

In some embodiments, $R^3$ is phenyl, or phenyl substituted with one or two members each independently selected from: Cl, F, $CH_3$, $CH(CH_3)_2$, $C(CH_3)_3$, $CF_3$, $OCH_3$, $OCH_2CH_3$, $OCF_3$, cyclopropyl, cyclopropyl substituted with $CF_3$, and cyclobutyl. In some embodiments, $R^3$ is

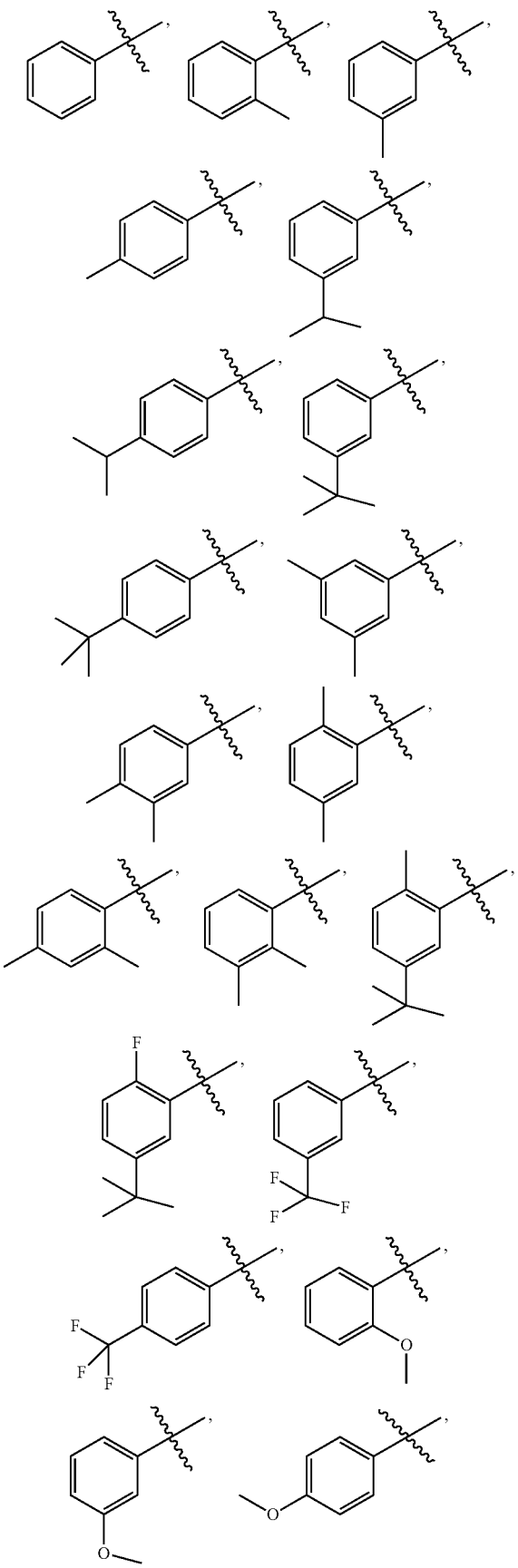

-continued

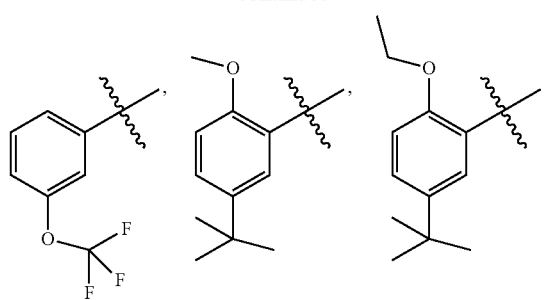

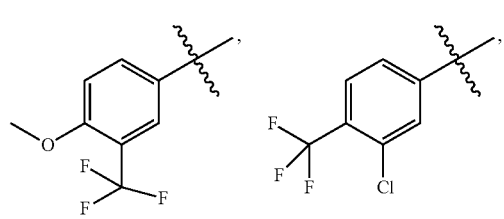

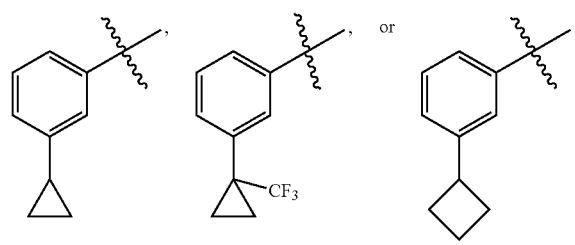

In some embodiments, R³ is

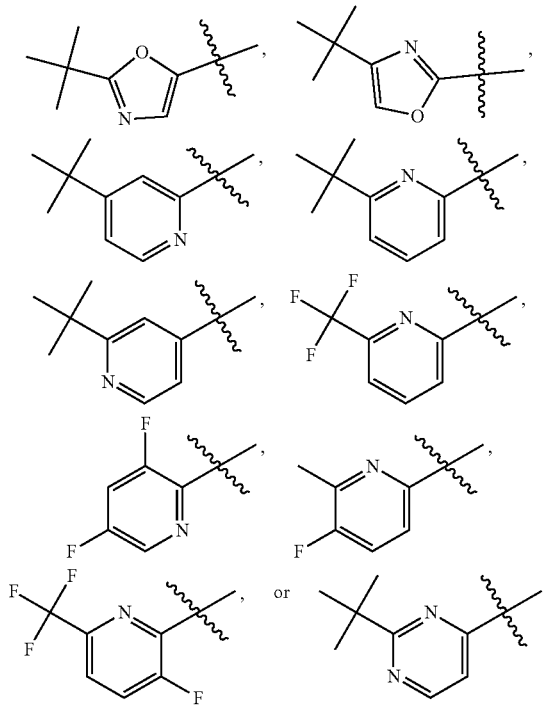

In some embodiments, R³ is

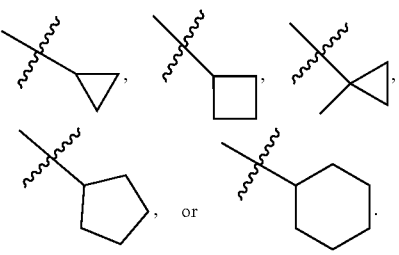

In some embodiments, R³ is 4-trifluoromethylphenyl, 3-isopropylphenyl, 4-isopropylphenyl, 2,4-dimethylphenyl, 3-tert-butylphenyl, 4-tert-butylphenyl, or 3-cyclopropylphenyl.

In some embodiments, R³ is phenyl; or phenyl substituted with one, two or three members each independently selected from: Cl, F, $C_{1-6}$alkyl, $C_{1-6}$haloalkyl, $C(CH_3)_2OH$, $OC_{1-6}$alkyl, $OC_{1-6}$haloalkyl, $SCH_3$, $Si(CH_3)_3$, $SF_5$, $N(CH_3)_2$, $C_{3-6}$cycloalkyl, $C_{3-6}$cycloalkyl substituted with $CH_3$, $OC_{3-6}$cycloalkyl, phenyl, O-phenyl, and O-pyridyl.

In some embodiments, R³ is phenyl substituted with one, two or three members each independently selected from: halo, $C_{1-6}$alkyl, $C_{1-6}$haloalkyl, $OC_{1-6}$alkyl, $OC_{1-6}$haloalkyl, $SCH_3$, $SF_5$, or $Si(CH_3)_3$.

In some embodiments, R³ is

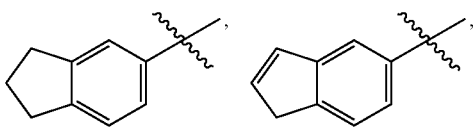

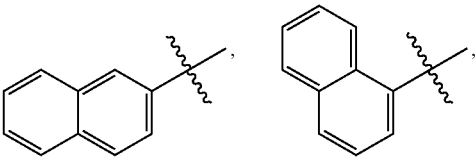

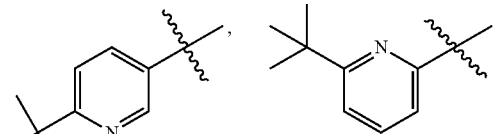

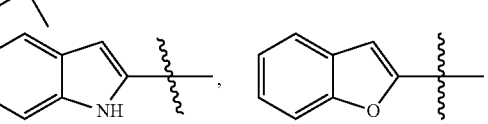

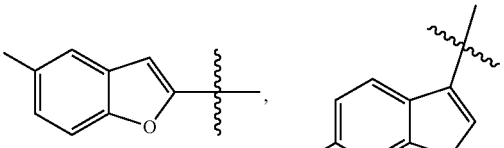

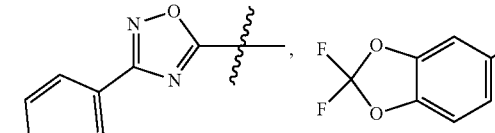

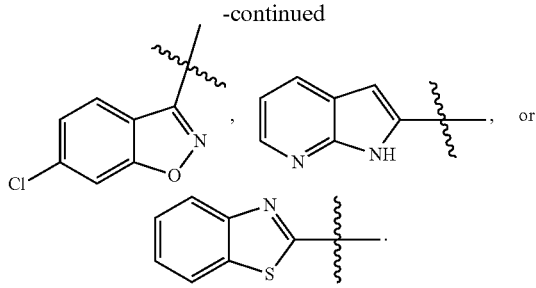

In some embodiments, R³ is 4-trifluoromethylphenyl, 3-trifluoromethoxyphenyl, 3-tert-butylphenyl, 4-tert-butylphenyl, or 3-(1-methylcyclopropyl)phenyl.

In some embodiments, R³ is benzyl; tert-butyl; cyclohexyl; phenyl substituted with 1-methylcyclopropyl or 1-trifluoromethylcyclopropyl, or fused with a cyclobutenyl or cyclohexenyl ring; pyridyl optionally substituted with trifluoromethyl, fluoro, or methyl; pyrimidinyl optionally substituted with tert-butyl; or oxazolyl optionally substituted with tert-butyl. In some embodiments, R³ is a bicyclic heteroaryl, optionally substituted as described herein. In some embodiments, R³ is phenyl, optionally substituted as described herein.

In some embodiments, n and o are each 1. In some embodiments, n and o are each 2. In some embodiments, n is 1 and o is 2. In some embodiments, m and p are each 1. In some embodiments, m and p are each 2. In some embodiments, m is 1 and p is 2. In some embodiments, m, n, o, and p are each 1. In some embodiments, m, n, and o are each 1 and o is 2. In some embodiments, m, n, and o are each 1 and p is 2. In some embodiments, n and o are each 2 and m and p are each 1. In some embodiments, n and o are each 1 and m and p are each 2. In some embodiments, n, o, and p are each 2 and m is 1.

A further embodiment of the current invention is a compound as shown below in Table 1.

TABLE 1

| Example # | Compound Name |
|---|---|
| 1 | (2s,4s)-2-(2-Phenyl-7-azaspiro[3.5]nonane-7-carbonyl)-7-oxa-5-azaspiro[3.4]octan-6-one; |
| 2 | (2s,4s)-2-(2-(3-(tert-Butyl)phenyl)-7-azaspiro[3.5]nonane-7-carbonyl)-7-oxa-5-azaspiro[3.4]octan-6-one; |
| 3 | (2s,4s)-2-(2-(p-Tolyl)-7-azaspiro[3.5]nonane-7-carbonyl)-7-oxa-5-azaspiro[3.4]octan-6-one; |
| 4 | (2s,4s)-2-(2-(o-Tolyl)-7-azaspiro[3.5]nonane-7-carbonyl)-7-oxa-5-azaspiro[3.4]octan-6-one; |
| 5 | (2s,4s)-2-[2-(3-Cyclopropylphenyl)-7-azaspiro[3.5]nonane-7-carbonyl)-7-oxa-5-azaspiro[3.4]octan-6-one; |
| 6 | (2s,4s)-2-[2-(3-Isopropylphenyl)-7-azaspiro[3.5]nonane-7-carbonyl)-7-oxa-5-azaspiro[3.4]octan-6-one; |
| 7 | (2s,4s)-2-[2-(m-Tolyl)-7-azaspiro[3.5]nonane-7-carbonyl)-7-oxa-5-azaspiro[3.4]octan-6-one; |
| 8 | (2s,4s)-2-[2-(3-Methoxyphenyl)-7-azaspiro[3.5]nonane-7-carbonyl)-7-oxa-5-azaspiro[3.4]octan-6-one; |
| 9 | (2s,4s)-2-[2-[3-(Trifluoromethoxy)phenyl]-7-azaspiro[3.5]nonane-7-carbonyl)-7-oxa-5-azaspiro[3.4]octan-6-one; |
| 10 | (2s,4s)-2-[2-(2,3-Dimethylphenyl)-7-azaspiro[3.5]nonane-7-carbonyl)-7-oxa-5-azaspiro[3.4]octan-6-one; |
| 11 | (2r,4s)-2-(2-(3-(tert-Butyl)phenyl)-7-azaspiro[3.5]nonane-7-carbonyl)-5-azaspiro[3.4]octan-6-one; |
| 12 | (2s,4s)-2-[2-(2,4-Dimethylphenyl)-7-azaspiro[3.5]nonane-7-carbonyl)-7-oxa-5-azaspiro[3.4]octan-6-one; |
| 13 | (2s,4s)-2-[2-(2-(Tert-butyl)pyridin-4-yl)-7-azaspiro[3.5]nonane-7-carbonyl)-7-oxa-5-azaspiro[3.4]octan-6-one; |
| 14 | (2r,4s)-2-(2-(5-(tert-Butyl)-2-methylphenyl)-7-azaspiro[3.5]nonane-7-carbonyl)-5-azaspiro[3.4]octan-6-one; |
| 15 | 2-[2-[3-(Trifluoromethyl)phenyl]-7-azaspiro[3.5]nonane-7-carbonyl)-5-azaspiro[3.4]octan-6-one; |
| 16 | (2r,4s)-2-(2-(6-(tert-Butyl)pyridin-2-yl)-7-azaspiro[3.5]nonane-7-carbonyl)-5-azaspiro[3.4]octan-6-one; |
| 17 | (2r,4s)-2-[2-[4-[1-(Trifluoromethyl)cyclopropyl]phenyl]-7-azaspiro[3.5]nonane-7-carbonyl)-5-azaspiro[3.4]octan-6-one; |
| 18 | (2r,4s)-2-[2-[3-Chloro-4-(trifluoromethyl)phenyl]-7-azaspiro[3.5]nonane-7-carbonyl)-5-azaspiro[3.4]octan-6-one; |
| 19 | (2r,4s)-2-[2-(2,5-Dimethylphenyl)-7-azaspiro[3.5]nonane-7-carbonyl)-5-azaspiro[3.4]octan-6-one; |
| 20 | (2r,4s)-2-[2-[4-Methoxy-3-(trifluoromethyl)phenyl]-7-azaspiro[3.5]nonane-7-carbonyl)-5-azaspiro[3.4]octan-6-one; |
| 21 | (2s,4s)-2-(2-(4-(tert-Butyl)pyridin-2-yl)-7-azaspiro[3.5]nonane-7-carbonyl)-7-oxa-5-azaspiro[3.4]octan-6-one; |
| 22 | (2r,4s)-2-(2-(5-(tert-Butyl)-2-fluorophenyl)-7-azaspiro[3.5]nonane-7-carbonyl)-5-azaspiro[3.4]octan-6-one; |
| 23 | (2r,4s)-2-(2-(5-(tert-Butyl)-2-ethoxyphenyl)-7-azaspiro[3.5]nonane-7-carbonyl)-5-azaspiro[3.4]octan-6-one; |
| 24 | (2r,4s)-2-[2-(o-Tolyl)-7-azaspiro[3.5]nonane-7-carbonyl)-5-azaspiro[3.4]octan-6-one; |
| 25 | (2r,4s)-2-[2-(3-Isopropylphenyl)-7-azaspiro[3.5]nonane-7-carbonyl)-5-azaspiro[3.4]octan-6-one; |
| 26 | (2r,4s)-2-[2-(2,3-Dimethylphenyl)-7-azaspiro[3.5]nonane-7-carbonyl)-5-azaspiro[3.4]octan-6-one; |

TABLE 1-continued

| Example # | Compound Name |
|---|---|
| 27 | (2r,4s)-2-(2-(5-(tert-Butyl)-2-methoxyphenyl)-7-azaspiro[3.5]nonane-7-carbonyl)-5-azaspiro[3.4]octan-6-one; |
| 28 | (2s,4s)-2-(2-(2,2-Difluorobenzo[d][1,3]dioxol-5-yl)-7-azaspiro[3.5]nonane-7-carbonyl)-7-oxa-5-azaspiro[3.4]octan-6-one; |
| 29 | (2s,4s)-2-[2-(2-Methoxyphenyl)-7-azaspiro[3.5]nonane-7-carbonyl)-7-oxa-5-azaspiro[3.4]octan-6-one; |
| 30 | (2s,4s)-2-[2-(4-Methoxyphenyl)-7-azaspiro[3.5]nonane-7-carbonyl)-7-oxa-5-azaspiro[3.4]octan-6-one; |
| 31 | (2s,4s)-2-(2-(6-(tert-Butyl)pyridin-2-yl)-7-azaspiro[3.5]nonane-7-carbonyl)-7-oxa-5-azaspiro[3.4]octan-6-one; |
| 32 | (2s,4s)-2-(2-(3-Fluoro-6-(trifluoromethyl)pyridin-2-yl)-7-azaspiro[3.5]nonane-7-carbonyl)-7-oxa-5-azaspiro[3.4]octan-6-one; |
| 33 | (2s,4s)-2-(2-(6-(Trifluoromethyl)pyridin-2-yl)-7-azaspiro[3.5]nonane-7-carbonyl)-7-oxa-5-azaspiro[3.4]octan-6-one; |
| 34 | (2s,4s)-2-(2-(5-Fluoro-6-methylpyridin-2-yl)-7-azaspiro[3.5]nonane-7-carbonyl)-7-oxa-5-azaspiro[3.4]octan-6-one; |
| 35 | (2s,4s)-2-(2-(2-(tert-Butyl)pyrimidin-4-yl)-7-azaspiro[3.5]nonane-7-carbonyl)-7-oxa-5-azaspiro[3.4]octan-6-one; |
| 36 | (2s,4s)-2-(2-(4-(tert-Butyl)oxazol-2-yl)-7-azaspiro[3.5]nonane-7-carbonyl)-7-oxa-5-azaspiro[3.4]octan-6-one; |
| 37 | (2s,4s)-2-[2-(2-(tert-Butyl)oxazol-5-yl)-7-azaspiro[3.5]nonane-7-carbonyl)-5-azaspiro[3.4]octan-6-one; |
| 38 | (2s,4s)-2-(2-(3,5-Difluoropyridin-2-yl)-7-azaspiro[3.5]nonane-7-carbonyl)-7-oxa-5-azaspiro[3.4]octan-6-one; |
| 39 | (rac)-(2s,4s)-2-(2-(4-(Trifluoromethyl)phenyl)-8-azaspiro[4.5]decane-8-carbonyl)-7-oxa-5-azaspiro[3.4]octan-6-one; |
| 40 | (rac)-(2s,4s)-8-Methyl-2-(2-(4-(trifluoromethyl)phenyl)-8-azaspiro[4.5]decane-8-carbonyl)-7-oxa-5-azaspiro[3.4]octan-6-one; |
| 41 | (rac)-(2s,4s)-2-(6-Phenyl-2-azaspiro[3.4]octane-2-carbonyl)-7-oxa-5-azaspiro[3.4]octan-6-one; |
| 42 | (2r,4S*)-2-((R*)-6-Phenyl-2-azaspiro[3.4]octane-2-carbonyl)-5-azaspiro[3.4]octan-6-one; |
| 43 | (2r,4R*)-2-((S*)-6-Phenyl-2-azaspiro[3.4]octane-2-carbonyl)-5-azaspiro[3.4]octan-6-one; |
| 44 | (rac)-(2s,4s)-2-(6-(4-(Trifluoromethyl)phenyl)-2-azaspiro[3.4]octane-2-carbonyl)-7-oxa-5-azaspiro[3.4]octan-6-one; |
| 45 | (2s,4s)-2-((R*)-6-(4-(Trifluoromethyl)phenyl)-2-azaspiro[3.4]octane-2-carbonyl)-7-oxa-5-azaspiro[3.4]octan-6-one; |
| 46 | (2s,4R*)-2-((S*)-6-(4-(Trifluoromethyl)phenyl)-2-azaspiro[3.4]octane-2-carbonyl)-7-oxa-5-azaspiro[3.4]octan-6-one; |
| 47 | (2r,4S*)-2-((R*)-6-(4-(Trifluoromethyl)phenyl)-2-azaspiro[3.4]octane-2-carbonyl)-5-azaspiro[3.4]octan-6-one; |
| 48 | (2r,4R*)-2-((S*)-6-(4-(Trifluoromethyl)phenyl)-2-azaspiro[3.4]octane-2-carbonyl)-5-azaspiro[3.4]octan-6-one; |
| 49 | (rac)-(2s,4s)-2-(6-(4-(tert-Butyl)phenyl)-2-azaspiro[3.4]octane-2-carbonyl)-7-oxa-5-azaspiro[3.4]octan-6-one; |
| 50 | (rac)-(2s,4s)-2-(6-(3-(tert-Butyl)phenyl)-2-azaspiro[3.4]octane-2-carbonyl)-7-oxa-5-azaspiro[3.4]octan-6-one; |
| 51 | (rac)-(2s,4s)-2-(6-(3-(tert-Butyl)phenyl)-2-azaspiro[3.4]octane-2-carbonyl)-8-methyl-7-oxa-5-azaspiro[3.4] octan-6-one; |
| 52 | (rac)-(2s,4s)-2-(6-Cyclopropyl-2-azaspiro[3.4]octane-2-carbonyl)-7-oxa-5-azaspiro[3.4]octan-6-one; |
| 53 | (rac)-(2s,4s)-2-(6-Cyclohexyl-2-azaspiro[3.4]octane-2-carbonyl)-7-oxa-5-azaspiro[3.4]octan-6-one; |
| 54 | (rac)-(2r,4s)-2-(6-Cyclohexyl-2-azaspiro[3.4]octane-2-carbonyl)-5-azaspiro[3.4]octan-6-one; |
| 55 | (rac)-(2s,4s)-2-(6-Cyclopentyl-2-azaspiro[3.4]octane-2-carbonyl)-7-oxa-5-azaspiro[3.4]octan-6-one; |
| 56 | (rac)-(2s,4s)-2-(6-Cyclobutyl-2-azaspiro[3.4]octane-2-carbonyl)-7-oxa-5-azaspiro[3.4]octan-6-one; |
| 57 | (rac)-(2s,4s)-2-(2-(3-(tert-Butyl)phenyl)-8-azaspiro[4.5]decane-8-carbonyl)-7-oxa-5-azaspiro[3.4]octan-6-one; |
| 58 | (rac)-(2s,4s)-2-(2-(4-(tert-Butyl)phenyl)-8-azaspiro[4.5]decane-8-carbonyl)-7-oxa-5-azaspiro[3.4]octan-6-one; |
| 59 | (2s,4s)-2-(2-(3-Isopropylphenyl)-6-azaspiro[3.4]octane-6-carbonyl)-7-oxa-5-azaspiro[3.4]octan-6-one; |
| 60 | (2s,4s)-2-(2-(3-(tert-Butyl)phenyl)-6-azaspiro[3.4]octane-6-carbonyl)-7-oxa-5-azaspiro[3.4]octan-6-one; |
| 61 | (rac)-(2s,4s)-2-(6-(3-Isopropylphenyl)-2-azaspiro[3.4]octane-2-carbonyl)-7-oxa-5-azaspiro[3.4]octan-6-one; |
| 62 | (rac)-(2r,4s)-2-(6-(3-Isopropylphenyl)-2-azaspiro[3.4]octane-2-carbonyl)-5-azaspiro[3.4]octan-6-one; |
| 63 | (rac)-(2s,4s)-2-(6-(4-Isopropylphenyl)-2-azaspiro[3.4]octane-2-carbonyl)-7-oxa-5-azaspiro[3.4]octan-6-one; |
| 64 | (2s,4s)-2-(2-Phenyl-6-azaspiro[3.4]octane-6-carbonyl)-7-oxa-5-azaspiro[3.4]octan-6-one; |

TABLE 1-continued

| Example # | Compound Name |
|---|---|
| 65 | (2s,4s)-2-(6-(3-(tert-Butyl)phenyl)-2-azaspiro[3.3]heptane-2-carbonyl)-7-oxa-5-azaspiro[3.4]octan-6-one; |
| 66 | (2s,4s)-2-(6-(m-Tolyl)-2-azaspiro[3.3]heptane-2-carbonyl)-7-oxa-5-azaspiro[3.4]octan-6-one; |
| 67 | (2s,4s)-2-(6-(3-Isopropylphenyl)-2-azaspiro[3.3]heptane-2-carbonyl)-7-oxa-5-azaspiro[3.4]octan-6-one; |
| 68 | (2s,4s)-2-(6-(3,4-Dimethylphenyl)-2-azaspiro[3.3]heptane-2-carbonyl)-7-oxa-5-azaspiro[3.4]octan-6-one; |
| 69 | (2s,4s)-2-(6-Cyclohexyl-2-azaspiro[3.3]heptane-2-carbonyl)-7-oxa-5-azaspiro[3.4]octan-6-one; |
| 70 | (2s,4s)-2-(6-(3,5-Dimethylphenyl)-2-azaspiro[3.3]heptane-2-carbonyl)-7-oxa-5-azaspiro[3.4]octan-6-one; |
| 71 | (2s,4s)-2-(6-(2,4-Dimethylphenyl)-2-azaspiro[3.3]heptane-2-carbonyl)-7-oxa-5-azaspiro[3.4]octan-6-one; |
| 72 | (2s,4s)-2-(6-(3-Cyclopropylphenyl)-2-azaspiro[3.3]heptane-2-carbonyl)-7-oxa-5-azaspiro[3.4]octan-6-one; |
| 73 | (2s,4s)-2-(6-(3-Cyclobutylphenyl)-2-azaspiro[3.3]heptane-2-carbonyl)-7-oxa-5-azaspiro[3.4]octan-6-one; |
| 74 | (2s,4s)-2-(6-(2,3-Dihydro-1H-inden-5-yl)-2-azaspiro[3.3]heptane-2-carbonyl)-7-oxa-5-azaspiro[3.4]octan-6-one; |
| 75 | (2s,4s)-2-(6-Phenyl-2-azaspiro[3.3]heptane-2-carbonyl)-7-oxa-5-azaspiro[3.4]octan-6-one; |
| 76 | (2s,4s)-2-(7-Phenyl-2-azaspiro[3.5]nonane-2-carbonyl)-7-oxa-5-azaspiro[3.4]octan-6-one; |
| 77 | (2s,4s)-2-(6-Cyclopentyl-2-azaspiro[3.3]heptane-2-carbonyl)-7-oxa-5-azaspiro[3.4]octan-6-one; |
| 78 | (2s,4s)-2-(6-Cyclobutyl-2-azaspiro[3.3]heptane-2-carbonyl)-7-oxa-5-azaspiro[3.4]octan-6-one; and |
| 79 | (2s,4s)-2-(6-(1-Methylcyclopropyl)-2-azaspiro[3.3]heptane-2-carbonyl)-7-oxa-5-azaspiro[3.4]octan-6-one; | and pharmaceutically acceptable salts, isotopes, N-oxides, solvates, and stereoisomers thereof.

A further embodiment of the current invention is a compound selected from:

(2r,4s)-2-(2-(6-(tert-Butyl)pyridin-2-yl)-7-azaspiro[3.5]nonane-7-carbonyl)-5-azaspiro[3.4]octan-6-one;

(2s,4s)-2-((R*)-6-(4-(Trifluoromethyl)phenyl)-2-azaspiro[3.4]octane-2-carbonyl)-7-oxa-5-azaspiro[3.4]octan-6-one;

(2s,4R*)-2-((S*)-6-(4-(Trifluoromethyl)phenyl)-2-azaspiro[3.4]octane-2-carbonyl)-7-oxa-5-azaspiro[3.4]octan-6-one; and (2s,4s)-2-(6-(3-(tert-Butyl)phenyl)-2-azaspiro[3.3]heptane-2-carbonyl)-7-oxa-5-azaspiro[3.4]octan-6-one;

and pharmaceutically acceptable salts, isotopes, N-oxides, solvates, and stereoisomers thereof.

An additional embodiment of the invention is a compound of Formula (I) having the Formula (IA):

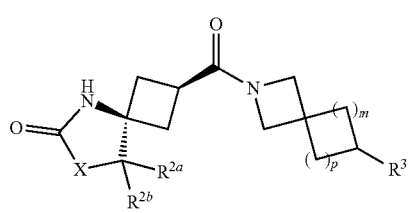

(IA)

wherein
X is CH$_2$ or O;
R$^{2a}$ and R$^{2b}$ are each independently selected from H and CH$_3$;
R$^3$ is selected from: C$_{3-6}$cycloalkyl; C$_{3-6}$cycloalkyl substituted with C$_{1-4}$alkyl; phenyl; phenyl substituted with one or two members each independently selected from: C$_{1-6}$alkyl, C$_{1-6}$haloalkyl, and C$_{3-6}$cycloalkyl; and

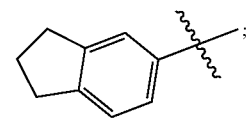 [SMILES: *c1ccc2c(c1)CCC2]

and
m and p are each independently 1 or 2;
or a pharmaceutically acceptable salt, isotope, N-oxide, solvate, or stereoisomer thereof.

An additional embodiment of the invention is a compound of Formula (I) having the Formula (IB):

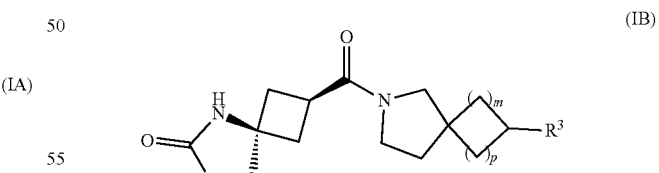

(IB)

wherein
X is O;
R$^3$ is selected from phenyl and phenyl substituted with C$_{1-6}$alkyl; and
m and p are each 1;
or a pharmaceutically acceptable salt, isotope, N-oxide, solvate, or stereoisomer thereof.

An additional embodiment of the invention is a compound of Formula (I) having the Formula (IC):

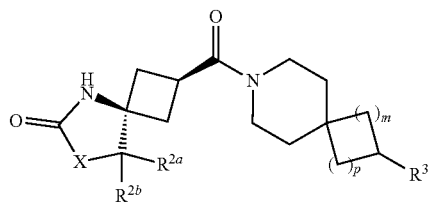

(IC)

wherein
X is $CH_2$ or O;
$R^{2a}$ and $R^{2b}$ are each independently selected from H and $CH_3$;
$R^3$ is selected from: $C_{3-6}$cycloalkyl; phenyl; phenyl substituted with one or two members each independently selected from: halo, $C_{1-6}$alkyl, $C_{1-6}$haloalkyl, $OC_{1-6}$alkyl, $OC_{1-6}$haloalkyl, and $C_{3-6}$cycloalkyl optionally substituted with $CH_3$ or $CF_3$; pyridyl substituted with one or two members each independently selected from: halo, $C_{1-6}$alkyl, and $C_{1-6}$haloalkyl; pyrimidinyl substituted with $C_{1-6}$alkyl;

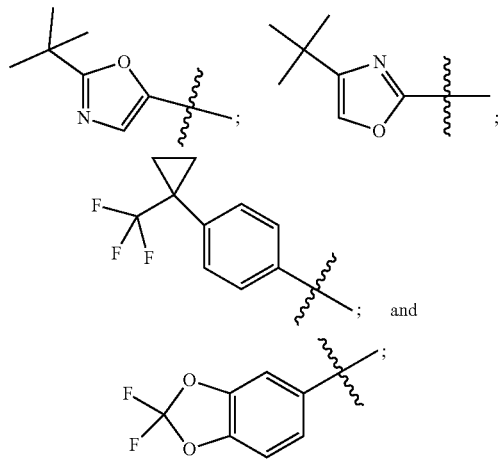

and
m and p are each independently 1 or 2;
or a pharmaceutically acceptable salt, isotope, N-oxide, solvate, or stereoisomer thereof.

An additional embodiment of the invention is a pharmaceutical composition comprising:
(A) a therapeutically effective amount of at least one compound selected from compounds of Formula (I) and pharmaceutically acceptable salts, isotopes, N-oxides, solvates, and stereoisomers of compounds of Formula (I); and
(B) at least one pharmaceutically acceptable excipient.

An additional embodiment of the invention is a pharmaceutical composition comprising a therapeutically effective amount of at least one compound selected from compounds in Table 1, including pharmaceutically acceptable salts, isotopes, N-oxides, solvates, and stereoisomers of compounds of Table 1, pharmaceutically acceptable prodrugs of compounds of Table 1, and pharmaceutically active metabolites of Table 1; and at least one pharmaceutically acceptable excipient.

An additional embodiment of the invention is a pharmaceutical composition comprising a therapeutically effective amount of at least one compound selected from compounds of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA); and at least one pharmaceutically acceptable excipient.

An additional embodiment of the invention is a pharmaceutical composition comprising a therapeutically effective amount of at least one compound selected from compounds of Formula (IB), as well as pharmaceutically acceptable salts, N-oxides or solvates of compounds of Formula (IB), pharmaceutically acceptable prodrugs of compounds of Formula (IB), and pharmaceutically active metabolites of Formula (IB); and at least one pharmaceutically acceptable excipient.

An additional embodiment of the invention is a pharmaceutical composition comprising a therapeutically effective amount of at least one compound selected from compounds of Formula (IC), as well as pharmaceutically acceptable salts, N-oxides or solvates of compounds of Formula (IC), pharmaceutically acceptable prodrugs of compounds of Formula (IC), and pharmaceutically active metabolites of Formula (IC); and at least one pharmaceutically acceptable excipient.

Also within the scope of the invention are enantiomers and diastereomers of the compounds of Formula (I) (as well as Formulas (IA), (IB), and (IC)). Also within the scope of the invention are the pharmaceutically acceptable salts, N-oxides or solvates of the compounds of Formula (I) (as well as Formulas (IA), (IB), and (IC)). Also within the scope of the invention are the pharmaceutically acceptable prodrugs of compounds of Formula (I) (as well as Formulas (IA), (IB), and (IC)), and pharmaceutically active metabolites of the compounds of Formula (I) (as well as Formulas (IA), (IB), and (IC)).

Also within the scope of the invention are isotopic variations of compounds of Formula (I) (as well as Formulas (IA), (IB), and (IC)), such as, e.g., deuterated compounds of Formula (I). Also within the scope of the invention are the pharmaceutically acceptable salts, N-oxides or solvates of the isotopic variations of the compounds of Formula (I) (as well as Formulas (IA), (IB), and (IC)). Also within the scope of the invention are the pharmaceutically acceptable prodrugs of the isotopic variations of the compounds of Formula (I) (as well as Formulas (IA), (IB), and (IC)), and pharmaceutically active metabolites of the isotopic variations of the compounds of Formula (I) (as well as Formulas (IA), (IB), and (IC)).

An additional embodiment of the invention is a method of treating a subject suffering from or diagnosed with a disease, disorder, or condition mediated by MGL receptor activity, comprising administering to a subject in need of such treatment a therapeutically effective amount of at least one compound selected from compounds of Formula (I) (as well as Formulas (IA), (IB), and (IC)), pharmaceutically acceptable salts, isotopes, N-oxides, solvates, and stereoisomers thereof, including enantiomers and diastereomers of the compounds of Formula (I) (as well as Formulas (IA), (IB), and (IC)), isotopic variations of the compounds of Formula (I) (as well as Formulas (IA), (IB), and (IC)), and pharmaceutically acceptable salts of all of the foregoing. Also described herein is the use of a compound of Formula (I), (IA), (IB), or (IC), or a pharmaceutically acceptable salt, isotope, N-oxide, solvate, or stereoisomer thereof in the preparation of a medicament. In some embodiments, the medicament is for treatment of a disease, disorder, or condition mediated by MGL receptor activity. Also described herein is a compound of Formula (I), (IA), (IB), or (IC), or a pharmaceutically acceptable salt, isotope, N-oxide, solvate, or stereoisomer thereof, for use in a method of treating a disease, disorder, or condition mediated by MGL receptor activity.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

TABLE 2

| Term | Acronym |
|---|---|
| [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate | $(Ir[dF(CF_3)ppy]_2(dtbpy))PF_6$ |
| Microliter | μL |
| Acetonitrile | ACN, MeCN |
| Aqueous | aq |
| Atmosphere | atm |
| tert-Butoxycarbonyl | BOC or Boc |
| Benzotriazol-1-yloxy-tris(dimethylamino)phosphonium hexafluorophosphate | BOP |
| Broad | br |
| Cerium (III) chloride | $CeCl_3$ |
| Diatomaceous Earth | Celite ® |
| Nickel(II) chloride hexahydrate | $NiCl_2 \cdot 6H_2O$ |
| 1,8-Diazabicyclo[5.4.0]undec-7-ene | DBU |
| N,N'-Dicyclohexylcarbodiimide | DCC |
| Methylene chloride or Dichloromethane | DCM |
| Diisobutylaluminum hydride | DIBAL-H |
| N-Ethyldiisopropylamine | DIPEA |
| 4-(Dimethylamino)pyridine | DMAP |
| 1,2-Dimethoxyethane | DME |
| Dimethylformamide | DMF |
| Dimethyl sulfoxide | DMSO |
| 1-Ethyl-3-(3-dimethylaminopropyl)carbodiimide | EDC, EDAC or EDCI |
| Electrospray ionization | ESI |
| Diethyl ether | Ether, $Et_2O$ |
| Ethyl Acetate | EtOAc, or EA |
| Ethanol | EtOH |
| Normal-phase silica gel chromatography | FCC |
| Grams | g |
| Hours | h, hr, hrs |
| 1-[Bis(dimethylamino)methylene]-1H-1,2,3-triazolo[4,5-b]pyridinium 3-oxide hexafluorophosphate | HATU |
| N,N,N',N'-Tetramethyl-O-(1H-benzotriazol-1-yl)uronium hexafluorophosphate | HBTU |
| hydroxybenzotriazole | HOBt |
| High-pressure liquid chromatography | HPLC |
| Hertz | Hz |
| Isopropyl alcohol | iPrOH, IPA |
| Liquid chromatography and mass spectrometry | LCMS |
| Light emitting diode | LED |
| Molar | M |
| Mass to charge ratio | m/z |
| Methanol | MeOH |
| Milligrams | mg |
| Megahertz | MHz |
| Minute | min |
| Milliliter | mL |
| Millimoles | mmol |
| Mass spectrometry | MS |
| Normal | N |
| Sodium hexamethyldisilazide | NaHMDS |
| Sodium acetate | NaOAc |
| n-Butyllithium | n-BuLi |
| Nickel(II) chloride ethylene glycol dimethyl ether complex | $NiCl_2(DME)$ |
| N-Methyl-2-pyrrolidone | NMP |
| Nuclear magnetic resonance | NMR |
| Triflate | OTf |
| Palladium on carbon | Pd/C |
| Bis(dibenzylideneacetone)palladium | $Pd(dba)_2$ |
| [1,1'-Bis(diphenylphosphino)ferrocene]dichloropalladium(II) | $Pd(dppf)Cl_2$ |
| Palladium (II) acetate | $Pd(OAc)_2$ |
| Palladium-tetrakis(triphenylphosphine) | $Pd(PPh_3)_4$ |
| Triphenylphosphine | $PPh_3$ |

TABLE 2-continued

| Term | Acronym |
| --- | --- |
| Parts per million | ppm |
| Precipitate | ppt |
| Polytetrafluoroethylene | PTFE |
| Bromotripyrrolidinophosphonium hexafluorophosphate | PyBroP ® |
| Reverse phase | RP |
| Rotations per minute | RPM |
| Retention time | $R_t$ |
| Room temperature | rt |
| Dicyclohexyl(2',6'-diisopropoxy-[1,1'-biphenyl]-2-yl)phosphine | RuPhos |
| Saturated | sat |
| Supercritical Fluid Chromatography | SFC |
| Temperature | T |
| 2,4,6-Tripropyl-1,3,5,2,4,6-trioxatriphosphorinane-2,4,6-trioxide | T3P ® |
| Triethylamine | TEA |
| Triethylsilane | TES |
| Trifluoroacetic acid | TFA |
| Trifluoroacetic anhydride | TFAA |
| Tetrahydrofuran | THF |
| Thin layer chromatography | TLC |
| Volume in milliliters of solvent per gram of substrate | V, or volumes |
| 2-Dicyclohexylphosphino-2',4',6'-triisopropylbiphenyl | XPhos |

PREPARATIVE EXAMPLES

Exemplary compounds useful in methods of the invention will now be described by reference to the illustrative synthetic schemes for their general preparation below and the specific examples to follow.

SCHEME 1

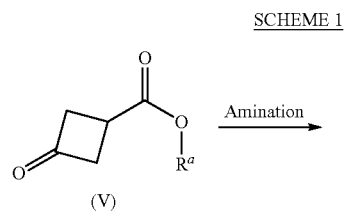

(V)

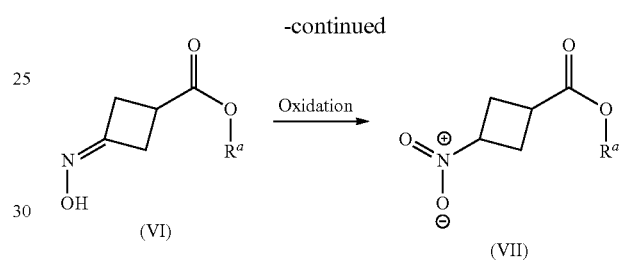

(VI) → (VII)

According to SCHEME 1, a compound of formula (V), where $R^a$ is $C_{1-4}$alkyl, is treated with hydroxylamine; using an additive such as sodium acetate (NaOAc), and the like; in a suitable solvent such as ethanol (EtOH), and the like; to provide a compound of formula (VI). A compound of formula (VII) is prepared from a compound of formula (VI) using an oxidant such as hydrogen peroxide, urea-hydrogen peroxide, and the like; in the presence of an activator such as trifluoroacetic anhydride (TFAA), and the like; in the presence of a base such as dibasic sodium phosphate, and the like; in a solvent such as acetonitrile (ACN), and the like.

SCHEME 2

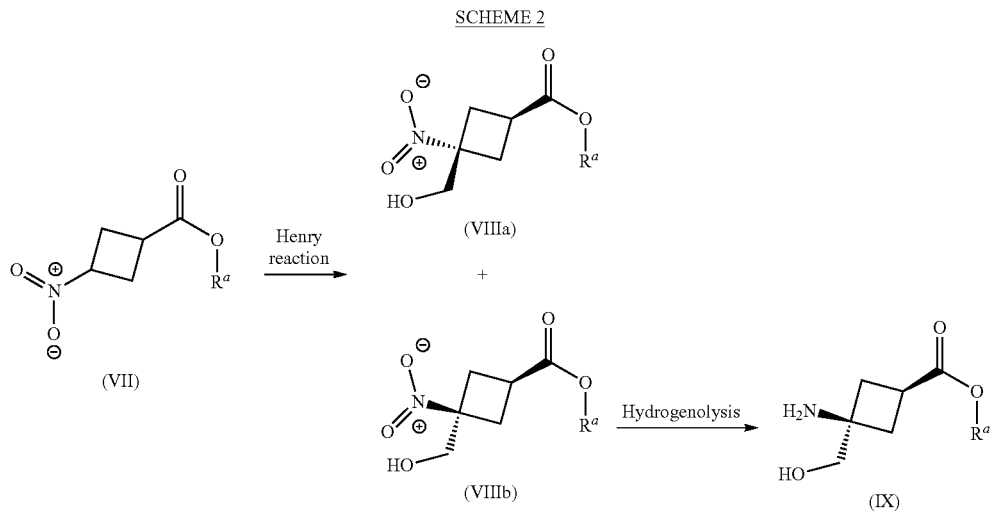

-continued

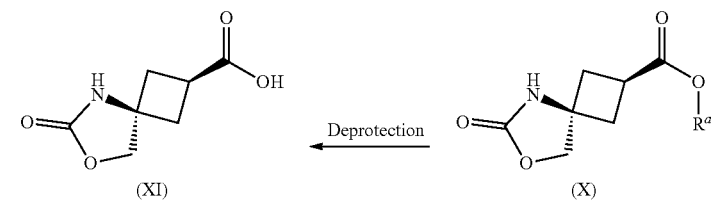

According to SCHEME 2, compounds of formula (VIIIa) and (VIIIb) are prepared by reacting a compound of formula (VII), $R^a$ is $C_{1-4}$alkyl, with formaldehyde in the presence of a base such as triethylamine (TEA), and the like; in a solvent such as ACN, and the like. A compound of formula (IX) is prepared by hydrogenolysis of a compound of formula (VIIIb) under an atmosphere of hydrogen gas ($H_2$) in the presence of a catalyst such as palladium on carbon (Pd/C), and the like; in a solvent such as ethyl acetate (EtOAc), EtOH, and the like. A compound of formula (X) is prepared by the reaction of a compound of formula (IX) with triphosgene in the presence of a base such as TEA, and the like; in a solvent such as tetrahydrofuran (THF), and the like. A compound of formula (XI) is prepared by the acidic deprotection of a compound of formula (X) using an acid such as trifluoroacetic acid (TFA), HCl in dioxane, and the like.

SCHEME 3

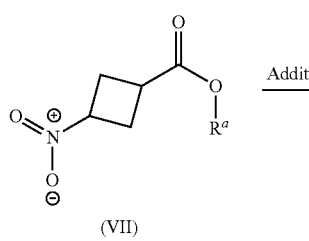

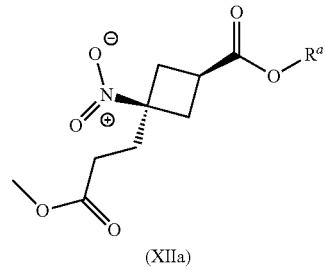

+

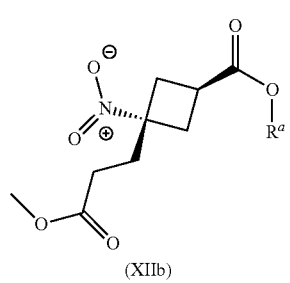

-continued

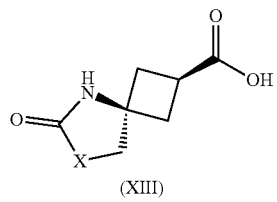

According to SCHEME 3, compounds of formula (XIIa) and formula (XIIb) are prepared by a Michael-type reaction between a compound of formula (VII), where $R^a$ is ethyl, and methyl acrylate; in the presence of a base such as 1,8-diazabicyclo[5.4.0]undec-7-ene (DBU), and the like; in a solvent such as ACN, and the like. Reductive ring closure of a compound of formula (XIIa) using a reducing agent such as sodium borohydride (NaBH$_4$), and the like; an additive such as nickel(II) chloride hexahydrate, and the like; in a suitable solvent such as methanol (MeOH), and the like; provides a compound of formula (XIII), where X is CH$_2$.

SCHEME 4

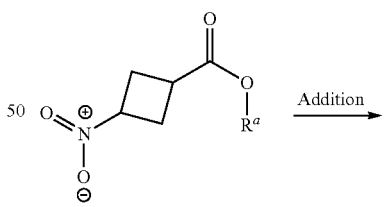

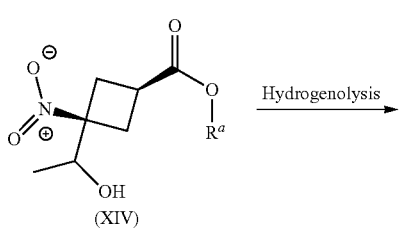

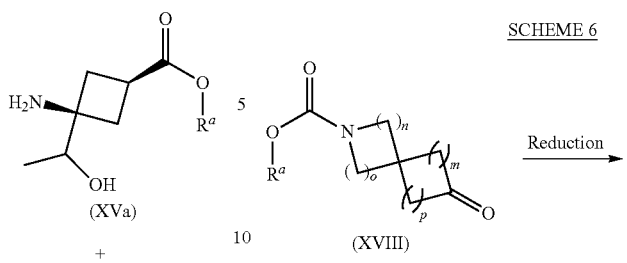

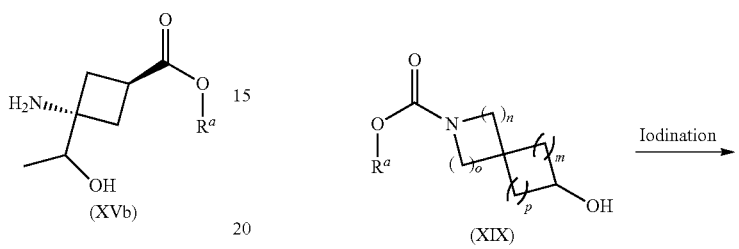

According to SCHEME 4, a compound of formula (XIV) is prepared by reacting a compound of formula (VII), where $R^a$ is $C_{1-4}$alkyl; with acetaldehyde in the presence of a base such as TEA, and the like; in a solvent such as ACN, and the like, at temperatures ranging from 0° C. to room temperature, for a period of 18 h. A compound of formula (XIV) is subjected to hydrogenolysis; employing conditions previously described, to provide compounds of formula (XVa) and (XVb).

SCHEME 5

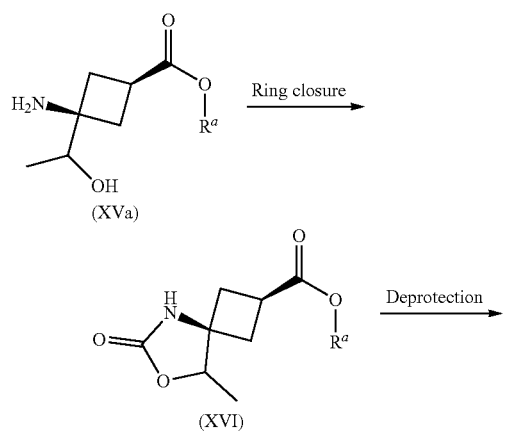

According to SCHEME 5, a compound of formula (XVa), where $R^a$ is $C_{1-4}$alkyl, is subjected to ring closure conditions with triphosgene, employing conditions previously described, to provide a compound of formula (XVI). A compound of formula (XVI) is subjected to acidic deprotection conditions previously described to provide a compound of formula (XVII), where X is O.

SCHEME 6

According to SCHEME 6, a compound of formula (XIX), wherein p and m are each independently 1 or 2; and n and o are each independently 1 or 2; and $R^a$ is tBu; is commercially available or synthetically accessible from a compound of formula (XVIII). Under conditions known to one skilled in the art, a compound of formula (XVIII) is reduced with a reducing agent such as $NaBH_4$, $LiAlH_4$, $LiBH_4$, diisobutylaluminum hydride (DIBAL-H), and the like; in a suitable solvent such as tetrahydrofuran (THF), methanol (MeOH), ethanol (EtOH), and the like; at temperatures ranging from −78 to 0° C.; for a period of 30 min to 16 h; to provide a compound of formula (XIX). A compound of formula (XX) is synthesized from a compound of formula (XIX), using iodine ($I_2$), employing an appropriate base such as imidazole; and triphenylphosphine ($PPh_3$); in a suitable solvent such as THF, and the like; in a temperature range of 0° C. to rt over a period of 1 h.

SCHEME 7

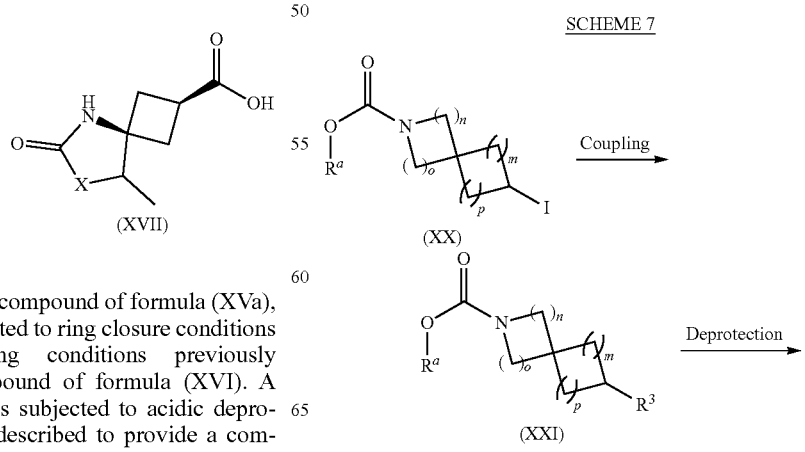

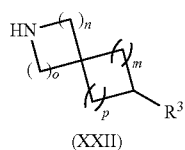

(XXII)

According to SCHEME 7, a compound of formula (XXI), wherein m is 1, p is 1 or 2; n and o are each independently 1 or 2, and $R^3$ is cycloalkyl or aryl; and $R^a$ is tBu; is prepared from a compound of formula (XX) either in flow or in batch with the appropriate commercially available or synthetically accessible suitably substituted aryl halide, boronic acid, or organomagnesium halide using catalysts such as palladium (II) acetate, bis(dibenzylideneacetone)palladium, cobalt (II) bromide, cobalt (II) acetylacetonate, nickel(II) acetylacetonate, nickel(II) iodide, and the like; and ligands such as dicyclohexyl(2',6'-diisopropoxy-[1,1'-biphenyl]-2-yl)phosphine (RuPhos), 2-dicyclohexylphosphino-2',4',6'-triisopropylbiphenyl (XPhos), N,N,N',N'-tetramethylethylenediamine, (1R,2R)-2-aminocyclohexanol and the like; with no base or an appropriate base such a sodium hexamethyldisilazide (NaHMDS) and the like; in a suitable solvent such as THF, over a period of 1-6 h at a temperature range of 0-50° C. Cleavage of the BOC protecting group on a compound of formula (XXI) is achieved according to procedures known to one skilled in the art, for example, under acidic conditions such as TFA/$CH_2Cl_2$, HCl/Dioxane, and the like, provides a compound of formula (XXII).

ether ($Et_2O$), and the like; to provide a compound of formula (XXIII) where $R^3$ is aryl or $C_{3-6}$cycloalkyl.

A compound of formula (XXIII) is reacted under acidic ionic reduction conditions such as TFA, using triethylsilane (TES) to reduce the alcohol and cleave the tert-butoxycarbonyl group to form a compound of formula (XXII).

In a similar fashion, a compound of formula (XVIII), where $R^a$ is $C_{1-4}$alkyl, m, n, and o are 1, and p is 2; is reacted under Grignard conditions as previously described with an organomagnesium halide such as cyclobutylmagnesium chloride, cyclopentylmagnesium chloride, and the like; with an additive such as $CeCl_3$, and the like; to provide a compound of formula (XXIII), where $R^3$ is $C_{3-6}$cycloalkyl. A compound of formula (XVIII), where $R^a$ is $C_{1-4}$alkyl, and m, n, o, and p are 1; is reacted under elimination conditions employing a dehydrating agent such as the Burgess reagent, and the like; to eliminate the alcohol and provide a compound of formula (XXIV). A compound of formula (XXII), where m, n, o, and p are 1 and $R^3$ is $C_3$-6cycloalkyl substituted with $C_{1-4}$alkyl, is prepared in two steps from a compound of formula (XXIV) where $R^3$ is $C_{3-6}$cycloalkyl substituted with $C_{1-4}$alkyl. For example, hydrogenation of a compound of formula (XXIV) is achieved employing conditions described, followed by deprotection of the Boc protecting group employing conditions known to one skilled in the art or as previously described, provides a compound of formula (XXII), where $R^3$ is $C_{3-6}$cycloalkyl substituted with $C_{1-4}$alkyl.

SCHEME 8

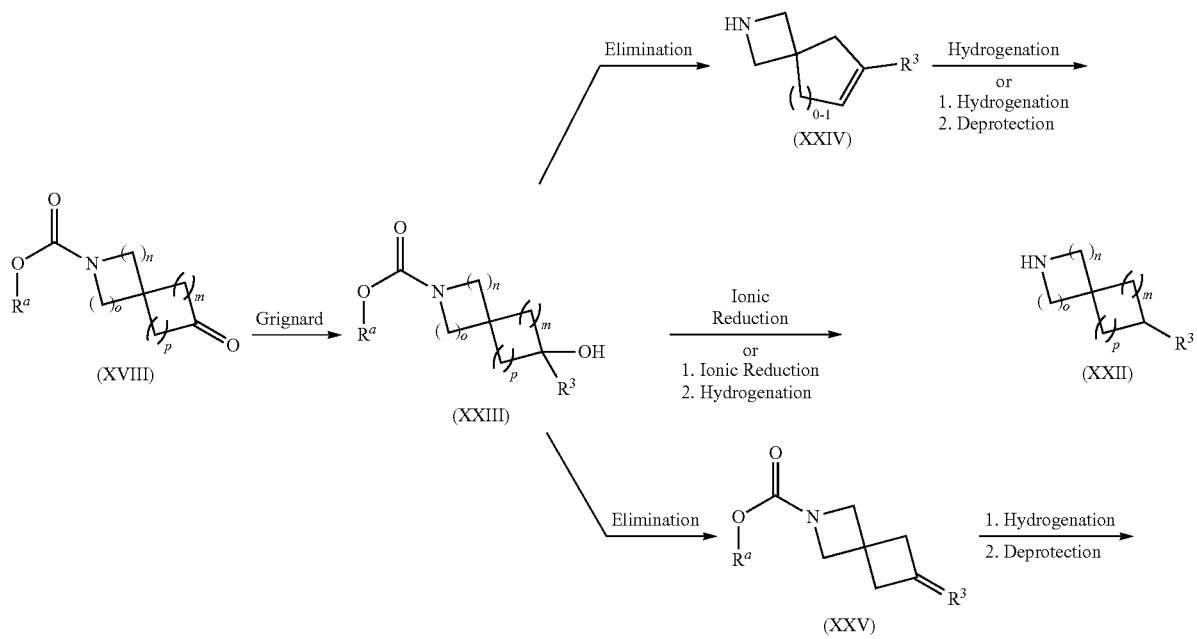

According to SCHEME 8, a compound of formula (XVIII), where n, m, o, p are each independently 1 or 2, and $R^a$ is $C_{1-4}$alkyl or benzyl; is reacted under conventional Grignard reaction conditions in the presence of an organomagnesium halide such as, phenylmagnesium bromide, and the like; with or without an additive such as $CeCl_3$, $LaCl_3$, and the like; in a suitable solvent such as THF or diethyl A compound of formula (XXIII) is reacted under elimination conditions such as TFA, using triethylsilane (TES) to eliminate the alcohol and cleave the tert-butoxycarbonyl group to form a compound of formula (XXIV). A compound of formula (XXIV) is reduced employing hydrogenation conditions in the presence of a palladium catalyst, including but not limited to, Pd on carbon, Pd(dppf)$Cl_2$ or Pd(PPh$_3$)$_4$; in a suitable solvent or solvent system such as DMF, methanol, dioxane/water, and the like; to provide a compound of formula (XXII), where $R^3$ is $C_{3-6}$cycloalkyl.

A compound of formula (XVIII), where $R^a$ is $C_{1-4}$alkyl, m, n, o, and p are 1; is reacted under Grignard conditions as previously described with an organomagnesium halide such as cyclohexylmagnesium bromide, and the like; to provide a compound of formula (XXV), where $R^3$ is $C_{3-6}$cycloalkyl. Alternately, a compound of formula (XVIII), m, n, o, and p are 1, and $R^a$ is $C_{1-4}$alkyl; is reacted under conventional Grignard reaction conditions employing conditions previously described, in the presence of an organomagnesium halide such as prop-1-en-2-ylmagnesium bromide. Subsequent cyclopropanation of the prop-1-en-2-yl, employing conditions such as diethylzinc; and diiodomethane; in a solvent such as DCM, and the like; provides a compound of formula (XXIII) where $R^3$ is $C_{3-6}$cycloalkyl substituted with $C_{1-4}$alkyl.

A compound of formula (XXIII), where $R^3$ is $C_{3-6}$cycloalkyl is reacted with a halogenating reagent such as thionyl chloride ($SOCl_2$) and the like; using a catalyst such as 4-(dimethylamino)pyridine (DMAP) and the like; in a suitable solvent such as pyridine and the like, to provide a compound of formula (XXV). A compound of formula (XXII), where m, n, o, and p are 1 and $R^3$ is $C_{3-6}$cycloalkyl is prepared in two steps from a compound of formula (XXV). In a first step, hydrogenation of a compound of formula (XXV) is achieved employing conditions previously described, followed by deprotection of the Boc protecting group employing conditions known to one skilled in the art or as previously described.

A compound of formula (XVIII), where $R^a$ is benzyl, n and o are 2, and m and p are 1; is reacted under Grignard conditions as previously described with a suitably substituted aryl organomagnesium halide such as phenylmagnesium bromide, to provide a compound of formula (XXIII), where $R^3$ is phenyl. Ionic reduction followed by hydrogenation employing conditions previously described affords a compound of formula (XXII), where $R^3$ is phenyl.

SCHEME 9

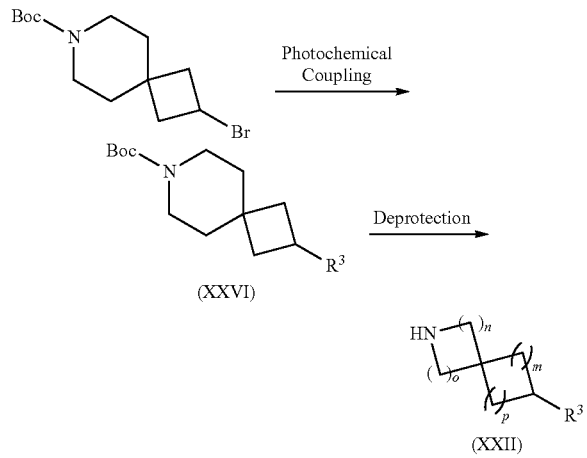

(XXVI)

(XXII)

According to SCHEME 9, tert-butyl 2-bromo-7-azaspiro[3.5]nonane-7-carboxylate is reacted under photochemical cross-coupling conditions in the presence of a commercially available or synthetically accessible appropriately substituted aryl or heteroaryl halide; with a photocatalyst such as (Ir[dF(CF$_3$)ppy]2(dtbpy))PF$_6$, and the like; a cross-coupling catalyst such as nickel(II) chloride ethylene glycol dimethyl ether complex (NiCl$_2$(DME)), and the like; a base such as 2,6-dimethylpyridine or potassium carbonate, and the like; a suitable additive such as tris(trimethylsilyl)silane or tris(trimethylsilyl)silanol, and the like; a suitable solvent such as 1,2-dimethoxyethane (DME) or dimethyl sulfoxide (DMSO), and the like; to provide a compound of formula (XXVI), where $R^3$ is a suitably substituted aryl or heteroaryl as defined in claim 1. A compound of formula (XXVI) is submitted to Boc deprotection, employing conditions previously described to provide a compound of formula (XXII), where n and o are 2, and m and p are 1.

SCHEME 10

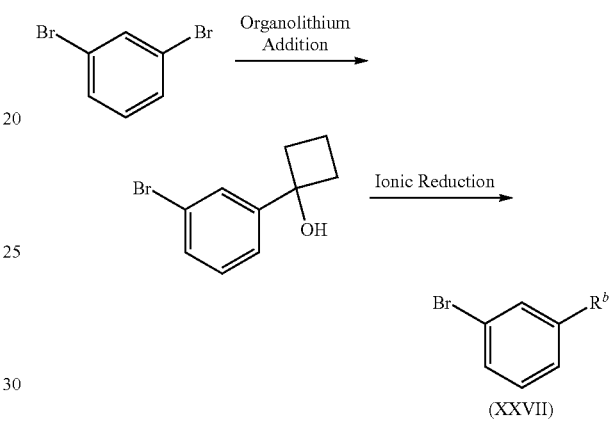

(XXVII)

According to SCHEME 10, a compound of formula (XXVII), where $R^b$ is $C_{3-6}$cycloalkyl, is commercially available or synthetically accessible in two steps from 1,3-dibromobenzene. For example, 1,3-dibromobenzene is reacted with a suitable lithiating reagent such as n-butyllithium (n-BuLi), and the like, in a suitable solvent such as THF, and the like; a temperatures ranging from −78° C. to −70° C.; followed by treatment with a ketone such as cyclobutanone and the like, to provide 1-(3-bromophenyl)cyclobutan-1-ol. Subsequent ionic reduction of 1-(3-bromophenyl)cyclobutan-1-ol employing conditions previously described, affords a compound of formula (XXVII), where $R^b$ is $C_{3-6}$cycloalkyl.

SCHEME 11

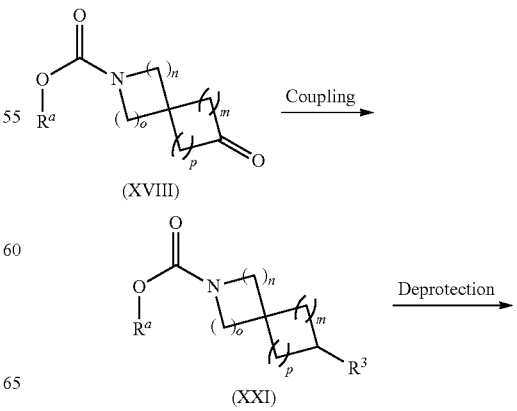

(XVIII)

(XXI)

-continued

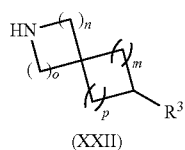

(XXII)

According to SCHEME 11, a compound of formula (XXI), where n, m and p are 1, o is 2, $R^3$ is phenyl, and $R^a$ is $C_{1-4}$alkyl; is synthesized from a compound of formula (XVIII) using 4-methylbenzenesulfonhydrazide; in a suitable solvent such as 1,4-dioxane, and the like; at a temperature of about 80° C.; for a period of 2-5 h; followed by addition of a suitable base such as potassium carbonate, and the like; and phenylboronic acid which is reacted at a temperature of about 110° C. for a period of 5-16 h. Cleavage of the BOC protecting group on a compound of formula (XXI) is achieved according to methods previously described to give a compound of formula (XXII).

SCHEME 12

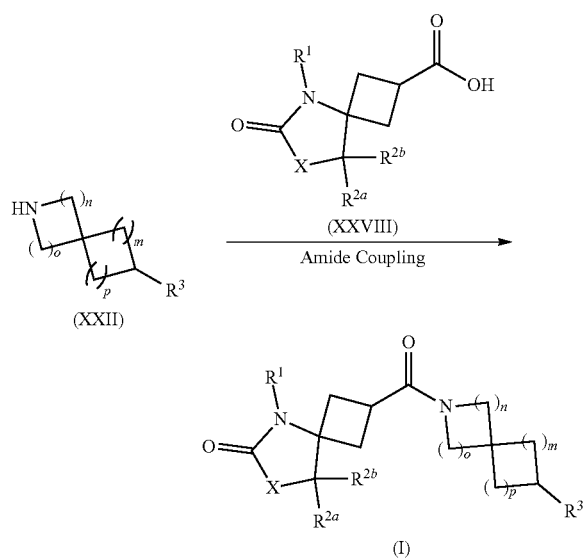

According to SCHEME 12, a compound of Formula (I), where $R^1$ is H and X is $CH_2$ or O and $R^{2a}$ and $R^{2b}$ are each independently H or $C_{1-4}$alkyl, is prepared from a compound of formula (XXII), where $R^3$ is cycloalkyl, aryl, heteroaryl, by conventional amide bond forming techniques such as coupling reactions which are well known to those skilled in the art (such as HATU (1-[bis(dimethylamino)methylene]-1H-1,2,3-triazolo[4,5-b]pyridinium 3-oxide hexafluorophosphate), BOP (benzotriazol-1-yloxy-tris(dimethylamino) phosphonium hexafluorophosphate), or conversion of the acid to an acid chloride). For example, reaction of a compound of formula (XXII), where m, n, o, and p are each independently 1 or 2; is reacted with a synthetically accessible suitably substituted carboxylic acid of formula (XXVII) (which includes compounds of formulas (XI), (XIII), and (XVII), where the acid is activated with an appropriate activating reagent, for example a carbodiimide, such as N,N'-dicyclohexylcarbodiimide (DCC) or 1-ethyl-3-(3-dimethylaminopropyl)carbodiimide (EDC, EDAC or EDCI) optionally in the presence of hydroxybenzotriazole (HOBt) and/or a catalyst such as 4-dimethylaminopyridine (DMAP); a halotrisaminophosphonium salt such as (benzotriazol-1-yloxy)tris(dimethylamino)phosphonium hexafluorophosphate (BOP), or bromotripyrrolidinophosphonium hexafluorophosphate (PyBroP®); a suitable pyridinium salt such as 2-chloro-1-methyl pyridinium chloride; or another suitable coupling agent such as N,N,N',N'-tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxid hexafluorophosphate (HATU), 2,4,6-tripropyl-1,3,5,2,4,6-trioxatriphosphorinane-2,4,6-trioxide (T3P®) and the like. Coupling reactions are conducted in a suitable solvent such as DCM, THF, DMF and the like, optionally in the presence of a tertiary amine such as N-methylmorpholine, N-ethyldiisopropylamine (DIPEA), or triethylamine (TEA), at a temperature ranging from 0° C. to rt, to provide a compound of Formula (I).

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16" PTFE tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

METHOD A. An Agilent HPLC with an Xterra Prep RP18 column (5 μM, 30×100 or 50×150 mm) or an)(Bridge C18 OBD column (5 μM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

METHOD B. A Shimadzu LC-8A Series HPLC with an Inertsil ODS-3 column (3 μm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

METHOD C. A Shimadzu LC-8A Series HPLC with an)(Bridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

METHOD D. A Gilson HPLC with an)(Bridge C18 column (51 μm, 100×50 mm), mobile phase of 5-99% ACN in 20 mM $NH_4OH$ over 10 min and then hold at 99 ACN for 2 min, at a flow rate of 80 mL/min.

or

METHOD E. An ACCQ Prep HPLC with an XBridge C18 OBD column (5 μM, 50×100), mobile phase of 5% ACN in $H_2O$ (both with 0.05% TFA) was held for 1 min, then a gradient of 5-95% ACN over 12 min, then held at 95% ACN for 2 min, with a flow rate of 80 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100 to 150 bar with a flow rate ranging from 40 to 60 mL/min. The column was heated to 35 to 40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, p=pentet, hept=heptet, dd=doublet of a doublet, dt=doublet of a triplet, pd=pentet of a doublet, ddd=doublet of a doublet of a doublet, tp=triplet of a pentet, td=triplet of a doublet, qd=quartet of a doublet, dq=doublet of a quartet, tt=triplet of a triplet, td=triplet of a doublet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 17.1 (CambridgeSoft Corp., Cambridge, MA) or OEMetaChem V1.4.0.4 (Open Eye).

Compounds designated as R* or S* are enantiopure compounds where the absolute configuration was not determined.

Intermediate 1: tert-Butyl 3-nitrocyclobutanecarboxylate

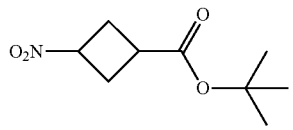

Step A: tert-Butyl 3-hydroxyiminocyclobutanecarboxylate. To a solution of tert-butyl 3-oxocyclobutane-1-carboxylate (100 g, 588 mmol) in ethanol (EtOH) (1.8 L) was added sodium acetate (NaOAc) (192 g, 2340 mmol) and hydroxylamine hydrochloride (81 g, 1166 mmol). The reaction mixture was stirred at reflux for 4 h then filtered through a pad of Celite® and the pad was washed with EtOH. The combined filtrates were evaporated and the residue was taken up in ethyl acetate (EtOAc) and washed with water and brine. The organic layer was dried over magnesium sulfate, filtered and concentrated to give the title compound (108 g, 584 mmol, 99% yield) as a white solid. MS (ESI): mass calcd. for $C_9H_{15}NO_3$ 185.1; m/z found, 186.2 $[M+H]^+$.

Step B: tert-Butyl 3-nitrocyclobutanecarboxylate. To a suspension of urea hydrogen peroxide (164 g, 1.74 mol) in acetonitrile (MeCN) (1 L) was added a solution of trifluoroacetic anhydride (TFAA) (245 mL, 1.75 mol) in MeCN (500 mL) dropwise over 1 h at −10° C. The reaction mixture was stirred at room temperature for 1 h. The solution was added to a solution of tert-butyl 3-hydroxyiminocyclobutanecarboxylate (108 g, 0.58 mol) and sodium phosphate dibasic (911 g, 6.42 mol) in MeCN (1 L) dropwise over 30 min at 80° C. The reaction mixture was stirred at 80° C. for 30 min then filtered through a pad of Celite® and the pad was washed with MeCN. The combined filtrates were diluted with EtOAc. The mixture was washed with water and brine. The organic layer was dried over magnesium sulfate, filtered and evaporated. The residue was purified by flash column chromatography (FCC) on silica (0-20% EtOAc in heptane) to give the title compound (89.6 g, 445 mmol, 76% yield) as a yellow oil as a 1.3:1 mixture of cis/trans isomers. Compound does not ionize with ESI LCMS.

Intermediate 2: Ethyl 3-nitrocyclobutanecarboxylate

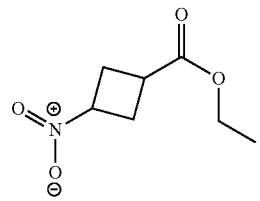

The title compound was prepared in a manner analogous to Intermediate 1 using ethyl 3-oxocyclobutane-1-carboxylate instead of tert-butyl 3-oxocyclobutane-1-carboxylate.

Compound does not ionize with ESI LCMS. ¹H NMR (300 MHz, Chloroform-d) δ 5.02-4.70 (m, 1H), 4.20 (q, J=7.2 Hz, 2H), 3.04-2.71 (m, 5H), 1.29 (t, J=7.0 Hz, 3H).

Intermediate 3: (2s,4s)-6-Oxo-7-oxa-5-azaspiro[3.4]octane-2-carboxylic acid

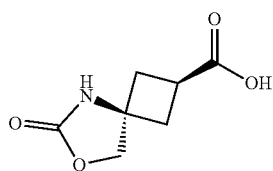 [SMILES: O=C1N[C@]2(CO1)C[C@H](C(=O)O)C2]

Step A: tert-Butyl (1s,3s)-3-(hydroxymethyl)-3-nitrocyclobutane-1-carboxylate. To a solution of tert-butyl 3-nitrocyclobutanecarboxylate (Intermediate 2, 89.6 g, 445 mmol) in MeCN (1 L) was added formaldehyde (37 wt % in water, 73 mL, 971 mmol). To the reaction mixture was added triethylamine (TEA) (62 mL, 444 mmol) dropwise at 0° C. and the reaction was stirred at room temperature for 2 h. The reaction mixture was evaporated and the residue was purified by FCC on silica (0-25% EtOAc in heptane) to give the title compound (38.2 g, 165 mmol, 37% yield) as a white powder. MS (ESI): mass calcd. for $C_{10}H_{17}NO_5$ 231.2; m/z found, 254.1 [M+Na]t trans-tert-Butyl 3-(hydroxymethyl)-3-nitro-cyclobutanecarboxylate was formed, but not isolated.

Step B: tert-Butyl (1s,3s)-3-amino-3-(hydroxymethyl)cyclobutane-1-carboxylate. To a solution of tert-butyl (1s,3s)-3-(hydroxymethyl)-3-nitro-cyclobutanecarboxylate (38.2 g, 165 mmol) in EtOAc (600 mL) was added 10% palladium on carbon (Pd/C) (1.9 g). The reaction mixture was stirred at 50° C. for 1 h under hydrogen ($H_2$) (10 bar). The reaction mixture was filtered through a pad of Celite®. To the filtrate was added 10% Pd/C (1.9 g). The reaction mixture was stirred at ° C. for 2 h under $H_2$ (10 bar). The reaction mixture was filtered through a pad of Celite® and the Celite® was washed with EtOAc. The combined filtrates were evaporated and the residue was triturated with diethyl ether ($Et_2O$) to give the title compound (18.6 g, 92.4 mmol, 55% yield) as a white powder. MS (ESI): mass calcd. for $C_{10}H_{19}NO_3$ 201.1; m/z found, 202.2 [M+H]⁺. ¹H NMR (300 MHz, DMSO-d6) δ 5.26-3.98 (m, 1H), 3.74-2.94 (m, 4H), 2.70-2.57 (m, 1H), 2.20-2.07 (m, 2H), 1.97-1.82 (m, 2H), 1.39 (s, 9H).

Step C: tert-Butyl (2s,4s)-6-oxo-7-oxa-5-azaspiro[3.4]octane-2-carboxylate. To a solution of tert-butyl (1s,3s)-3-amino-3-(hydroxymethyl)cyclobutane-1-carboxylate (18.6 g, 92.4 mmol) in tetrahydrofuran (THF) (300 mL) was added TEA (26 mL, 186 mmol). To the mixture was added a solution of triphosgene (9.6 g, 32.4 mmol) in THF (200 mL) dropwise at −10° C. and stirred at room temperature for 1 h. The reaction mixture poured into saturated sodium bicarbonate (600 mL) and the mixture was extracted with EtOAc. The combined organic layers were dried over magnesium sulfate, filtered and evaporated. The residue was triturated with $Et_2O$ to give the title compound (17.7 g, 77.9 mmol, 84% yield) as a white powder. MS (ESI): mass calcd. for $C_{11}H_{17}NO_4$ 227.1; m/z found, 228.2 [M+H]⁺.

Step D: (2s,4s)-6-Oxo-7-oxa-5-azaspiro[3.4]octane-2-carboxylic acid. To trifluoroacetic acid (TFA) (180 mL, 235 mmol) was added tert-butyl (2s,4s)-6-oxo-7-oxa-5-azaspiro [3.4]octane-2-carboxylate (17.7 g, 77.9 mmol) in portions at 0° C. The reaction mixture was stirred at room temperature for 1 h. The reaction mixture was evaporated and the residue was triturated with $Et_2O$ to afford the title compound (12.9 g, 75.4 mmol, 96% yield) as a white powder. MS (ESI): mass calcd. for $C_7H9NO_3$ 171.0; m/z found, 172.1 [M+H]⁺. ¹H NMR (500 MHz, DMSO-d6) δ 12.26 (br s, 1H), 8.08 (s, 1H), 4.34 (s, 2H), 2.79-2.66 (m, 1H), 2.43-2.29 (m, 4H).

Intermediate 4: (2r,4s)-6-Oxo-5-azaspiro[3.4]octane-2-carboxylic acid

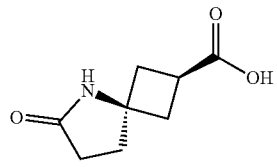 [SMILES: O=C1CC[C@]2(C[C@H](C(=O)O)C2)N1]

Step A: Ethyl (1r,3s)-3-(3-methoxy-3-oxopropyl)-3-nitrocyclobutane-1-carboxylate. To a solution of ethyl 3-nitrocyclobutanecarboxylate (Intermediate 2, 16.6 g, 95.6 mmol) in MeCN (145 mL) was added methyl acrylate (10.3 mL, 114 mmol). To the reaction mixture was added 1,8-diazabicyclo[5.4.0]undec-7-ene (7.1 mL, 47.6 mmol) dropwise at 0° C. and the reaction mixture was stirred at 0° C. for 1 h. The reaction mixture was diluted with saturated ammonium chloride and EtOAc and the layers were separated. The organic layer was dried over magnesium sulfate, filtered and evaporated. The residue was purified by FCC on silica (0-15% EtOAc in heptane) to give the title compound (13.6 g, 52.6 mmol, 55% yield) as a colorless liquid. MS (ESI): mass calcd. for $C_{11}H_{17}NO_6$ 259.1; m/z found, 282.1 [M+Na]t ¹H NMR (300 MHz, Chloroform-d) δ 4.17 (q, J=7.1 Hz, 2H), 3.70 (s, 3H), 3.12-2.79 (m, 3H), 2.69-2.49 (m, 2H), 2.48-2.21 (m, 4H), 1.27 (t, J=7.1 Hz, 3H).

Step B: (2r,4s)-6-Oxo-5-azaspiro[3.4]octane-2-carboxylic acid. To a solution of ethyl (1r,3s)-3-(3-methoxy-3-oxopropyl)-3-nitrocyclobutane-1-carboxylate (13.6 g, 52.6 mmol) in methanol (MeOH) (133 mL) was added nickel(II) chloride hexahydrate (12.5 g, 52.6 mmol). To the reaction mixture was added sodium borohydride ($NaBH_4$) (10 g, 264 mmol) in small portions at −10° C. and the reaction mixture was stirred at 0° C. for 1 h. To the reaction mixture was added aqueous potassium carbonate (47 mL, 141 mmol, 3 M) dropwise at 0° C. (pH 10) and the reaction mixture was stirred at 0° C. for 1 h. The reaction mixture was filtered through a pad of Celite® and the pad was washed with EtOH. The combined filtrates were evaporated. The residue was purified by FCC on silica eluting with chloroform:methanol:acetic acid (100:0:0→9:1:1) to give the title compound (4.8 g, 28.2 mmol, 53% yield) as an off-white powder. MS (ESI): mass calcd. for $C_8H_{11}NO_3$ 169.1; m/z found, 170.1 [M+H]⁺. ¹H NMR (300 MHz, DMSO-d6) δ 7.97 (br s, 1H), 4.01-2.94 (m, 1H), 2.82-2.65 (m, 1H), 2.36-2.01 (m, 8H).

Intermediate 5: (2s,4s)-8-Methyl-6-oxo-7-oxa-5-azaspiro[3.4]octane-2-carboxylic acid

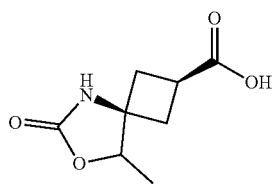

Step A: tert-Butyl 3-(1-hydroxyethyl)-3-nitro-cyclobutanecarboxylate. To a solution of tert-butyl 3-nitrocyclobutanecarboxylate (Intermediate 1, 11.7 g, 58.1 mmol) in MeCN (120 mL) was added acetaldehyde (19.6 mL, 349 mmol). To the reaction mixture was added TEA (8.1 mL, 58 mmol) dropwise at 0° C. and the reaction mixture was stirred at room temperature for 18 h. The reaction mixture was concentrated and the residue was purified by FCC on silica (0-20% EtOAc in heptane) to give the title compound (10.5 g, 42.8 mmol) as a colorless oil. MS (ESI): mass calcd. for $C_{11}H_{19}NO_5$ 245.1; m/z found, 263.2 $[M+H+NH_3]^+$.

Step B: tert-Butyl (1s,3s)-3-amino-3-(1-hydroxyethyl)cyclobutane-1-carboxylate. To a solution of a tert-butyl 3-(1-hydroxyethyl)-3-nitro-cyclobutanecarboxylate (10.5 g, 42.8 mmol) in EtOAc (110 mL) was added 10% Pd/C (1 g). The reaction mixture was stirred at 50° C. for 1 h under $H_2$ (10 bar). The reaction mixture was filtered through a pad of Celite®. To the filtrate was added 10% Pd/C (500 mg) and the reaction mixture was stirred at 50° C. for 2 h under $H_2$ (10 bar). The reaction mixture was filtered through a pad of Celite® and the pad was washed with EtOAc. The combined filtrates were evaporated and the residue was purified by FCC on silica eluting with chloroform:methanol:ammonium hydroxide (1:0:0→9:1:0.05) to give the title compound (3.6 g, 16.7 mmol, 39% yield) as a yellow oil. MS (ESI): mass calcd. for $C_{11}H_2INO_3$ 215.2; m/z found, 216.3 $[M+H]^+$. $^1H$ NMR (300 MHz, Chloroform-d) δ 3.83-3.64 (m, 1H), 2.80-2.61 (m, 1H), 2.54 (br s, 2H), 2.52-2.27 (m, 3H), 2.14-1.93 (m, 2H), 1.45 (s, 9H), 1.22-1.13 (m, 3H). Additional fractions from the same purification were collected to give tert-butyl (1r,3r)-3-amino-3-(1-hydroxyethyl)cyclobutanecarboxylate (550 mg, crude) as a yellow oil.

Step C: tert-Butyl (2s,4s)-8-methyl-6-oxo-7-oxa-5-azaspiro[3.4]octane-2-carboxylate. To a solution of tert-butyl (1s,3s)-3-amino-3-(1-hydroxyethyl)cyclobutane-1-carboxylate (15.2 g, 70.4 mmol) in THF (240 mL) was added TEA (20 mL, 143 mmol). To the mixture was added a solution of triphosgene (7.3 g, 24.6 mmol) in THF (170 mL) dropwise at −10° C. and the reaction mixture was stirred at room temperature for 1 h. The reaction mixture poured into saturated sodium bicarbonate and extracted with EtOAc. The combined organic layers were dried over magnesium sulfate, filtered and evaporated. The residue was purified by FCC on silica (0-35% EtOAc in heptane) to give the title compound (6.1 g, 25.3 mmol, 35% yield) as a white powder. MS (ESI): mass calcd. for $C_{12}H_{19}NO_4$ 241.1; m/z found, 242.2 $[M+H]^+$.

Step D: (2s,4s)-8-Methyl-6-oxo-7-oxa-5-azaspiro[3.4]octane-2-carboxylic acid. To TFA (60 mL, 784 mmol) was added tert-butyl (2s,4s)-8-methyl-6-oxo-7-oxa-5-azaspiro[3.4]octane-2-carboxylate (6.1 g, 25.3 mmol) in portions at 0° C. and the reaction mixture was stirred at room temperature for 1 h. The reaction mixture was evaporated and the residue was triturated with $Et_2O$ to give the title compound (4.3 g, 23.2 mmol, 91% yield) as a white powder. MS (ESI): mass calcd. for $C_8H_{11}NO_4$ 185.1; m/z found, 186.1 $[M+H]^+$. $^1H$ NMR (500 MHz, DMSO-$d_6$) δ 12.23 (br s, 1H), 7.94 (s, 1H), 4.50 (q, J=6.4 Hz, 1H), 2.68-2.59 (m, 1H), 2.53-2.46 (m, 1H), 2.41-2.35 (m, 1H), 2.32-2.24 (m, 1H), 2.17 (dd, J=12.0, 10.1 Hz, 1H), 1.30 (d, J=6.5 Hz, 3H).

Intermediate 6: Benzyl 2-hydroxy-2-phenyl-7-azaspiro[3.5]nonane-7-carboxylate

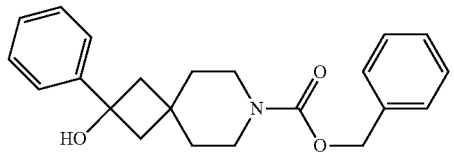 [SMILES: O=C(OCc1ccccc1)N1CCC2(CC1)CC(O)(c1ccccc1)C2]

Benzyl 2-oxo-7-azaspiro[3.5]nonane-7-carboxylate (200 mg, 0.73 mmol) was dissolved in diethyl ether and cooled to −78° C. Phenylmagnesium bromide (1 M in $Et_2O$, 0.95 mL, 0.95 mmol) was added dropwise with stirring. The reaction mixture was stirred at −78° C. for 4 hours, quenched with saturated aqueous $NH_4Cl$, and partitioned between water and DCM. The aqueous layer was extracted twice with DCM and the combined organics were concentrated and purified on silica gel (0-100% EA/hexanes) to obtain 131 mg (51% yield) of the desired product. MS (ESI): mass calcd. for $C_{22}H_{25}NO_3$ 351.2; m/z found, 352.0 $[M+H]^+$.

Intermediate 7: Benzyl 2-phenyl-7-azaspiro[3.5]nonane-7-carboxylate

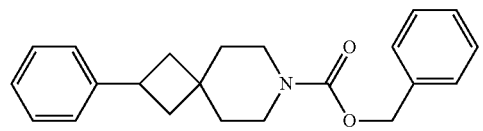 [SMILES: O=C(OCc1ccccc1)N1CCC2(CC1)CC(c1ccccc1)C2]

Benzyl 2-hydroxy-2-phenyl-7-azaspiro[3.5]nonane-7-carboxylate (Intermediate 6, 131 mg, 0.37 mmol) and triethylsilane (0.60 mL, 3.7 mmol) were dissolved in dry DCM and TFA (0.29 mL, 3.7 mmol) was added dropwise. The reaction mixture was stirred at r.t. for two hours, concentrated, and purified on silica gel to obtain 101 mg (81% yield) of the desired product. MS (ESI): mass calcd. for $C_{22}H_{25}NO_2$ 335.2; m/z found, 336 $[M+H]^+$.

Intermediate 8: 2-Phenyl-7-azaspiro[3.5]nonane

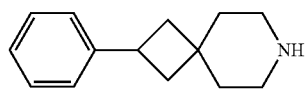 [SMILES: c1ccc(C2CC3(CCNCC3)C2)cc1]

Benzyl 2-phenyl-7-azaspiro[3.5]nonane-7-carboxylate (Intermediate 7, 101 mg, 0.30 mmol) was dissolved in 10 mL ethyl acetate and 10% palladium on carbon (100 mg) was added. The reaction vessel was evacuated and backfilled with hydrogen gas, and the reaction mixture was stirred at r.t. for two hours, then filtered through Celite®, and concentrated. Obtained 39 mg (0.19 mmol, 64% yield) of the title compound, which was used directly in subsequent transformations. MS (ESI): mass calcd. for $C_{14}H_{19}N$ 201.2; m/z found, 202.1 $[M+H]^+$.

Intermediate 9: tert-Butyl 2-(3-(tert-butyl)phenyl)-7-azaspiro[3.5]nonane-7-carboxylate

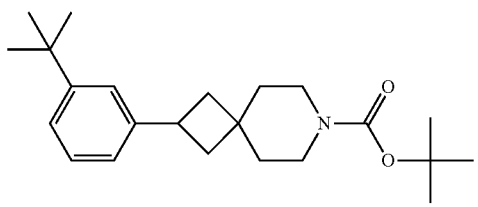

Nickel(II) chloride ethylene glycol dimethyl ether complex (7.2 mg, 0.033 mmol) and 4,4'-di-tert-butyl-2,2'-bipyridine (10.6 mg, 0.039 mmol) were dissolved in DME and stirred for ten minutes. To a separate vessel were added tert-butyl 2-bromo-7-azaspiro[3.5]nonane-7-carboxylate (100 mg, 0.30 mmol), $(Ir[dF(CF_3)ppy]2(dtbpy))PF_6$ (3.7 mg, 0.0033 mmol), 2,6-dimethylpyridine (0.19 mL, 1.64 mmol), 1-bromo-3-tert-butylbenzene (105 mg, 0.49 mmol), and tris(trimethylsilyl)silane (0.20 mL, 0.66 mmol). The solution of nickel(II) complex was added to the second reaction vessel and the mixture was sparged with $N_2$ for 10 minutes, sealed with parafilm, and stirred overnight in a Pennoc 450 nm photoreactor (LED: 100% power, fan: max, stirring: 700 RPM). The reaction mixture was concentrated, dissolved in dichloromethane, and purified on silica gel (0-30% EA/hexanes) to yield a mixture of the desired product and silane byproducts (238 mg total mass). This mixture was carried on to the next step without further purification. MS (ESI): mass calcd. for $C_{23}H_{35}NO_2$ 357.3; m/z found, 302.1 $[M+2H-tBu]^+$.

Intermediate 10: tert-Butyl 2-(4-methylphenyl)-7-azaspiro[3.5]nonane-7-carboxylate

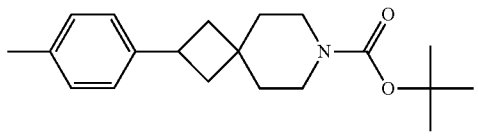 [SMILES: Cc1ccc(C2CC3(CCN(C(=O)OC(C)(C)C)CC3)C2)cc1]

The title compound was prepared in a manner analogous to tert-butyl 2-(3-(tert-butyl)phenyl)-7-azaspiro[3.5]nonane-7-carboxylate (Intermediate 9), using 1-bromo-4-methylbenzene in place of 1-bromo-3-tert-butylbenzene. MS (ESI): mass calcd. for $C_{21}H_3INO_2$ 315.2; m/z found, 260.1 $[M+2H-tBu]^+$.

Intermediate 11: tert-Butyl 2-(2-methylphenyl)-7-azaspiro[3.5]nonane-7-carboxylate

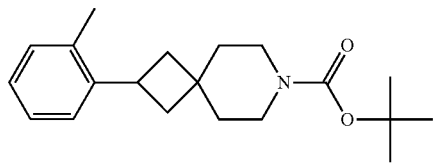 [SMILES: Cc1ccccc1C1CC2(CCN(C(=O)OC(C)(C)C)CC2)C1]

The title compound was prepared in a manner analogous to tert-butyl 2-(3-(tert-butyl)phenyl)-7-azaspiro[3.5]nonane-7-carboxylate (Intermediate 9), using 1-bromo-2-methylbenzene in place of 1-bromo-3-tert-butylbenzene. MS (ESI): mass calcd. for $C_{21}H_3INO_2$ 315.2; m/z found, 260.1 $[M+2H-tBu]^+$.

Intermediate 12: tert-Butyl 2-(3-cyclopropylphenyl)-7-azaspiro[3.5]nonane-7-carboxylate

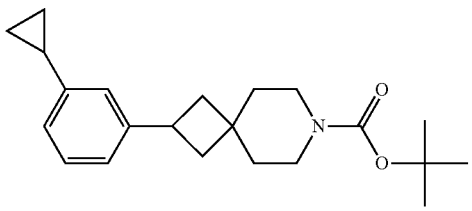 [SMILES: CC(C)(C)OC(=O)N1CCC2(CC1)CC(c1cccc(C3CC3)c1)C2]

The title compound was prepared in a manner analogous to tert-butyl 2-(3-(tert-butyl)phenyl)-7-azaspiro[3.5]nonane-7-carboxylate (Intermediate 9), using 1-bromo-3-cyclopropylbenzene in place of 1-bromo-3-tert-butylbenzene. MS (ESI): mass calcd. for $C_{21}H_3INO_2$ 341.2; m/z found, 286.1 $[M+2H-tBu]^+$.

Intermediate 13: tert-Butyl 2-(3-isopropylphenyl)-7-azaspiro[3.5]nonane-7-carboxylate

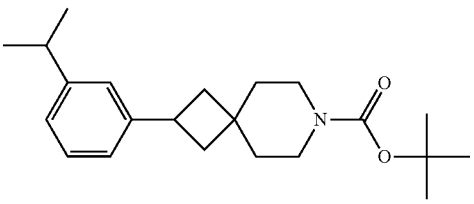 [SMILES: CC(C)c1cccc(C2CC3(CCN(C(=O)OC(C)(C)C)CC3)C2)c1]

The title compound was prepared in a manner analogous to tert-butyl 2-(3-(tert-butyl)phenyl)-7-azaspiro[3.5]nonane-7-carboxylate (Intermediate 9), using 1-bromo-3-isopropylbenzene in place of 1-bromo-3-tert-butylbenzene. MS (ESI): mass calcd. for $C_{21}H_3INO_2$ 343.3; m/z found, 288.0 $[M+2H-tBu]^+$.

Intermediate 14: tert-Butyl 2-(3-methylphenyl)-7-azaspiro[3.5]nonane-7-carboxylate

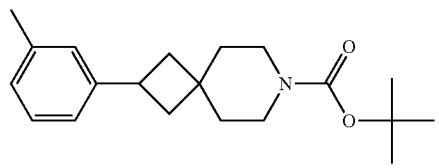 [SMILES: Cc1cccc(C2CC3(CCN(C(=O)OC(C)(C)C)CC3)C2)c1]

The title compound was prepared in a manner analogous to tert-butyl 2-(3-(tert-butyl)phenyl)-7-azaspiro[3.5]nonane-7-carboxylate (Intermediate 9), using 1-bromo-3-methylbenzene in place of 1-bromo-3-tert-butylbenzene. MS (ESI): mass calcd. for $C_{20}H_{29}NO_2$ 315.2; m/z found, 260.1 [M+2H-tBu]$^+$.

Intermediate 15: tert-Butyl 2-(3-methoxyphenyl)-7-azaspiro[3.5]nonane-7-carboxylate

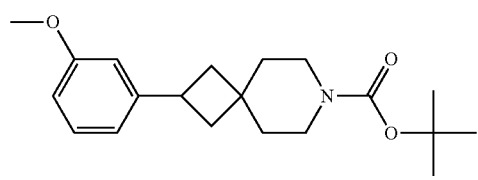 [SMILES: COc1cccc(C2CC3(CCN(C(=O)OC(C)(C)C)CC3)C2)c1]

The title compound was prepared in a manner analogous to tert-butyl 2-(3-(tert-butyl)phenyl)-7-azaspiro[3.5]nonane-7-carboxylate (Intermediate 9), using 3-bromoanisole in place of 1-bromo-3-tert-butylbenzene. MS (ESI): mass calcd. for $C_{20}H29NO_3$ 331.2; m/z found, 276.0 [M+2H-tBu]$^+$.

Intermediate 16: tert-Butyl 2-(3-trifluoromethoxyphenyl)-7-azaspiro[3.5]nonane-7-carboxylate

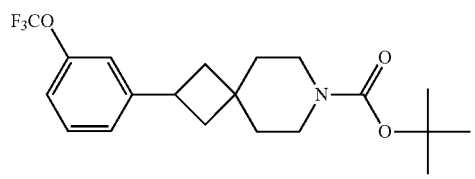 [SMILES: CC(C)(C)OC(=O)N1CCC2(CC1)CC(c1cccc(OC(F)(F)F)c1)C2]

The title compound was prepared in a manner analogous to tert-butyl 2-(3-(tert-butyl)phenyl)-7-azaspiro[3.5]nonane-7-carboxylate (Intermediate 9), using 1-bromo-3-trifluoromethoxybenzene in place of 1-bromo-3-tert-butylbenzene. MS (ESI): mass calcd. for $C_{20}H_{26}F_3NO_3$ 385.2; m/z found, 330.0 [M+2H-tBu]$^+$.

Intermediate 17: tert-Butyl 2-(2,3-dimethylphenyl)-7-azaspiro[3.5]nonane-7-carboxylate

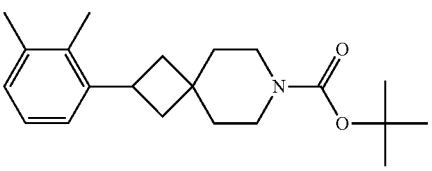 [SMILES: Cc1cccc(C2CC3(CCN(C(=O)OC(C)(C)C)CC3)C2)c1C]

The title compound was prepared in a manner analogous to tert-butyl 2-(3-(tert-butyl)phenyl)-7-azaspiro[3.5]nonane-7-carboxylate (Intermediate 9), using 1-bromo-2,3-dimethylbenzene in place of 1-bromo-3-tert-butylbenzene. MS (ESI): mass calcd. for $C_{21}H_3INO_2$ 329.2; m/z found, 274.0 [M+2H-tBu]$^+$.

Intermediate 18: tert-Butyl 2-(2,4-dimethylphenyl)-7-azaspiro[3.5]nonane-7-carboxylate

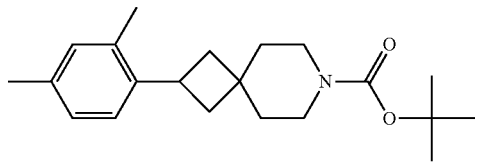 [SMILES: Cc1ccc(C2CC3(CCN(C(=O)OC(C)(C)C)CC3)C2)c(C)c1]

The title compound was prepared in a manner analogous to tert-butyl 2-(3-(tert-butyl)phenyl)-7-azaspiro[3.5]nonane-7-carboxylate (Intermediate 9), using 1-bromo-2,4-dimethylbenzene in place of 1-bromo-3-tert-butylbenzene. MS (ESI): mass calcd. for $C_{21}H_{31}NO_2$ 329.2; m/z found, 274.2 [M+2H-tBu]$^+$.

Intermediate 19: tert-Butyl 2-(2-(tert-butyl)pyridin-4-yl)-7-azaspiro[3.5]nonane-7-carboxylate

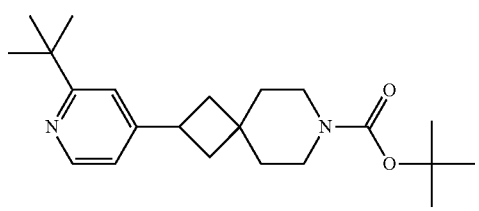 [SMILES: CC(C)(C)OC(=O)N1CCC2(CC1)CC(c1ccnc(C(C)(C)C)c1)C2]

The title compound was prepared in a manner analogous to tert-butyl 2-(3-(tert-butyl)phenyl)-7-azaspiro[3.5]nonane-7-carboxylate (Intermediate 9), using 4-bromo-2-(tert-butyl)pyridine in place of 1-bromo-3-tert-butylbenzene. MS (ESI): mass calcd. for $C_{22}H_{34}N_2O_2$ 358.3; m/z found, 359.3 [M+H]$^+$.

Intermediate 20: tert-Butyl 2-(5-(tert-butyl)-2-methylphenyl)-7-azaspiro[3.5]nonane-7-carboxylate

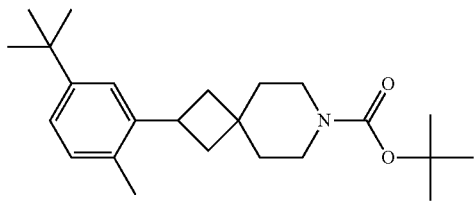 [SMILES: Cc1ccc(C(C)(C)C)cc1C1CC2(CCN(C(=O)OC(C)(C)C)CC2)C1]

The title compound was prepared in a manner analogous to tert-butyl 2-(3-(tert-butyl)phenyl)-7-azaspiro[3.5]nonane-7-carboxylate (Intermediate 9), using 2-bromo-4-(tert-butyl)-1-methylbenzene in place of 1-bromo-3-tert-butylbenzene. MS (ESI): mass calcd. for $C_{24}H_{37}NO_2$ 371.3; m/z found, 316.2 [M+2H-tBu]$^+$.

Intermediate 21: tert-Butyl 2-(3-trifluoromethylphenyl)-7-azaspiro[3.5]nonane-7-carboxylate

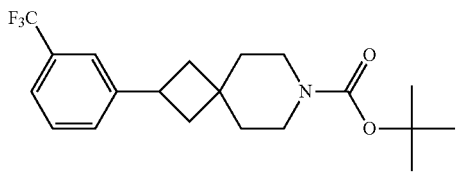 [SMILES: CC(C)(C)OC(=O)N1CCC2(CC1)CC(c1cccc(C(F)(F)F)c1)C2]

The title compound was prepared in a manner analogous to tert-butyl 2-(3-(tert-butyl)phenyl)-7-azaspiro[3.5]nonane-7-carboxylate (Intermediate 9), using 3-trifluoromethylbromobenzene in place of 1-bromo-3-tert-butylbenzene. MS (ESI): mass calcd. for $C_{20}H_{26}F_3NO_2$ 369.2; m/z found, 314.1 [M+2H-tBu]$^+$.

Intermediate 22: tert-Butyl 2-(2,5-dimethylphenyl)-7-azaspiro[3.5]nonane-7-carboxylate

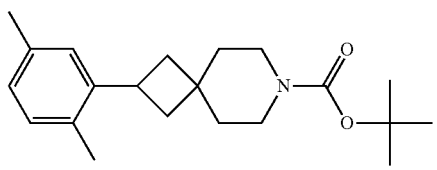 [SMILES: Cc1ccc(C)c(C2CC3(CCN(C(=O)OC(C)(C)C)CC3)C2)c1]

The title compound was prepared in a manner analogous to tert-butyl 2-(3-(tert-butyl)phenyl)-7-azaspiro[3.5]nonane-7-carboxylate (Intermediate 9), using 1-bromo-2,5-dimethylbenzene in place of 1-bromo-3-tert-butylbenzene. MS (ESI): mass calcd. for $C_{21}H_{31}NO_2$ 329.2; m/z found, 274.2 [M+2H-tBu]$^+$.

Intermediate 23: tert-Butyl 2-(6-(tert-butyl)pyridin-2-yl)-7-azaspiro[3.5]nonane-7-carboxylate

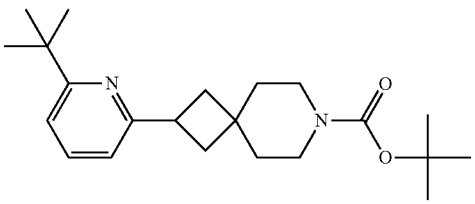 [SMILES: CC(C)(C)OC(=O)N1CCC2(CC1)CC(c1cccc(C(C)(C)C)n1)C2]

The title compound was prepared in a manner analogous to tert-butyl 2-(3-(tert-butyl)phenyl)-7-azaspiro[3.5]nonane-7-carboxylate (Intermediate 9), using 2-bromo-6-(tert-butyl)pyridine in place of 1-bromo-3-tert-butylbenzene. MS (ESI): mass calcd. for $C_{22}H_{34}N_2O_2$ 358.3; m/z found, 359.3 [M+H]$^+$.

Intermediate 24: tert-Butyl 2-(4-(1-(trifluoromethyl)cyclopropyl)phenyl)-7-azaspiro[3.5]nonane-7-carboxylate

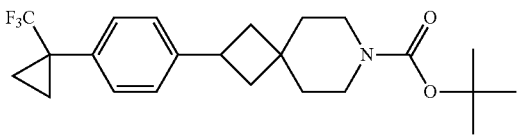

The title compound was prepared in a manner analogous to tert-butyl 2-(3-(tert-butyl)phenyl)-7-azaspiro[3.5]nonane-7-carboxylate (Intermediate 9), using 1-bromo-4-(1-(trifluoromethyl)cyclopropyl)benzene in place of 1-bromo-3-tert-butylbenzene. MS (ESI): mass calcd. for $C_{23}H_{30}F_3NO_2$ 409.2; m/z found, 354.2 [M+2H-tBu]$^+$.

Intermediate 25: tert-Butyl 2-(3-chloro-4-(trifluoromethyl)phenyl)-7-azaspiro[3.5]nonane-7-carboxylate

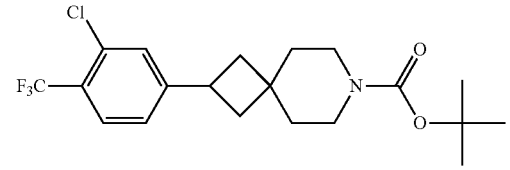 [SMILES: CC(C)(C)OC(=O)N1CCC2(CC1)CC(c1ccc(C(F)(F)F)c(Cl)c1)C2]

The title compound was prepared in a manner analogous to tert-butyl 2-(3-(tert-butyl)phenyl)-7-azaspiro[3.5]nonane-7-carboxylate (Intermediate 9), using 4-bromo-2-chloro-1-(trifluoromethyl)benzene in place of 1-bromo-3-tert-butylbenzene. MS (ESI): mass calcd. for $C_{20}H_{25}ClF_3NO_2$ 403.2; m/z found, 348.1 [M+2H-tBu]$^+$.

Intermediate 26: tert-Butyl 2-(4-methoxy-3-(trifluoromethyl)phenyl)-7-azaspiro[3.5]nonane-7-carboxylate

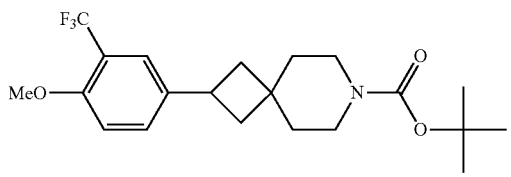 [SMILES: COc1ccc(C2CC3(CCN(C(=O)OC(C)(C)C)CC3)C2)cc1C(F)(F)F]

The title compound was prepared in a manner analogous to tert-butyl 2-(3-(tert-butyl)phenyl)-7-azaspiro[3.5]nonane-7-carboxylate (Intermediate 9), using 4-bromo-1-methoxy-2-(trifluoromethyl)benzene in place of 1-bromo-3-tert-butylbenzene. MS (ESI): mass calcd. for $C_{21}H_{31}ClF_3NO_3$ 399.2; m/z found, 344.2 [M+2H-tBu]$^+$.

Intermediate 27: tert-Butyl 2-(4-(tert-butyl)pyridin-2-yl)-7-azaspiro[3.5]nonane-7-carboxylate

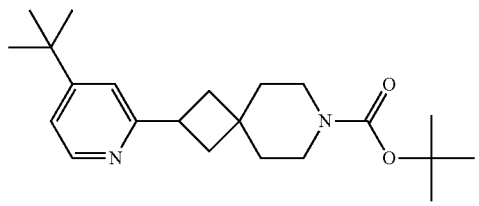

The title compound was prepared in a manner analogous to tert-butyl 2-(3-(tert-butyl)phenyl)-7-azaspiro[3.5]nonane-7-carboxylate (Intermediate 9), using 2-bromo-4-(tert-butyl)pyridine in place of 1-bromo-3-tert-butylbenzene. MS (ESI): mass calcd. for $C_{22}H_{34}N_2O_2$ 358.3; m/z found, 359.2 [M+H]$^+$.

Intermediate 28: tert-Butyl 2-(5-(tert-butyl)-2-fluorophenyl)-7-azaspiro[3.5]nonane-7-carboxylate

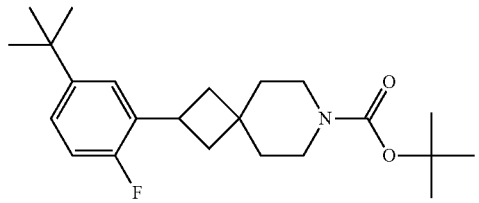 [SMILES: CC(C)(C)OC(=O)N1CCC2(CC1)CC(c1cc(C(C)(C)C)ccc1F)C2]

The title compound was prepared in a manner analogous to tert-butyl 2-(3-(tert-butyl)phenyl)-7-azaspiro[3.5]nonane-7-carboxylate (Intermediate 9), using 2-bromo-4-(tert-butyl)-1-fluorobenzene in place of 1-bromo-3-tert-butylbenzene. MS (ESI): mass calcd. for $C_{23}H_{34}FNO_2$ 375.2; m/z found, 320.2 [M+2H-tBu]$^+$.

Intermediate 29: tert-Butyl 2-(5-(tert-butyl)-2-ethoxyphenyl)-7-azaspiro[3.5]nonane-7-carboxylate

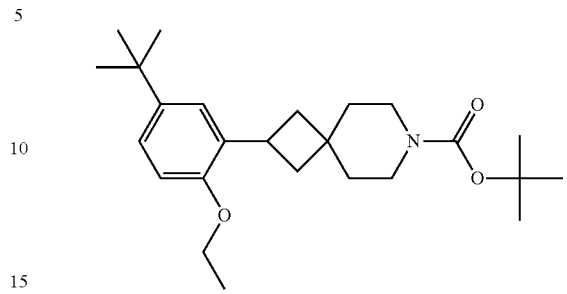

The title compound was prepared in a manner analogous to tert-butyl 2-(3-(tert-butyl)phenyl)-7-azaspiro[3.5]nonane-7-carboxylate (Intermediate 9), using 2-bromo-4-(tert-butyl)-2-ethoxybenzene in place of 1-bromo-3-tert-butylbenzene. MS (ESI): mass calcd. for $C_{25}H_{39}NO_3$ 401.3; m/z found, 346.2 [M+2H-tBu]$^+$.

Intermediate 30: tert-Butyl 2-(5-(tert-butyl)-2-methoxyphenyl)-7-azaspiro[3.5]nonane-7-carboxylate

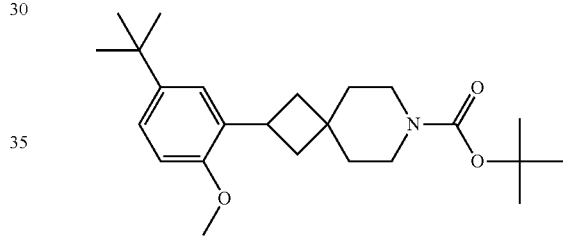

The title compound was prepared in a manner analogous to tert-butyl 2-(3-(tert-butyl)phenyl)-7-azaspiro[3.5]nonane-7-carboxylate (Intermediate 9), using 2-bromo-4-(tert-butyl)-2-methoxybenzene in place of 1-bromo-3-tert-butylbenzene. MS (ESI): mass calcd. for $C_{24}H_{37}NO_3$ 387.3; m/z found, 332.2 [M+2H-tBu]$^+$.

Intermediate 31: tert-Butyl 2-(2,2-difluorobenzo[d][1,3]dioxol-5-yl)-7-azaspiro[3.5]nonane-7-carboxylate

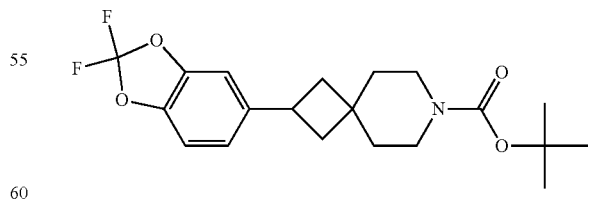

The title compound was prepared in a manner analogous to tert-butyl 2-(3-(tert-butyl)phenyl)-7-azaspiro[3.5]nonane-7-carboxylate (Intermediate 9), using 5-bromo-2,2-difluorobenzo[d][1,3]dioxole in place of 1-bromo-3-tert-butylbenzene. MS (ESI): mass calcd. for $C_{20}H_{25}F_2NO_4$ 381.2; m/z found, 326.0 [M+2H-tBu]$^+$.

Intermediate 32: tert-Butyl 2-(2-methoxyphenyl)-7-azaspiro[3.5]nonane-7-carboxylate

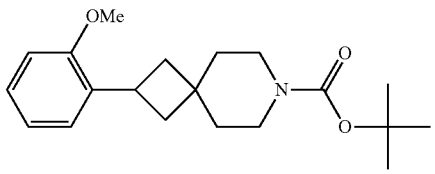 [SMILES: COc1ccccc1C1CC2(CCN(C(=O)OC(C)(C)C)CC2)C1]

The title compound was prepared in a manner analogous to tert-butyl 2-(3-(tert-butyl)phenyl)-7-azaspiro[3.5]nonane-7-carboxylate (Intermediate 9), using 1-bromo-2-methoxybenzene in place of 1-bromo-3-tert-butylbenzene. MS (ESI): mass calcd. for $C_{20}H_{29}NO_3$ 331.2; m/z found, 276.1 $[M+2H-tBu]^+$.

Intermediate 33: tert-Butyl 2-(4-methoxyphenyl)-7-azaspiro[3.5]nonane-7-carboxylate

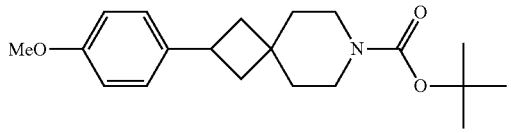 [SMILES: COc1ccc(C2CC3(CCN(C(=O)OC(C)(C)C)CC3)C2)cc1]

The title compound was prepared in a manner analogous to tert-butyl 2-(3-(tert-butyl)phenyl)-7-azaspiro[3.5]nonane-7-carboxylate (Intermediate 9), using 1-bromo-4-methoxybenzene in place of 1-bromo-3-tert-butylbenzene. MS (ESI): mass calcd. for $C_{20}H_{29}NO_3$ 331.2; m/z found, 276.1 $[M+2H-tBu]^+$.

Intermediate 34: tert-Butyl 2-(3-fluoro-6-(trifluoromethyl)pyridin-2-yl)-7-azaspiro[3.5]nonane-7-carboxylate

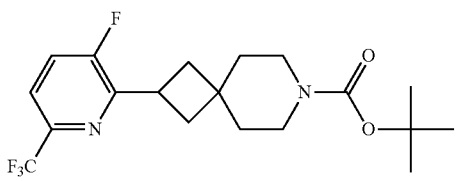 [SMILES: CC(C)(C)OC(=O)N1CCC2(CC1)CC(c1nc(C(F)(F)F)ccc1F)C2]

The title compound was prepared in a manner analogous to tert-butyl 2-(3-(tert-butyl)phenyl)-7-azaspiro[3.5]nonane-7-carboxylate (Intermediate 9), using 2-bromo-3-fluoro-6-(trifluoromethyl)pyridine in place of 1-bromo-3-tert-butylbenzene. MS (ESI): mass calcd. for $C_{19}H_{24}F_4N_2O_2$ 388.2; m/z found, 333.1 $[M+2H-tBu]^+$.

Intermediate 35: tert-Butyl 2-(6-(trifluoromethyl)pyridin-2-yl)-7-azaspiro[3.5]nonane-7-carboxylate

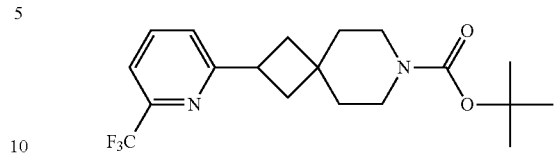

The title compound was prepared in a manner analogous to tert-butyl 2-(3-(tert-butyl)phenyl)-7-azaspiro[3.5]nonane-7-carboxylate (Intermediate 9), using 2-bromo-6-(trifluoromethyl)pyridine in place of 1-bromo-3-tert-butylbenzene. MS (ESI): mass calcd. for $C_{19}H_{25}F_3N_2O_2$ 370.2; m/z found, 315.1 $[M+2H-tBu]^+$.

Intermediate 36: tert-Butyl 2-(5-fluoro-6-methylpyridin-2-yl)-7-azaspiro[3.5]nonane-7-carboxylate

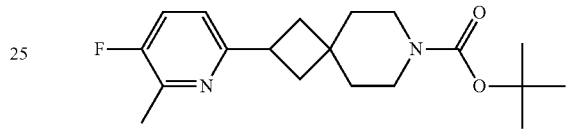

The title compound was prepared in a manner analogous to tert-butyl 2-(3-(tert-butyl)phenyl)-7-azaspiro[3.5]nonane-7-carboxylate (Intermediate 9), using 6-bromo-3-fluoro-2-methylpyridine in place of 1-bromo-3-tert-butylbenzene. MS (ESI): mass calcd. for $C_{19}H_{27}FN_2O_2$ 334.2; m/z found, 335.3 $[M+H]^+$.

Intermediate 37: tert-Butyl 2-(2-(tert-butyl)pyrimidin-4-yl)-7-azaspiro[3.5]nonane-7-carboxylate

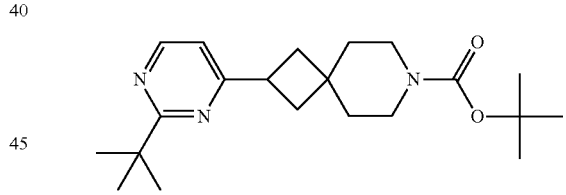

The title compound was prepared in a manner analogous to tert-butyl 2-(3-(tert-butyl)phenyl)-7-azaspiro[3.5]nonane-7-carboxylate (Intermediate 9), using 4-bromo-2-(tert-butyl)pyrimidine in place of 1-bromo-3-tert-butylbenzene. MS (ESI): mass calcd. for $C_{21}H_{33}N_3O_2$ 359.3; m/z found, 360.3 $[M+H]^+$.

Intermediate 38: tert-Butyl 2-(4-(tert-butyl)oxazol-2-yl)-7-azaspiro[3.5]nonane-7-carboxylate

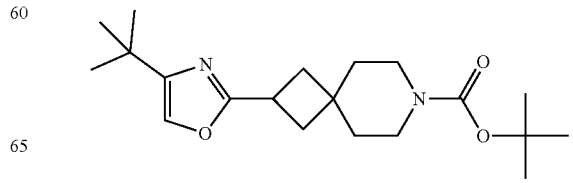

The title compound was prepared in a manner analogous to tert-butyl 2-(3-(tert-butyl)phenyl)-7-azaspiro[3.5]nonane-7-carboxylate (Intermediate 9), using 2-bromo-4-(tert-butyl)oxazole in place of 1-bromo-3-tert-butylbenzene. MS (ESI): mass calcd. for $C_{20}H_{32}N_2O_3$ 348.2; m/z found, 293.2 [M+2H-tBu]$^+$.

Intermediate 39: tert-Butyl 2-(2-(tert-butyl)oxazol-5-yl)-7-azaspiro[3.5]nonane-7-carboxylate

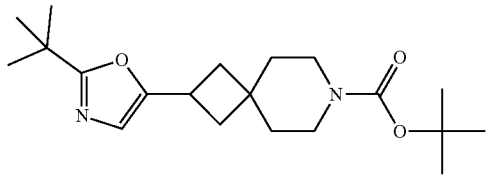 [SMILES: CC(C)(C)OC(=O)N1CCC2(CC1)CC(c1cnc(C(C)(C)C)o1)C2]

The title compound was prepared in a manner analogous to tert-butyl 2-(3-(tert-butyl)phenyl)-7-azaspiro[3.5]nonane-7-carboxylate (Intermediate 9), using 5-bromo-2-(tert-butyl)oxazole in place of 1-bromo-3-tert-butylbenzene. MS (ESI): mass calcd. for $C_{20}H_{32}N_2O_3$ 348.2; m/z found, 349.3 [M+H]$^+$.

Intermediate 40: tert-Butyl 2-(3,5-difluoropyridin-2-yl)-7-azaspiro[3.5]nonane-7-carboxylate

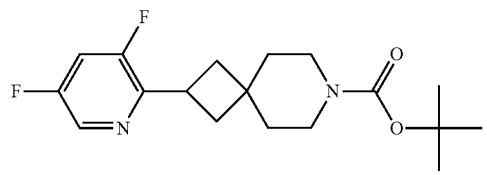 [SMILES: CC(C)(C)OC(=O)N1CCC2(CC1)CC(c1ncc(F)cc1F)C2]

The title compound was prepared in a manner analogous to tert-butyl 2-(3-(tert-butyl)phenyl)-7-azaspiro[3.5]nonane-7-carboxylate (Intermediate 9), using 2-bromo-3,5-difluoropyridine in place of 1-bromo-3-tert-butylbenzene. MS (ESI): mass calcd. for $C_{18}H_{24}F_2N_2O_2$ 338.2; m/z found, 283.1 [M+2H-tBu]$^+$.

Intermediate 41: tert-Butyl 2-iodo-8-azaspiro[4.5]decane-8-carboxylate

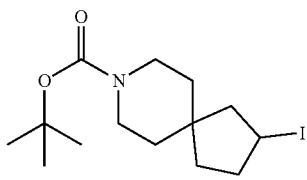 [SMILES: CC(C)(C)OC(=O)N1CCC2(CCC(I)C2)CC1]

Step A: tert-Butyl 2-hydroxy-8-azaspiro[4.5]decane-8-carboxylate. Sodium borohydride (NaBH$_4$) (239 mg, 6.32 mmol) was added portion-wise to a solution of tert-butyl 2-oxo-8-azaspiro[4.5]decane-8-carboxylate (800 mg, 3.16 mmol) in methanol (MeOH) (60 mL) at 0° C. The mixture was stirred at rt for 6 h. The solvent was evaporated under reduced pressure, and the residue was re-dissolved in ethyl acetate (EtOAc) and washed with hydrochloric acid (HCl) (0.1 N) and brine. The organic phase was separated, dried, filtered and evaporated under reduced pressure to afford the title compound that was used without further purification in the next step (841 mg, 100% yield). MS (ESI): mass calcd. for $C_{14}H_{25}NO_3$, 255.2; m/z found, 256.2 [M+H]$^+$.

Step B: tert-Butyl 2-iodo-8-azaspiro[4.5]decane-8-carboxylate. Iodine (I2) (962 mg, 3.79 mmol) was added portion-wise to a solution of tert-butyl 2-hydroxy-8-azaspiro[4.5]decane-8-carboxylate (807 mg, 3.16 mmol), imidazole (323 mg, 4.74 mmol), and triphenylphosphine (PPh$_3$) (995 mg, 3.79 mmol) in tetrahydrofuran (THF) (5.9 mL) at 0° C. The mixture was stirred for 1 h at rt. Excess I$_2$ was quenched with 10% Na$_2$S$_2$O$_3$. The aqueous phase was extracted with EtOAc and the combined organics were dried over MgSO$_4$. Solids were removed by filtration and the solvent was evaporated under reduced pressure. The residue was purified by flash column chromatography (FCC) on silica (EtOAc in heptane 0-15%) affording the title compound as a colorless oil (719 mg, 62% yield). MS (ESI): mass calcd. for $C_{14}H_{25}INO_2$, 365.2; m/z found, 366.1 [M+H]$^+$.

Intermediate 42: tert-Butyl 6-iodo-2-azaspiro[3.4]octane-2-carboxylate

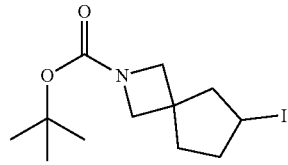 [SMILES: CC(C)(C)OC(=O)N1CC2(CCC(I)C2)C1]

The title compound was prepared in a manner analogous to Intermediate 41, Step B using tert-butyl 6-hydroxy-2-azaspiro[3.4]octane-2-carboxylate instead of tert-butyl 2-hydroxy-8-azaspiro[4.5]decane-8-carboxylate. MS (ESI): mass calcd. for $C_{12}H_{20}INO_2$, 337.2; m/z found, 338.1 [M+H]$^+$.

Intermediate 43: tert-Butyl 6-phenyl-2-azaspiro[3.4]octane-2-carboxylate

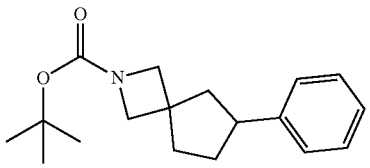 [SMILES: CC(C)(C)OC(=O)N1CC2(CCC(c3ccccc3)C2)C1]

A solution of tert-butyl 6-iodo-2-azaspiro[3.4]octane-2-carboxylate (Intermediate 42, 435 mg, 1.29 mmol) in THF (2.6 mL) was flowed through a column containing activated zinc at 40° C. at 0.25 mL/min. The outcoming solution was collected in a sealed vial containing bromobenzene (68 µL, 0.645 mmol), palladium (II) acetate (7.2 mg, 0.032 mmol) and dicyclohexyl(2',6'-diisopropoxy-[1,1'-biphenyl]-2-yl)phosphine (RuPhos) (30 mg, 0.064 mmol). The mixture was stirred at 50° C. for 90 minutes. Then, a 1:1 solution of saturated NH$_4$Cl and NH$_3$ (37% in water) was added and the mixture was extracted with EtOAc. The organic phase was separated, dried over Na$_2$SO$_4$, filtered and the solvent removed in vacuo. The residue was purified by FCC on silica (0-100% EtOAc in heptane) to afford the title compound (174 mg, 70% pure, 66% yield). MS (ESI): mass calcd. for $C_{18}H_{25}NO_2$, 287.4; m/z found, 288.3 $[M+H]^+$.

Intermediate 44: tert-Butyl (S*)-6-phenyl-2-azaspiro[3.4]octane-2-carboxylate

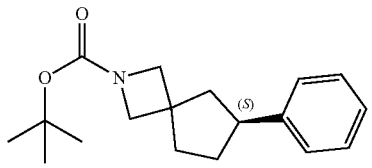

The title compound was prepared by chiral supercritical fluid chromatography of tert-butyl 6-phenyl-2-azaspiro[3.4]octane-2-carboxylate (Intermediate 43) (Stationary phase: Chiralpak IG 5 μm 250*30 mm, Mobile phase: 90% $CO_2$, 10% MeOH). MS (ESI): mass calcd. for $C_{18}H_{25}NO_2$, 287.2; m/z found, 288.0 $[M+H]^+$.

Intermediate 45: tert-Butyl (R*)-6-phenyl-2-azaspiro[3.4]octane-2-carboxylate

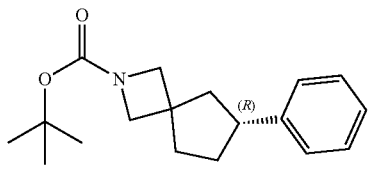

The title compound was prepared by chiral supercritical fluid chromatography of tert-butyl 6-phenyl-2-azaspiro[3.4]octane-2-carboxylate (Intermediate 43) (Stationary phase: Chiralpak IG 5 μm 250*30 mm, Mobile phase: 90% $CO_2$, 10% MeOH). MS (ESI): mass calcd. for $C_{18}H_{25}NO_2$, 287.2; m/z found, 288.1 $[M+H]^+$.

Intermediate 46: tert-Butyl 6-(4-(trifluoromethyl)phenyl)-2-azaspiro[3.4]octane-2-carboxylate

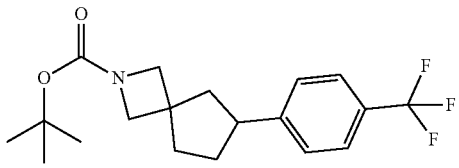 [SMILES: CC(C)(C)OC(=O)N1CC2(CCC(c3ccc(C(F)(F)F)cc3)C2)C1]

The title compound was prepared in a manner analogous to tert-butyl 6-phenyl-2-azaspiro[3.4]octane-2-carboxylate (Intermediate 43) using 4-bromobenzotrifluoride instead of bromobenzene. MS (ESI): mass calcd. for $C_{19}H_{24}F_3NO_2$, 355.1; m/z found, 356.3 $[M+H]^+$.

Intermediate 47: tert-Butyl (S*)-6-(4-(trifluoromethyl)phenyl)-2-azaspiro[3.4]octane-2-carboxylate

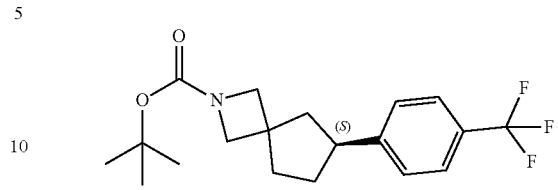

The title compound was prepared by chiral supercritical fluid chromatography of tert-butyl 6-(4-(trifluoromethyl)phenyl)-2-azaspiro[3.4]octane-2-carboxylate (Intermediate 46) (Stationary phase: Chiralpak IG 5 μm 250*30 mm, Mobile phase: 95% $CO_2$, 5% MeOH). MS (ESI): mass calcd. for $C_{19}H_{24}F_3NO_2$, 355.1; m/z found, 341.1 [M-tBu+2H+MeCN]$^+$.

Intermediate 48: tert-Butyl (R*)-6-(4-(trifluoromethyl)phenyl)-2-azaspiro[3.4]octane-2-carboxylate

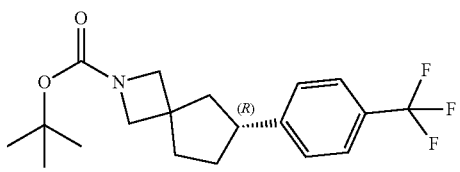

The title compound was prepared by chiral supercritical fluid chromatography of tert-butyl 6-(4-(trifluoromethyl)phenyl)-2-azaspiro[3.4]octane-2-carboxylate (Intermediate 46) (Stationary phase: Chiralpak IG 5 μm 250*30 mm, Mobile phase: 95% $CO_2$, 5% MeOH). MS (ESI): mass calcd. for $C_{19}H_{24}F_3NO_2$, 355.1; m/z found, 341.1 [M-tBu+2H+MeCN]$^+$.

Intermediate 49: 6-Phenyl-2-azaspiro[3.3]heptane, trifluoroacetate salt

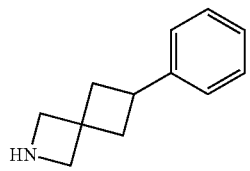 [SMILES: c1ccc(C2CC3(CNC3)C2)cc1]

Step A: tert-butyl 6-Hydroxy-6-phenyl-2-azaspiro[3.3]heptane-2-carboxylate. Phenylmagnesium bromide (2 M in THF, 376 μL, 753 μmol) was added dropwise to a −78° C. stirring solution of tert-butyl 6-oxo-2-azaspiro[3.3]heptane-2-carboxylate (70.0 mg, 331 μmol) in THF (1.7 mL). After the end of the addition, the ice bath was removed and the reaction mixture was stirred at room temperature. After 30 min, the reaction mixture was quenched by the addition of sat'd aq. $NH_4Cl$ (10 mL) and the resulting aqueous mixture was extracted with EtOAc (3×10 mL). The combined organic extracts were dried over $Na_2SO_4$ and concentrated in vacuo. Purification of the resulting crude product by flash column chromatography on silica (0-100% EtOAc/Hex)

afforded the title product (90.7 mg, 313 μmol, 95% yield) as a white solid which was used in step B without further purification. MS (ESI): mass calcd. for $C_{17}H_{23}NO_3$, 289.2; m/z found, 234.2 [M-tBu+2E1]$^+$.

Step B: 6-Phenyl-2-azaspiro[3.3]heptane, trifluoroacetate salt. tert-Butyl 6-hydroxy-6-phenyl-2-azaspiro[3.3]heptane-2-carboxylate (90.0 mg, 311 μmol) was dissolved in trifluoroacetic acid (TFA) (1.07 mL) and the resulting solution was stirred at rt for 5 min. Triethylsilane (149 μL, 933 μmol) was added dropwise. After the end of the addition, the reaction mixture was stirred vigorously at room temperature for 2 h. Solvent was subsequently removed in vacuo to give the crude title product which was used without further purification. MS (ESI): mass calcd. for $C_{12}H_{15}N$, 173.2; m/z found, 174.1 [M+H]$^+$.

Intermediate 50: tert-Butyl 6-iodo-2-azaspiro[3.3]heptane-2-carboxylate

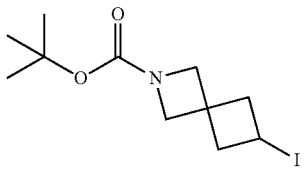

Step A: tert-Butyl 6-hydroxy-2-azaspiro[3.3]heptane-2-carboxylate. Sodium borohydride (NaBH$_4$) (1.80 g, 47.3 mmol) was added in portions to a 0° C. solution consisting of tert-butyl 6-oxo-2-azaspiro[3.3]heptane-2-carboxylate (5.00 g, 23.7 mmol) in methanol (50 mL). The resultant mixture was stirred at 0° C. for 30 min before quenching with the sat. NaHCO$_3$ and extracting twice with ethyl acetate. The combined organic extracts were washed with brine, dried over anhydrous Na$_2$SO$_4$, and concentrated to afford the title compound (4.86 g, 96% yield) as a white solid, which was used in the next step without further purification. $^1$H NMR (400 MHz, CDCl$_3$) δ 4.24-4.11 (m, 1H), 3.88 (d, J=7.2 Hz, 4H), 2.54 (ddd, J=2.8, 6.8, 10.0 Hz, 2H), 2.11-2.02 (m, 2H), 1.93 (br s, 1H), 1.43 (s, 9H).

Step B: tert-Butyl 6-iodo-2-azaspiro[3.3]heptane-2-carboxylate. tert-Butyl 6-hydroxy-2-azaspiro[3.3]heptane-2-carboxylate (4.86 g, 22.8 mmol), toluene (50 mL), PPh$_3$ (112 g, 45.6 mmol), 1H-imidazole (4.65 g, 68.4 mmol), and I2 (8.68 g, 34.2 mmol) were combined. The resultant mixture was stirred at 100° C. for 1 hour before cooling to room temperature, quenching with sat. aq. Na$_2$SO$_3$ and extracting twice with ethyl acetate. The combined organic extracts were washed with brine, dried over anhydrous Na$_2$SO$_4$, and purified by FCC (eluent:petroleum ether:ethyl acetate=1:0 to 5:1) to afford the title compound (6.24 g, 85% yield) as a white solid. MS (ESI): mass calcd. for $C_{11}H_{18}INO_2$ 323.0 m/z, found 267.9 [M-tBu+2H]$^+$.

Intermediate 51: 1-Bromo-3-cyclobutylbenzene

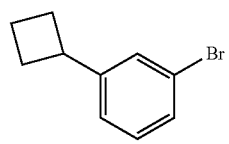 [SMILES: Brc1cccc(C2CCC2)c1]

Step A: 1-(3-Bromophenyl)cyclobutan-1-ol. n-BuLi (1.88 mL, 2.5 M in hexane, 4.71 mmol) was added drop-wise to a -70° C. solution of 1,3-dibromobenzene (1.11 g, 4.71 mmol) in dry THF (12 mL) under Na. The resultant mixture was stirred at -78° C. for 30 minutes and then treated with cyclobutanone (300 mg, 4.28 mmol). The reaction mixture was stirred at -78° C. for 2 hours before pouring it into sat. aq. NH$_4$Cl and extracting twice with ethyl acetate. The combined organic extracts were washed with brine, dried over anhydrous Na$_2$SO$_4$, concentrated, and purified by FCC (eluent:petroleum ether:ethyl acetate=1:0 to 9:1) to afford the title compound (811 mg, 83% yield) as a yellow oil. $^1$H NMR (400 MHz, CDCl$_3$) δ 7.70 (t, J=2.0 Hz, 1H), 7.50-7.44 (m, 2H), 7.31-7.28 (m, 1H), 2.63-2.54 (m, 2H), 2.45-2.36 (m, 2H), 2.14-2.03 (m, 2H), 1.84-1.70 (m, 1H).

Step B: 1-Bromo-3-cyclobutylbenzene. Boron trifluoride etherate (312 mg, 2.20 mmol) was added drop-wise to a -70° C. solution of 1-(3-bromophenyl)cyclobutanol (200 mg, 0.88 mmol) and triethylsilane (256 mg, 2.20 mmol) in dichloromethane (2 mL) under Na. The resultant mixture was stirred at -70° C. for 2 hours before pouring it into sat. NaHCO$_3$ and extracting twice with dichloromethane. The combined organic extracts were washed with brine, dried over anhydrous Na$_2$SO$_4$, concentrated, and purified by FCC (eluent:petroleum ether:ethyl acetate=1:0 to 30:1) to afford the title compound (160 mg, 86% yield) as a yellow oil. $^1$H NMR (400 MHz, CDCl$_3$) δ 7.36 (s, 1H), 7.30 (td, J=2.0, 7.2 Hz, 1H), 7.19-7.10 (m, 2H), 3.56-3.48 (m, 1H), 2.41-2.29 (m, 2H), 2.18-1.97 (m, 3H), 1.92-1.81 (m, 1H).

Intermediate 52: 7-Phenyl-2-azaspiro[3.5]nonane, trifluoroacetate salt

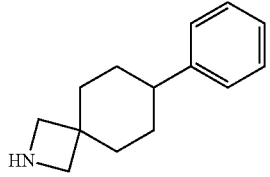 [SMILES: c1ccc(C2CCC3(CC2)CNC3)cc1]

The title compound was prepared in a manner analogous to 6-phenyl-2-azaspiro[3.3]heptane, trifluoroacetate salt (Intermediate 49), except using tert-butyl 7-oxo-2-azaspiro[3.5]nonane-2-carboxylate instead of tert-butyl 6-oxo-2-azaspiro[3.3]heptane-2-carboxylate in step A. MS (ESI): mass calcd. for $C_{14}H_{19}N$, 201.2; m/z found, 202.2 [M+H]$^+$.

Example 1: (2s,4s)-2-(2-Phenyl-7-azaspiro[3.5]nonane-7-carbonyl)-7-oxa-5-azaspiro[3.4]octan-6-one

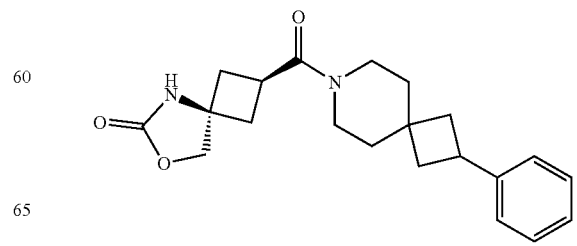

(2s,4s)-6-Oxo-7-oxa-5-azaspiro[3.4]octane-2-carboxylic acid (Intermediate 3, 20 mg, 0.117 mmol) and DIPEA (60 µL, 0.350 mmol) were dissolved in DMF (1 mL). HATU (69 mg, 0.175 mmol) and 2-phenyl-7-azaspiro[3.5]nonane (Intermediate 8, 28 mg, 0.140 mmol) were added and the reaction mixture was stirred at r.t. for 1 hour, then purified by reverse phase basic HPLC (Gilson, 0-100% MeCN/water, NH$_4$OH modifier) to obtain 24.8 mg (0.070 mmol, 60% yield) of the title compound. MS (ESI): mass calcd. for C$_{21}$H$_{26}$N$_2$O$_3$, 354.2; m/z found, 355.0 [M+H]$^+$. $^1$H NMR (500 MHz, Chloroform-d) δ 7.31 (dd, J=8.3, 6.9 Hz, 2H), 7.23-7.16 (m, 3H), 5.69 (s, 1H), 4.39-4.34 (m, 2H), 3.67-3.43 (m, 3H), 3.38-3.20 (m, 2H), 3.08-2.95 (m, 1H), 2.67-2.59 (m, 2H), 2.52-2.42 (m, 2H), 2.38-2.28 (m, 2H), 2.00-1.88 (m, 2H), 1.79-1.67 (m, 2H), 1.54-1.49 (m, 2H).

Example 2: (2s,4s)-2-(2-(3-(tert-Butyl)phenyl)-7-azaspiro[3.5]nonane-7-carbonyl)-7-oxa-5-azaspiro[3.4]octan-6-one

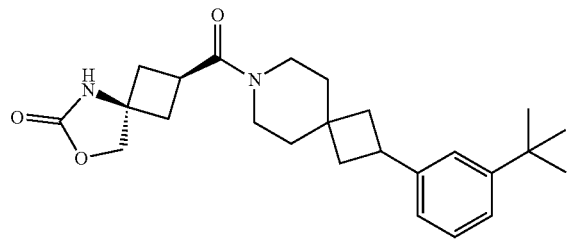 [SMILES: CC(C)(C)c1cccc(C2CC3(CCN(C(=O)[C@H]4C[C@]5(COC(=O)N5)C4)CC3)C2)c1]

A solution of tert-butyl 2-(3-(tert-butyl)phenyl)-7-azaspiro[3.5]nonane-7-carboxylate (Intermediate 9) in 4N HCl/dioxane (1 mL) was stirred for 30 minutes and concentrated. The residue was dissolved in DMF (1 mL), (2s,4s)-6-oxo-7-oxa-5-azaspiro[3.4]octane-2-carboxylic acid (Intermediate 3, 20 mg, 0.117 mmol), DIPEA (0.10 mL, 0.580 mmol), and HATU (69 mg, mmol) were added, and the reaction mixture was stirred for 1 hour then purified by reverse phase basic HPLC (Gilson, 0-100% MeCN/water, NH$_4$OH modifier) to obtain 17.1 mg (0.042 mmol, 36% yield) of the title compound. MS (ESI): mass calcd. for C$_{25}$H$_{34}$N$_2$O$_3$, 410.3; m/z found, 411.1 [M+H]$^+$. $^1$H NMR (400 MHz, Chloroform-d) δ 7.26 (s, 3H), 7.09-7.01 (m, 1H), 5.64 (s, 1H), 4.42-4.28 (m, 2H), 3.67-3.46 (m, 3H), 3.40-3.20 (m, 2H), 3.09-2.95 (m, 1H), 2.69-2.57 (m, 2H), 2.54-2.42 (m, 2H), 2.40-2.28 (m, 2H), 2.02-1.88 (m, 2H), 1.81-1.70 (m, 2H), 1.57-1.50 (m, 2H), 1.32 (s, 9H).

Example 3: (2s,4s)-2-(2-(p-Tolyl)-7-azaspiro[3.5]nonane-7-carbonyl)-7-oxa-5-azaspiro[3.4]octan-6-one

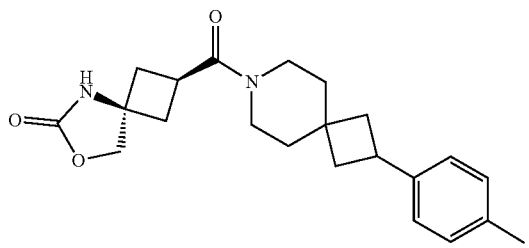 [SMILES: Cc1ccc(C2CC3(CCN(C(=O)[C@H]4C[C@]5(COC(=O)N5)C4)CC3)C2)cc1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(4-methylphenyl)-7-azaspiro[3.5]nonane-7-carboxylate (Intermediate 10) in place of tert-butyl 2-(3-(tert-butyl)phenyl)-7-azaspiro[3.5]nonane-7-carboxylate (Intermediate 9). MS (ESI): mass calcd. for C$_{22}$H$_{28}$N$_2$O$_3$, 368.2; m/z found, 369.0 [M+H]$^+$. $^1$H NMR (400 MHz, Chloroform-d) δ 7.16-7.08 (m, 4H), 5.65 (s, 1H), 4.42-4.33 (m, 2H), 3.69-3.58 (m, 1H), 3.57-3.40 (m, 2H), 3.38-3.30 (m, 1H), 3.27-3.19 (m, 1H), 3.12-2.91 (m, 1H), 2.72-2.58 (m, 2H), 2.54-2.40 (m, 2H), 2.36-2.24 (m, 4H), 1.98-1.85 (m, 2H), 1.77-1.61 (m, 2H), 1.60-1.46 (m, 3H).

Example 4: (2s,4s)-2-(2-(o-Tolyl)-7-azaspiro[3.5]nonane-7-carbonyl)-7-oxa-5-azaspiro[3.4]octan-6-one

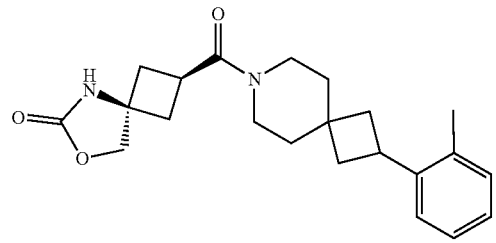 [SMILES: Cc1ccccc1C1CC2(CCN(C(=O)[C@H]3C[C@]4(COC(=O)N4)C3)CC2)C1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(2-methylphenyl)-7-azaspiro[3.5]nonane-7-carboxylate (Intermediate 11) in place of tert-butyl 2-(3-(tert-butyl)phenyl)-7-azaspiro[3.5]nonane-7-carboxylate (Intermediate 9). MS (ESI): mass calcd. for C$_{22}$H$_{28}$N$_2$O$_3$, 368.2; m/z found, 369.0 [M+H]$^+$. $^1$H NMR (400 MHz, Chloroform-d) δ 7.25-7.09 (m, 4H), 5.66 (s, 1H), 4.40-4.24 (m, 2H), 3.71-3.58 (m, 2H), 3.55-3.46 (m, 1H), 3.42-3.35 (m, 1H), 3.30-3.22 (m, 1H), 3.12-2.90 (m, 1H), 2.69-2.57 (m, 2H), 2.54-2.44 (m, 2H), 2.39-2.26 (m, 2H), 2.27-2.19 (m, 3H), 2.00-1.87 (m, 2H), 1.83-1.73 (m, 2H), 1.53-1.48 (m, 2H).

Example 5: (2s,4s)-2-[2-(3-Cyclopropylphenyl)-7-azaspiro[3.5]nonane-7-carbonyl)-7-oxa-5-azaspiro[3.4]octan-6-one

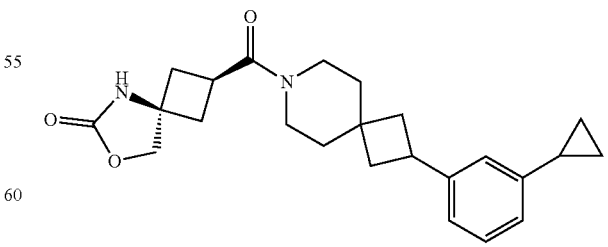

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(3-cyclopropylphenyl)-

7-azaspiro[3.5]nonane-7-carboxylate (Intermediate 12) in place of tert-butyl 2-(3-(tert-butyl)phenyl)-7-azaspiro[3.5]nonane-7-carboxylate (Intermediate 9). MS (ESI): mass calcd. for $C_{24}H_{30}N_2O_3$, 394.2; m/z found, 395.1 [M+H]$^+$. $^1$H NMR (400 MHz, Chloroform-d) δ 7.20 (t, J=7.6 Hz, 1H), 7.02-6.94 (m, 1H), 6.94-6.81 (m, 2H), 5.80 (s, 1H), 4.40-4.35 (m, 2H), 3.66-3.58 (m, 1H), 3.59-3.42 (m, 2H), 3.39-3.32 (m, 1H), 3.27-3.20 (m, 1H), 3.08-2.87 (m, 1H), 2.69-2.58 (m, 2H), 2.53-2.41 (m, 2H), 2.37-2.19 (m, 2H), 1.99-1.84 (m, 3H), 1.79-1.68 (m, 2H), 1.58-1.48 (m, 2H), 0.98-0.90 (m, 2H), 0.74-0.64 (m, 2H).

Example 6: (2s,4s)-2-[2-(3-Isopropylphenyl)-7-azaspiro[3.5]nonane-7-carbonyl)-7-oxa-5-azaspiro[3.4]octan-6-one

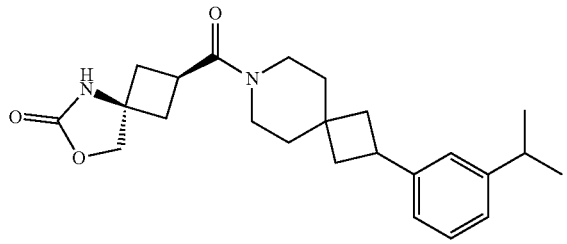 [SMILES: CC(C)c1cccc(C2CC3(CCN(C(=O)[C@H]4C[C@]5(COC(=O)N5)C4)CC3)C2)c1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(3-isopropylphenyl)-7-azaspiro[3.5]nonane-7-carboxylate (Intermediate 13) in place of tert-butyl 2-(3-(tert-butyl)phenyl)-7-azaspiro[3.5]nonane-7-carboxylate (Intermediate 9). MS (ESI): mass calcd. for $C_{24}H_{32}N_2O_3$, 396.2; m/z found, 397.0 [M+H]$^+$. $^1$H NMR (400 MHz, Chloroform-d) δ 7.26-7.20 (m, 1H), 7.11-6.98 (m, 3H), 5.70 (s, 1H), 4.37 (d, J=6.4 Hz, 2H), 3.66-3.61 (m, 1H), 3.58-3.45 (m, 2H), 3.40-3.33 (m, 1H), 3.26-3.20 (m, 1H), 3.11-2.96 (m, 1H), 2.94-2.83 (m, 1H), 2.70-2.60 (m, 2H), 2.54-2.41 (m, 2H), 2.38-2.25 (m, 2H), 2.02-1.86 (m, 2H), 1.79-1.68 (m, 2H), 1.55-1.49 (m, 2H), 1.25 (d, J=6.9 Hz, 6H).

Example 7: (2s,4s)-2-[2-(m-Tolyl)-7-azaspiro[3.5]nonane-7-carbonyl)-7-oxa-5-azaspiro[3.4]octan-6-one

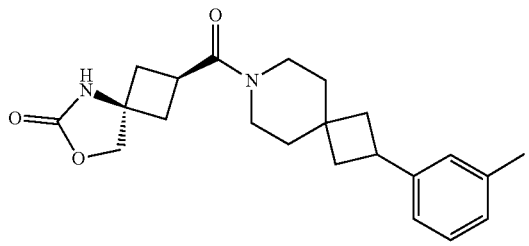 [SMILES: Cc1cccc(C2CC3(CCN(C(=O)[C@H]4C[C@]5(COC(=O)N5)C4)CC3)C2)c1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(3-methylphenyl)-7-azaspiro[3.5]nonane-7-carboxylate (Intermediate 14) in place of tert-butyl 2-(3-(tert-butyl)phenyl)-7-azaspiro[3.5]nonane-7-carboxylate (Intermediate 9). MS (ESI): mass calcd. for $C_{22}H_{28}N_2O_3$, 368.2; m/z found, 369.2 [M+H]$^+$. $^1$H NMR (400 MHz, Chloroform-d) δ 7.12 (t, J=7.9 Hz, 1H), 6.92 (d, J=5.7 Hz, 3H), 5.69 (s, 1H), 4.34-4.25 (m, 2H), 3.61-3.50 (m, 1H), 3.48-3.37 (m, 2H), 3.33-3.26 (m, 1H), 3.20-3.08 (m, 1H), 3.02-2.84 (m, 1H), 2.63-2.51 (m, 2H), 2.45-2.34 (m, 2H), 2.29-2.14 (m, 5H), 1.85 (q, J=11.4 Hz, 2H), 1.69-1.61 (m, 2H), 1.49-1.39 (m, 2H).

Example 8: (2s,4s)-2-[2-(3-Methoxyphenyl)-7-azaspiro[3.5]nonane-7-carbonyl)-7-oxa-5-azaspiro[3.4]octan-6-one

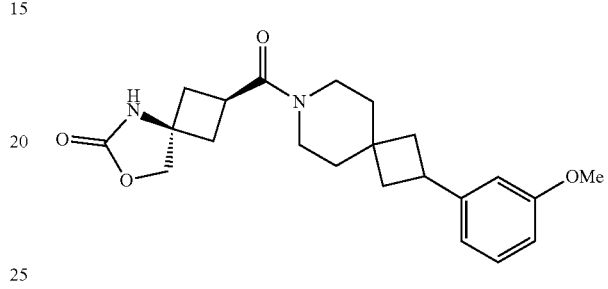

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(3-methoxyphenyl)-7-azaspiro[3.5]nonane-7-carboxylate (Intermediate 15) in place of tert-butyl 2-(3-(tert-butyl)phenyl)-7-azaspiro[3.5]nonane-7-carboxylate (Intermediate 9). MS (ESI): mass calcd. for $C_{22}H_{28}N_2O_4$, 384.2; m/z found, 385.2 [M+H]$^+$. $^1$H NMR (400 MHz, Chloroform-d) δ 7.15 (dd, J=9.2, 7.7 Hz, 1H), 6.75-6.70 (m, 1H), 6.68-6.62 (m, 2H), 5.60 (s, 1H), 4.29 (s, 2H), 3.73 (s, 3H), 3.63-3.05 (m, 5H), 3.01-2.81 (m, 1H), 2.62-2.50 (m, 2H), 2.44-2.33 (m, 2H), 2.23 (t, J=10.2 Hz, 2H), 1.85 (t, J=10.2 Hz, 2H), 1.69-1.59 (m, 2H), 1.47-1.41 (m, 2H).

Example 9: (2s,4s)-2-[2-[3-(Trifluoromethoxy)phenyl]-7-azaspiro[3.5]nonane-7-carbonyl)-7-oxa-5-azaspiro[3.4]octan-6-one

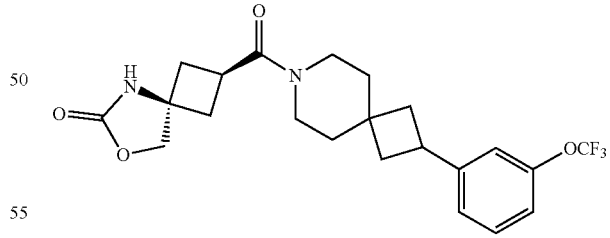

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(3-(trifluoromethoxy)phenyl)-7-azaspiro[3.5]nonane-7-carboxylate (Intermediate 16) in place of tert-butyl 2-(3-(tert-butyl)phenyl)-7-azaspiro[3.5]nonane-7-carboxylate (Intermediate 9). MS (ESI): mass calcd. for $C_{22}H_{25}F_3N_2O_4$, 438.2; m/z found, 439.2 [M+H]$^+$. $^1$H NMR (400 MHz, Chloroform-d) δ 7.41-7.31 (m, 1H), 7.17-7.11 (m, 1H), 7.10-6.99 (m, 2H), 5.81 (s, 1H), 4.42-

4.36 (m, 2H), 3.69-3.49 (m, 3H), 3.42-3.36 (m, 1H), 3.30-3.23 (m, 1H), 3.12-2.95 (m, 1H), 2.74-2.62 (m, 2H), 2.55-2.45 (m, 2H), 2.42-2.26 (m, 2H), 2.03-1.91 (m, 2H), 1.81-1.68 (m, 2H), 1.58-1.50 (m, 2H).

Example 10: (2s,4s)-2-[2-(2,3-Dimethylphenyl)-7-azaspiro[3.5]nonane-7-carbonyl)-7-oxa-5-azaspiro[3.4]octan-6-one

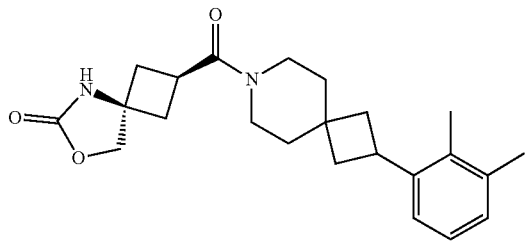 [SMILES: Cc1cccc(C2CC3(CCN(C(=O)[C@H]4C[C@]5(COC(=O)N5)C4)CC3)C2)c1C]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(2,3-dimethylphenyl)-7-azaspiro[3.5]nonane-7-carboxylate (Intermediate 17) in place of tert-butyl 2-(3-(tert-butyl)phenyl)-7-azaspiro[3.5]nonane-7-carboxylate (Intermediate 9). MS (ESI): mass calcd. for $C_{23}H_{30}N_2O_3$, 382.2; m/z found, 383.2 [M+H]$^+$. $^1$H NMR (400 MHz, Chloroform-d) δ 7.05-6.92 (m, 3H), 5.62 (s, 1H), 4.29 (d, J=8.3 Hz, 2H), 3.69-3.51 (m, 2H), 3.50-3.23 (m, 2H), 3.21-3.07 (m, 1H), 3.03-2.86 (m, 1H), 2.64-2.51 (m, 2H), 2.47-2.34 (m, 2H), 2.30-2.22 (m, 2H), 2.20 (s, 3H), 2.05 (s, 3H), 1.93-1.81 (m, 2H), 1.74-1.63 (m, 2H), 1.46-1.38 (m, 2H).

Example 11: (2r,4s)-2-(2-(3-(tert-Butyl)phenyl)-7-azaspiro[3.5]nonane-7-carbonyl)-5azaspiro[3.4]octan-6-one

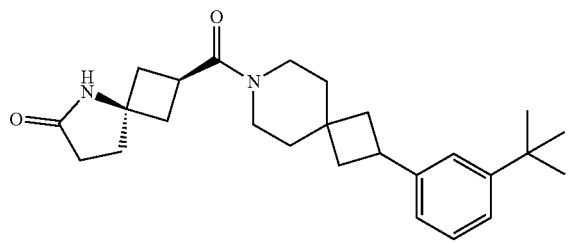 [SMILES: CC(C)(C)c1cccc(C2CC3(CCN(C(=O)[C@H]4C[C@]5(CCC(=O)N5)C4)CC3)C2)c1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{26}H_{36}N_2O_2$, 408.3; m/z found, 409.3 [M+H]$^+$. $^1$H NMR (400 MHz, Chloroform-d) δ 7.18 (s, 2H), 6.96 (d, J=7.0 Hz, 1H), 5.76 (s, 1H), 3.56-3.51 (m, 1H), 3.51-3.35 (m, 2H), 3.35-3.26 (m, 1H), 3.21-3.12 (m, 1H), 3.02-2.85 (m, 1H), 2.53-2.40 (m, 2H), 2.34-2.21 (m, 5H), 2.15 (q, J=7.6 Hz, 2H), 1.86 (q, J=11.3 Hz, 2H), 1.65 (q, J=6.7, 5.9 Hz, 2H), 1.47 (s, 4H), 1.24 (s, 9H).

Example 12: (2s,4s)-2-[2-(2,4-Dimethylphenyl)-7-azaspiro[3.5]nonane-7-carbonyl)-7-oxa-5-azaspiro[3.4]octan-6-one

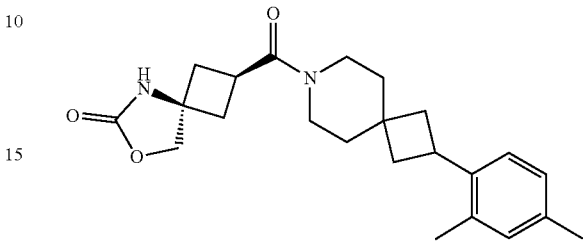

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(2,4-dimethylphenyl)-7-azaspiro[3.5]nonane-7-carboxylate (Intermediate 18) in place of tert-butyl 2-(3-(tert-butyl)phenyl)-7-azaspiro[3.5]nonane-7-carboxylate (Intermediate 9). MS (ESI): mass calcd. for $C_{23}H_{30}N_2O_3$, 382.2; m/z found, 383.2 [M+H]$^+$. $^1$H NMR (400 MHz, Chloroform-d) δ 7.10-6.79 (m, 3H), 5.60 (s, 1H), 4.38-4.20 (m, 2H), 3.63-3.11 (m, 6H), 3.02-2.86 (m, 1H), 2.63-2.51 (m, 2H), 2.47-2.33 (m, 2H), 2.26-2.16 (m, 4H), 2.12 (s, 3H), 1.95-1.78 (m, 2H), 1.73-1.54 (m, 2H), 1.45-1.37 (m, 2H).

Example 13: (2s,4s)-2-[2-(2-(Tert-butyl)pyridin-4-yl)-7-azaspiro[3.5]nonane-7-carbonyl)-7-oxa-5-azaspiro[3.4]octan-6-one

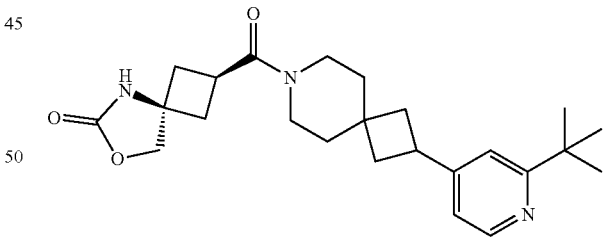

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(2-(tert-butyl)pyridin-4-yl)-7-azaspiro[3.5]nonane-7-carboxylate (Intermediate 19) in place of tert-butyl 2-(3-(tert-butyl)phenyl)-7-azaspiro[3.5]nonane-7-carboxylate (Intermediate 9). MS (ESI): mass calcd. for $C_{24}H_{33}N_3O_3$, 411.3; m/z found, 412.3 [M+H]$^+$. $^1$H NMR (400 MHz, Chloroform-d) δ 8.71 (s, 1H), 7.44-7.31 (m, 2H), 5.74 (s, 1H), 4.42-4.20 (m, 2H), 3.75-3.12 (m, 5H), 3.05-2.83 (m, 1H), 2.61-2.48 (m, 2H), 2.46-2.26 (m, 4H), 2.09-1.80 (m, 2H), 1.75-1.64 (m, 2H), 1.64-1.40 (m, 11H).

Example 14: (2r,4s)-2-(2-(5-(tert-Butyl)-2-methylphenyl)-7-azaspiro[3.5]nonane-7-carbonyl)-5-azaspiro[3.4]octan-6-one

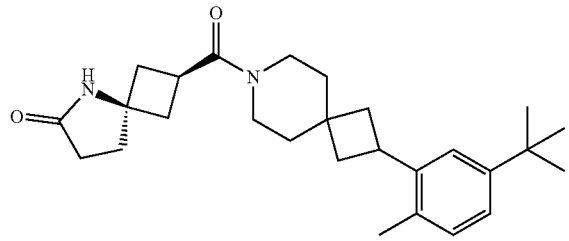 [SMILES: Cc1ccc(C(C)(C)C)cc1C1CC2(CCN(C(=O)[C@H]3C[C@]4(CCC(=O)N4)C3)CC2)C1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(5-(tert-butyl)-2-methylphenyl)-7-azaspiro[3.5]nonane-7-carboxylate (Intermediate 20) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{27}H_{38}N_2O_2$, 422.3; m/z found, 423.3 [M+H]$^+$. $^1$H NMR (500 MHz, Chloroform-d) δ 7.27-7.22 (m, 1H), 7.17 (dd, J=7.9, 2.1 Hz, 1H), 7.08 (d, J=7.9 Hz, 1H), 6.15 (s, 1H), 3.65 (s, 2H), 3.51 (s, 1H), 3.41 (s, 1H), 3.28 (s, 1H), 3.12-2.94 (m, 1H), 2.62-2.49 (m, 2H), 2.43-2.32 (m, 8H), 2.32-2.18 (m, 5H), 1.98 (s, 2H), 1.63-1.50 (m, 2H), 1.35 (s, 9H).

Example 15: 2-[2-[3-(Trifluoromethyl)phenyl]-7-azaspiro[3.5]nonane-7-carbonyl)-5-azaspiro[3.4]octan-6-one

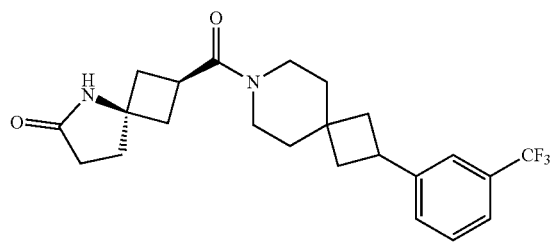

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(3-(trifluoromethyl)phenyl)-7-azaspiro[3.5]nonane-7-carboxylate (Intermediate 21) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{23}H_{27}F_3N_2O_2$, 420.2; m/z found, 421.2 [M+H]$^+$. $^1$H NMR (500 MHz, Chloroform-d) δ 7.41-7.26 (m, 4H), 6.01 (s, 1H), 3.56 (d, J=19.6 Hz, 2H), 3.42 (d, J=5.9 Hz, 1H), 3.31 (s, 1H), 3.19 (s, 1H), 2.97 (d, J=16.1 Hz, 1H), 2.52-2.42 (m, 2H), 2.31 (dd, J=11.3, 4.4 Hz, 6H), 2.16 (t, J=7.8 Hz, 2H), 1.87 (d, J=9.9 Hz, 2H), 1.67 (s, 2H), 1.51-1.46 (m, 2H).

Example 16: (2r,4s)-2-(2-(6-(tert-Butyl)pyridin-2-yl)-7-azaspiro[3.5]nonane-7-carbonyl)-5-azaspiro[3.4]octan-6-one

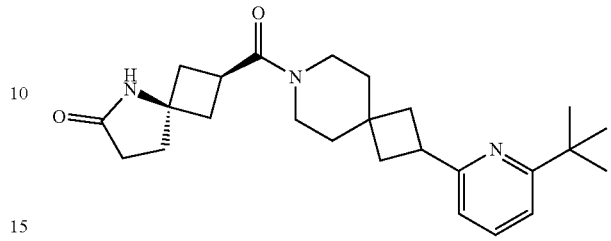

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(6-(tert-butyl)-pyridin-2-yl)-7-azaspiro[3.5]nonane-7-carboxylate (Intermediate 23) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{25}H_{35}N_3O_2$, 409.3; m/z found, 410.3 [M+H]$^+$. $^1$H NMR (500 MHz, Chloroform-d) δ 7.55-7.45 (m, 1H), 7.14 (d, J=7.8 Hz, 1H), 6.89 (t, J=6.6 Hz, 1H), 5.97 (s, 1H), 3.67-3.50 (m, 3H), 3.41-3.35 (m, 1H), 3.31-3.25 (m, 1H), 3.04 (dp, J=11.2, 8.5 Hz, 1H), 2.60-2.49 (m, 2H), 2.43-2.34 (m, 4H), 2.29-2.19 (m, 6H), 1.73 (t, J=5.8 Hz, 2H), 1.64 (d, J=4.2 Hz, 2H), 1.39 (d, J=1.9 Hz, 9H).

Example 17: (2r,4s)-2-[2-[4-[1-(Trifluoromethyl)cyclopropyl]phenyl]-7-azaspiro[3.5]nonane-7-carbonyl)-5-azaspiro[3.4]octan-6-one

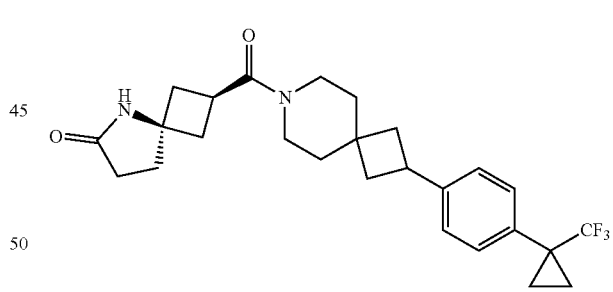

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(4-(1-(trifluoromethyl)cyclopropyl)phenyl)-7-azaspiro[3.5]nonane-7-carboxylate (Intermediate 24) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{26}H_{31}F_3N_2O_2$, 460.2; m/z found, 461.2 [M+H]$^+$. $^1$H NMR (400 MHz, Chloroform-d) δ 7.31 (d, J=8.1 Hz, 2H), 7.09 (d, J=8.1 Hz, 2H), 5.84 (s, 1H), 3.66-2.84 (m, 7H), 2.44 (dd, J=11.8, 9.3 Hz, 2H), 2.35-2.19

(m, 5H), 2.15 (t, J=7.8 Hz, 2H), 1.85 (s, 2H), 1.64 (s, 2H), 1.44 (s, 2H), 1.29-1.14 (m, 2H), 0.98-0.87 (m, 2H).

Example 18: (2r,4s)-2-[2-[3-Chloro-4-(trifluoromethyl)phenyl]-7-azaspiro[3.5]nonane-7-carbonyl]-5-azaspiro[3.4]octan-6-one

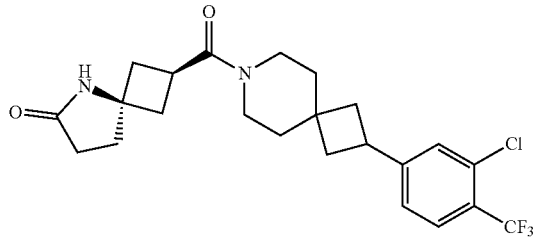 [SMILES: O=C1CC[C@]2(C[C@H](C(=O)N3CCC4(CC3)CC(c3ccc(C(F)(F)F)c(Cl)c3)C4)C2)N1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(3-chloro-4-(trifluoromethyl)phenyl)-7-azaspiro[3.5]nonane-7-carboxylate (Intermediate 25) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{23}H_{26}ClF_3N_2O_2$, 454.2; m/z found, 455.1 [M+H]$^+$. $^1$H NMR (400 MHz, Chloroform-d) δ 7.63 (d, J=8.2 Hz, 1H), 7.37-7.32 (m, 1H), 7.18 (d, J=8.1 Hz, 1H), 5.90 (s, 1H), 3.68-3.48 (m, 3H), 3.40 (d, J=6.1 Hz, 1H), 3.28 (t, J=5.7 Hz, 1H), 3.13-2.95 (m, 1H), 2.55 (t, J=8.6 Hz, 2H), 2.39 (t, J=8.4 Hz, 6H), 2.25 (q, J=7.0 Hz, 2H), 1.95 (q, J=11.2 Hz, 2H), 1.76 (d, J=5.7 Hz, 2H), 1.55 (d, J=4.9 Hz, 2H).

Example 19: (2r,4s)-2-[2-(2,5-Dimethylphenyl)-7-azaspiro[3.5]nonane-7-carbonyl)-5-azaspiro[3.4]octan-6-one

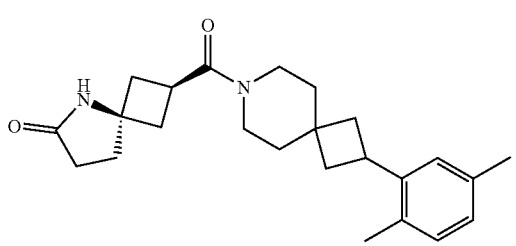 [SMILES: Cc1ccc(C)c(C2CC3(CCN(C(=O)[C@H]4C[C@]5(CCC(=O)N5)C4)CC3)C2)c1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(2,5-dimethylphenyl)-7-azaspiro[3.5]nonane-7-carboxylate (Intermediate 22) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{24}H_{32}N_2O_2$, 380.2; m/z found, 381.2 [M+H]$^+$. $^1$H NMR (400 MHz, Chloroform-d) δ 7.04 (d, J=6.9 Hz, 2H), 6.95 (d, J=8.1 Hz, 1H), 5.89 (s, 1H), 3.64 (d, J=8.8 Hz, 2H), 3.52 (s, 1H), 3.40 (s, 1H), 3.27 (s, 1H), 3.04 (s, 1H), 2.55 (t, J=10.3 Hz, 2H), 2.48-2.17 (m, 14H), 1.96 (s, 2H), 1.78 (s, 2H), 1.54 (s, 2H).

Example 20: (2r,4s)-2-[2-[4-Methoxy-3-(trifluoromethyl)phenyl]-7-azaspiro[3.5]nonane-7-carbonyl)-5-azaspiro[3.4]octan-6-one

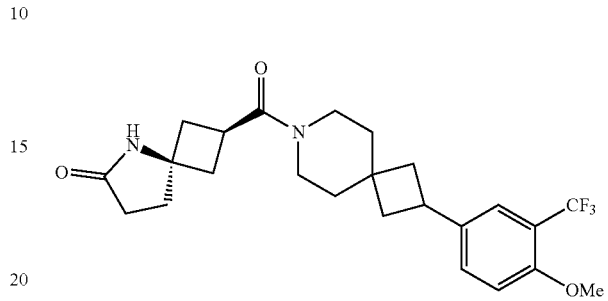

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(4-methoxy-3-(trifluoromethyl)phenyl)-7-azaspiro[3.5]nonane-7-carboxylate (Intermediate 26) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{24}H_{29}F_3N_2O_3$, 450.2; m/z found, 451.1 [M+H]$^+$. $^1$H NMR (400 MHz, Chloroform-d) δ 7.40 (s, 1H), 7.33 (t, J=7.8 Hz, 1H), 6.97 (d, J=8.5 Hz, 1H), 5.88 (s, 1H), 3.91 (s, 3H), 3.63 (t, J=5.7 Hz, 1H), 3.56-3.49 (m, 2H), 3.39 (t, J=5.6 Hz, 1H), 3.27 (t, J=5.7 Hz, 1H), 3.04 (dt, J=12.6, 8.5 Hz, 1H), 2.64-2.48 (m, 2H), 2.46-2.30 (m, 6H), 2.30-2.23 (m, 2H), 1.91 (q, J=11.5 Hz, 2H), 1.75 (q, J=6.3 Hz, 2H), 1.59 (s, 2H).

Example 21: (2s,4s)-2-(2-(4-(tert-Butyl)pyridin-2-yl)-7-azaspiro[3.5]nonane-7-carbonyl)-7-oxa-5-azaspiro[3.4]octan-6-one

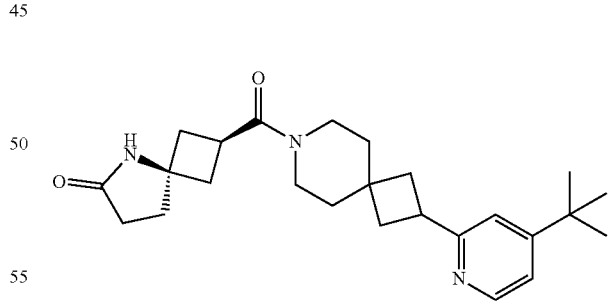

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(4-(tert-butyl)pyridin-2-yl)-7-azaspiro[3.5]nonane-7-carboxylate (Intermediate 27) in place of tert-butyl 2-(3-(tert-butyl)phenyl)-7-azaspiro[3.5]nonane-7-carboxylate (Intermediate 9). MS (ESI): mass calcd. for $C_{24}H_{33}N_3O_3$, 411.3; m/z found, 412.3 [M+H]$^+$. $^1$H NMR (400 MHz, Chloroform-d) δ 8.47-8.35 (m, 1H), 7.18 (s, 2H), 5.57 (s, 1H), 4.34-4.26 (m, 2H), 3.62-3.52 (m, 1H), 3.48-3.39 (m, 1H), 3.33-3.26 (m, 1H), 3.22-3.11 (m, 1H), 3.03-2.88 (m, 1H), 2.62-2.51 (m, 2H), 2.47-2.34 (m, 2H), 2.32-2.07 (m, 3H), 1.76-1.64 (m, 2H), 1.62-1.36 (m, 4H), 1.26-1.23 (m, 9H).

Example 22: (2r,4s)-2-(2-(5-(tert-Butyl)-2-fluorophenyl)-7-azaspiro[3.5]nonane-7-carbonyl)-5-azaspiro[3.4]octan-6-one

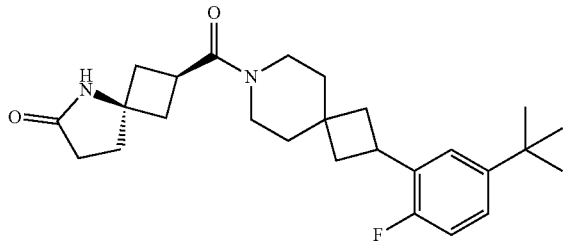 [SMILES: CC(C)(C)c1ccc(F)c(C2CC3(CCN(C(=O)[C@H]4C[C@]5(CCC(=O)N5)C4)CC3)C2)c1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(5-(tert-butyl)-2-fluorophenyl)-7-azaspiro[3.5]nonane-7-carboxylate (Intermediate 28) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{26}H_{35}FN_2O_2$, 426.3; m/z found, 427.3 [M+H]$^+$. $^1$H NMR (400 MHz, Chloroform-d) δ 7.10 (dd, J=9.1, 6.1 Hz, 2H), 6.83 (t, J=9.5 Hz, 1H), 5.78 (s, 1H), 3.64-3.50 (m, 2H), 3.45-3.38 (m, 1H), 3.29 (t, J=5.6 Hz, 1H), 3.17 (t, J=5.7 Hz, 1H), 2.94 (dt, J=15.8, 8.2 Hz, 1H), 2.45 (td, J=11.2, 9.7, 4.4 Hz, 2H), 2.35-2.19 (m, 6H), 2.15 (q, J=7.7 Hz, 2H), 2.01-1.87 (m, 2H), 1.67 (q, J=6.3 Hz, 2H), 1.48 (s, 2H), 1.23 (s, 9H).

Example 23: (2r,4s)-2-(2-(5-(tert-Butyl)-2-ethoxyphenyl)-7-azaspiro[3.5]nonane-7-carbonyl)-5-azaspiro[3.4]octan-6-one

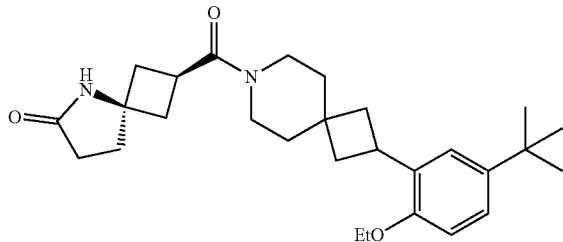 [SMILES: CCOc1ccc(C(C)(C)C)cc1C1CC2(CCN(C(=O)[C@H]3C[C@]4(CCC(=O)N4)C3)CC2)C1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(5-(tert-butyl)-2-ethoxyphenyl)-7-azaspiro[3.5]nonane-7-carboxylate (Intermediate 29) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{28}H_{40}N_2O_3$, 452.3; m/z found, 453.3 [M+H]$^+$. $^1$H NMR (400 MHz, Chloroform-d) δ 7.13-7.05 (m, 2H), 6.66 (d, J=9.1 Hz, 1H), 5.82 (s, 1H), 3.92 (q, J=6.9 Hz, 2H), 3.72-3.08 (m, 6H), 3.04-2.83 (m, 1H), 2.45 (dd, J=11.8, 9.5 Hz, 2H), 2.29 (t, J=7.7 Hz, 3H), 2.25-2.10 (m, 4H), 1.88 (t, J=10.6 Hz, 2H), 1.67 (t, J=5.7 Hz, 2H), 1.43 (t, J=5.7 Hz, 2H), 1.31 (t, J=7.0 Hz, 3H), 1.23 (s, 9H).

Example 24: (2r,4s)-2-[2-(o-Tolyl)-7-azaspiro[3.5]nonane-7-carbonyl]-5-azaspiro[3.4]octan-6-one

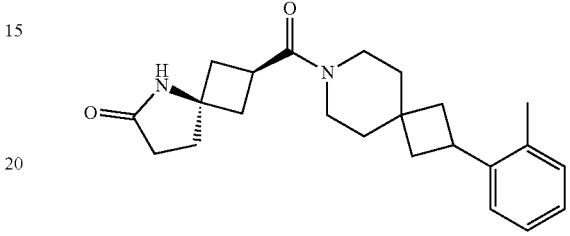

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(2-methylphenyl)-7-azaspiro[3.5]nonane-7-carboxylate (Intermediate 11) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{23}H_{30}N_2O_2$, 366.2; m/z found, 367.2 [M+H]$^+$. $^1$H NMR (400 MHz, Chloroform-d) δ 7.16-7.08 (m, 2H), 7.07-6.99 (m, 2H), 5.87 (s, 1H), 3.62-3.46 (m, 2H), 3.45-3.37 (m, 1H), 3.31-3.28 (m, 1H), 3.21-3.12 (m, 1H), 3.01-2.85 (m, 1H), 2.50-2.39 (m, 2H), 2.35-2.19 (m, 6H), 2.15 (s, 5H), 1.94-1.80 (m, 2H), 1.73-1.63 (m, 2H), 1.47-1.41 (m, 2H).

Example 25: (2r,4s)-2-[2-(3-Isopropylphenyl)-7-azaspiro[3.5]nonane-7-carbonyl)-5-azaspiro[3.4]octan-6-one

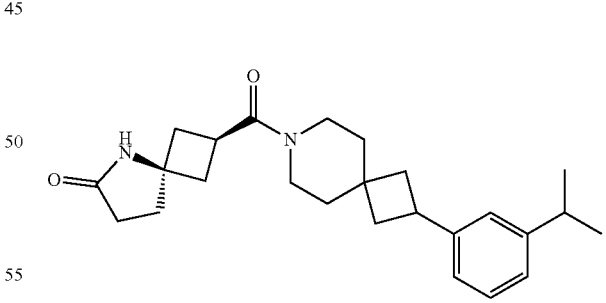

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(3-isopropylphenyl)-7-azaspiro[3.5]nonane-7-carboxylate (Intermediate 13) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{25}H_{34}N_2O_2$, 394.3; m/z found, 395.3 [M+H]$^+$. $^1$H NMR (400 MHz, Chloroform-d) δ 7.18-7.11 (m, 1H), 7.02-6.91 (m, 3H), 5.82 (s, 1H), 3.58-3.35 (m, 3H), 3.29 (s, 1H), 3.17 (s, 1H), 3.01-2.87 (m, 1H), 2.81 (p, J=6.9 Hz, 1H), 2.45 (t, J=10.3 Hz, 2H), 2.34-2.19 (m, 6H), 2.15 (d, J=6.7 Hz, 2H), 1.86 (d, J=10.4 Hz, 2H), 1.65 (s, 2H), 1.46 (s, 2H), 1.17 (d, J=6.9 Hz, 6H).

Example 26: (2r,4s)-2-[2-(2,3-Dimethylphenyl)-7-azaspiro[3.5]nonane-7-carbonyl)-5-azaspiro[3.4]octan-6-one

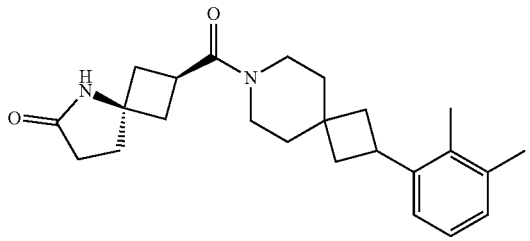 [SMILES: Cc1cccc(C2CC3(CCN(C(=O)[C@H]4C[C@]5(CCC(=O)N5)C4)CC3)C2)c1C]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(2,3-dimethylphenyl)-7-azaspiro[3.5]nonane-7-carboxylate (Intermediate 17) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{24}H_{32}N_2O_2$, 380.2; m/z found, 381.3 [M+H]$^+$. $^1$H NMR (400 MHz, Chloroform-d) δ 7.05-6.97 (m, 2H), 6.94 (dd, J=6.4, 2.6 Hz, 1H), 5.85 (s, 1H), 3.69-3.47 (m, 2H), 3.35 (d, J=36.7 Hz, 2H), 3.16 (s, 1H), 2.93 (s, 1H), 2.45 (dd, J=11.8, 9.1 Hz, 2H), 2.36-2.10 (m, 11H), 2.05 (s, 3H), 1.87 (d, J=10.7 Hz, 2H), 1.68 (d, J=6.4 Hz, 2H), 1.41 (t, J=5.7 Hz, 2H).

Example 27: (2r,4s)-2-(2-(5-(tert-Butyl)-2-methoxyphenyl)-7-azaspiro[3.5]nonane-7-carbonyl)-5-azaspiro[3.4]octan-6-one

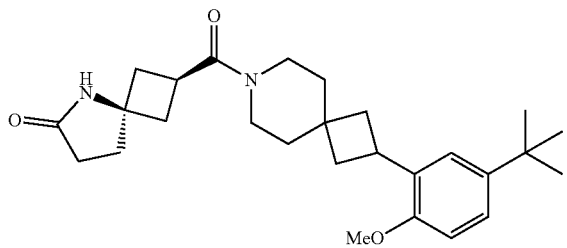 [SMILES: COc1ccc(C(C)(C)C)cc1C1CC2(CCN(C(=O)[C@H]3C[C@]4(CCC(=O)N4)C3)CC2)C1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(5-(tert-butyl)-2-methoxyphenyl)-7-azaspiro[3.5]nonane-7-carboxylate (Intermediate 30) in place of tert-butyl 2-(3-(tert-butyl)phenyl)-7-azaspiro[3.5]nonane-7-carboxylate (Intermediate 9) and (2r,4s)-6-oxo-5-azaspiro[3.4]octane-2-carboxylic acid (Intermediate 4) in place of (2s,4s)-6-oxo-7-oxa-5-azaspiro[3.4]octane-2-carboxylic acid (Intermediate 3). MS (ESI): mass calcd. for $C_{27}H_{38}N_2O_3$, 438.3; m/z found, 439.3 [M+H]$^+$. $^1$H NMR (400 MHz, Chloroform-d) δ 7.14-7.05 (m, 2H), 6.68 (d, J=8.9 Hz, 1H), 5.86 (s, 1H), 3.71 (s, 3H), 3.58 (q, J=9.1 Hz, 1H), 3.41 (s, 6H), 3.01-2.87 (m, 1H), 2.52-2.40 (m, 2H), 2.35-2.24 (m, 3H), 2.24-2.05 (m, 3H), 1.86 (t, J=10.7 Hz, 2H), 1.67 (t, J=5.7 Hz, 2H), 1.43 (t, J=5.7 Hz, 2H), 1.23 (s, 9H).

Example 28: (2s,4s)-2-(2-(2,2-Difluorobenzo[d][1,3]dioxol-5-yl)-7-azaspiro[3.5]nonane-7-carbonyl)-7-oxa-5-azaspiro[3.4]octan-6-one

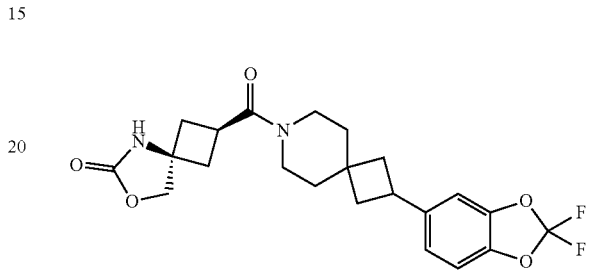

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(2,2-difluorobenzo[d][1,3]dioxol-5-yl)-7-azaspiro[3.5]nonane-7-carboxylate (Intermediate 31) in place of tert-butyl 2-(3-(tert-butyl)phenyl)-7-azaspiro[3.5]nonane-7-carboxylate (Intermediate 9). MS (ESI): mass calcd. for $C_{22}H_{24}F_2N_2O_5$, 434.2; m/z found, 435.1 [M+H]$^+$. $^1$H NMR (400 MHz, Chloroform-d) δ 6.89 (d, J=8.2 Hz, 1H), 6.82 (d, J=1.7 Hz, 1H), 6.81-6.74 (m, 1H), 5.76 (s, 1H), 4.33-4.23 (m, 2H), 3.57-3.51 (m, 1H), 3.48-3.35 (m, 2H), 3.33-3.22 (m, 1H), 3.20-3.10 (m, 1H), 3.01-2.83 (m, 1H), 2.63-2.50 (m, 2H), 2.46-2.33 (m, 2H), 2.30-2.13 (m, 2H), 1.87-1.73 (m, 2H), 1.70-1.60 (m, 2H), 1.50-1.40 (m, 2H).

Example 29: (2s,4s)-2-[2-(2-Methoxyphenyl)-7-azaspiro[3.5]nonane-7-carbonyl)-7-oxa-5-azaspiro[3.4]octan-6-one

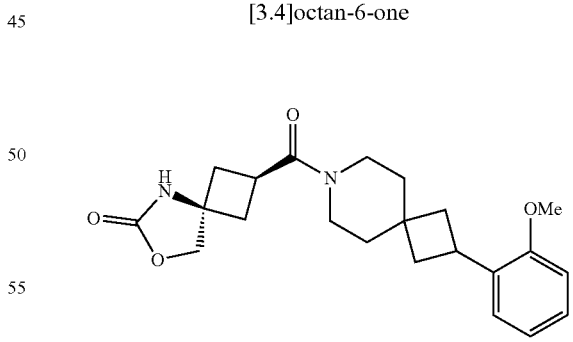

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(2-methoxyphenyl)-7-azaspiro[3.5]nonane-7-carboxylate (Intermediate 32) in place of tert-butyl 2-(3-(tert-butyl)phenyl)-7-azaspiro[3.5]nonane-7-carboxylate (Intermediate 9). MS (ESI): mass calcd. for $C_{22}H_{28}N_2O_4$, 384.2; m/z found, 385.2 [M+H]$^+$. $^1$H NMR (400 MHz, Chloroform-d) δ 7.10 (d, J=7.6 Hz, 2H), 6.86 (t, J=7.3 Hz, 1H), 6.75 (d, J=7.9 Hz, 1H), 5.58 (s, 1H), 4.29 (s, 2H), 3.73 (s, 3H), 3.61 (dd, J=17.8, 8.6 Hz, 1H), 3.35 (q, J=58.6, 56.0 Hz, 4H), 2.93 (s, 1H), 2.61-2.48 (m, 2H), 2.44-2.33 (m, 2H), 2.20 (t, J=10.2 Hz, 2H), 1.83 (t, J=Hz, 2H), 1.67 (s, 2H), 1.43 (t, J=5.8 Hz, 2H).

Example 30: (2s,4s)-2-[2-(4-Methoxyphenyl)-7-azaspiro[3.5]nonane-7-carbonyl)-7-oxa-5-azaspiro[3.4]octan-6-one

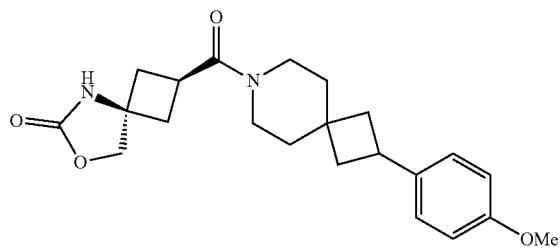 [SMILES: COc1ccc(C2CC3(CCN(C(=O)[C@H]4C[C@]5(COC(=O)N5)C4)CC3)C2)cc1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(4-methoxyphenyl)-7-azaspiro[3.5]nonane-7-carboxylate (Intermediate 11) in place of tert-butyl 2-(3-(tert-butyl)phenyl)-7-azaspiro[3.5]nonane-7-carboxylate (Intermediate 9). MS (ESI): mass calcd. for $C_{22}H_{28}N_2O_4$, 384.2; m/z found, 385.1 [M+H]$^+$. $^1$H NMR (400 MHz, Chloroform-d) δ 7.07-6.95 (m, 2H), 6.81-6.69 (m, 2H), 5.67 (s, 1H), 4.29 (s, 2H), 3.71 (s, 3H), 3.53 (s, 1H), 3.40 (dd, J=11.0, 7.1 Hz, 2H), 3.27 (s, 1H), 3.16 (s, 1H), 2.92 (s, 1H), 2.60-2.50 (m, 2H), 2.46-2.35 (m, 2H), 2.21 (t, J=10.1 Hz, 2H), 1.82 (d, J=10.5 Hz, 2H), 1.64 (s, 2H), 1.45 (s, 2H).

Example 31: (2s,4s)-2-(2-(6-(tert-Butyl)pyridin-2-yl)-7-azaspiro[3.5]nonane-7-carbonyl)-7-oxa-5-azaspiro[3.4]octan-6-one

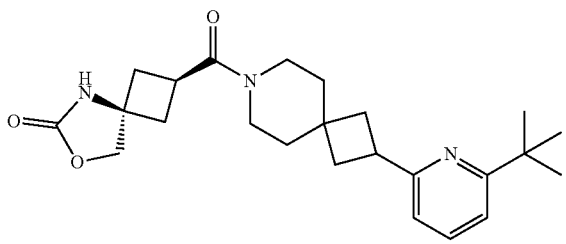 [SMILES: CC(C)(C)c1cccc(C2CC3(CCN(C(=O)[C@H]4C[C@]5(COC(=O)N5)C4)CC3)C2)n1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(6-(tert-butyl)pyridin-2-yl)-7-azaspiro[3.5]nonane-7-carboxylate (Intermediate 23) in place of tert-butyl 2-(3-(tert-butyl)phenyl)-7-azaspiro[3.5]nonane-7-carboxylate (Intermediate 9). MS (ESI): mass calcd. for $C_{24}H_{33}N_3O_3$, 411.3; m/z found, 412.3 [M+H]$^+$. $^1$H NMR (400 MHz, Chloroform-d) δ 7.44-7.33 (m, 1H), 7.10-6.95 (m, 1H), 6.85-6.69 (m, 1H), 5.66 (s, 1H), 4.38-4.07 (m, 2H), 3.61-3.36 (m, 3H), 3.32-3.22 (m, 1H), 3.22-3.12 (m, 1H), 3.02-2.87 (m, 1H), 2.62-2.50 (m, 2H), 2.47-2.34 (m, 2H), 2.22-2.09 (m, 4H), 1.69-1.53 (m, 4H), 1.29 (s, 9H).

Example 32: (2s,4s)-2-(2-(3-Fluoro-6-(trifluoromethyl)pyridin-2-yl)-7-azaspiro[3.5]nonane-7-carbonyl)-7-oxa-5-azaspiro[3.4]octan-6-one

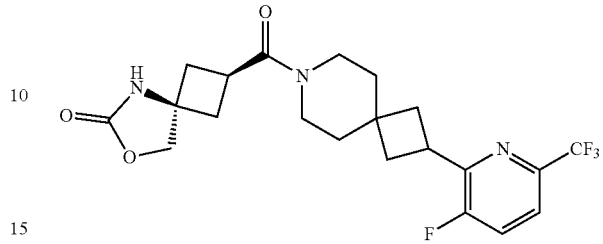

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(2,3-dimethylphenyl)-7-azaspiro[3.5]nonane-7-carboxylate (Intermediate 34) in place of tert-butyl 2-(3-fluoro-6-(trifluoromethyl)pyridin-2-yl)-7-azaspiro[3.5]nonane-7-carboxylate (Intermediate 9). MS (ESI): mass calcd. for $C_{21}H_{23}F_4N_3O_3$, 441.2; m/z found, 442.2 [M+H]$^+$. $^1$H NMR (400 MHz, Chloroform-d) δ 7.52-7.44 (m, 1H), 7.42-7.31 (m, 1H), 5.66 (s, 1H), 4.35-4.24 (m, 2H), 3.98-3.76 (m, 1H), 3.59-3.48 (m, 1H), 3.49-3.39 (m, 1H), 3.31-3.22 (m, 1H), 3.24-3.13 (m, 1H), 2.99-2.87 (m, 1H), 2.63-2.53 (m, 2H), 2.47-2.33 (m, 1H), 2.28-2.10 (m, 5H), 1.73-1.63 (m, 2H), 1.57-1.52 (m, 2H).

Example 33: (2s,4s)-2-(2-(6-(Trifluoromethyl)pyridin-2-yl)-7-azaspiro[3.5]nonane-7-carbonyl)-7-oxa-5-azaspiro[3.4]octan-6-one

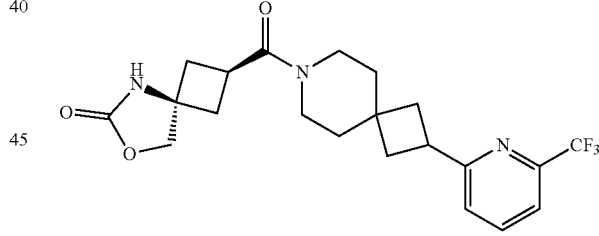

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(6-(trifluoromethyl)pyridin-2-yl)-7-azaspiro[3.5]nonane-7-carboxylate (Intermediate in place of tert-butyl 2-(3-(tert-butyl)phenyl)-7-azaspiro[3.5]nonane-7-carboxylate (Intermediate 9). MS (ESI): mass calcd. for $C_{21}H_{24}F_3N_3O_3$, 423.2; m/z found, 424.2 [M+H]$^+$. $^1$H NMR (400 MHz, Chloroform-d) δ 7.76-7.62 (m, 1H), 7.46-7.39 (m, 1H), 7.31-7.19 (m, 1H), 5.73 (s, 1H), 4.41-4.23 (m, 2H), 3.69-3.57 (m, 1H), 3.55-3.51 (m, 1H), 3.47-3.37 (m, 1H), 3.33-3.23 (m, 1H), 3.22-3.11 (m, 1H), 3.01-2.87 (m, 1H), 2.63-2.52 (m, 2H), 2.47-2.30 (m, 2H), 2.27-2.19 (m, 2H), 2.16-2.02 (m, 2H), 1.69-1.59 (m, 2H), 1.52 (s, 2H).

Example 34: (2s,4s)-2-(2-(5-Fluoro-6-methylpyridin-2-yl)-7-azaspiro[3.5]nonane-7-carbonyl)-7-oxa-5-azaspiro[3.4]octan-6-one

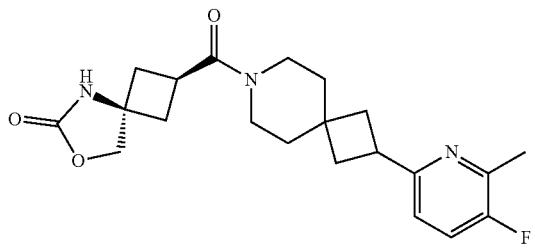 [SMILES: Cc1nc(C2CC3(CCN(C(=O)[C@H]4C[C@]5(COC(=O)N5)C4)CC3)C2)ccc1F]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(5-fluoro-6-methylpyridin-2-yl)-7-azaspiro[3.5]nonane-7-carboxylate (Intermediate 36) in place of tert-butyl 2-(3-(tert-butyl)phenyl)-7-azaspiro[3.5]nonane-7-carboxylate (Intermediate 9). MS (ESI): mass calcd. for $C_{21}H_{26}FN_3O_3$, 387.2; m/z found, 388.2 [M+H]$^+$. $^1$H NMR (400 MHz, Chloroform-d) δ 7.19-7.10 (m, 1H), 6.97-6.82 (m, 1H), 5.63 (s, 1H), 4.41-4.24 (m, 2H), 3.61-3.49 (m, 2H), 3.47-3.38 (m, 1H), 3.33-3.24 (m, 1H), 3.20-3.13 (m, 1H), 3.02-2.87 (m, 1H), 2.61-2.50 (m, 2H), 2.48-2.33 (m, 5H), 2.28-2.17 (m, 2H), 2.05-1.93 (m, 2H), 1.69-1.61 (m, 2H), 1.59-1.49 (m, 2H).

Example 35: (2s,4s)-2-(2-(2-(tert-Butyl)pyrimidin-4-yl)-7-azaspiro[3.5]nonane-7-carbonyl)-7-oxa-5-azaspiro[3.4]octan-6-one

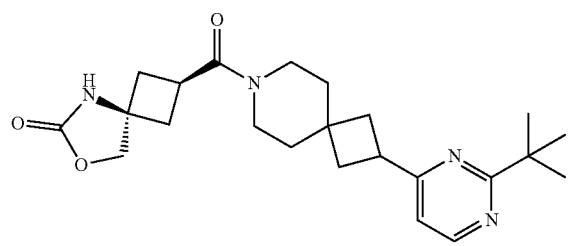 [SMILES: CC(C)(C)c1nccc(C2CC3(CCN(C(=O)[C@H]4C[C@]5(COC(=O)N5)C4)CC3)C2)n1]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(2-(tert-butyl)pyrimidin-4-yl)-7-azaspiro[3.5]nonane-7-carboxylate (Intermediate 37) in place of tert-butyl 2-(3-(tert-butyl)phenyl)-7-azaspiro[3.5]nonane-7-carboxylate (Intermediate 9). MS (ESI): mass calcd. for $C_{23}H_{32}N_4O_3$, 412.2; m/z found, 413.3 [M+H]$^+$. $^1$H NMR (400 MHz, Chloroform-d) δ 8.53-8.32 (m, 1H), 6.90-6.78 (m, 1H), 5.63 (s, 1H), 4.35-4.24 (m, 2H), 3.57-3.50 (m, 1H), 3.50-3.37 (m, 2H), 3.31-3.26 (m, 1H), 3.23-3.17 (m, 1H), 3.00-2.85 (m, 1H), 2.60-2.52 (m, 2H), 2.47-2.32 (m, 2H), 2.23-2.05 (m, 4H), 1.68-1.58 (m, 2H), 1.58-1.50 (m, 2H), 1.34 (s, 9H).

Example 36: (2s,4s)-2-(2-(4-(tert-Butyl)oxazol-2-yl)-7-azaspiro[3.5]nonane-7-carbonyl)-7-oxa-5-azaspiro[3.4]octan-6-one

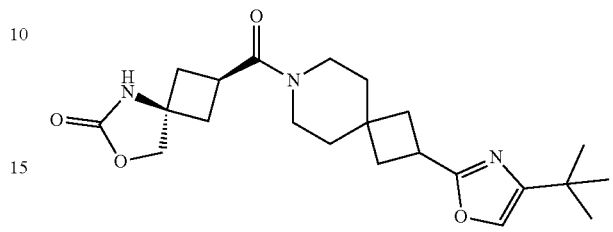

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(4-(tert-butyl)oxazol-2-yl)-7-azaspiro[3.5]nonane-7-carboxylate (Intermediate 38) in place of tert-butyl 2-(3-(tert-butyl)phenyl)-7-azaspiro[3.5]nonane-7-carboxylate (Intermediate 9). MS (ESI): mass calcd. for $C_{22}H_{31}N_3O_4$, 401.2; m/z found, 402.3 [M+H]$^+$. $^1$H NMR (400 MHz, Chloroform-d) δ 7.17-7.12 (m, 1H), 5.62 (s, 1H), 4.34-4.21 (m, 2H), 3.60-3.47 (m, 2H), 3.46-3.39 (m, 1H), 3.26-3.21 (m, 1H), 3.19-3.12 (m, 1H), 3.00-2.83 (m, 1H), 2.60-2.51 (m, 2H), 2.46-2.33 (m, 2H), 2.26-2.06 (m, 4H), 1.63-1.51 (m, 4H), 1.17 (s, 9H).

Example 37: (2s,4s)-2-[2-(2-(tert-Butyl)oxazol-5-yl)-7-azaspiro[3.5]nonane-7-carbonyl)-7-oxa-5-azaspiro[3.4]octan-6-one

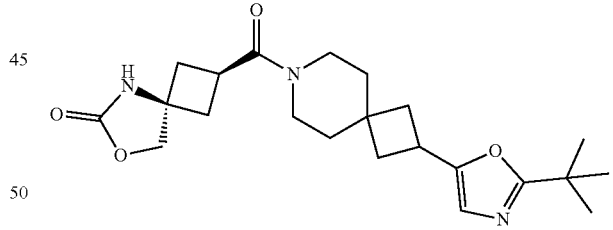

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(4-(tert-butyl)oxazol-5-yl)-7-azaspiro[3.5]nonane-7-carboxylate (Intermediate 39) in place of tert-butyl 2-(3-(tert-butyl)phenyl)-7-azaspiro[3.5]nonane-7-carboxylate (Intermediate 9). MS (ESI): mass calcd. for $C_{22}H_{31}N_3O_4$, 401.2; m/z found, 402.3 [M+H]$^+$. $^1$H NMR (400 MHz, Chloroform-d) δ 6.56-6.47 (m, 1H), 5.58 (s, 1H), 4.36-4.25 (m, 2H), 3.55-3.47 (m, 1H), 3.46-3.40 (m, 2H), 3.30-3.22 (m, 1H), 3.22-3.14 (m, 1H), 3.00-2.84 (m, 1H), 2.61-2.49 (m, 2H), 2.46-2.35 (m, 2H), 2.21-2.10 (m, 2H), 1.98-1.84 (m, 2H), 1.66-1.56 (m, 2H), 1.53-1.47 (m, 2H), 1.28 (s, 9H).

Example 38: (2s,4s)-2-(2-(3,5-Difluoropyridin-2-yl)-7-azaspiro[3.5]nonane-7-carbonyl)-7-oxa-5-azaspiro[3.4]octan-6-one

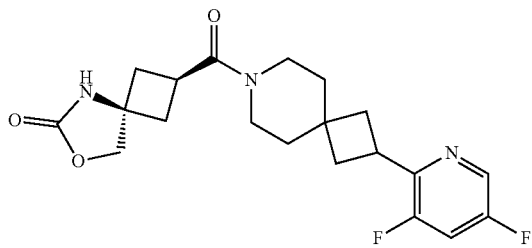 [SMILES: O=C1N[C@]2(CO1)C[C@H](C(=O)N1CCC3(CC1)CC(c1ncc(F)cc1F)C3)C2]

The title compound was prepared in a manner analogous to (2s,4s)-2-(2-(3-(tert-butyl)phenyl)-7-azaspiro[3.5]nonane-7-carbonyl)-7-oxa-5-azaspiro[3.4]octan-6-one (Example 2) except using tert-butyl 2-(3,5-difluoropyridin-2-yl)-7-azaspiro[3.5]nonane-7-carboxylate (Intermediate 40) in place of tert-butyl 2-(3-(tert-butyl)phenyl)-7-azaspiro[3.5]nonane-7-carboxylate (Intermediate 9). MS (ESI): mass calcd. for $C_{20}H_{23}F_2N_3O_3$, 391.2; m/z found, 392.2 [M+H]$^+$. $^1$H NMR (400 MHz, Chloroform-d) δ 8.30-8.18 (m, 1H), 7.10-6.98 (m, 1H), 5.63 (s, 1H), 4.34-4.21 (m, 2H), 3.84-3.68 (m, 1H), 3.58-3.52 (m, 1H), 3.47-3.41 (m, 1H), 3.31-3.22 (m, 1H), 3.22-3.15 (m, 1H), 3.01-2.86 (m, 1H), 2.61-2.50 (m, 2H), 2.45-2.35 (m, 2H), 2.27-2.07 (m, 4H), 1.72-1.58 (m, 2H), 1.55-1.48 (m, 2H).

Example 39: (rac)-(2s,4s)-2-(2-(4-(Trifluoromethyl)phenyl)-8-azaspiro[4.5]decane-8-carbonyl)-7-oxa-5-azaspiro[3.4]octan-6-one

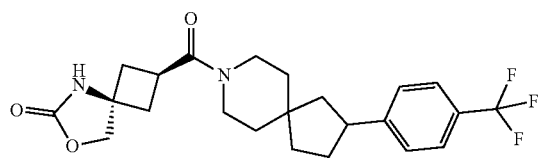 [SMILES: O=C1N[C@]2(CO1)C[C@H](C(=O)N1CCC3(CCC(c4ccc(C(F)(F)F)cc4)C3)CC1)C2]

Step A: tert-Butyl 2-(4-(trifluoromethyl)phenyl)-8-azaspiro[4.5]decane-8-carboxylate. A solution of tert-butyl 2-iodo-8-azaspiro[4.5]decane-8-carboxylate (Intermediate 41, 719 mg, 1.97 mmol) in THF (3.9 mL) was flowed through a column containing activated zinc at 40° C. (flow rate 0.5 mL/min). The outcoming solution was collected in a vial containing 4-bromobenzotrifluoride (0.18 mL, 1.31 mmol), bis(dibenzylideneacetone)palladium (Pd(dba)$_2$) (38 mg, 0.066 mmol) and 2-dicyclohexylphosphino-2',4',6'-triisopropylbiphenyl (XPhos) (47 mg, 0.098 mmol). The mixture was stirred at 50° C. for 4 h. Then, a 1:1 solution of saturated NH$_4$Cl and NH$_3$ (37% in water) was added and the mixture was extracted with EtOAc. The organic phase was separated, dried over Na$_2$SO$_4$, filtered and the solvent removed in vacuo. The residue was purified by FCC on silica (0-15% EtOAc in heptane) to afford the title compound as a yellow sticky oil (156 mg, 31% yield). MS (ESI): mass calcd. for $C_{21}H_{28}F_3NO_2$, 383.2; m/z found, 369.2 [M-tBu+2H+MeCN]$^+$.

Step B: 2-(4-(Trifluoromethyl)phenyl)-8-azaspiro[4.5]decane hydrochloride. To tert-butyl 2-(4-(trifluoromethyl)phenyl)-8-azaspiro[4.5]decane-8-carboxylate (10 mg, 0.026 mmol) in MeOH (52 µL) was added HCl in 1,4-dioxane (4 M, 65 µL). This was heated to 45° C. for 1 h before concentrating under reduced pressure. The title compound was used without further purification in the next step. MS (ESI): mass calcd. for $C_{16}H_{20}F_3N$, 283.2; m/z found, 284.1 [M+H]$^+$.

Step C: (rac)-(2s,4s)-2-(2-(4-(Trifluoromethyl)phenyl)-8-azaspiro[4.5]decane-8-carbonyl)-7-oxa-5-azaspiro[3.4]octan-6-one. 2-(4-(Trifluoromethyl)phenyl)-8-azaspiro[4.5]decane hydrochloride was taken up in dimethylformamide (DMF) (0.26 mL) and to this was added (2s,4s)-6-oxo-7-oxa-5-azaspiro[3.4]octane-2-carboxylic acid (Intermediate 3, 4 mg, 0.026 mmol), diisopropylethylamine (DIPEA) (14 µL, 0.078 mmol), and 1-[bis(dimethylamino)methylene]-1H-1,2,3-triazolo[4,5-b]pyridinium 3-oxide hexafluorophosphate (HATU) (11 mg, 0.029 mmol). This was stirred at room temperature for 1 hour. The reaction was filtered through a PTFE filter with MeOH and purified via reverse phase HPLC (5-95% MeCN in 20 mM NH$_4$OH in water) to afford the title compound (11 mg, 97% yield). MS (ESI): mass calcd. for $C_{23}H_{27}F_3N_2O_3$, 436.2; m/z found, 437.2 [M+H]$^+$. $^1$H NMR (400 MHz, Chloroform-d) δ 7.54 (d, J=8.1 Hz, 2H), 7.35-7.30 (m, 2H), 5.89 (s, 1H), 4.37 (d, J=1.8 Hz, 2H), 3.70-3.53 (m, 2H), 3.34 (dt, J=11.0, 5.6 Hz, 2H), 3.28-3.13 (m, 1H), 3.01 (pd, J=8.0, 3.1 Hz, 1H), 2.69-2.60 (m, 2H), 2.52-2.42 (m, 2H), 2.21-2.01 (m, 2H), 1.82-1.69 (m, 2H), 1.60-1.42 (m, 6H).

Example 40: (rac)-(2s,4s)-8-Methyl-2-(2-(4-(trifluoromethyl)phenyl)-8-azaspiro[4.5]decane-8-carbonyl)-7-oxa-5-azaspiro[3.4]octan-6-one

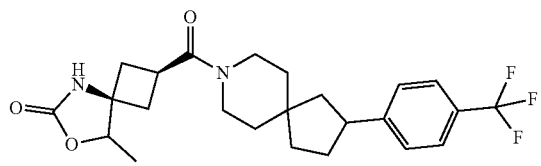

The title compound was prepared in a manner analogous to Example 39 using (2s,4s)-8-methyl-6-oxo-7-oxa-5-azaspiro[3.4]octane-2-carboxylic acid (Intermediate 5) instead of (2s,4s)-6-oxo-7-oxa-5-azaspiro[3.4]octane-2-carboxylic acid (Intermediate 3) in Step C. MS (ESI): mass calcd. for $C_{24}H_{29}F_3N_2O_3$, 450.2; m/z found, 451.2 [M+H]$^+$. $^1$H NMR (400 MHz, Chloroform-d) δ 7.54 (d, J=8.1 Hz, 2H), 7.33 (d, J=8.0 Hz, 2H), 5.89 (s, 1H), 4.54-4.46 (m, 1H), 3.71-3.53 (m, 2H), 3.33 (dt, J=10.9, 5.8 Hz, 2H), 3.28-3.12 (m, 1H), 3.01-2.91 (m, 1H), 2.71-2.56 (m, 2H), 2.44-2.33 (m, 2H), 2.21-2.01 (m, 2H), 1.84-1.69 (m, 2H), 1.59-1.47 (m, 6H), 1.46-1.41 (m, 3H).

Example 41: (rac)-(2s,4s)-2-(6-Phenyl-2-azaspiro[3.4]octane-2-carbonyl)-7-oxa-5-azaspiro[3.4]octan-6-one

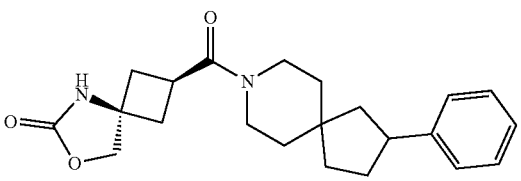 [SMILES: O=C1N[C@]2(CO1)C[C@H](C(=O)N1CCC3(CCC(c4ccccc4)C3)CC1)C2]

The title compound was prepared in a manner analogous to Steps B and C of Example 39 using tert-butyl 6-phenyl-2-azaspiro[3.4]octane-2-carboxylate (Intermediate 43) instead of tert-butyl 2-(4-(trifluoromethyl)phenyl)-8-azaspiro[4.5]decane-8-carboxylate in Step B. MS (ESI): mass calcd. for C$_{20}$H$_{24}$N$_2$O$_3$, 340.2; m/z found, 341.2 [M+H]$^+$. $^1$H NMR (400 MHz, Chloroform-d) δ 7.34-7.27 (m, 2H), 7.20 (td, J=6.4, 1.6 Hz, 3H), 6.49 (d, J=9.2 Hz, 1H), 4.33 (d, J=0.8 Hz, 2H), 4.09-3.85 (m, 4H), 3.19-3.02 (m, 1H), 2.76-2.65 (m, 1H), 2.65-2.56 (m, 2H), 2.48-2.37 (m, 2H), 2.32 (td, J=13.5, 7.4 Hz, 1H), 2.22-1.84 (m, 5H).

Example 42: (2r,4S*)-2-((R*)-6-Phenyl-2-azaspiro[3.4]octane-2-carbonyl)-5-azaspiro[3.4]octan-6-one

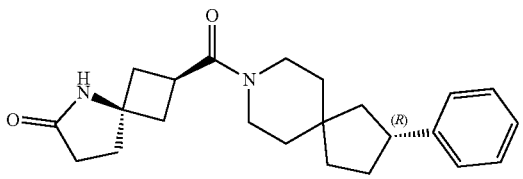

The title compound was prepared in a manner analogous to Steps B and C of Example 39 using tert-butyl (R*)-6-phenyl-2-azaspiro[3.4]octane-2-carboxylate (Intermediate 45) instead of tert-butyl 2-(4-(trifluoromethyl)phenyl)-8-azaspiro[4.5]decane-8-carboxylate in Step B and (2r,4s)-6-oxo-5-azaspiro[3.4]octane-2-carboxylic acid (Intermediate 4) instead of (2s,4s)-6-oxo-7-oxa-5-azaspiro[3.4]octane-2-carboxylic acid (Intermediate 3) in Step C. MS (ESI): mass calcd. for C$_{21}$H$_{26}$N$_2$O$_2$, 338.2; m/z found, 339.2 [M+H]$^+$. $^1$H NMR (500 MHz, Chloroform-d) δ 7.32-7.27 (m, 2H), 7.23-7.16 (m, 3H), 6.34 (s, 1H), 4.05-3.83 (m, 4H), 3.10 (s, 1H), 2.75 (p, J=8.1 Hz, 1H), 2.53-2.46 (m, 2H), 2.38-2.26 (m, 5H), 2.19 (dd, J=8.4, 7.3 Hz, 2H), 2.18-2.10 (m, 1H), 2.10-2.02 (m, 1H), 2.04-1.94 (m, 1H), 1.88 (s, 1H), 1.79-1.67 (m, 1H).

Example 43: (2r,4R*)-2-((S*)-6-Phenyl-2-azaspiro[3.4]octane-2-carbonyl)-5-azaspiro[3.4]octan-6-one

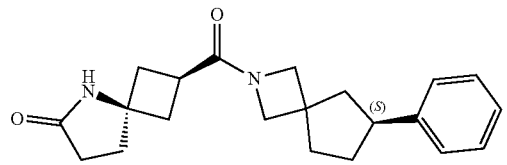

The title compound was prepared in a manner analogous to Steps B and C of Example 39 using tert-butyl (S*)-6-phenyl-2-azaspiro[3.4]octane-2-carboxylate (Intermediate 44) instead of tert-butyl 2-(4-(trifluoromethyl)phenyl)-8-azaspiro[4.5]decane-8-carboxylate in Step B and (2r,4s)-6-oxo-5-azaspiro[3.4]octane-2-carboxylic acid (Intermediate 4) instead of (2s,4s)-6-oxo-7-oxa-5-azaspiro[3.4]octane-2-carboxylic acid (Intermediate 3) in Step C. MS (ESI): mass calcd. for C$_{21}$H$_{26}$N$_2$O$_2$, 338.2; m/z found, 339.2 [M+H]$^+$. $^1$H NMR (500 MHz, Chloroform-d) δ 7.33-7.27 (m, 2H), 7.23-7.16 (m, 3H), 6.35 (s, 1H), 4.04-3.84 (m, 4H), 3.10 (s, 1H), 2.74 (p, J=8.1 Hz, 1H), 2.54-2.45 (m, 2H), 2.38-2.25 (m, 5H), 2.22-2.10 (m, 3H), 2.10-1.94 (m, 2H), 1.89 (s, 1H), 1.79-1.67 (m, 1H).

Example 44: (rac)-(2s,4s)-2-(6-(4-(Trifluoromethyl)phenyl)-2-azaspiro[3.4]octane-2-carbonyl)-7-oxa-5-azaspiro[3.4]octan-6-one

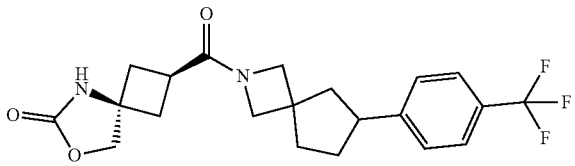 [SMILES: O=C1N[C@]2(CO1)C[C@H](C(=O)N1CC3(CCC(c4ccc(C(F)(F)F)cc4)C3)C1)C2]

The title compound was prepared in a manner analogous to Steps B and C of Example 39 using tert-butyl 6-(4-(trifluoromethyl)phenyl)-2-azaspiro[3.4]octane-2-carboxylate (Intermediate 46) instead of tert-butyl 2-(4-(trifluoromethyl)phenyl)-8-azaspiro[4.5]decane-8-carboxylate in Step B. MS (ESI): mass calcd. for C$_{21}$H$_{23}$F$_3$N$_2$O$_3$, 408.2; m/z found, 409.2 [M+H]$^+$. $^1$H NMR (400 MHz, Chloroform-d) δ 7.55 (d, J=8.1 Hz, 2H), 7.30 (d, J=8.0 Hz, 2H), 6.56 (d, J=10.5 Hz, 1H), 4.33 (s, 2H), 4.05-3.86 (m, 4H), 3.24-3.07 (m, 1H), 2.74-2.66 (m, 1H), 2.66-2.57 (m, 2H), 2.49-2.28 (m, 3H), 2.25-1.66 (m, 5H).

Example 45: (2s,4s)-2-((R*)-6-(4-(Trifluoromethyl)phenyl)-2-azaspiro[3.4]octane-2-carbonyl)-7-oxa-5-azaspiro[3.4]octan-6-one

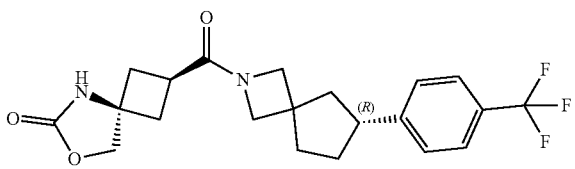

The title compound was prepared in a manner analogous to Steps B and C of Example 39 using tert-butyl (R*)-6-(4-(trifluoromethyl)phenyl)-2-azaspiro[3.4]octane-2-carboxylate (Intermediate 48) instead of tert-butyl 2-(4-(trifluoromethyl)phenyl)-8-azaspiro[4.5]decane-8-carboxylate in Step B. MS (ESI): mass calcd. for C$_{21}$H$_{23}$F$_3$N$_2$O$_3$, 408.2; m/z found, 409.1 [M+H]$^+$. $^1$H NMR (500 MHz, Chloroform-d) δ 7.55 (d, J=8.1 Hz, 2H), 7.30 (d, J=7.9 Hz, 2H), 6.60 (d, J=13.9 Hz, 1H), 4.33 (s, 2H), 4.05-3.87 (m, 4H), 3.24-3.07 (m, 1H), 2.74-2.66 (m, 1H), 2.66-2.56 (m, 2H), 2.48-2.39 (m, 2H), 2.39-2.30 (m, 1H), 2.24-2.13 (m, 1H), 2.13-1.96 (m, 2H), 1.96-1.84 (m, 1H), 1.80-1.65 (m, 1H).

Example 46: (2s,4R*)-2-((S*)-6-(4-(Trifluoromethyl)phenyl)-2-azaspiro[3.4]octane-2-carbonyl)-7-oxa-5-azaspiro[3.4]octan-6-one

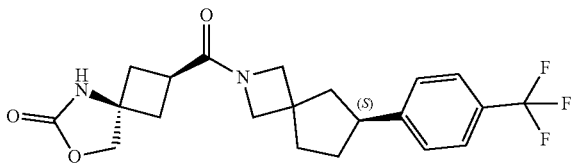

The title compound was prepared in a manner analogous to Steps B and C of Example 39 using tert-butyl (S*)-6-(4-(trifluoromethyl)phenyl)-2-azaspiro[3.4]octane-2-carboxylate (Intermediate 47) instead of tert-butyl 2-(4-(trifluoromethyl)phenyl)-8-azaspiro[4.5]decane-8-carboxylate in Step B. MS (ESI): mass calcd. for $C_{21}H_{23}F_3N_2O_3$, 408.2; m/z found, 409.2 [M+H]+. 1H NMR (500 MHz, Chloroform-d) δ 7.55 (d, J=8.1 Hz, 2H), 7.30 (d, J=7.9 Hz, 2H), 6.62 (d, J=14.6 Hz, 1H), 4.33 (s, 2H), 4.05-3.89 (m, 4H), 3.24-3.07 (m, 1H), 2.74-2.66 (m, 1H), 2.66-2.58 (m, 2H), 2.48-2.39 (m, 2H), 2.39-2.30 (m, 1H), 2.23-2.13 (m, 1H), 2.13-1.96 (m, 2H), 1.96-1.84 (m, 1H), 1.80-1.66 (m, 1H).

Example 47: (2r,4S*)-2-((R*)-6-(4-(Trifluoromethyl)phenyl)-2-azaspiro[3.4]octane-2-carbonyl)-5azaspiro[3.4]octan-6-one

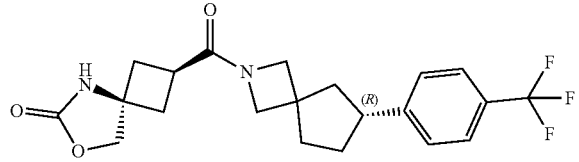

The title compound was prepared from in a manner analogous to Steps B and C of Example 39 using tert-butyl (R*)-6-(4-(trifluoromethyl)phenyl)-2-azaspiro[3.4]octane-2-carboxylate (Intermediate 48) instead of tert-butyl 2-(4-(trifluoromethyl)phenyl)-8-azaspiro[4.5]decane-8-carboxylate in Step B and (2r,4s)-6-oxo-5-azaspiro[3.4]octane-2-carboxylic acid (Intermediate 4) instead of (2s,4s)-6-oxo-7-oxa-5-azaspiro[3.4]octane-2-carboxylic acid (Intermediate 3) in Step C. MS (ESI): mass calcd. for $C_{22}H_{25}F_3N_2O_2$, 406.2; m/z found, 407.2 [M+H]+. 1H NMR (500 MHz, Chloroform-d) δ 7.57-7.51 (m, 2H), 7.30 (d, J=8.0 Hz, 2H), 6.44 (s, 1H), 4.08-3.84 (m, 4H), 3.16 (s, 1H), 2.74 (p, J=8.1 Hz, 1H), 2.54-2.46 (m, 2H), 2.39-2.28 (m, 5H), 2.23-2.13 (m, 3H), 2.14-1.97 (m, 2H), 1.89 (s, 1H), 1.80-1.66 (m, 1H).

Example 48: (2r,4R*)-2-((S*)-6-(4-(Trifluoromethyl)phenyl)-2-azaspiro[3.4]octane-2-carbonyl)-5azaspiro[3.4]octan-6-one

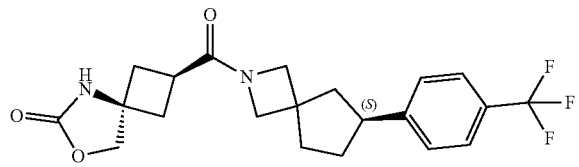

The title compound was prepared in a manner analogous to Steps B and C of Example 39 using tert-butyl (S*)-6-(4-(trifluoromethyl)phenyl)-2-azaspiro[3.4]octane-2-carboxylate (Intermediate 47) instead of tert-butyl 2-(4-(trifluoromethyl)phenyl)-8-azaspiro[4.5]decane-8-carboxylate in Step B and (2r,4s)-6-oxo-5-azaspiro[3.4]octane-2-carboxylic acid (Intermediate 4) instead of (2s,4s)-6-oxo-7-oxa-5-azaspiro[3.4]octane-2-carboxylic acid (Intermediate 3) in Step C. MS (ESI): mass calcd. for $C_{22}H_{25}F_3N_2O_2$, 406.2; m/z found, 407.2 [M+H]+. 1H NMR (500 MHz, Chloroform-d) δ 7.56-7.51 (m, 2H), 7.32-7.27 (m, 2H), 6.40 (s, 1H), 4.05-3.85 (m, 4H), 3.16 (s, 1H), 2.74 (p, J=8.1 Hz, 1H), 2.54-2.47 (m, 2H), 2.40-2.29 (m, 5H), 2.23-2.12 (m, 3H), 2.12-1.97 (m, 2H), 1.90 (s, 1H), 1.80-1.66 (m, 1H).

Example 49: (rac)-(2s,4s)-2-(6-(4-(tert-Butyl)phenyl)-2-azaspiro[3.4]octane-2-carbonyl)-7-oxa-5-azaspiro[3.4]octan-6-one

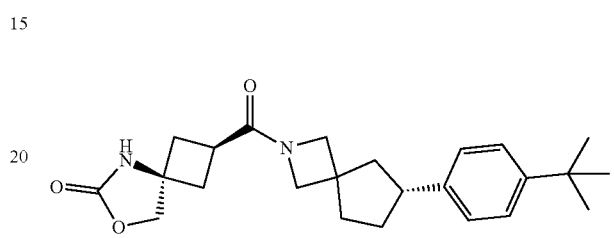

The title compound was prepared in a manner analogous to Example 39 using tert-butyl 6-iodo-2-azaspiro[3.4]octane-2-carboxylate (Intermediate 42) instead of tert-butyl 2-iodo-8-azaspiro[4.5]decane-8-carboxylate (Intermediate 41) and 1-bromo-4-tert-butylbenzene instead of 4-bromobenzotrifluoride in Step A. MS (ESI): mass calcd. for $C_{24}H_{32}N_2O_3$, 396.2; m/z found, 397.2 [M+H]+. 1H NMR (400 MHz, Chloroform-d) δ 7.35-7.29 (m, 2H), 7.15-7.09 (m, 2H), 6.37 (d, J=7.7 Hz, 1H), 4.33 (s, 2H), 4.03-3.86 (m, 4H), 3.16-3.00 (m, 1H), 2.76-2.67 (m, 1H), 2.64-2.55 (m, 2H), 2.48-2.38 (m, 2H), 2.30 (td, J=13.9, 7.4 Hz, 1H), 2.19-1.82 (m, 4H), 1.80-1.68 (m, 1H), 1.31 (s, 9H).

Example 50: (rac)-(2s,4s)-2-(6-(3-(tert-Butyl)phenyl)-2-azaspiro[3.4]octane-2-carbonyl)-7-oxa-5-azaspiro[3.4]octan-6-one

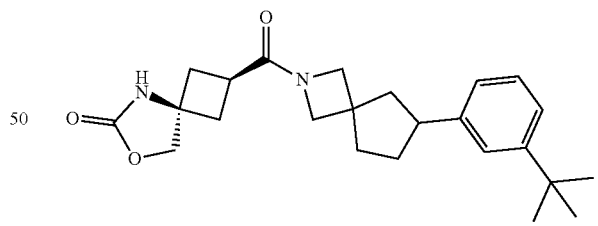

The title compound was prepared in a manner analogous to Example 39 using tert-butyl 6-iodo-2-azaspiro[3.4]octane-2-carboxylate (Intermediate 42) instead of tert-butyl 2-iodo-8-azaspiro[4.5]decane-8-carboxylate (Intermediate 41) and 1-bromo-3-tert-butylbenzene instead of 4-bromobenzotrifluoride in Step A. MS (ESI): mass calcd. for $C_{24}H_{32}N_2O_3$, 396.2; m/z found, 397.2 [M+H]+. 1H NMR (400 MHz, Chloroform-d) δ 7.25-7.22 (m, 2H), 7.20 (s, 1H), 7.04-6.98 (m, 1H), 6.36 (d, J=9.7 Hz, 1H), 4.33 (s, 2H), 4.04-3.88 (m, 4H), 3.19-3.01 (m, 1H), 2.77-2.67 (m, 1H), 2.65-2.55 (m, 2H), 2.49-2.39 (m, 2H), 2.32 (td, J=13.5, 7.3 Hz, 1H), 2.21-1.85 (m, 4H), 1.82-1.68 (m, 1H), 1.32 (s, 9H).

Example 51: (rac)-(2s,4s)-2-(6-(3-(tert-Butyl)phenyl)-2-azaspiro[3.4]octane-2-carbonyl)-8-methyl-7-oxa-5-azaspiro[3.4]octan-6-one

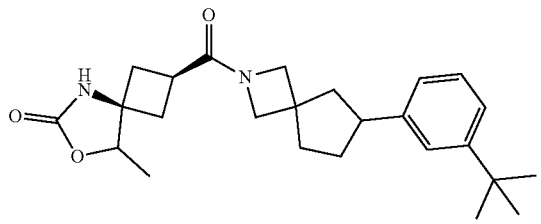

The title compound was prepared in a manner analogous to Example 39 using tert-butyl 6-iodo-2-azaspiro[3.4]octane-2-carboxylate (Intermediate 42) instead of tert-butyl 2-iodo-8-azaspiro[4.5]decane-8-carboxylate (Intermediate 41) and 1-bromo-3-tert-butylbenzene instead of 4-bromobenzotrifluoride in Step A and (2s,4s)-8-methyl-6-oxo-7-oxa-5-azaspiro[3.4]octane-2-carboxylic acid (Intermediate 5) instead of (2s,4s)-6-oxo-7-oxa-5-azaspiro[3.4]octane-2-carboxylic acid (Intermediate 3) in Step C. MS (ESI): mass calcd. for $C_{25}H_{34}N_2O_3$, 410.3; m/z found, 411.3 $[M+H]^+$. $^1H$ NMR (400 MHz, Chloroform-d) δ 7.25-7.22 (m, 2H), 7.21 (dt, J=3.2, 1.5 Hz, 1H), 7.04-6.98 (m, 1H), 6.39 (d, J=7.3 Hz, 1H), 4.49-4.41 (m, 1H), 4.04-3.87 (m, 4H), 3.19-3.01 (m, 1H), 2.73-2.58 (m, 2H), 2.58-2.48 (m, 1H), 2.42-2.25 (m, 3H), 2.22-1.83 (m, 4H), 1.81-1.68 (m, 1H), 1.41 (dt, J=6.5, 1.5 Hz, 3H), 1.32 (s, 9H).

Example 52: (rac)-(2s,4s)-2-(6-Cyclopropyl-2-azaspiro[3.4]octane-2-carbonyl)-7-oxa-5-azaspiro[3.4]octan-6-one

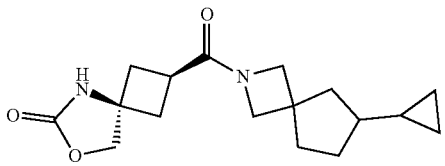 [SMILES: O=C1N[C@]2(CO1)C[C@H](C(=O)N1CC3(CCC(C4CC4)C3)C1)C2]

Step A: tert-Butyl 6-cyclopropyl-2-azaspiro[3.4]octane-2-carboxylate. Cyclopropylmagnesium bromide (0.75 mL, 0.75 mmol) was added to a solution of tert-butyl 6-iodo-2-azaspiro[3.4]octane-2-carboxylate (Intermediate 42, 169 mg, 0.50 mmol), cobalt (II) acetylacetonate (4.5 mg, 0.018 mmol) and N,N,N',N'-tetramethylethylenediamine (58 mg, 0.50 mmol) in THF (0.6 mL) at 0° C. The mixture was stirred at this temperature for 1 h. The reaction was quenched with $NH_4Cl/NH_3$ and the organic phase was separated, dried, filtered and evaporated under reduced pressure. The crude was purified by FCC on silica (EtOAc:DCM:Heptane 0/30/70 to 50/50/0) affording the title compound as a colorless oil (89 mg, 50% pure, 35% yield).

Step B: 6-Cyclopropyl-2-azaspiro[3.4]octan-2-ium chloride. To tert-butyl 6-cyclopropyl-2-azaspiro[3.4]octane-2-carboxylate (45 mg, 50% pure, 0.179 mmol) in MeOH (100 μL) was added HCl in 1,4-dioxane (4 M, 0.45 mL). This was heated to 45° C. for 1 h before concentrating under reduced pressure. The title compound was used without further purification in the next step. MS (ESI): mass calcd. for $C_{10}H_{17}N$, 151.1; m/z found, 152.1 $[M+H]^+$.

Step C: (rac)-(2s,4s)-2-(6-Cyclopropyl-2-azaspiro[3.4]octane-2-carbonyl)-7-oxa-5-azaspiro[3.4]octan-6-one. 6-Cyclopropyl-2-azaspiro[3.4]octan-2-ium chloride was taken up in DMF (0.9 mL) and to this was added (2s,4s)-6-oxo-7-oxa-5-azaspiro[3.4]octane-2-carboxylic acid (Intermediate 3, 31 mg, 0.179 mmol), DIPEA (94 μL, 0.537 mmol), and HATU (77 mg, 0.197 mmol). This was stirred at room temperature for 1 hour. The reaction was filtered through a PTFE filter with MeOH and purified via reverse phase HPLC (5-95% MeCN in 20 mM $NH_4OH$ in water) to afford the title compound (10 mg, 18% yield). MS (ESI): mass calcd. for $C_{17}H_{24}N_2O_3$, 304.2; m/z found, 305.2 $[M+H]^+$. $^1H$ NMR (400 MHz, Chloroform-d) δ 6.53 (d, J=7.5 Hz, 1H), 4.32 (d, J=2.5 Hz, 2H), 3.98-3.84 (m, 2H), 3.84 (s, 1H), 3.79 (s, 1H), 2.74-2.64 (m, 1H), 2.64-2.54 (m, 2H), 2.45-2.36 (m, 2H), 2.04-1.92 (m, 1H), 1.92-1.71 (m, 3H), 1.64-1.51 (m, 1H), 1.46-1.26 (m, 2H), 0.65-0.52 (m, 1H), 0.44-0.35 (m, 2H), 0.08--0.01 (m, 2H).

Example 53: (rac)-(2s,4s)-2-(6-Cyclohexyl-2-azaspiro[3.4]octane-2-carbonyl)-7-oxa-5-azaspiro[3.4]octan-6-one

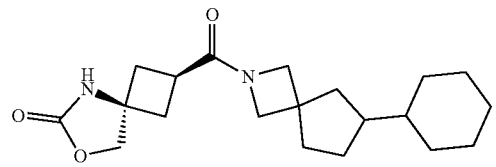 [SMILES: O=C1N[C@]2(CO1)C[C@H](C(=O)N1CC3(CCC(C4CCCCC4)C3)C1)C2]

Step A: tert-Butyl 6-cyclohexyl-2-azaspiro[3.4]octane-2-carboxylate. Cyclohexylmagnesium chloride (1 mL, 1 mmol) was added to a solution of tert-butyl 6-iodo-2-azaspiro[3.4]octane-2-carboxylate (Intermediate 42, 169 mg, 0.5 mmol), nickel(II) acetylacetonate (13 mg, 0.05 mmol), 4-fluorostyrene (12 μL, 0.1 mmol) and tetrabutylammonium iodide (554 mg, 1.5 mmol) in THF (0.41 mL) and N-methyl-2-pyrrolidone (NMP) (0.24 mL) at 0° C. The mixture was stirred at this temperature for 4 h at rt. The reaction was quenched with saturated $NH_4Cl$ solution and extracted with EtOAc. The combined organic layers were washed with brine, separated, dried, and evaporated under reduced pressure to give a crude residue which was purified by FCC on silica (20-80% DCM in heptane) to obtain the title compound as a colorless oil (87 mg, 45% pure, 27% yield). MS (ESI): mass calcd. for $C_{18}H_{31}NO_2$, 293.2; m/z found, 294.2 $[M+H]^+$.

Step B: 6-Cyclohexyl-2-azaspiro[3.4]octan-2-ium chloride. To tert-butyl 6-cyclohexyl-2-azaspiro[3.4]octane-2-carboxylate (44 mg, 45% pure, 0.15 mmol) in MeOH (100 μL) was added HCl in 1,4-dioxane (4 M, 0.38 mL). This was heated to 45° C. for 1 h before concentrating under reduced pressure. The title compound was used without further purification in the next step. MS (ESI): mass calcd. for $C_{13}H_{23}N$, 193.2; m/z found, 194.2 $[M+H]^+$.

Step C: (rac)-(2s,4s)-2-(6-Cyclohexyl-2-azaspiro[3.4]octane-2-carbonyl)-7-oxa-5-azaspiro[3.4]octan-6-one. 6-Cyclohexyl-2-azaspiro[3.4]octan-2-ium chloride was taken up in DMF (0.75 mL) and to this was added (2s,4s)-6-oxo-7-oxa-5-azaspiro[3.4]octane-2-carboxylic acid (Intermediate 3, 26 mg, 0.15 mmol), DIPEA (79 μL, 0.45 mmol), and HATU (65 mg, 0.16 mmol). This was stirred at room temperature for 1.5 hour. The reaction was filtered through a PTFE filter with MeOH and purified via reverse phase HPLC (5-95% MeCN in 20 mM NH$_4$OH in water) to afford the title compound (20 mg, 39% yield). MS (ESI): mass calcd. for C$_{20}$H$_{30}$N$_2$O$_3$, 346.2; m/z found, 347.2 [M+H]$^+$. $^1$H NMR (500 MHz, Chloroform-d) δ 6.58 (d, J=Hz, 1H), 4.32 (d, J=1.7 Hz, 2H), 3.84 (dd, J=31.7, 21.3 Hz, 4H), 2.72-2.63 (m, 1H), 2.63-2.56 (m, 2H), 2.44-2.35 (m, 2H), 2.01-1.89 (m, 1H), 1.87-1.74 (m, 4H), 1.74-1.51 (m, 1.47-1.35 (m, 1H), 1.32-1.09 (m, 4H), 1.06-0.96 (m, 1H), 0.94-0.80 (m, 2H).

Example 54: (rac)-(2r,4s)-2-(6-Cyclohexyl-2-azaspiro[3.4]octane-2-carbonyl)-5-azaspiro[3.4]octan-6-one

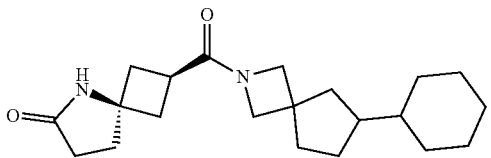 [SMILES: O=C1CC[C@]2(C[C@H](C(=O)N3CC4(CCC(C5CCCCC5)C4)C3)C2)N1]

The title compound was prepared in a manner analogous to Example 53 using (2r,4s)-6-oxo-5-azaspiro[3.4]octane-2-carboxylic acid (Intermediate 4) instead of (2s,4s)-6-oxo-7-oxa-5-azaspiro[3.4]octane-2-carboxylic acid (Intermediate 3) in Step C. MS (ESI): mass calcd. for C$_{21}$H$_{32}$N$_2$O$_2$, 344.2; m/z found, 345.3 [M+H]$^+$. $^1$H NMR (400 MHz, Chloroform-d) δ 6.18 (s, 1H), 3.91-3.74 (m, 4H), 2.72 (pd, J=8.1, 3.8 Hz, 1H), 2.52-2.43 (m, 2H), 2.38-2.26 (m, 4H), 2.21-2.14 (m, 2H), 2.01-1.88 (m, 1H), 1.87-1.66 (m, 7H), 1.57 (q, J=9.1, 8.4 Hz, 2H), 1.47-1.34 (m, 1H), 1.34-1.10 (m, 4H), 1.10-0.96 (m, 1H), 0.96-0.80 (m, 2H).

Example 55: (rac)-(2s,4s)-2-(6-Cyclopentyl-2-azaspiro[3.4]octane-2-carbonyl)-7-oxa-5-azaspiro[3.4]octan-6-one

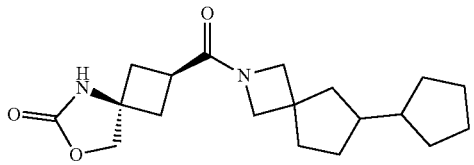 [SMILES: O=C1N[C@]2(CO1)C[C@H](C(=O)N1CC3(CCC(C4CCCC4)C3)C1)C2]

Step A: tert-Butyl 6-cyclopentyl-6-hydroxy-2-azaspiro[3.4]octane-2-carboxylate. In an oven-dried flask under N$_2$, 2-boc-6-oxo-2-azaspiro[3.4]octane (100 mg, 0.439 mmol) was taken up in anhydrous THF (0.3 M). Cerium (III) chloride (CeCl$_3$) (162 mg, 0.659 mmol) was added and this was stirred for 1 h at room temperature. The reaction was cooled to 0° C. and cyclopentylmagnesium bromide (2 M in THF, 0.33 mL) was added dropwise. The reaction was allowed to warm to rt and stirred for 16 h. The reaction was quenched with saturated aqueous NH$_4$Cl, extracted with EtOAc, dried over Na$_2$SO$_4$, filtered, and concentrated under reduced pressure. Purification via FCC on silica (0-60% EtOAc in hexane) afforded the title compound (33 mg, 25% yield). MS (ESI): mass calcd. for C$_{17}$H$_{29}$NO$_3$, 295.2; m/z found, 222.2 [M+H-tBu-OH]$^+$.

Step B: 6-Cyclopentyl-2-azaspiro[3.4]octan-2-ium 2,2,2-trifluoroacetate. tert-Butyl 6-cyclopentyl-6-hydroxy-2-azaspiro[3.4]octane-2-carboxylate (33 mg, 0.112 mmol) was taken up in trifluoroacetic acid (TFA) (0.75 mL) and stirred for 5 min at rt. Triethylsilane (TES) (54 µL, mmol) was added and this was stirred for 2 h at rt before concentrating under reduced pressure. The title compound was used without further purification in the next step. MS (ESI): mass calcd. for C$_{12}$H$_{21}$N, 179.2; m/z found, 180.2 [M+H]$^+$.

Step C: (rac)-(2s,4s)-2-(6-Cyclopentyl-2-azaspiro[3.4]octane-2-carbonyl)-7-oxa-5-azaspiro[3.4]octan-6-one. 6-Cyclopentyl-2-azaspiro[3.4]octan-2-ium 2,2,2-trifluoroacetate (16 mg, 0.054 mmol) and (2s,4s)-6-oxo-7-oxa-5-azaspiro[3.4]octane-2-carboxylic acid (Intermediate 3, 9 mg, 0.054 mmol) were taken up in DMF (0.15 M). DIPEA (38 µL, 0.218 mmol) and HATU (26 mg, 0.066 mmol) were added and the reaction was stirred at rt for 72 h. The crude mixture was filtered through a PTFE filter with MeOH and purified via reverse phase HPLC (5-95% MeCN in 20 mM NH$_4$OH in water) to afford the title compound (12 mg, 66% yield). MS (ESI): mass calcd. for C$_{19}$H$_{28}$N$_2$O$_3$, 332.2; m/z found, 333.3 [M+H]$^+$. $^1$H NMR (400 MHz, Chloroform-d) δ 6.58 (d, J=4.7 Hz, 1H), 4.32 (d, J=1.1 Hz, 2H), 3.92-3.77 (m, 4H), 2.73-2.63 (m, 1H), 2.64-2.56 (m, 2H), 2.46-2.36 (m, 2H), 1.97 (td, J=13.4, 7.2 Hz, 1H), 1.88-1.65 (m, 6H), 1.65-1.38 (m, 6H), 1.34-1.21 (m, 1H), 1.16-0.99 (m, 2H).

Example 56: (rac)-(2s,4s)-2-(6-Cyclobutyl-2-azaspiro[3.4]octane-2-carbonyl)-7-oxa-5-azaspiro[3.4]octan-6-one

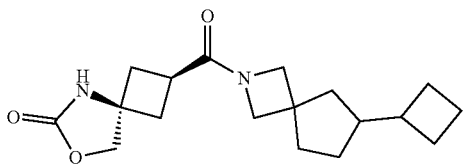 [SMILES: O=C1N[C@]2(CO1)C[C@H](C(=O)N1CC3(CCC(C4CCC4)C3)C1)C2]

Step A: tert-Butyl 6-cyclobutyl-6-hydroxy-2-azaspiro[3.4]octane-2-carboxylate. In an oven-dried flask under N$_2$, 2-boc-6-oxo-2-azaspiro[3.4]octane (50 mg, 0.22 mmol) was taken up in anhydrous THF (0.6 M). CeCl$_3$ (81 mg, 0.33 mmol) was added and this was stirred for 45 min at room temperature. The reaction was cooled to 0° C. and cyclobutylmagnesium chloride (0.5 M in THF, 0.66 mL) was added dropwise. The reaction was allowed to warm to rt and stirred for 6 h. The reaction was quenched with saturated aqueous NH$_4$Cl, extracted with EtOAc, dried over Na$_2$SO$_4$, filtered, and concentrated under reduced pressure. Purification via FCC on silica (0-100% EtOAc in hexane) afforded the title compound (33 mg, 53% yield). MS (ESI): mass calcd. for C$_{16}$H$_{27}$NO$_3$, 281.2; m/z found, 208.2 [M+H-tBu-OH]$^+$.

Step B: 6-Cyclobutyl-2-azaspiro[3.4]oct-6-en-2-ium 2,2,2-trifluoroacetate. tert-Butyl 6-cyclobutyl-6-hydroxy-2-azaspiro[3.4]octane-2-carboxylate (26 mg, 0.092 mmol) was taken up in TFA (0.62 mL) and stirred for 5 min at rt. TES (45 µL, 0.277 mmol) was added and this was stirred for 1 h at rt before concentrating under reduced pressure. The title compound was used without further purification in the next step. MS (ESI): mass calcd. for CHI-117N, 163.1; m/z found, 164.2 [M+H]$^+$.

Step C: 6-Cyclobutyl-2-azaspiro[3.4]octan-2-ium 2,2,2-trifluoroacetate. 6-Cyclobutyl-2-azaspiro[3.4]oct-6-en-2-ium 2,2,2-trifluoroacetate (26 mg, 0.094 mmol) was taken up in ethanol (EtOH) (0.9 mL). Palladium on carbon (Pd/C) (10 mg, 0.009 mmol) was added and the reaction vessel was evacuated and left under a hydrogen (H₂) balloon to stir at rt for 16 h. The reaction mixture was filtered through Celite® with MeOH and concentrated under reduced pressure. The title compound was used without further purification in the next step. MS (ESI): mass calcd. for $C_{11}H_{19}N$, 165.2; m/z found, 166.2 [M+H]⁺.

Step D: (rac)-(2s,4s)-2-(6-Cyclobutyl-2-azaspiro[3.4]octane-2-carbonyl)-7-oxa-5-azaspiro[3.4]octan-6-one. 6-Cyclobutyl-2-azaspiro[3.4]octan-2-ium 2,2,2-trifluoroacetate (26 mg, 0.093 mmol) and (2s,4s)-6-oxo-7-oxa-5-azaspiro [3.4]octane-2-carboxylic acid (Intermediate 3, 17 mg, 0.098 mmol) were taken up in DMF (0.6 mL). DIPEA (48 µL, 0.279 mmol) and HATU (40 mg, 0.102 mmol) were added and the reaction was stirred at rt for 2 h. The reaction mixture was filtered through a PTFE filter with MeOH and purified via reverse phase HPLC (5-95% MeCN in 20 mM NH₄OH in water) to afford the title compound (5 mg, 17% yield). MS (ESI): mass calcd. for $C_{18}E126N_2O_3$, 318.2; m/z found, 319.3 [M+H]⁺. ¹H NMR (400 MHz, Chloroform-d) δ 6.34 (s, 1H), 4.32 (s, 2H), 3.76-3.59 (m, 4H), 2.75-2.63 (m, 1H), 2.63-2.51 (m, 2H), 2.47-2.35 (m, 2H), 1.89 (d, J=15.9 Hz, 2H), 1.80-1.48 (m, 9H), 1.48-1.27 (m, 3H).

Example 57: (rac)-(2s,4s)-2-(2-(3-(tert-Butyl)phenyl)-8-azaspiro[4.5]decane-8-carbonyl)-7-oxa-5-azaspiro[3.4]octan-6-one

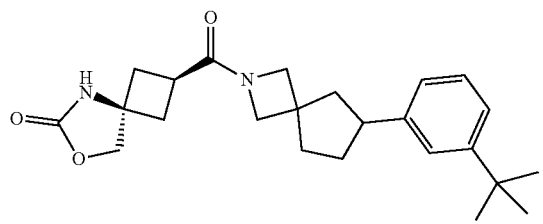 [SMILES: CC(C)(C)c1cccc(C2CCC3(C2)CN(C(=O)[C@H]2C[C@]4(COC(=O)N4)C2)C3)c1]

Step A: tert-Butyl 2-(3-(tert-butyl)phenyl)-2-hydroxy-8-azaspiro[4.5]decane-8-carboxylate. In an oven-dried flask under N₂, tert-butyl 2-oxo-8-azaspiro[4.5]decane-8-carboxylate (100 mg, mmol) was taken up in anhydrous THF (1.9 mL) and cooled to −78° C. 3-tert-Butylphenylmagnesium bromide (0.5 M in THF, 1.12 mL) was added dropwise. This was allowed to warm to rt and stirred 1.5 h before being quenched with saturated aqueous NH₄Cl and extracted with EtOAc. The combined organic layers were dried over Na₂SO₄, filtered, and concentrated under reduced pressure. Purification via FCC on silica (0-100% EtOAc in hexane) provided the title compound (68 mg, 47% yield). MS (ESI): mass calcd. for $C_{24}H_{37}NO_3$, 387.3; m/z found, 332.2 [M-tBu+2H]⁺.

Step B: 2-(3-(tert-Butyl)phenyl)-8-azaspiro[4.5]decan-8-ium 2,2,2-trifluoroacetate. tert-Butyl 2-(3-(tert-butyl)phenyl)-2-hydroxy-8-azaspiro[4.5]decane-8-carboxylate (68 mg, 0.175 mmol) was taken up in TFA (0.58 mL) and stirred for 5 min at rt. TES (85 µL) was added and this was stirred for 1 h at rt before concentrating under reduced pressure. The title compound was used without further purification in the next step. MS (ESI): mass calcd. for $C_{19}H_{29}N$, 271.2; m/z found, 272.2 [M+H]⁺.

Step C: (rac)-(2s,4s)-2-(2-(3-(tert-Butyl)phenyl)-8-azaspiro[4.5]decane-8-carbonyl)-7-oxa-5-azaspiro[3.4]octan-6-one. 2-(3-(tert-Butyl)phenyl)-8-azaspiro[4.5]decan-8-ium 2,2,2-trifluoroacetate (20 mg, 0.052 mmol) and (2s,4s)-6-oxo-7-oxa-5-azaspiro[3.4]octane-2-carboxylic acid (Intermediate 3, 10 mg, 0.057 mmol) were taken up in DMF (0.5 mL). DIPEA (27 µL, 0.156 mmol) and HATU (24 mg, 0.062 mmol) were added and the reaction was stirred at rt for 3 h. The reaction mixture was filtered through a PTFE filter with MeOH and purified via reverse phase HPLC (5-95% MeCN in 20 mM NH₄OH in water) to afford the title compound (16 mg, 73% yield). MS (ESI): mass calcd. for $C_{26}H_{36}N_2O_3$, 424.3; m/z found, 425.3 [M+H]⁺. ¹H NMR (400 MHz, Chloroform-d) δ 7.25-7.20 (m, 3H), 7.08-7.02 (m, 1H), 6.19 (d, J=5.6 Hz, 1H), 4.38 (d, J=2.1 Hz, 2H), 3.67-3.52 (m, 2H), 3.40-3.27 (m, 2H), 3.23-3.07 (m, 1H), 3.07-2.93 (m, 1H), 2.72-2.61 (m, 2H), 2.52-2.40 (m, 2H), 2.19-2.00 (m, 2H), 1.84-1.67 (m, 3H), 1.66-1.44 (m, 5H), 1.32 (s, 9H).

Example 58: (rac)-(2s,4s)-2-(2-(4-(tert-Butyl)phenyl)-8-azaspiro[4.5]decane-8-carbonyl)-7-oxa-5-azaspiro[3.4]octan-6-one

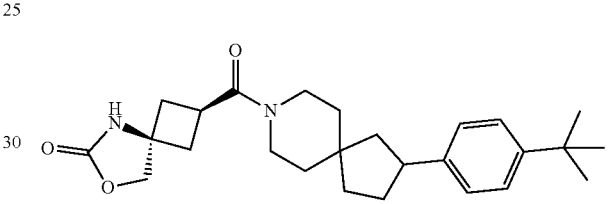

The title compound was prepared in a manner analogous to Example 57 using 4-tert-butylphenylmagnesium bromide instead of 3-tert-butylphenylmagnesium bromide in Step A. MS (ESI): mass calcd. for $C_{26}H_{36}N_2O_3$, 424.3; m/z found, 425.3 [M+H]⁺. ¹H NMR (400 MHz, Chloroform-d) δ 7.35-7.28 (m, 2H), 7.19-7.13 (m, 2H), 6.10 (d, J=4.7 Hz, 1H), 4.37 (d, J=1.9 Hz, 2H), 3.66-3.49 (m, 2H), 3.40-3.25 (m, 2H), 3.21-3.06 (m, 1H), 2.99 (pd, J=8.1, 3.7 Hz, 1H), 2.71-2.61 (m, 2H), 2.51-2.39 (m, 2H), 2.17-1.96 (m, 2H), 1.82-1.65 (m, 3H), 1.65-1.41 (m, 5H), 1.31 (s, 9H).

Example 59: (2s,4s)-2-(2-(3-Isopropylphenyl)-6-azaspiro[3.4]octane-6-carbonyl)-7-oxa-5-azaspiro[3.4]octan-6-one

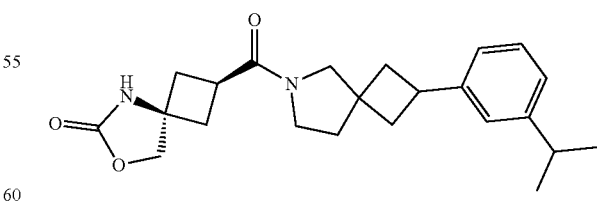

The title compound was prepared in a manner analogous to Example 57 using tert-butyl 2-oxo-6-azaspiro[3.4]octane-6-carboxylate instead of tert-butyl 2-oxo-8-azaspiro[4.5]decane-8-carboxylate and 3-isopropylphenylmagnesium bromide instead of 3-tert-butylphenylmagnesium bromide in Step A. MS (ESI): mass calcd. for $C_{23}H_{30}N_2O_3$, 382.2; m/z found, 383.3 [M+H]⁺. ¹H NMR (400 MHz, Chloroform-d) δ 7.25-7.19 (m, 1H), 7.12-7.05 (m, 1H), 7.05-6.97 (m, 2H), 6.41-6.23 (m, 1H), 4.41-4.30 (m, 2H), 3.67-3.25 (m, 5H), 2.88 (qd, J=18.0, 15.3, 10.0 Hz, 2H), 2.72-2.58 (m, 2H), 2.57-2.29 (m, 4H), 2.28-2.09 (m, 2H), 2.09-1.82 (m, 2H), 1.25 (dd, J=6.9, 1.3 Hz, 6H).

Example 60: (2s,4s)-2-(2-(3-(tert-Butyl)phenyl)-6-azaspiro[3.4]octane-6-carbonyl)-7-oxa-5-azaspiro[3.4]octan-6-one

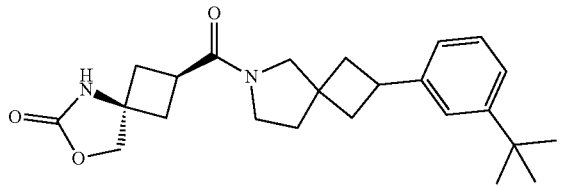 [SMILES: CC(C)(C)c1cccc(C2CC3(CCN(C(=O)[C@H]4C[C@]5(COC(=O)N5)C4)C3)C2)c1]

The title compound was prepared in a manner analogous to Example 57 using tert-butyl 2-oxo-6-azaspiro[3.4]octane-6-carboxylate instead of tert-butyl 2-oxo-8-azaspiro[4.5]decane-8-carboxylate in Step A. MS (ESI): mass calcd. for C₂₄H₃₂N₂O₃, 396.2; m/z found, 397.3 [M+H]⁺. ¹H NMR (400 MHz, Chloroform-d) δ 7.26-7.21 (m, 2H), 7.21-7.16 (m, 1H), 7.05-6.99 (m, 1H), 6.21 (d, J=25.8 Hz, 1H), 4.40-4.30 (m, 2H), 3.68-3.26 (m, 5H), 2.98-2.78 (m, 1H), 2.70-2.58 (m, 2H), 2.55-2.30 (m, 4H), 2.26-2.10 (m, 2H), 2.10-1.83 (m, 2H), 1.32 (d, J=1.3 Hz, 9H).

Example 61: (rac)-(2s,4s)-2-(6-(3-Isopropylphenyl)-2-azaspiro[3.4]octane-2-carbonyl)-7-oxa-5-azaspiro[3.4]octan-6-one

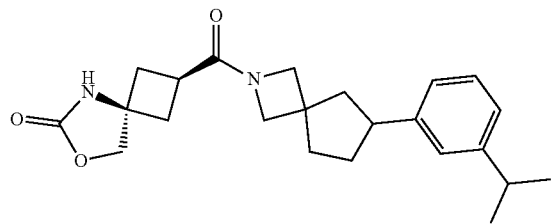 [SMILES: CC(C)c1cccc(C2CCC3(C2)CN(C(=O)[C@H]2C[C@]4(COC(=O)N4)C2)C3)c1]

The title compound was prepared in a manner analogous to Example 57 using 2-boc-6-oxo-2-azaspiro[3.4]octane instead of tert-butyl 2-oxo-8-azaspiro[4.5]decane-8-carboxylate and 3-isopropylphenylmagnesium bromide instead of 3-tert-butylphenylmagnesium bromide in Step A. MS (ESI): mass calcd. for C₂₃H₃₀N₂O₃, 382.2; m/z found, 383.2 [M+H]⁺. ¹H NMR (400 MHz, Chloroform-d) δ 7.23 (t, J=7.6 Hz, 1H), 7.10-6.98 (m, 3H), 6.61-6.51 (m, 1H), 4.33 (s, 2H), 4.03-3.87 (m, 4H), 3.17-3.00 (m, 1H), 2.88 (hept, J=6.9 Hz, 1H), 2.75-2.66 (m, 1H), 2.66-2.58 (m, 2H), 2.48-2.37 (m, 2H), 2.31 (td, J=13.5, 7.3 Hz, 1H), 2.20-1.83 (m, 4H), 1.80-1.67 (m, 1H), 1.24 (d, J=6.9 Hz, 6H).

Example 62: (rac)-(2r,4S)-2-(6-(3-Isopropylphenyl)-2-azaspiro[3.4]octane-2-carbonyl)-5-azaspiro[3.4]octan-6-one

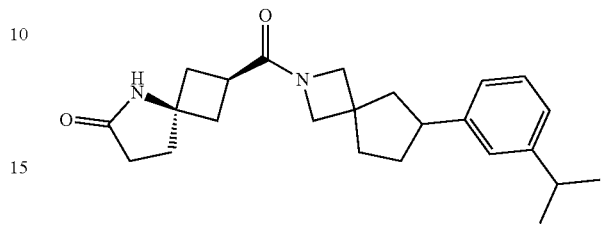

The title compound was prepared in a manner analogous to Example 57 using 2-boc-6-oxo-2-azaspiro[3.4]octane instead of tert-butyl 2-oxo-8-azaspiro[4.5]decane-8-carboxylate and 3-isopropylphenylmagnesium bromide instead of 3-tert-butylphenylmagnesium bromide in Step A and (2r,4s)-6-oxo-5-azaspiro[3.4]octane-2-carboxylic acid (Intermediate 4) instead of (2s,4s)-6-oxo-7-oxa-5-azaspiro[3.4]octane-2-carboxylic acid (Intermediate 3) in Step C. MS (ESI): mass calcd. for C₂₄H₃₂N₂O₂, 380.2; m/z found, 381.2 [M+H]⁺. ¹H NMR (400 MHz, Chloroform-d) δ 7.23 (t, J=7.6 Hz, 1H), 7.09-6.98 (m, 3H), 6.38 (s, 1H), 4.04-3.84 (m, 4H), 3.09 (dp, J=18.1, 8.8 Hz, 1H), 2.87 (hept, J=6.9 Hz, 1H), 2.75 (p, J=8.1 Hz, 1H), 2.55-2.45 (m, 2H), 2.38-2.25 (m, 5H), 2.22-2.16 (m, 2H), 2.16-1.82 (m, 4H), 1.81-1.66 (m, 1H), 1.24 (d, J=6.9 Hz, 6H).

Example 63: (rac)-(2s,4s)-2-(6-(4-Isopropylphenyl)-2-azaspiro[3.4]octane-2-carbonyl)-7-oxa-5-azaspiro[3.4]octan-6-one

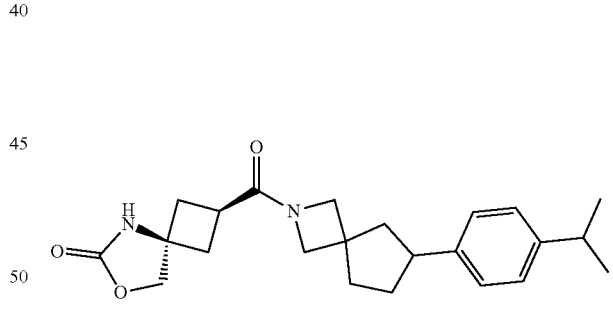

The title compound was prepared in a manner analogous to Example 57 using 2-boc-6-oxo-2-azaspiro[3.4]octane instead of tert-butyl 2-oxo-8-azaspiro[4.5]decane-8-carboxylate and 4-isopropylphenylmagnesium bromide instead of 3-tert-butylphenylmagnesium bromide in Step A. MS (ESI): mass calcd. for C₂₃H₃₀N₂O₃, 382.2; m/z found, 383.2 [M+H]⁺. ¹H NMR (400 MHz, Chloroform-d) δ 7.16 (d, J=8.2 Hz, 2H), 7.11 (d, J=8.3 Hz, 2H), 6.55 (d, J=7.9 Hz, 1H), 4.33 (s, 2H), 4.02-3.86 (m, 4H), 3.16-2.97 (m, 1H), 2.88 (hept, J=6.9 Hz, 1H), 2.75-2.66 (m, 1H), 2.66-2.57 (m, 2H), 2.48-2.36 (m, 2H), 2.30 (td, J=13.6, 7.3 Hz, 1H), 2.19-1.83 (m, 4H), 1.76-1.64 (m, 1H), 1.24 (d, J=6.9 Hz, 6H).

Example 64: (2s,4s)-2-(2-Phenyl-6-azaspiro[3.4]
octane-6-carbonyl)-7-oxa-5-azaspiro[3.4]octan-6-
one

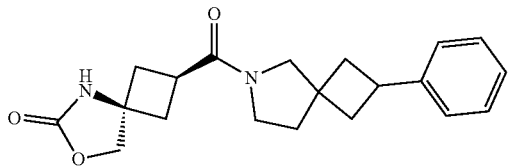 [SMILES: O=C1N[C@]2(CO1)C[C@H](C(=O)N1CCC3(CC(c4ccccc4)C3)C1)C2]

Step A: tert-Butyl 2-phenyl-6-azaspiro[3.4]octane-6-carboxylate. tert-Butyl 2-oxo-6-azaspiro[3.4]octane-6-carboxylate (100 mg, 0.444 mmol) and 4-methylbenzenesulfonhydrazide (85 mg, 0.444 mmol) were taken up in 1,4-dioxane (0.9 mL) and heated to 80° C. for 2.5 h. Potassium carbonate (K2CO₃) (92 mg, 0.666 mmol) and phenylboronic acid (85 mg, 0.666 mmol) were added and this was heated to 110° C. for 10 h. The reaction was quenched with saturated aqueous NaHCO₃ and extracted with EtOAc. The combined organic layers were dried over Na₂SO₄, filtered, and concentrated under reduced pressure. Purification via FCC on silica (0-20% EtOAc in hexane) afforded the title compound (13 mg, 10% yield). MS (ESI): mass calcd. for $C_{18}H_{25}NO_2$, 287.2; m/z found, 232.2 [M-tBu+2H]⁺.

Step B: 2-Phenyl-6-azaspiro[3.4]octan-6-ium chloride. To tert-butyl 2-phenyl-6-azaspiro[3.4]octane-6-carboxylate (13 mg, 0.045 mmol) in MeOH (91 µL) was added HCl in 1,4-dioxane (4 M, 0.11 mL). This was heated to 45° C. for 1 h before concentrating under reduced pressure. The title compound was used without further purification in the next step. MS (ESI): mass calcd. for $C_{13}H_{17}N$, 187.1; m/z found, 188.1 [M+H]⁺.

Step C: (2s,4s)-2-(2-Phenyl-6-azaspiro[3.4]octane-6-carbonyl)-7-oxa-5-azaspiro[3.4]octan-6-one. 2-Phenyl-6-azaspiro[3.4]octan-6-ium chloride was taken up in DMF (0.45 mL) and to this was added (2s,4s)-6-oxo-7-oxa-5-azaspiro[3.4]octane-2-carboxylic acid (Intermediate 3, 8 mg, mmol), DIPEA (24 µL, 0.136 mmol), and HATU (19.5 mg, 0.050 mmol). This was stirred at room temperature for 16 hours. The reaction was filtered through a PTFE filter with MeOH and purified via reverse phase HPLC (5-95% MeCN in 20 mM NH₄OH in water) to afford the title compound (11 mg, 75% yield). MS (ESI): mass calcd. for $C_{20}H_{24}N_2O_3$, 340.2; m/z found, 341.2 [M+H]⁺. ¹H NMR (400 MHz, Chloroform-d) δ 7.31 (td, J=7.6, 3.7 Hz, 2H), 7.19 (dd, J=7.6, 4.4 Hz, 3H), 6.49-6.34 (m, 1H), 4.41-4.29 (m, 2H), 3.70-3.26 (m, 5H), 2.87 (dp, J=31.6, 8.2 Hz, 1H), 2.76-2.57 (m, 2H), 2.57-2.29 (m, 4H), 2.28-2.10 (m, 2H), 2.10-1.82 (m, 2H).

Example 65: (2s,4s)-2-(6-(3-(tert-Butyl)phenyl)-2-
azaspiro[3.3]heptane-2-carbonyl)-7-oxa-5-azaspiro
[3.4]octan-6-one

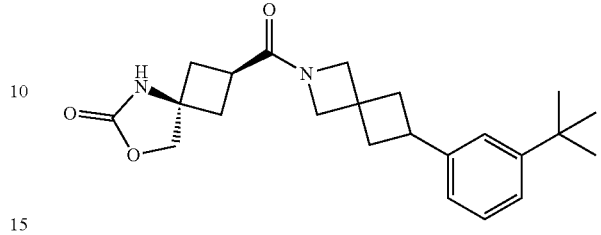

Step A: tert-Butyl 6-(3-(tert-butyl)phenyl)-2-azaspiro[3.3]heptane-2-carboxylate. (3-(tert-Butyl)phenyl)boronic acid (881 mg, 4.95 mmol), (1R,2R)-2-aminocyclohexanol (57 mg, 0.495 mmol), and nickel(II) iodide (155 mg, 0.495 mmol) were dissolved in isopropanol (10 mL). The resultant mixture was stirred at 25° C. for 30 minutes under N₂ atmosphere and then treated with NaHMDS (4.95 mL, 1M in THF, 4.95 mmol). The resultant mixture was stirred for 10 minutes under nitrogen atmosphere, followed by adding a solution of tert-butyl 6-iodo-2-azaspiro[3.3]heptane-2-carboxylate (Intermediate 50, 800 mg, 2.47 mmol) in isopropanol (5 mL). The resultant mixture was stirred at 70° C. for 14 hours under nitrogen atmosphere, then concentrated and purified by FCC (eluent:petroleum ether:ethyl acetate=1:0 to 5:1) to afford the title compound (800 mg, 67% yield) as light-yellow oil. MS (ESI): mass calcd. for $C_{21}H_{31}NO_2$ 329.2 m/z, found 274.2 [M-tBu+2H]⁺. ¹H NMR (400 MHz, CDCl₃) δ 7.26-7.20 (m, 2H), 7.19-7.12 (m, 1H), 7.03-6.97 (m, 1H), 4.06 (s, 2H), 3.85 (s, 2H), 3.45-3.31 (m, 1H), 2.61-2.54 (m, 2H), 2.33-2.24 (m, 2H), 1.44 (s, 9H), 1.31 (s, 9H).

Step B: 6-(3-(tert-Butyl)phenyl)-2-azaspiro[3.3]heptane. tert-Butyl 6-(3-(tert-butyl)phenyl)-2-azaspiro[3.3]heptane-2-carboxylate (300 mg, 0.628 mmol) was dissolved in a mixture of TFA (1 mL) and DCM (1 mL). The resultant mixture was stirred at room temperature for 2 hours and then concentrated to give the title compound (150 mg, crude) as a yellow oil, which was used in the next step without further purification. MS (ESI): mass calcd. for $C_{16}H_{23}N$ 229.2 m/z, found 230.2 [M+H]⁺.

Step C: (2s,4s)-2-(6-(3-(tert-Butyl)phenyl)-2-azaspiro[3.3]heptane-2-carbonyl)-7-oxa-5-azaspiro[3.4]octan-6-one. HATU (333 mg, 0.876 mmol) was added to a solution of (2s,4s)-6-oxo-7-oxa-5-azaspiro[3.4]octane-2-carboxylic acid (75 mg, 0.438 mmol), 6-(3-(tert-butyl)phenyl)-2-azaspiro[3.3]heptane (150 mg, crude), and DIPEA (283 mg, 2.19 mmol) in DMF (5 mL). The resultant mixture was stirred at room temperature for 12 hours, poured into H₂O, and extracted 2× with ethyl acetate. The combined organic extracts were washed with brine, dried over anhydrous Na₂SO₄, and purified by FCC (eluent:dichloromethane:methanol=1:0 to then re-purified by reverse-phase HPLC using a Boston Prime C18, 150 mm×30 mm×5 µm column (eluent:55% to 85% (v/v) CH₃CN and H₂O with 0.04% NH₃ and 10 mM NH₄HCO₃) to afford the title compound (89.3 mg, 53% yield) as a white solid. MS (ESI): mass calcd. for $C_{23}H_{30}N_2O_3$, 382.2; m/z found, 383.1 [M+H]⁺. ¹H NMR (400 MHz, CDCl₃) δ 7.40-7.30 (m, 3H), 7.12-7.08 (m, 1H), 6.65 (br s, 1H), 4.44 (d, J=6.0 Hz, 2H), 4.32 (s, 1H), 4.26 (s, 1H), 4.10 (s, 1H), 4.05 (s, 1H), 3.61-3.43 (m, 1H), 2.86-2.67 (m, 5H), 2.57-2.39 (m, 4H), 1.42 (s, 9H).

Example 66: (2s,4s)-2-(6-(m-Tolyl)-2-azaspiro[3.3]heptane-2-carbonyl)-7-oxa-5-azaspiro[3.4]octan-6-one

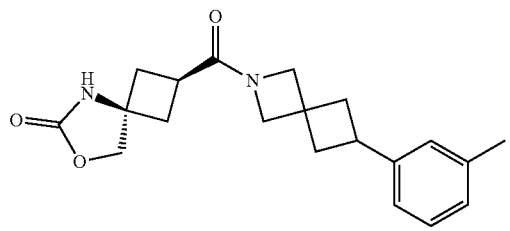 [SMILES: Cc1cccc(C2CC3(C2)CN(C(=O)[C@H]2C[C@]4(COC(=O)N4)C2)C3)c1]

The title compound was prepared in a manner analogous to (2s,4s)-2-(6-(3-(tert-butyl)phenyl)-2-azaspiro[3.3]heptane-2-carbonyl)-7-oxa-5-azaspiro[3.4]octan-6-one (Example 65), except using m-tolylboronic acid in place of 3-(tert-butyl)phenylboronic acid. MS (ESI): mass calcd. for $C_{24}H_{24}N_2O_3$, 340.2; m/z found, 341.1 [M+H]$^+$. $^1$H NMR (400 MHz, CDCl$_3$) δ 7.24-7.17 (m, 1H), 7.05-6.94 (m, 3H), 6.63 (br d, J=7.6 Hz, 1H), 4.35 (d, J=5.6 Hz, 2H), 4.24-4.13 (m, 2H), 3.98 (d, J=17.2 Hz, 2H), 3.47-3.32 (m, 1H), 2.77-2.53 (m, 5H), 2.48-2.27 (m, 7H).

Example 67: (2s,4s)-2-(6-(3-Isopropylphenyl)-2-azaspiro[3.3]heptane-2-carbonyl)-7-oxa-5-azaspiro[3.4]octan-6-one

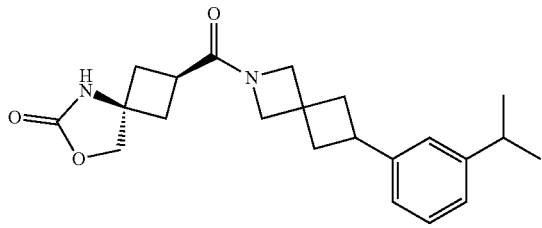 [SMILES: CC(C)c1cccc(C2CC3(C2)CN(C(=O)[C@H]2C[C@]4(COC(=O)N4)C2)C3)c1]

The title compound was prepared in a manner analogous to (2s,4s)-2-(6-(3-(tert-butyl)phenyl)-2-azaspiro[3.3]heptane-2-carbonyl)-7-oxa-5-azaspiro[3.4]octan-6-one (Example 65), except using 3-isopropylphenylboronic acid in place of 3-(tert-butyl)phenylboronic acid. MS (ESI): mass calcd. for $C_{22}H_{28}N_2O_3$, 368.2; m/z found, 369.1 [M+H]$^+$. $^1$H NMR (400 MHz, CDCl$_3$) δ 7.26-7.22 (m, 1H), 7.09 (d, J=7.6 Hz, 1H), 7.02-6.98 (m, 2H), 6.27 (br s, 1H), 4.34 (d, J=5.6 Hz, 2H), 4.23-4.15 (m, 2H), 3.98 (d, J=18.8 Hz, 2H), 3.50-3.34 (m, 1H), 2.89 (td, J=6.8, 14.0 Hz, 1H), 2.75-2.56 (m, 5H), 2.50-2.29 (m, 4H), 1.25 (d, J=6.8 Hz, 6H).

Example 68: (2s,4s)-2-(6-(3,4-Dimethylphenyl)-2-azaspiro[3.3]heptane-2-carbonyl)-7-oxa-5-azaspiro[3.4]octan-6-one

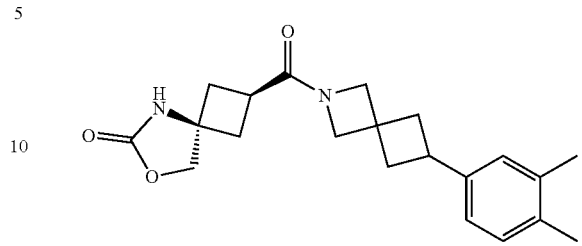

The title compound was prepared in a manner analogous to (2s,4s)-2-(6-(3-(tert-butyl)phenyl)-2-azaspiro[3.3]heptane-2-carbonyl)-7-oxa-5-azaspiro[3.4]octan-6-one (Example 65), except using 3,4-dimethylphenylboronic acid in place of 3-(tert-butyl)phenylboronic acid. MS (ESI): mass calcd. for $C_{21}H_{26}N_2O_3$, 354.2; m/z found, 355.1 [M+H]$^+$. $^1$H NMR (400 MHz, CDCl$_3$) δ 7.07 (d, J=7.6 Hz, 1H), 6.95-6.88 (m, 2H), 6.35 (br s, 1H), 4.33 (d, J=5.6 Hz, 2H), 4.22-4.12 (m, 2H), 4.00-3.91 (m, 2H), 3.45-3.28 (m, 1H), 2.76-2.65 (m, 1H), 2.62-2.52 (m, 4H), 2.48-2.39 (m, 2H), 2.35-2.27 (m, 2H), 2.24 (d, J=6.8 Hz, 6H).

Example 69: (2s,4s)-2-(6-Cyclohexyl-2-azaspiro[3.3]heptane-2-carbonyl)-7-oxa-5-azaspiro[3.4]octan-6-one

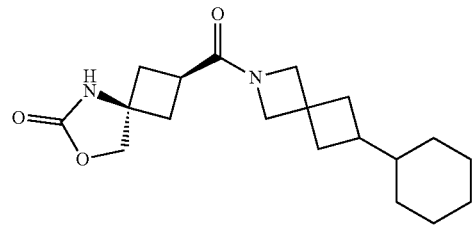 [SMILES: O=C1N[C@]2(CO1)C[C@H](C(=O)N1CC3(CC(C4CCCCC4)C3)C1)C2]

Step A: tert-Butyl 6-cyclohexyl-6-hydroxy-2-azaspiro[3.3]heptane-2-carboxylate. Cyclohexylmagnesium bromide (7.1 mL, 1 M in THF, 7.10 mmol) was added drop-wise to a cooled (−65° C., dry ice/acetone) solution of tert-butyl 6-oxo-2-azaspiro[3.3]heptane-2-carboxylate (1.0 g, 4.73 mmol) in THF (20 mL). The resultant mixture was stirred for 4 hours with gradual warming to room temperature before quenching with sat. aq. NH$_4$Cl and extracting twice with ethyl acetate. The combined organic extracts were washed with brine, dried over anhydrous Na$_2$SO$_4$, and purified by FCC (eluent:petroleum ether:ethyl acetate=1:0 to 3:1) to afford the title compound (498 mg, 36% yield) as a white solid. $^1$H NMR (400 MHz, CDCl$_3$) δ 3.96 (s, 2H), 3.84 (s, 2H), 2.31 (br d, J=13.2 Hz, 2H), 2.10 (br d, J=12.8 Hz, 2H), 1.80 (br d, J=12.4 Hz, 2H), 1.68 (br d, J=12.4 Hz, 3H), 1.43 (s, 9H), 1.28-1.11 (m, 4H), 1.06-0.93 (m, 2H).

Step B: tert-Butyl 6-cyclohexylidene-2-azaspiro[3.3]heptane-2-carboxylate. Thionyl chloride (SOCl$_2$) (245 μL, 3.37 mmol) was added to a 0° C. mixture of tert-butyl 6-cyclohexyl-6-hydroxy-2-azaspiro[3.3]heptane-2-carboxylate (498 mg, 1.69 mmol) and DMAP (20.6 mg, 0.169 mmol) in pyridine (10 mL). The resultant mixture was stirred for 2 hours with gradual warming to room temperature to give a yellow solution before quenching with sat. NaHCO$_3$ and extracting twice with ethyl acetate. The combined organic extracts were washed with brine, dried over anhydrous Na$_2$SO$_4$, and purified by FCC (eluent:petroleum ether:ethyl acetate=1:0 to 10:1) to afford the title compound (341 mg, 73% yield) as a white solid. ¹H NMR (400 MHz, CDCl₃) δ 3.91 (s, 4H), 2.76 (s, 4H), 1.94-1.88 (m, 4H), 1.52-1.44 (m, 6H), 1.43 (s, 9H).

Step C: tert-Butyl 6-cyclohexyl-2-azaspiro[3.3]heptane-2-carboxylate. tert-Butyl 6-cyclohexylidene-2-azaspiro[3.3]heptane-2-carboxylate (341 mg, 1.23 mmol) and wet Pd/C (200 mg, 10% wt, 0.189 mmol) were combined in MeOH (10 mL). The suspension was stirred under H₂ (15 psi) at room temperature for 2 hours, filtered through a pad of Celite® and concentrated to afford the title compound (320 mg, 93% yield) as colorless oil. ¹H NMR (400 MHz, CDCl₃) δ 3.90 (s, 2H), 3.75 (s, 2H), 2.22-2.08 (m, 2H), 1.79-1.72 (m, 3H), 1.69-1.58 (m, 5H), 1.42 (s, 9H), 1.20-1.01 (m, 4H), 0.77-0.64 (m, 2H).

Step D: 6-Cyclohexyl-2-azaspiro[3.3]heptane. tert-Butyl 6-cyclohexyl-2-azaspiro[3.3]heptane-2-carboxylate (150 mg, 0.537 mmol) was dissolved in a mixture of TFA (2 mL) and dichloromethane (4 mL). The mixture was stirred at room temperature for 2 hours and then concentrated to afford the title compound (160 mg, as TFA salt crude) as a yellow oil, which was used in the next step without further purification. ¹H NMR (400 MHz, CDCl₃) δ 8.28 (br s, 1H), 4.16-4.10 (m, 2H), 3.97 (br s, 2H), 2.34-2.26 (m, 2H), 1.90-1.77 (m, 3H), 1.70-1.58 (m, 1.19-0.99 (m, 4H), 0.78-0.65 (m, 2H).

Step E: (2s,4s)-2-(6-Cyclohexyl-2-azaspiro[3.3]heptane-2-carbonyl)-7-oxa-5-azaspiro[3.4]octan-6-one. HATU (222 mg, 0.584 mmol) was added to a solution of (2s,4s)-6-oxo-7-oxa-5-azaspiro[3.4]octane-2-carboxylic acid (50 mg, 0.292 mmol), 6-cyclohexyl-2-azaspiro[3.3]heptane (160 mg, crude), and DIPEA (189 mg, 1.46 mmol) in DMF (10 mL). The resultant mixture was stirred at room temperature for 3 hours before pouring it into H₂O and extracting twice with ethyl acetate. The combined organic extracts were washed with brine, dried over anhydrous Na₂SO₄, filtered, and concentrated. The residue was purified by FCC (eluent: dichloromethane:methanol=1:0 to 10:1) followed by preparative HPLC using a Welch Xtimate C18, 100 mm×40 mm×3 μm column (eluent:50% to 60% (v/v) CH₃CN and H₂O with 0.225% HCOOH) to afford the title compound (58.4 mg, 60% yield) as a white solid. MS (ESI): mass calcd. for C₁₉H₂₈N₂O₃, 332.2; m/z found, 333.1 [M+H]⁺. ¹H NMR (400 MHz, CDCl₃) δ 6.26 (br s, 1H), 4.32 (d, J=1.2 Hz, 2H), 4.07-3.97 (m, 2H), 3.91-3.82 (m, 2H), 2.71-2.61 (m, 1H), 2.59-2.52 (m, 2H), 2.46-2.38 (m, 2H), 2.24-2.14 (m, 2H), 1.87-1.75 (m, 3H), 1.73-1.63 (m, 1.20-1.00 (m, 4H), 0.79-0.64 (m, 2H).

Example 70: (2s,4s)-2-(6-(3,5-Dimethylphenyl)-2-azaspiro[3.3]heptane-2-carbonyl)-7-oxa-5-azaspiro[3.4]octan-6-one

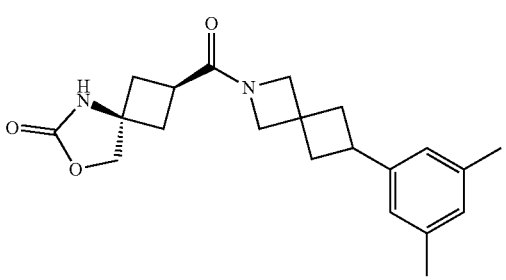 [SMILES: Cc1cc(C)cc(C2CC3(C2)CN(C(=O)[C@H]2C[C@]4(COC(=O)N4)C2)C3)c1]

The title compound was prepared in a manner analogous to (2s,4s)-2-(6-(3-(tert-butyl)phenyl)-2-azaspiro[3.3]heptane-2-carbonyl)-7-oxa-5-azaspiro[3.4]octan-6-one (Example 65), except using 3,5-dimethylphenylboronic acid in place of 3-(tert-butyl)phenylboronic acid. MS (ESI): mass calcd. for C₂₁H₂₆N₂O₃, 354.2; m/z found, 355.1 [M+H]⁺. ¹H NMR (400 MHz, CDCl₃) δ 6.85 (s, 1H), 6.77 (s, 2H), 6.30 (br s, 1H), 4.33 (d, J=5.2 Hz, 2H), 4.23-4.12 (m, 2H), 4.00-3.91 (m, 2H), 3.44-3.26 (m, 1H), 2.78-2.63 (m, 1H), 2.62-2.51 (m, 4H), 2.49-2.39 (m, 2H), 2.37-2.24 (m, 8H).

Example 71: (2s,4s)-2-(6-(2,4-Dimethylphenyl)-2-azaspiro[3.3]heptane-2-carbonyl)-7-oxa-5-azaspiro[3.4]octan-6-one

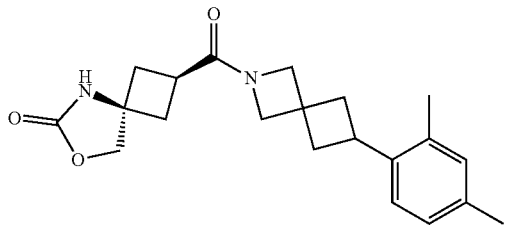 [SMILES: Cc1ccc(C2CC3(C2)CN(C(=O)[C@H]2C[C@]4(COC(=O)N4)C2)C3)c(C)c1]

The title compound was prepared in a manner analogous to (2s,4s)-2-(6-(3-(tert-butyl)phenyl)-2-azaspiro[3.3]heptane-2-carbonyl)-7-oxa-5-azaspiro[3.4]octan-6-one (Example 65), except using 2,4-dimethylphenylboronic acid in place of 3-(tert-butyl)phenylboronic acid. MS (ESI): mass calcd. for C₂₁H₂₆N₂O₃, 354.2; m/z found, 355.1 [M+H]⁺. ¹H NMR (400 MHz, CDCl₃) δ 7.06-6.94 (m, 3H), 6.26 (br s, 1H), 4.33 (d, J=5.6 Hz, 2H), 4.26-4.14 (m, 2H), 3.99-3.89 (m, 2H), 3.55-3.40 (m, 1H), 2.77-2.55 (m, 5H), 2.49-2.40 (m, 2H), 2.34-2.25 (m, 5H), 2.19 (d, J=3.6 Hz, 3H).

Example 72: (2s,4s)-2-(6-(3-Cyclopropylphenyl)-2-azaspiro[3.3]heptane-2-carbonyl)-7-oxa-5-azaspiro[3.4]octan-6-one

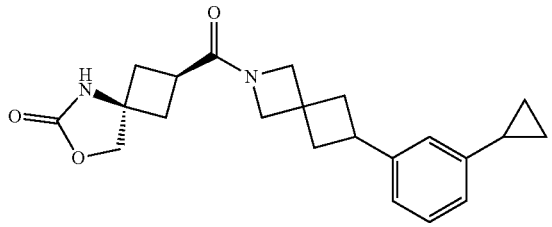 [SMILES: O=C1N[C@]2(CO1)C[C@H](C(=O)N1CC3(CC(c4cccc(C5CC5)c4)C3)C1)C2]

Step A: tert-Butyl 6-(3-cyclopropylphenyl)-6-hydroxy-2-azaspiro[3.3]heptane-2-carboxylate. n-BuLi (0.49 mL, 2.5 M in hexanes, 1.23 mmol) was added drop-wise to a −78° C. solution of 1-bromo-3-cyclopropylbenzene (224 mg, 1.14 mmol) in THF (5 mL). The resultant mixture was stirred for 0.5 hours at −78° C. and then treated with a solution of tert-butyl 6-oxo-2-azaspiro[3.3]heptane-2-carboxylate (200 mg, 0.947 mmol) in THF (5 mL). The mixture was stirred for another 2 hours before pouring it into sat. aq. NH₄Cl and extracting with three times with ethyl acetate. The combined organic extracts were dried over anhydrous Na₂SO₄, filtered, concentrated, and purified by FCC (eluent:petroleum ether: ethyl acetate=1:0 to 3:1) to afford the title compound (230 mg, 71% yield) as a yellow solid. MS (ESI): mass calcd. for $C_{20}H_{27}NO_3$ 329.2 m/z, found 659.4 $[2M+H]^+$. $^1H$ NMR (400 MHz, $CDCl_3$) δ 7.26-7.24 (m, 1H), 7.20-7.12 (m, 2H), 6.98 (d, J=8.0 Hz, 1H), 4.08 (s, 2H), 3.82 (s, 2H), 2.80-2.73 (m, 2H), 2.58-2.52 (m, 2H), 2.05 (s, 1H), 1.44 (s, 9H), 1.27 (t, J=7.2 Hz, 1H), 1.03-0.95 (m, 2H), 0.74-0.68 (m, 2H).

Step B: 6-(3-cyclopropylphenyl)-2-azaspiro[3.3]heptane. tert-Butyl 6-(3-cyclopropylphenyl)-6-hydroxy-2-azaspiro [3.3]heptane-2-carboxylate (230 mg, 0.674 mmol) was dissolved in TFA (1 mL). The resultant mixture was stirred for 20 minutes before treating with triethylsilane (235 mg, 2.02 mmol). The mixture was stirred for another 2 hours and then concentrated to afford the title compound (220 mg, crude) as colorless oil which was used in the next step without further purification. MS (ESI): $C_{15}H_{19}N$ 213.2 m/z, found 214.1 $[M+H]^+$.

Step C: (2s,4s)-2-(6-(3-Cyclopropylphenyl)-2-azaspiro [3.3]heptane-2-carbonyl)-7-oxa-5-azaspiro[3.4]octan-6-one. HATU (222 mg, 0.584 mmol) was added to a solution of (2s,4s)-6-oxo-7-oxa-5-azaspiro[3.4]octane-2-carboxylic acid (Intermediate 3, 50 mg, 0.292 mmol), 6-(3-cyclopropylphenyl)-2-azaspiro[3.3]heptane (220 mg, 0.672 mmol) and DIPEA (0.24 mL, 1.46 mmol) in DMF (10 mL). The resultant mixture was stirred at room temperature for 16 hours before pouring it into sat. aq. $NH_4Cl$ and extracting three times with ethyl acetate. The combined organic extracts were washed three times with brine, dried over anhydrous $Na_2SO_4$, filtered and concentrated. The residue was purified by FCC (eluent:dichloromethane:methyl alcohol=1:0 to 97:3) followed by preparative HPLC using a Phenomenex Gemini-NX, 80 mm×30 mm×3 column (eluent:41% to 51% (v/v) $CH_3CN$ and $H_2O$ with 10 mM $NH_4HCO_3$) to afford the title compound (37.9 mg, 35% yield) as a white solid. MS (ESI): mass calcd. for $C_{22}H_{26}N_2O_3$, 366.2; m/z found, 367.1 $[M+H]^+$. $^1H$ NMR (400 MHz, $CDCl_3$) δ 7.23-7.18 (m, 1H), 6.96 (d, J=7.6 Hz, 1H), 6.92-6.87 (m, 2H), 6.19 (br s, 1H), 4.34 (d, J=5.2 Hz, 2H), 4.23-4.13 (m, 2H), 3.97 (d, J=19.2 Hz, 2H), 3.48-3.32 (m, 1H), 2.78-2.66 (m, 1H), 2.65-2.54 (m, 4H), 2.51-2.41 (m, 2H), 2.39-2.26 (m, 2H), 1.92-1.84 (m, 1H), 0.99-0.93 (m, 2H), 0.72-0.66 (m, 2H).

Example 73: (2s,4s)-2-(6-(3-Cyclobutylphenyl)-2-azaspiro[3.3]heptane-2-carbonyl)-7-oxa-5-azaspiro [3.4]octan-6-one

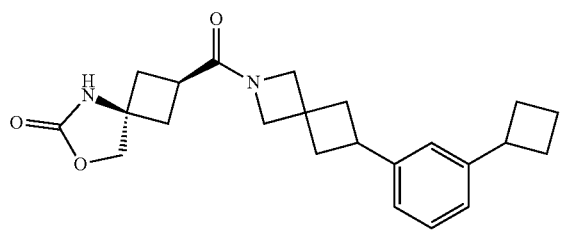 [SMILES: O=C1N[C@]2(CO1)C[C@H](C(=O)N1CC3(CC(c4cccc(C5CCC5)c4)C3)C1)C2]

The title compound was prepared in a manner analogous to (2s,4s)-2-(6-(3-cyclopropylphenyl)-2-azaspiro[3.3]heptane-2-carbonyl)-7-oxa-5-azaspiro[3.4]octan-6-one (Example 72), except using 1-bromo-3-cyclobutylbenzene (Intermediate 51) in place of 1-bromo-3-cyclopropylbenzene. MS (ESI): mass calcd. for $C_{23}H_{28}N_2O_3$, 380.2; m/z found, 381.1 $[M+H]^+$. $^1H$ NMR (400 MHz, $CDCl_3$) δ 7.26-7.22 (m, 1H), 7.07 (d, J=8.0 Hz, 1H), 7.00-6.96 (m, 2H), 6.34 (br s, 1H), 4.34 (s, 1H), 4.32 (s, 1H), 4.21 (s, 1H), 4.15 (s, 1H), 3.99 (s, 1H), 3.94 (s, 1H), 3.52 (quin, J=8.8 Hz, 1H), 3.47-3.32 (m, 1H), 2.77-2.65 (m, 1H), 2.64-2.55 (m, 4H), 2.48-2.40 (m, 2H), 2.39-2.28 (m, 4H), 2.19-2.08 (m, 2H), 2.08-1.97 (m, 1H), 1.89-1.79 (m, 1H).

Example 74: (2s,4s)-2-(6-(2,3-Dihydro-1H-inden-5-yl)-2-azaspiro[3.3]heptane-2-carbonyl)-7-oxa-5-azaspiro[3.4]octan-6-one

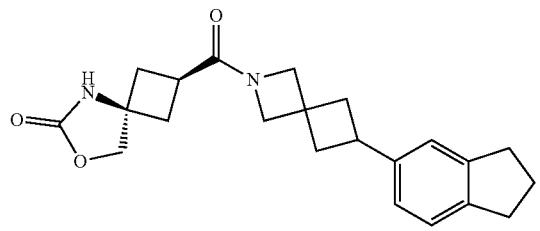 [SMILES: O=C1N[C@]2(CO1)C[C@H](C(=O)N1CC3(CC(c4ccc5c(c4)CCC5)C3)C1)C2]

The title compound was prepared in a manner analogous to (2s,4s)-2-(6-(3-(tert-butyl)phenyl)-2-azaspiro[3.3]heptane-2-carbonyl)-7-oxa-5-azaspiro[3.4]octan-6-one (Example 65), except using (2,3-dihydro-1H-inden-5-yl)boronic acid in place of 3-(tert-butyl)phenylboronic acid. MS (ESI): mass calcd. for $C_{22}H_{26}N_2O_3$, 366.2; m/z found, 367.1 $[M+H]^+$. $^1H$ NMR (400 MHz, $CDCl_3$) δ 7.16 (d, J=7.6 Hz, 1H), 7.04 (br s, 1H), 6.93 (d, J=7.6 Hz, 1H), 6.22 (br s, 1H), 4.33 (d, J=4.8 Hz, 2H), 4.24-4.11 (m, 2H), 4.01-3.91 (m, 2H), 3.47-3.31 (m, 1H), 2.92-2.83 (m, 4H), 2.77-2.65 (m, 1H), 2.63-2.53 (m, 4H), 2.49-2.40 (m, 2H), 2.37-2.25 (m, 2H), 2.11-2.02 (m, 2H).

Example 75: (2s,4s)-2-(6-Phenyl-2-azaspiro[3.3] heptane-2-carbonyl)-7-oxa-5-azaspiro[3.4]octan-6-one

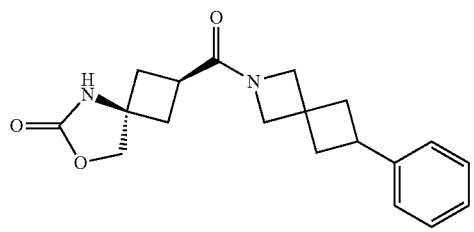 [SMILES: O=C1N[C@]2(CO1)C[C@H](C(=O)N1CC3(CC(c4ccccc4)C3)C1)C2]

Triethylamine (110 μL, 794 μmol) was added dropwise to a stirring 0° C. mixture of 6-phenyl-2-azaspiro[3.3]heptane (Intermediate 49, 25.0 mg, 87.0 μmol), (2s,4s)-6-oxo-7-oxa-5-azaspiro[3.4]octane-2-carboxylic acid (Intermediate 3, 14.9 mg, 87.0 μmol) and HATU (41.0 mg, 95.7 μmol) in N,N-dimethylacetamide (870 The reaction mixture was allowed to stir at room temperature for 14 h and subsequently diluted with water (1 mL). Purification by reverse-phase HPLC (MeCN/$H_2O$, 0.05% TFA) afforded the title product (23.4 mg, 71.7 μmol, 82% yield). MS (ESI): mass calcd. for $C_{19}H_{22}N_2O_3$, 326.2; m/z found, 327.2 $[M+H]^+$. $^1H$ NMR (500 MHz, Methanol-d4) δ 7.34-7.25 (m, 2H), 7.24-7.13 (m, 3H), 4.48 (d, J=10.6 Hz, 2H), 4.32 (s, 1H), 4.13 (s, 1H), 4.09 (s, 1H), 3.90 (s, 1H), 3.50-3.39 (m, 1H), 2.91-2.78 (m, 1H), 2.66-2.29 (m, 8H).

Example 76: (2s,4s)-2-(7-Phenyl-2-azaspiro[3.5]nonane-2-carbonyl)-7-oxa-5-azaspiro[3.4]octan-6-one

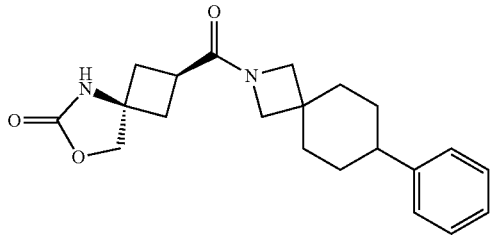 [SMILES: O=C1N[C@]2(CO1)C[C@H](C(=O)N1CC3(CCC(c4ccccc4)CC3)C1)C2]

The title compound was prepared in a manner analogous to (2s,4s)-2-(6-phenyl-2-azaspiro[3.3]heptane-2-carbonyl)-7-oxa-5-azaspiro[3.4]octan-6-one (Example 75), except using 7-phenyl-2-azaspiro[3.5]heptane (Intermediate 52), instead of 6-phenyl-2-azaspiro[3.3]heptane (Intermediate 49). MS (ESI): mass calcd. for $C_{21}H_{26}N_2O_3$, 354.2; m/z found, 355.2 [M+H]$^+$. $^1$H NMR (500 MHz, Methanol-d4) δ 7.32-7.12 (m, 5H), 4.49 (d, J=5.38 Hz, 2H), 3.96 (s, 1H), 3.83 (s, 1H), 3.77 (s, 1H), 3.64 (s, 1H), 2.95-2.82 (m, 1H), 2.59-2.39 (m, 5H), 2.07-1.98 (m, 2H), 1.88-1.79 (m, 2H), 1.68 (m, 2H), 1.58-1.44 (m, 2H).

Example 77: (2s,4s)-2-(6-Cyclopentyl-2-azaspiro[3.3]heptane-2-carbonyl)-7-oxa-5-azaspiro[3.4]octan-6-one

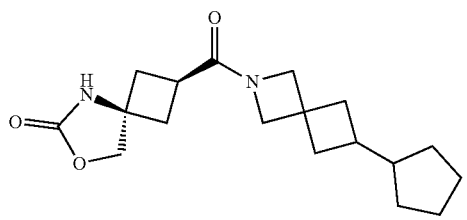 [SMILES: O=C1N[C@]2(CO1)C[C@H](C(=O)N1CC3(CC(C4CCCC4)C3)C1)C2]

The title compound was prepared in a manner analogous to Example 69 using cyclopentylmagnesium bromide instead of cyclohexylmagnesium bromide in Step A. MS (ESI): mass calcd. for $C_{18}E126N_2O_3$, 318.2; m/z found, 319.1 [M+H]$^+$. $^1$H NMR (400 MHz, CDCl$_3$) δ 6.21 (br s, 1H), 4.32 (d, J=1.2 Hz, 2H), 4.06 (s, 1H), 4.00 (s, 1H), 3.94 (s, 1H), 3.88 (s, 1H), 2.74-2.64 (m, 1H), 2.59-2.52 (m, 2H), 2.47-2.39 (m, 2H), 2.28-2.18 (m, 2H), 2.05-1.91 (m, 1H), 1.89-1.63 (m, 5H), 1.58-1.48 (m, 4H), 1.10-0.99 (m, 2H).

Example 78: (2s,4s)-2-(6-Cyclobutyl-2-azaspiro[3.3]heptane-2-carbonyl)-7-oxa-5-azaspiro[3.4]octan-6-one

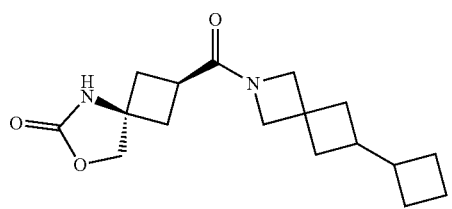 [SMILES: O=C1N[C@]2(CO1)C[C@H](C(=O)N1CC3(CC(C4CCC4)C3)C1)C2]

The title compound was prepared in a manner analogous to Example 69 using cyclobutylmagnesium bromide instead of cyclohexylmagnesium bromide in Step A. MS (ESI): mass calcd. for $C_{17}H_{24}N_2O_3$, 304.2; m/z found, 305.1 [M+H]$^+$. $^1$H NMR (400 MHz, CDCl$_3$) δ 6.21 (br s, 1H), 4.32 (d, J=1.2 Hz, 2H), 4.08-3.84 (m, 4H), 2.74-2.63 (m, 1H), 2.59-2.52 (m, 2H), 2.48-2.39 (m, 2H), 2.32-2.12 (m, 4H), 2.01-1.90 (m, 2H), 1.88-1.74 (m, 4H), 1.59-1.49 (m, 2H).

Example 79: (2s,4s)-2-(6-(1-Methylcyclopropyl)-2-azaspiro[3.3]heptane-2-carbonyl)-7-oxa-5-azaspiro[3.4]octan-6-one

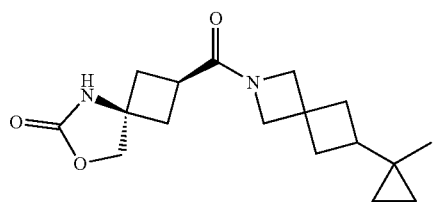 [SMILES: CC1(C2CC3(C2)CN(C(=O)[C@H]2C[C@]4(COC(=O)N4)C2)C3)CC1]

Step A: tert-Butyl 6-hydroxy-6-(prop-1-en-2-yl)-2-azaspiro[3.3]heptane-2-carboxylate. Prop-1-en-2-ylmagnesium bromide (0.5 M in THF, 7.1 mL, 3.55 mmol) was added dropwise to a −78° C. solution of tert-butyl 6-oxo-2-azaspiro[3.3]heptane-2-carboxylate (500 mg, 2.37 mmol) in THF (20 mL). The resultant mixture was stirred for 2 hours before being quenched with sat. aq. NH$_4$Cl and extracted with EtOAc. The combined organic extracts were washed with brine, dried over anhydrous Na$_2$SO$_4$, filtered, and concentrated under reduced pressure. The resulting residue was purified by FCC (0-30% EtOAc in ether) to afford the title compound as a white solid (270 mg, 45% yield). MS (ESI): mass calcd. for $C_{14}H_{23}NO_3$, 253.2; m/z found, 197.9 [M+2H-tBu]$^+$.

Step B: tert-Butyl 6-hydroxy-6-(1-methylcyclopropyl)-2-azaspiro[3.3]heptane-2-carboxylate. A solution of TFA (0.41 mL, 5.33 mmol) in DCM (2.0 mL) was added dropwise to a 0° C. solution of diethylzinc (1M in hexanes, 5.3 mL, 5.33 mmol) in DCM (2.0 mL). The resultant mixture was stirred for 20 min before being treated with a solution of diiodomethane (0.43 mL, 5.33 mmol) in DCM (2.0 mL) and stirred for an additional 20 min. Finally, a solution of tert-butyl 6-hydroxy-6-(prop-1-en-2-yl)-2-azaspiro[3.3]heptane-2-carboxylate (270 mg, 1.07 mmol) in DCM (4.0 mL) was added to the reaction mixture, and the reaction mixture was stirred for 30 min. The reaction mixture was quenched with sat. aq. NH$_4$Cl and extracted with EtOAc. The combined organic extracts were washed with sat. aq. NaHCO$_3$ and brine, dried over Na$_2$SO$_4$, filtered, and concentrated under reduced pressure. Purification of the resulting residue by FCC (0-40% EtOAc in ether) afforded the title compound as a white solid (220 mg, 34% yield). MS (ESI): mass calcd. for $C_{15}H_{25}NO_3$, 267.2; m/z found, 212.0 [M+2H-tBu]$^+$.

Step C: tert-Butyl 6-(1-methylcyclopropyl)-2-azaspiro[3.3]hept-5-ene-2-carboxylate. To a solution of tert-butyl 6-hydroxy-6-(1-methylcyclopropyl)-2-azaspiro[3.3]heptane-2-carboxylate (220 mg, 0.823 mmol) in toluene (3.0 mL) was added Burgess reagent (methyl N-(triethylammoniumsulfonyl)carbamate) (294 mg, 1.23 mmol), and the reaction mixture was heated to 120° C. and stirred for 16 hours. The reaction mixture was cooled to rt, then poured into sat. aq. NaHCO$_3$ and extracted with EtOAc. The combined organic extracts were washed with brine, dried over anhydrous Na₂SO₄, filtered, and concentrated under reduced pressure. Purification of the resulting residue (FCC, SiO₂, 0-10% EtOAc in ether) afforded the title compound as a colorless oil (70 mg, 34% yield).

Step D: tert-Butyl 6-(1-methylcyclopropyl)-2-azaspiro[3.3]heptane-2-carboxylate. A solution of tert-Butyl 6-(1-methylcyclopropyl)-2-azaspiro[3.3]hept-5-ene-2-carboxylate (850 mg, 3.41 mmol) and wet Pd/C (80 mg, 10 wt. %) in EtOAc (20 mL) was stirred under H₂ (15 psi) at rt for 2 hours. The reaction mixture was filtered through a pad of Celite® and the pad was washed with EtOAc. The resulting filtrate was concentrated under reduced pressure, and the resulting residue was purified by RP-HPLC (30-90% ACN in H₂O with 0.05% NH₃) to afford the title product as a colorless oil (102 mg, 12% yield).

Step E: 6-(1-Methylcyclopropyl)-2-azaspiro[3.3]heptane. TFA (1.5 mL, 19.7 mmol) was added dropwise to a solution of tert-butyl 6-(1-methylcyclopropyl)-2-azaspiro[3.3]heptane-2-carboxylate (102 mg, 0.406 mmol) in DCM (5.0 mL). The resultant mixture was stirred at rt for 1 hour. The reaction mixture was concentrated under reduced pressure to afford the title compound (100 mg) as a brown oil, which was used in the next step without further purification.

Step F: (2s,4s)-2-(6-(1-Methylcyclopropyl)-2-azaspiro[3.3]heptane-2-carbonyl)-7-oxa-5-azaspiro[3.4]octan-6-one. HATU (215 mg, 0.566 mmol) was added to a solution of (2s,4s)-6-oxo-7-oxa-5-azaspiro[3.4]octane-2-carboxylic acid (Intermediate 3, 64.5 mg, 0.377 mmol), 6-(1-methylcyclopropyl)-2-azaspiro[3.3]heptane (100 mg, 0.377 mmol) and DIPEA (0.31 mL, 1.89 mmol) in DMF (10 mL). The resultant mixture was stirred at rt for 16 hours. The reaction mixture was poured into sat. aq. NH₄Cl and extracted with EtOAc. The combined organic extracts were washed with brine, dried over anhydrous Na₂SO₄, filtered, and concentrated under reduced pressure. The resulting residue was purified by RP-HPLC (31-61% ACN in H₂O with 10 mM NH₄HCO₃) to afford the title compound (110 mg, 96% yield). MS (ESI): mass calcd. for $C_{17}H_{24}N_2O_3$, 304.2; m/z found, 305.1 [M+H]⁺. ¹H NMR (400 MHz, CDCl₃) δ 6.12 (br s, 1H), 4.32 (s, 2H), 4.08-3.99 (m, 2H), 3.93-3.83 (m, 2H), 2.73-2.65 (m, 1H), 2.58-2.51 (m, 2H), 2.49-2.40 (m, 2H), 2.27-2.15 (m, 1H), 2.08 (q, J=10.0 Hz, 2H), 1.81-1.68 (m, 2H), 0.98 (s, 3H), 0.29-0.23 (m, 2H), 0.21-0.15 (m, 2H).

Biological Data

The assay used to measure the in vitro activity of MGL is adapted from the assay used for another serine hydrolase (FAAH) described in Wilson et al., 2003 (A high-throughput-compatible assay for determining the activity of fatty acid amide hydrolase. Wilson S J, Lovenberg T W, Barbier A J. Anal Biochem. 2003 Jul. 15; 318(2):270-5.). The assay consists of combining endogenously expressed MGL from HeLa cells with test compounds, adding [glycerol-1,3-³H]-oleoyl glycerol, incubating for one hour, and then measuring the amount of cleaved [1,3-³H]-glycerol that passes through an activated carbon filter. The amount of cleaved, tritiated glycerol passing through the carbon filter is proportional to the activity of the MGL enzyme in a particular well/test condition.

Standard conditions for this assay combine 300 nM [Glycerol-1,3-³H]-oleoyl glycerol with human MGL from HeLa cells and test compounds for one hour, after which the reaction is filtered through activated carbon and tritium is measured in the flow through. The test compound concentration in screening mode is 10 μM, while the highest compound concentration in IC₅₀ assays is determined empirically. MGL is the predominant hydrolase in HeLa cells/cell homogenates.

TABLE 3

| Example # | Compound Name | MGL IC₅₀ (nM) |
|---|---|---|
| 1 | (2s,4s)-2-(2-Phenyl-7-azaspiro[3.5]nonane-7-carbonyl)-7-oxa-5-azaspiro[3.4]octan-6-one; | 2.8 |
| 2 | (2s,4s)-2-(2-(3-(tert-Butyl)phenyl)-7-azaspiro[3.5]nonane-7-carbonyl)-7-oxa-5-azaspiro[3.4]octan-6-one; | 0.014 |
| 3 | (2s,4s)-2-(2-(p-Tolyl)-7-azaspiro[3.5]nonane-7-carbonyl)-7-oxa-5-azaspiro[3.4]octan-6-one; | 1.8 |
| 4 | (2s,4s)-2-(2-(o-Tolyl)-7-azaspiro[3.5]nonane-7-carbonyl)-7-oxa-5-azaspiro[3.4]octan-6-one; | 1.6 |
| 5 | (2s,4s)-2-[2-(3-Cyclopropylphenyl)-7-azaspiro[3.5]nonane-7-carbonyl)-7-oxa-5-azaspiro[3.4]octan-6-one; | 0.088 |
| 6 | (2s,4s)-2-[2-(3-Isopropylphenyl)-7-azaspiro[3.5]nonane-7-carbonyl)-7-oxa-5-azaspiro[3.4]octan-6-one; | 0.041 |
| 7 | (2s,4s)-2-[2-(m-Tolyl)-7-azaspiro[3.5]nonane-7-carbonyl)-7-oxa-5-azaspiro[3.4]octan-6-one; | 1.1 |
| 8 | (2s,4s)-2-[2-(3-Methoxyphenyl)-7-azaspiro[3.5]nonane-7-carbonyl)-7-oxa-5-azaspiro[3.4]octan-6-one; | 3.6 |
| 9 | (2s,4s)-2-[2-[3-(Trifluoromethoxy)phenyl]-7-azaspiro[3.5]nonane-7-carbonyl)-7-oxa-5-azaspiro[3.4]octan-6-one; | 0.094 |
| 10 | (2s,4s)-2-[2-(2,3-Dimethylphenyl)-7-azaspiro[3.5]nonane-7-carbonyl)-7-oxa-5-azaspiro[3.4]octan-6-one; | 0.11 |
| 11 | (2r,4s)-2-(2-(3-(tert-Butyl)phenyl)-7-azaspiro[3.5]nonane-7-carbonyl)-5-azaspiro[3.4]octan-6-one; | 0.082 |
| 12 | (2s,4s)-2-[2-(2,4-Dimethylphenyl)-7-azaspiro[3.5]nonane-7-carbonyl)-7-oxa-5-azaspiro[3.4]octan-6-one; | 0.048 |
| 13 | (2s,4s)-2-[2-(2-(Tert-butyl)pyridin-4-yl)-7-azaspiro[3.5]nonane-7-carbonyl)-7-oxa-5-azaspiro[3.4]octan-6-one; | 0.54 |
| 14 | (2r,4s)-2-(2-(5-(tert-Butyl)-2-methylphenyl)-7-azaspiro[3.5]nonane-7-carbonyl)-5-azaspiro[3.4]octan-6-one; | 0.027 |
| 15 | 2-[2-[3-(Trifluoromethyl)phenyl]-7-azaspiro[3.5]nonane-7-carbonyl)-5-azaspiro[3.4]octan-6-one; | 4.1 |
| 16 | (2r,4s)-2-(2-(6-(tert-Butyl)pyridin-2-yl)-7-azaspiro[3.5]nonane-7-carbonyl)-5-azaspiro[3.4]octan-6-one; | 0.36 |

TABLE 3-continued

| Example # | Compound Name | MGL IC$_{50}$ (nM) |
|---|---|---|
| 17 | (2r,4s)-2-[2-[4-[1-(Trifluoromethyl)cyclopropyl]phenyl]-7-azaspiro[3.5]nonane-7-carbonyl)-5-azaspiro[3.4]octan-6-one; | 8.6 |
| 18 | (2r,4s)-2-[2-(3-Chloro-4-(trifluoromethyl)phenyl]-7-azaspiro[3.5]nonane-7-carbonyl)-5-azaspiro[3.4]octan-6-one; | 1.7 |
| 19 | (2r,4s)-2-[2-(2,5-Dimethylphenyl)-7-azaspiro[3.5]nonane-7-carbonyl)-5-azaspiro[3.4]octan-6-one; | 2.4 |
| 20 | (2r,4s)-2-[2-[4-Methoxy-3-(trifluoromethyl)phenyl]-7-azaspiro[3.5]nonane-7-carbonyl)-5-azaspiro[3.4]octan-6-one; | 3.3 |
| 21 | (2s,4s)-2-(2-(4-(tert-Butyl)pyridin-2-yl)-7-azaspiro[3.5]nonane-7-carbonyl)-7-oxa-5-azaspiro[3.4]octan-6-one; | 0.90 |
| 22 | (2r,4s)-2-(2-(5-(tert-Butyl)-2-fluorophenyl)-7-azaspiro[3.5]nonane-7-carbonyl)-5-azaspiro[3.4]octan-6-one; | 0.82 |
| 23 | (2r,4s)-2-(2-(5-(tert-Butyl)-2-ethoxyphenyl)-7-azaspiro[3.5]nonane-7-carbonyl)-5-azaspiro[3.4]octan-6-one; | 0.49 |
| 24 | (2r,4s)-2-[2-(o-Tolyl)-7-azaspiro[3.5]nonane-7-carbonyl)-5-azaspiro[3.4]octan-6-one; | 12 |
| 25 | (2r,4s)-2-[2-(3-Isopropylphenyl)-7-azaspiro[3.5]nonane-7-carbonyl)-5-azaspiro[3.4]octan-6-one; | 1.4 |
| 26 | (2r,4s)-2-[2-(2,3-Dimethylphenyl)-7-azaspiro[3.5]nonane-7-carbonyl)-5-azaspiro[3.4]octan-6-one; | 4.4 |
| 27 | (2r,4s)-2-(2-(5-(tert-Butyl)-2-methoxyphenyl)-7-azaspiro[3.5]nonane-7-carbonyl)-5-azaspiro[3.4]octan-6-one; | 0.40 |
| 28 | (2s,4s)-2-(2-(2,2-Difluorobenzo[d][1,3]dioxol-5-yl)-7-azaspiro[3.5]nonane-7-carbonyl)-7-oxa-5-azaspiro[3.4]octan-6-one; | 1.1 |
| 29 | (2s,4s)-2-[2-(2-Methoxyphenyl)-7-azaspiro[3.5]nonane-7-carbonyl)-7-oxa-5-azaspiro[3.4]octan-6-one; | 1.8 |
| 30 | (2s,4s)-2-[2-(4-Methoxyphenyl)-7-azaspiro[3.5]nonane-7-carbonyl)-7-oxa-5-azaspiro[3.4]octan-6-one; | 6.4 |
| 31 | (2s,4s)-2-(2-(6-(tert-Butyl)pyridin-2-yl)-7-azaspiro[3.5]nonane-7-carbonyl)-7-oxa-5-azaspiro[3.4]octan-6-one; | 0.095 |
| 32 | (2s,4s)-2-(2-(3-Fluoro-6-(trifluoromethyl)pyridin-2-yl)-7-azaspiro[3.5]nonane-7-carbonyl)-7-oxa-5-azaspiro[3.4]octan-6-one; | 0.86 |
| 33 | (2s,4s)-2-(2-(6-(Trifluoromethyl)pyridin-2-yl)-7-azaspiro[3.5]nonane-7-carbonyl)-7-oxa-5-azaspiro[3.4]octan-6-one; | 4.4 |
| 34 | (2s,4s)-2-(2-(5-Fluoro-6-methylpyridin-2-yl)-7-azaspiro[3.5]nonane-7-carbonyl)-7-oxa-5-azaspiro[3.4]octan-6-one; | 5.9 |
| 35 | (2s,4s)-2-(2-(2-(tert-Butyl)pyrimidin-4-yl)-7-azaspiro[3.5]nonane-7-carbonyl)-7-oxa-5-azaspiro[3.4]octan-6-one; | 0.35 |
| 36 | (2s,4s)-2-(2-(4-(tert-Butyl)oxazol-2-yl)-7-azaspiro[3.5]nonane-7-carbonyl)-7-oxa-5-azaspiro[3.4]octan-6-one; | 2.7 |
| 37 | (2s,4s)-2-[2-(2-(tert-Butyl)oxazol-5-yl)-7-azaspiro[3.5]nonane-7-carbonyl)-7-oxa-5-azaspiro[3.4]octan-6-one; | 1.4 |
| 38 | (2s,4s)-2-(2-(3,5-Difluoropyridin-2-yl)-7-azaspiro[3.5]nonane-7-carbonyl)-7-oxa-5-azaspiro[3.4]octan-6-one; | 5.7 |
| 39 | (rac)-(2s,4s)-2-(2-(4-(Trifluoromethyl)phenyl)-8-azaspiro[4.5]decane-8-carbonyl)-7-oxa-5-azaspiro[3.4]octan-6-one; | 0.039 |
| 40 | (rac)-(2s,4s)-8-Methyl-2-(2-(4-(trifluoromethyl)phenyl)-8-azaspiro[4.5]decane-8-carbonyl)-7-oxa-5-azaspiro[3.4]octan-6-one; | 0.23 |
| 41 | (rac)-(2s,4s)-2-(6-Phenyl-2-azaspiro[3.4]octane-2-carbonyl)-7-oxa-5-azaspiro[3.4]octan-6-one; | 11 |
| 42 | (2r,4S*)-2-((R*)-6-Phenyl-2-azaspiro[3.4]octane-2-carbonyl)-5-azaspiro[3.4]octan-6-one; | 31 |
| 43 | (2r,4R*)-2-((S*)-6-Phenyl-2-azaspiro[3.4]octane-2-carbonyl)-5-azaspiro[3.4]octan-6-one; | 34 |
| 44 | (rac)-(2s,4s)-2-(6-(4-(Trifluoromethyl)phenyl)-2-azaspiro[3.4]octane-2-carbonyl)-7-oxa-5-azaspiro[3.4]octan-6-one; | 0.32 |
| 45 | (2s,4s)-2-((R*)-6-(4-(Trifluoromethyl)phenyl)-2-azaspiro[3.4]octane-2-carbonyl)-7-oxa-5-azaspiro[3.4]octan-6-one; | 0.25 |
| 46 | (2s,4R*)-2-((S*)-6-(4-(Trifluoromethyl)phenyl)-2-azaspiro[3.4]octane-2-carbonyl)-7-oxa-5-azaspiro[3.4]octan-6-one; | 0.10 |
| 47 | (2r,4S*)-2-((R*)-6-(4-(Trifluoromethyl)phenyl)-2-azaspiro[3.4]octane-2-carbonyl)-5-azaspiro[3.4]octan-6-one; | 1.5 |
| 48 | (2r,4R*)-2-((S*)-6-(4-(Trifluoromethyl)phenyl)-2-azaspiro[3.4]octane-2-carbonyl)-5-azaspiro[3.4]octan-6-one; | 0.87 |
| 49 | (rac)-(2s,4s)-2-(6-(4-(tert-Butyl)phenyl)-2-azaspiro[3.4]octane-2-carbonyl)-7-oxa-5-azaspiro[3.4]octan-6-one; | 0.11 |
| 50 | (rac)-(2s,4s)-2-(6-(3-(tert-Butyl)phenyl)-2-azaspiro[3.4]octane-2-carbonyl)-7-oxa-5-azaspiro[3.4]octan-6-one; | 0.086 |
| 51 | (rac)-(2s,4s)-2-(6-(3-(tert-Butyl)phenyl)-2-azaspiro[3.4]octane-2-carbonyl)-8-methyl-7-oxa-5-azaspiro[3.4]octan-6-one; | 1.0 |
| 52 | (rac)-(2s,4s)-2-(6-Cyclopropyl-2-azaspiro[3.4]octane-2-carbonyl)-7-oxa-5-azaspiro[3.4]octan-6-one; | 27 |
| 53 | (rac)-(2s,4s)-2-(6-Cyclohexyl-2-azaspiro[3.4]octane-2-carbonyl)-7-oxa-5-azaspiro[3.4]octan-6-one; | 0.71 |
| 54 | (rac)-(2r,4s)-2-(6-Cyclohexyl-2-azaspiro[3.4]octane-2-carbonyl)-5-azaspiro[3.4]octan-6-one; | 3.2 |

TABLE 3-continued

| Example # | Compound Name | MGL IC$_{50}$ (nM) |
|---|---|---|
| 55 | (rac)-(2s,4s)-2-(6-Cyclopentyl-2-azaspiro[3.4]octane-2-carbonyl)-7-oxa-5-azaspiro[3.4]octan-6-one; | 1.1 |
| 56 | (rac)-(2s,4s)-2-(6-Cyclobutyl-2-azaspiro[3.4]octane-2-carbonyl)-7-oxa-5-azaspiro[3.4]octan-6-one; | 18 |
| 57 | (rac)-(2s,4s)-2-(2-(3-(tert-Butyl)phenyl)-8-azaspiro[4.5]decane-8-carbonyl)-7-oxa-5-azaspiro[3.4]octan-6-one; | 0.10 |
| 58 | (rac)-(2s,4s)-2-(2-(4-(tert-Butyl)phenyl)-8-azaspiro[4.5]decane-8-carbonyl)-7-oxa-5-azaspiro[3.4]octan-6-one; | 0.11 |
| 59 | (2s,4s)-2-(2-(3-Isopropylphenyl)-6-azaspiro[3.4]octane-6-carbonyl)-7-oxa-5-azaspiro[3.4]octan-6-one; | 0.87 |
| 60 | (2s,4s)-2-(2-(3-(tert-Butyl)phenyl)-6-azaspiro[3.4]octane-6-carbonyl)-7-oxa-5-azaspiro[3.4]octan-6-one; | 0.28 |
| 61 | (rac)-(2s,4s)-2-(6-(3-Isopropylphenyl)-2-azaspiro[3.4]octane-2-carbonyl)-7-oxa-5-azaspiro[3.4]octan-6-one; | 0.17 |
| 62 | (rac)-(2r,4s)-2-(6-(3-Isopropylphenyl)-2-azaspiro[3.4]octane-2-carbonyl)-5-azaspiro[3.4]octan-6-one; | 1.8 |
| 63 | (rac)-(2s,4s)-2-(6-(4-Isopropylphenyl)-2-azaspiro[3.4]octane-2-carbonyl)-7-oxa-5-azaspiro[3.4]octan-6-one; | 0.10 |
| 64 | (2s,4s)-2-(2-Phenyl-6-azaspiro[3.4]octane-6-carbonyl)-7-oxa-5-azaspiro[3.4]octan-6-one; | 13 |
| 65 | (2s,4s)-2-(6-(3-(tert-Butyl)phenyl)-2-azaspiro[3.3]heptane-2-carbonyl)-7-oxa-5-azaspiro[3.4]octan-6-one; | 0.097 |
| 66 | (2s,4s)-2-(6-(m-Tolyl)-2-azaspiro[3.3]heptane-2-carbonyl)-7-oxa-5-azaspiro[3.4]octan-6-one; | 3.8 |
| 67 | (2s,4s)-2-(6-(3-Isopropylphenyl)-2-azaspiro[3.3]heptane-2-carbonyl)-7-oxa-5-azaspiro[3.4]octan-6-one; | 0.28 |
| 68 | (2s,4s)-2-(6-(3,4-Dimethylphenyl)-2-azaspiro[3.3]heptane-2-carbonyl)-7-oxa-5-azaspiro[3.4]octan-6-one; | 1.0 |
| 69 | (2s,4s)-2-(6-Cyclohexyl-2-azaspiro[3.3]heptane-2-carbonyl)-7-oxa-5-azaspiro[3.4]octan-6-one; | 0.90 |
| 70 | (2s,4s)-2-(6-(3,5-Dimethylphenyl)-2-azaspiro[3.3]heptane-2-carbonyl)-7-oxa-5-azaspiro[3.4]octan-6-one; | 1.3 |
| 71 | (2s,4s)-2-(6-(2,4-Dimethylphenyl)-2-azaspiro[3.3]heptane-2-carbonyl)-7-oxa-5-azaspiro[3.4]octan-6-one; | 3.2 |
| 72 | (2s,4s)-2-(6-(3-Cyclopropylphenyl)-2-azaspiro[3.3]heptane-2-carbonyl)-7-oxa-5-azaspiro[3.4]octan-6-one; | 0.30 |
| 73 | (2s,4s)-2-(6-(3-Cyclobutylphenyl)-2-azaspiro[3.3]heptane-2-carbonyl)-7-oxa-5-azaspiro[3.4]octan-6-one; | 0.21 |
| 74 | (2s,4s)-2-(6-(2,3-Dihydro-1H-inden-5-yl)-2-azaspiro[3.3]heptane-2-carbonyl)-7-oxa-5-azaspiro[3.4]octan-6-one; | 0.62 |
| 75 | (2s,4s)-2-(6-Phenyl-2-azaspiro[3.3]heptane-2-carbonyl)-7-oxa-5-azaspiro[3.4]octan-6-one; | 48 |
| 76 | (2s,4s)-2-(7-Phenyl-2-azaspiro[3.5]nonane-2-carbonyl)-7-oxa-5-azaspiro[3.4]octan-6-one; | 0.73 |
| 77 | (2s,4s)-2-(6-Cyclopentyl-2-azaspiro[3.3]heptane-2-carbonyl)-7-oxa-5-azaspiro[3.4]octan-6-one; | 1.9 |
| 78 | (2s,4s)-2-(6-Cyclobutyl-2-azaspiro[3.3]heptane-2-carbonyl)-7-oxa-5-azaspiro[3.4]octan-6-one; and | 4.9 |
| 79 | (2s,4s)-2-(6-(1-Methylcyclopropyl)-2-azaspiro[3.3]heptane-2-carbonyl)-7-oxa-5-azaspiro[3.4]octan-6-one. | 6.5 |

NT means not tested.

What is claimed is:

1. A method of treating a subject suffering from or diagnosed with a disease, disorder, or condition mediated by MGL receptor activity, comprising administering to a subject in need of such treatment a therapeutically effective amount of a compound of Formula (I):

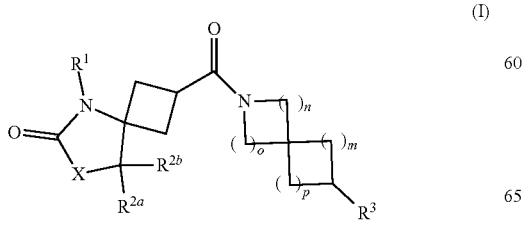

(I)

wherein
X is CH$_2$ or O;
R$^1$ is H;
R$^{2a}$ and R$^{2b}$ are each independently selected from H and C$_{1-4}$alkyl;
R$^3$ is selected from:
(i) phenyl, benzyl, or monocyclic heteroaryl, each optionally substituted with one, two, or three substituents selected from: halo, C$_{1-6}$alkyl, C$_{1-6}$haloalkyl, C$_{1-6}$alkyl-OH, OC$_{1-6}$alkyl, OC$_{1-6}$haloalkyl, SC$_{1-6}$alkyl, SF$_5$, Si(CH$_3$)$_3$, NR$^a$R$^b$, C$_{3-6}$cycloalkyl, OC$_{3-6}$cycloalkyl, phenyl, O-phenyl, and O-pyridyl, wherein each cycloalkyl, phenyl, or pyridyl is optionally substituted with one or two C$_{1-4}$alkyl, C$_{1-4}$haloalkyl, or halo groups; or two adjacent ring substituents on the phenyl, benzyl, or monocyclic heteroaryl, taken together with the atoms to which they are attached form a fused monocyclic C$_{5-6}$cycloalkyl or heterocycloalkyl ring, each ring optionally substituted with one or two $C_{1-4}$alkyl, $C_{1-4}$haloalkyl, or halo groups;
  wherein $R^a$ and $R^b$ are each independently H or $C_{1-4}$alkyl;
(ii) a bicyclic heteroaryl optionally substituted with $C_{1-4}$alkyl or halo; and
(iii) $C_{3-6}$alkyl or $C_{3-6}$cycloalkyl optionally substituted with $C_{1-4}$alkyl, $C_{1-4}$haloalkyl, or halo; and
n, m, o, and p are each independently 1 or 2;
or a pharmaceutically acceptable salt, isotope, N-oxide, or stereoisomer thereof.

2. The method of claim 1, wherein
$R^3$ is selected from: $C_{3-6}$cycloalkyl; $C_{3-6}$cycloalkyl substituted with $C_{1-4}$alkyl; phenyl; phenyl substituted with one or two members each independently selected from: halo, $C_{1-6}$alkyl, $C_{1-6}$ haloalkyl, $OC_{1-6}$alkyl, $OC_{1-6}$haloalkyl, and $C_{3-6}$cycloalkyl optionally substituted with $CH_3$ or $CF_3$; pyridyl substituted with one or two members each independently selected from: halo, $C_{1-6}$alkyl, and $C_{1-6}$haloalkyl; pyrimidinyl substituted with $C_{1-6}$alkyl;

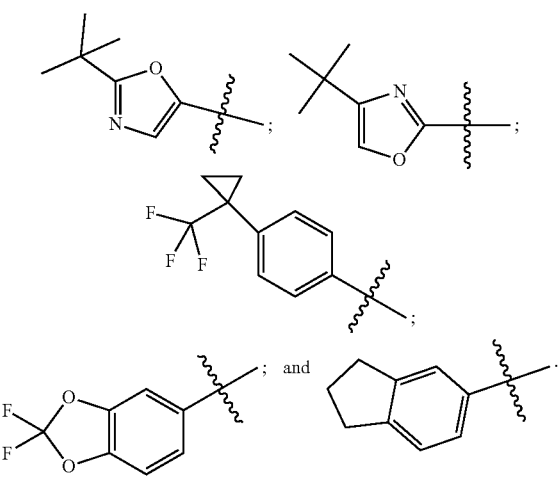

3. The method of claim 1, wherein X is $CH_2$.
4. The method of claim 1, wherein X is O.
5. The method of claim 1, wherein (a) $R^{2a}$ and $R^{2b}$ are each H; of (b) $R^{2a}$ and $R^{2b}$ are each $CH_3$; or (c) $R^{2a}$ is H and $R^{2b}$ is $CH_3$.
6. The method of claim 1, wherein $R^3$ is:
(a) cyclopropyl, cyclobutyl, cyclopentyl or cyclohexyl;
(b)

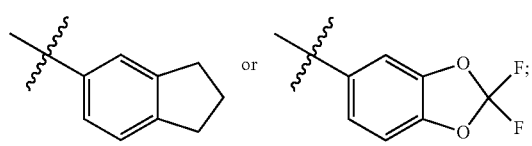 [SMILES: *c1ccc2c(c1)CCC2 ; *c1ccc2c(c1)OC(F)(F)O2]

(c) $R^3$ is phenyl, or phenyl substituted with one or two members each independently selected from: Cl, F, $CH_3$, $CH(CH_3)_2$, $C(CH_3)_3$, $CF_3$, $OCH_3$, $OCH_2CH_3$, $OCF_3$, cyclopropyl, cyclopropyl substituted with $CF_3$, and cyclobutyl;

(d)

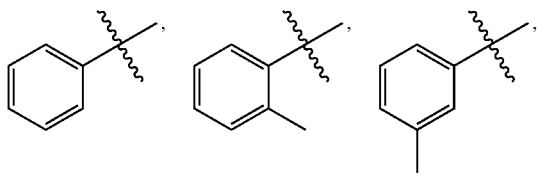

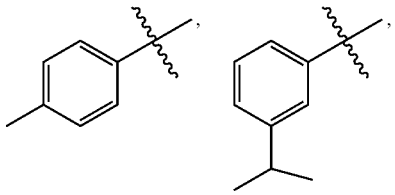

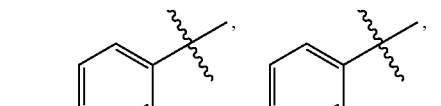

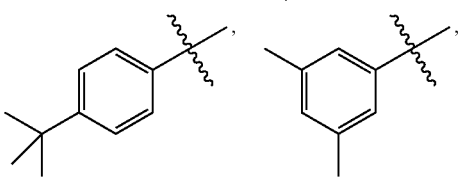

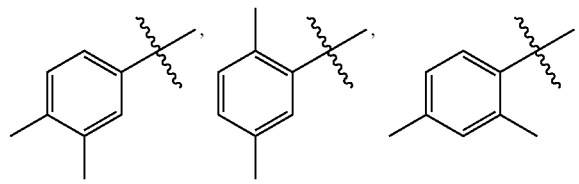

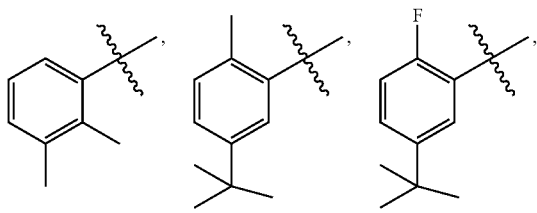

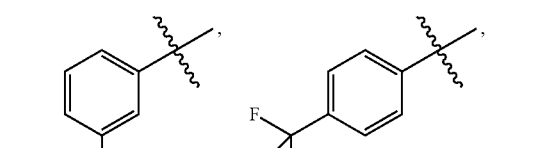

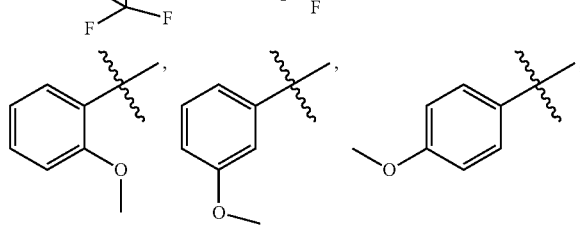

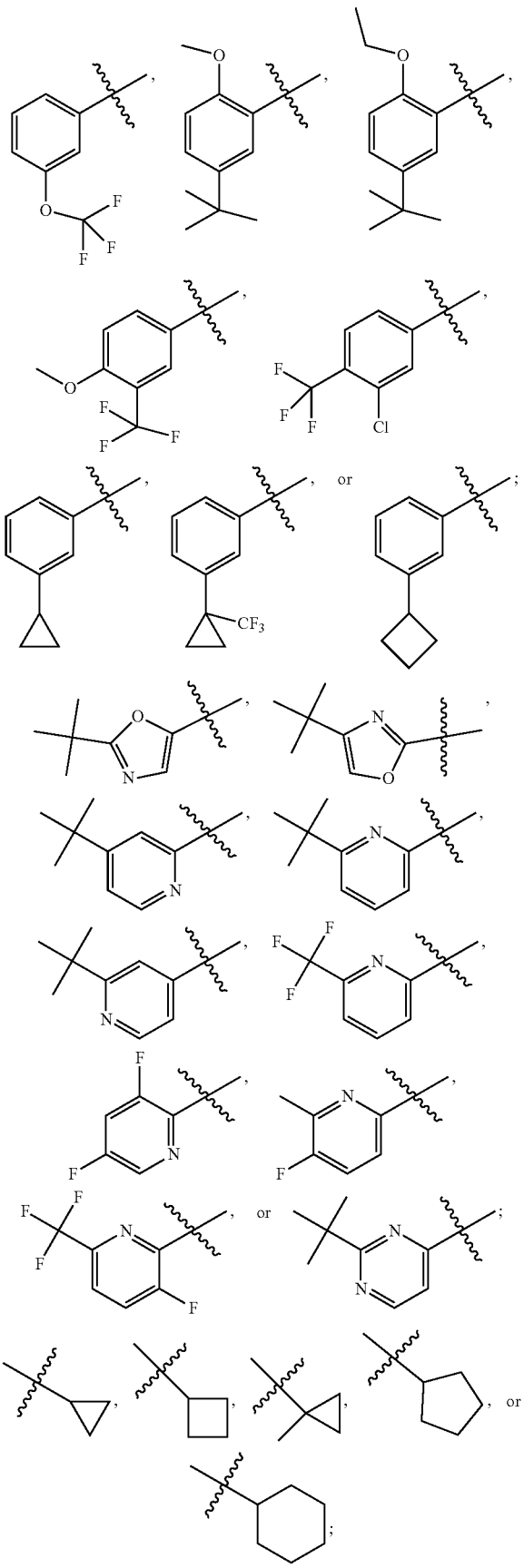

or (g) 4-trifluoromethylphenyl, 3-isopropylphenyl, 4-isopropylphenyl, 2,4-dimethylphenyl, 3-tert-butylphenyl, 4-tert-butylphenyl, or 3-cyclopropylphenyl.

7. The method of claim 1, wherein:
(a) n and o are each 1;
(b) n and o are each 2;
(c) n is 1 and o is 2;
(d) m and p are each 1;
(e) m and p are each 2;
(f) m is 1 and p is 2;
(g) m, n, o, and p are each 1;
(h) m, n, and p are each 1 and o is 2;
(i) m, n, and o are each 1 and p is 2;
(j) n and o are each 2 and m and p are each 1;
(k) n and o are each 1 and m and p are each 2; or
(l) n, o, and p are each 2 and m is 1.

8. A method of treating a subject suffering from or diagnosed with a disease, disorder, or condition mediated by MGL receptor activity, comprising administering to a subject in need of such treatment a therapeutically effective amount of a compound selected from:

(2s,4s)-2-(2-Phenyl-7-azaspiro[3.5]nonane-7-carbonyl)-7-oxa-5-azaspiro[3.4]octan-6-one;

(2s,4s)-2-(2-(3-(tert-Butyl)phenyl)-7-azaspiro[3.5]nonane-7-carbonyl)-7-oxa-5-azaspiro[3.4]octan-6-one;

(2s,4s)-2-(2-(p-Tolyl)-7-azaspiro[3.5]nonane-7-carbonyl)-7-oxa-5-azaspiro[3.4]octan-6-one;

(2s,4s)-2-(2-(o-Tolyl)-7-azaspiro[3.5]nonane-7-carbonyl)-7-oxa-5-azaspiro[3.4]octan-6-one;

(2s,4s)-2-[2-(3-Cyclopropylphenyl)-7-azaspiro[3.5]nonane-7-carbonyl)-7-oxa-5-azaspiro[3.4]octan-6-one;

(2s,4s)-2-[2-(3-Isopropylphenyl)-7-azaspiro[3.5]nonane-7-carbonyl)-7-oxa-5-azaspiro[3.4]octan-6-one;

(2s,4s)-2-[2-(m-Tolyl)-7-azaspiro[3.5]nonane-7-carbonyl)-7-oxa-5-azaspiro[3.4]octan-6-one;

(2s,4s)-2-[2-(3-Methoxyphenyl)-7-azaspiro[3.5]nonane-7-carbonyl)-7-oxa-5-azaspiro[3.4]octan-6-one;

(2s,4s)-2-[2-[3-(Trifluoromethoxy)phenyl]-7-azaspiro[3.5]nonane-7-carbonyl)-7-oxa-5-azaspiro[3.4]octan-6-one;

(2s,4s)-2-[2-(2,3-Dimethylphenyl)-7-azaspiro[3.5]nonane-7-carbonyl)-7-oxa-5-azaspiro[3.4]octan-6-one;

(2r,4s)-2-[2-(3-(tert-Butyl)phenyl)-7-azaspiro[3.5]nonane-7-carbonyl)-5-azaspiro[3.4]octan-6-one;

(2s,4s)-2-[2-(2,4-Dimethylphenyl)-7-azaspiro[3.5]nonane-7-carbonyl)-7-oxa-5-azaspiro[3.4]octan-6-one;

(2s,4s)-2-[2-(2-(Tert-butyl)pyridin-4-yl)-7-azaspiro[3.5]nonane-7-carbonyl)-7-oxa-5-azaspiro[3.4]octan-6-one;

(2r,4s)-2-[2-(5-(tert-Butyl)-2-methylphenyl)-7-azaspiro[3.5]nonane-7-carbonyl)-5-azaspiro[3.4]octan-6-one;

2-[2-[3-(Trifluoromethyl)phenyl]-7-azaspiro[3.5]nonane-7-carbonyl)-5-azaspiro[3.4]octan-6-one;

(2r,4s)-2-(2-(6-(tert-Butyl)pyridin-2-yl)-7-azaspiro[3.5]nonane-7-carbonyl)-5-azaspiro[3.4]octan-6-one;

(2r,4s)-2-[2-[4-[1-(Trifluoromethyl)cyclopropyl]phenyl]-7-azaspiro[3.5]nonane-7-carbonyl)-5-azaspiro[3.4]octan-6-one;

(2r,4s)-2-[2-[3-Chloro-4-(trifluoromethyl)phenyl]-7-azaspiro[3.5]nonane-7-carbonyl)-5-azaspiro[3.4]octan-6-one;

(2r,4s)-2-[2-(2,5-Dimethylphenyl)-7-azaspiro[3.5]nonane-7-carbonyl)-5-azaspiro[3.4]octan-6-one;

(2r,4s)-2-[2-[4-Methoxy-3-(trifluoromethyl)phenyl]-7-azaspiro[3.5]nonane-7-carbonyl)-5-azaspiro[3.4]octan-6-one;

(2s,4s)-2-(2-(4-(tert-Butyl)pyridin-2-yl)-7-azaspiro[3.5]nonane-7-carbonyl)-7-oxa-5-azaspiro[3.4]octan-6-one;

(2r,4s)-2-(2-(5-(tert-Butyl)-2-fluorophenyl)-7-azaspiro[3.5]nonane-7-carbonyl)-5-azaspiro[3.4]octan-6-one;
(2r,4s)-2-(2-(5-(tert-Butyl)-2-ethoxyphenyl)-7-azaspiro[3.5]nonane-7-carbonyl)-5-azaspiro[3.4]octan-6-one;
(2r,4s)-2-[2-(o-Tolyl)-7-azaspiro[3.5]nonane-7-carbonyl]-5-azaspiro[3.4]octan-6-one;
(2r,4s)-2-[2-(3-Isopropylphenyl)-7-azaspiro[3.5]nonane-7-carbonyl)-5-azaspiro[3.4]octan-6-one;
(2r,4s)-2-[2-(2,3-Dimethylphenyl)-7-azaspiro[3.5]nonane-7-carbonyl)-5-azaspiro[3.4]octan-6-one;
(2r,4s)-2-(2-(5-(tert-Butyl)-2-methoxyphenyl)-7-azaspiro[3.5]nonane-7-carbonyl)-5-azaspiro[3.4]octan-6-one;
(2s,4s)-2-(2-(2,2-Difluorobenzo[d][1,3]dioxol-5-yl)-7-azaspiro[3.5]nonane-7-carbonyl)-7-oxa-5-azaspiro[3.4]octan-6-one;
(2s,4s)-2-[2-(2-Methoxyphenyl)-7-azaspiro[3.5]nonane-7-carbonyl)-7-oxa-5-azaspiro[3.4]octan-6-one;
(2s,4s)-2-[2-(4-Methoxyphenyl)-7-azaspiro[3.5]nonane-7-carbonyl)-7-oxa-5-azaspiro[3.4]octan-6-one;
(2s,4s)-2-(2-(6-(tert-Butyl)pyridin-2-yl)-7-azaspiro[3.5]nonane-7-carbonyl)-7-oxa-5-azaspiro[3.4]octan-6-one;
(2s,4s)-2-(2-(3-Fluoro-6-(trifluoromethyl)pyridin-2-yl)-7-azaspiro[3.5]nonane-7-carbonyl)-7-oxa-5-azaspiro[3.4]octan-6-one;
(2s,4s)-2-(2-(6-(Trifluoromethyl)pyridin-2-yl)-7-azaspiro[3.5]nonane-7-carbonyl)-7-oxa-5-azaspiro[3.4]octan-6-one;
(2s,4s)-2-(2-(5-Fluoro-6-methylpyridin-2-yl)-7-azaspiro[3.5]nonane-7-carbonyl)-7-oxa-5-azaspiro[3.4]octan-6-one;
(2s,4s)-2-(2-(2-(tert-Butyl)pyrimidin-4-yl)-7-azaspiro[3.5]nonane-7-carbonyl)-7-oxa-5-azaspiro[3.4]octan-6-one;
(2s,4s)-2-(2-(4-(tert-Butyl)oxazol-2-yl)-7-azaspiro[3.5]nonane-7-carbonyl)-7-oxa-5-azaspiro[3.4]octan-6-one;
(2s,4s)-2-[2-(2-(tert-Butyl)oxazol-5-yl)-7-azaspiro[3.5]nonane-7-carbonyl)-7-oxa-5-azaspiro[3.4]octan-6-one;
(2s,4s)-2-(2-(3,5-Difluoropyridin-2-yl)-7-azaspiro[3.5]nonane-7-carbonyl)-7-oxa-5-azaspiro[3.4]octan-6-one;
(rac)-(2s,4s)-2-(2-(4-(Trifluoromethyl)phenyl)-8-azaspiro[4.5]decane-8-carbonyl)-7-oxa-5-azaspiro[3.4]octan-6-one;
(rac)-(2s,4s)-8-Methyl-2-(2-(4-(trifluoromethyl)phenyl)-8-azaspiro[4.5]decane-8-carbonyl)-7-oxa-5-azaspiro[3.4]octan-6-one;
(rac)-(2s,4s)-2-(6-Phenyl-2-azaspiro[3.4]octane-2-carbonyl)-7-oxa-5-azaspiro[3.4]octan-6-one;
(2r,4S*)-2-((R*)-6-Phenyl-2-azaspiro[3.4]octane-2-carbonyl)-5-azaspiro[3.4]octan-6-one;
(2r,4R*)-2-((S*)-6-Phenyl-2-azaspiro[3.4]octane-2-carbonyl)-5-azaspiro[3.4]octan-6-one;
(rac)-(2s,4s)-2-(6-(4-(Trifluoromethyl)phenyl)-2-azaspiro[3.4]octane-2-carbonyl)-7-oxa-5-azaspiro[3.4]octan-6-one;
(2s,4s)-2-((R*)-6-(4-(Trifluoromethyl)phenyl)-2-azaspiro[3.4]octane-2-carbonyl)-7-oxa-5-azaspiro[3.4]octan-6-one;
(2s,4R*)-2-((S*)-6-(4-(Trifluoromethyl)phenyl)-2-azaspiro[3.4]octane-2-carbonyl)-7-oxa-5-azaspiro[3.4]octan-6-one;
(2r,4S*)-2-((R*)-6-(4-(Trifluoromethyl)phenyl)-2-azaspiro[3.4]octane-2-carbonyl)-5-azaspiro[3.4]octan-6-one;
(2r,4R*)-2-((S*)-6-(4-(Trifluoromethyl)phenyl)-2-azaspiro[3.4]octane-2-carbonyl)-5-azaspiro[3.4]octan-6-one;
(rac)-(2s,4s)-2-(6-(4-(tert-Butyl)phenyl)-2-azaspiro[3.4]octane-2-carbonyl)-7-oxa-5-azaspiro[3.4]octan-6-one;
(rac)-(2s,4s)-2-(6-(3-(tert-Butyl)phenyl)-2-azaspiro[3.4]octane-2-carbonyl)-7-oxa-5-azaspiro[3.4]octan-6-one;
(rac)-(2s,4s)-2-(6-(3-(tert-Butyl)phenyl)-2-azaspiro[3.4]octane-2-carbonyl)-8-methyl-7-oxa-5-azaspiro[3.4]octan-6-one;
(rac)-(2s,4s)-2-(6-Cyclopropyl-2-azaspiro[3.4]octane-2-carbonyl)-7-oxa-5-azaspiro[3.4]octan-6-one;
(rac)-(2s,4s)-2-(6-Cyclohexyl-2-azaspiro[3.4]octane-2-carbonyl)-7-oxa-5-azaspiro[3.4]octan-6-one;
(rac)-(2r,4s)-2-(6-Cyclohexyl-2-azaspiro[3.4]octane-2-carbonyl)-5-azaspiro[3.4]octan-6-one;
(rac)-(2s,4s)-2-(6-Cyclopentyl-2-azaspiro[3 0.4]octane-2-carbonyl)-7-oxa-5-azaspiro[3.4]octan-6-one;
(rac)-(2s,4s)-2-(6-Cyclobutyl-2-azaspiro[3.4]octane-2-carbonyl)-7-oxa-5-azaspiro[3.4]octan-6-one;
(rac)-(2s,4s)-2-(2-(3-(tert-Butyl)phenyl)-8-azaspiro[4.5]decane-8-carbonyl)-7-oxa-5-azaspiro[3.4]octan-6-one;
(rac)-(2s,4s)-2-(2-(4-(tert-Butyl)phenyl)-8-azaspiro[4.5]decane-8-carbonyl)-7-oxa-5-azaspiro[3.4]octan-6-one;
(2s,4s)-2-(2-(3-Isopropylphenyl)-6-azaspiro[3.4]octane-6-carbonyl)-7-oxa-5-azaspiro[3.4]octan-6-one;
(2s,4s)-2-(2-(3-(tert-Butyl)phenyl)-6-azaspiro[3.4]octane-6-carbonyl)-7-oxa-5-azaspiro[3.4]octan-6-one;
(rac)-(2s,4s)-2-(6-(3-Isopropylphenyl)-2-azaspiro[3.4]octane-2-carbonyl)-7-oxa-5-azaspiro[3.4]octan-6-one;
(rac)-(2r,4s)-2-(6-(3-Isopropylphenyl)-2-azaspiro[3.4]octane-2-carbonyl)-5-azaspiro[3.4]octan-6-one;
(rac)-(2s,4s)-2-(6-(4-Isopropylphenyl)-2-azaspiro[3.4]octane-2-carbonyl)-7-oxa-5-azaspiro[3.4]octan-6-one;
(2s,4s)-2-(2-Phenyl-6-azaspiro[3.4]octane-6-carbonyl)-7-oxa-5-azaspiro[3.4]octan-6-one;
(2s,4s)-2-(6-(3-(tert-Butyl)phenyl)-2-azaspiro[3.3]heptane-2-carbonyl)-7-oxa-5-azaspiro[3.4]octan-6-one;
(2s,4s)-2-(6-(m-Tolyl)-2-azaspiro[3.3]heptane-2-carbonyl)-7-oxa-5-azaspiro[3.4]octan-6-one;
(2s,4s)-2-(6-(3-Isopropylphenyl)-2-azaspiro[3.3]heptane-2-carbonyl)-7-oxa-5-azaspiro[3.4]octan-6-one;
(2s,4s)-2-(6-(3,4-Dimethylphenyl)-2-azaspiro[3.3]heptane-2-carbonyl)-7-oxa-5-azaspiro[3.4]octan-6-one;
(2s,4s)-2-(6-Cyclohexyl-2-azaspiro[3.3]heptane-2-carbonyl)-7-oxa-5-azaspiro[3.4]octan-6-one;
(2s,4s)-2-(6-(3,5-Dimethylphenyl)-2-azaspiro[3.3]heptane-2-carbonyl)-7-oxa-5-azaspiro[3.4]octan-6-one;
(2s,4s)-2-(6-(2,4-Dimethylphenyl)-2-azaspiro[3.3]heptane-2-carbonyl)-7-oxa-5-azaspiro[3.4]octan-6-one;
(2s,4s)-2-(6-(3-Cyclopropylphenyl)-2-azaspiro[3.3]heptane-2-carbonyl)-7-oxa-5-azaspiro[3.4]octan-6-one;
(2s,4s)-2-(6-(3-Cyclobutylphenyl)-2-azaspiro[3.3]heptane-2-carbonyl)-7-oxa-5-azaspiro[3.4]octan-6-one;
(2s,4s)-2-(6-(2,3-Dihydro-1H-inden-5-yl)-2-azaspiro[3.3]heptane-2-carbonyl)-7-oxa-5-azaspiro[3.4]octan-6-one;
(2s,4s)-2-(6-Phenyl-2-azaspiro[3.3]heptane-2-carbonyl)-7-oxa-5-azaspiro[3.4]octan-6-one;
(2s,4s)-2-(7-Phenyl-2-azaspiro[3.5]nonane-2-carbonyl)-7-oxa-5-azaspiro[3.4]octan-6-one;
(2s,4s)-2-(6-Cyclopentyl-2-azaspiro[3.3]heptane-2-carbonyl)-7-oxa-5-azaspiro[3.4]octan-6-one;
(2s,4s)-2-(6-Cyclobutyl-2-azaspiro[3.3]heptane-2-carbonyl)-7-oxa-5-azaspiro[3.4]octan-6-one; and
(2s,4s)-2-(6-(1-Methylcyclopropyl)-2-azaspiro[3.3]heptane-2-carbonyl)-7-oxa-5-azaspiro[3.4]octan-6-one;
and pharmaceutically acceptable salts, isotopes, N-oxides, and stereoisomers thereof.

9. The method of claim 8, wherein the compound is selected from:
- (2r,4s)-2-(2-(6-(tert-Butyl)pyridin-2-yl)-7-azaspiro[3.5]nonane-7-carbonyl)-5-azaspiro[3.4]octan-6-one;
- (2s,4s)-2-((R*)-6-(4-(Trifluoromethyl)phenyl)-2-azaspiro[3.4]octane-2-carbonyl)-7-oxa-5-azaspiro[3.4]octan-6-one;
- (2s,4R*)-2-((S*)-6-(4-(Trifluoromethyl)phenyl)-2-azaspiro[3.4]octane-2-carbonyl)-7-oxa-5-azaspiro[3.4]octan-6-one; and
- (2s,4s)-2-(6-(3-(tert-Butyl)phenyl)-2-azaspiro[3.3]heptane-2-carbonyl)-7-oxa-5-azaspiro[3.4]octan-6-one;

and pharmaceutically acceptable salts, isotopes, N-oxides, solvates, and stereoisomers.

10. The method of claim 1, wherein the compound comprises the structure of Formula (IA):

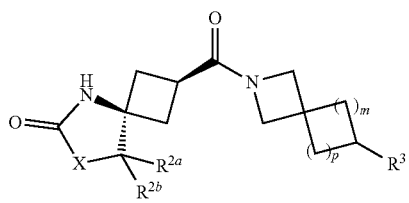
(IA)

wherein
X is CH$_2$ or O;
R$^{2a}$ and R$^{2b}$ are each independently selected from H and CH$_3$;
R$^3$ is selected from: C$_{3-6}$cycloalkyl; C$_{3-6}$cycloalkyl substituted with C$_{1-4}$alkyl; phenyl; phenyl substituted with one or two members each independently selected from: C$_{1-6}$alkyl, C$_{1-6}$haloalkyl, and C$_{3-6}$cycloalkyl; and

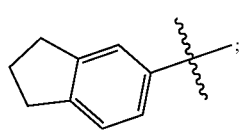 [SMILES: *c1ccc2c(c1)CCC2]

and
m and p are each independently 1 or 2;
or a pharmaceutically acceptable salt, isotope, N-oxide, or stereoisomer thereof.

11. The method of claim 1, wherein the compound comprises the structure of Formula (TB):

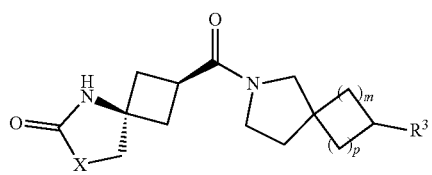
(IB)

wherein
X is O;
R$^3$ is selected from: phenyl and phenyl substituted with C$_{1-6}$alkyl; and
m and p are each 1;

or a pharmaceutically acceptable salt, isotope, N-oxide, or stereoisomer thereof.

12. The method of claim 1, wherein the compound comprises the structure of Formula (IC):

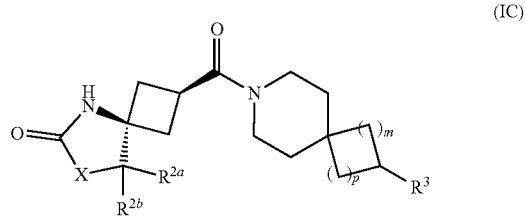
(IC)

wherein
X is CH$_2$ or O;
R$^{2a}$ and R$^{2b}$ are each independently selected from H and CH$_3$;
R$^3$ is selected from: C$_{3-6}$cycloalkyl; phenyl; phenyl substituted with one or two members each independently selected from: halo, C$_{1-6}$alkyl, C$_{1-6}$haloalkyl, OC$_{1-6}$alkyl, OC$_{1-6}$haloalkyl, and C$_{3-6}$cycloalkyl; pyridyl substituted with one or two members each independently selected from: halo, C$_{1-6}$alkyl, and C$_{1-6}$haloalkyl; pyrimidinyl substituted with C$_{1-6}$alkyl;

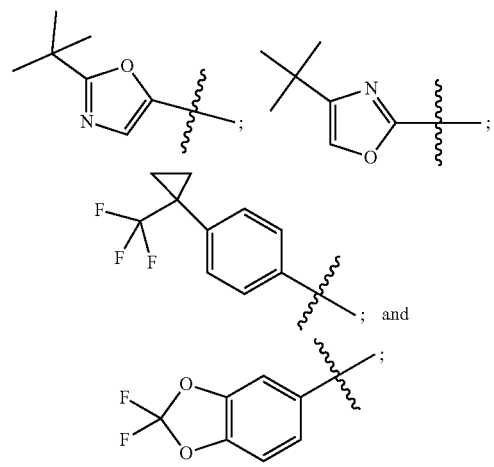

and
m and p are each independently 1 or 2;
or a pharmaceutically acceptable salt, isotope, N-oxide, or stereoisomer thereof.

13. The method of claim 1, wherein the MGL receptor mediated disease, disorder, or condition is selected from: pain, psychiatric conditions, neurological conditions, cancers, and eye conditions.

14. The method of claim 1, wherein the MGL receptor mediated disease, disorder or condition is selected from: major depressive disorder, treatment resistant depression, anxious depression, autism spectrum disorders, Asperger syndrome, and bipolar disorder.

15. The method of claim 1, wherein the MGL receptor mediated disease, disorder or condition is inflammatory pain.

* * * * *